US009417238B2

(12) United States Patent
Reich et al.

(10) Patent No.: US 9,417,238 B2
(45) Date of Patent: *Aug. 16, 2016

(54) POSTERIOR SEGMENT DRUG DELIVERY

(71) Applicant: ForSight Vision4, Inc., Menlo Park, CA (US)

(72) Inventors: Cary J. Reich, Menlo Park, CA (US); Michael Barrett, Menlo Park, CA (US); Randolph E. Campbell, Menlo Park, CA (US); Kathleen C. Farinas, Menlo Park, CA (US)

(73) Assignee: ForSight Vision4, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/080,700

(22) Filed: Nov. 14, 2013

(65) Prior Publication Data

US 2014/0073714 A1 Mar. 13, 2014

Related U.S. Application Data

(63) Continuation of application No. 13/831,695, filed on Mar. 15, 2013, now Pat. No. 8,808,727, which is a continuation of application No. 12/696,678, filed on Jan. 29, 2010, now Pat. No. 8,399,006.

(60) Provisional application No. 61/299,282, filed on Jan. 28, 2010, provisional application No. 61/284,832, filed on Dec. 24, 2009, provisional application No. 61/261,717, filed on Nov. 16, 2009, provisional application No. 61/174,887, filed on May 1, 2009, provisional application No. 61/148,375, filed on Jan. 29, 2009.

(51) Int. Cl.
*A61M 37/00* (2006.01)
*A61M 31/00* (2006.01)
*E21B 49/10* (2006.01)
*G01N 33/558* (2006.01)
*A61F 9/00* (2006.01)
*A61K 9/00* (2006.01)
*A61K 31/57* (2006.01)
*A61K 31/573* (2006.01)

(52) U.S. Cl.
CPC ............ *G01N 33/558* (2013.01); *A61F 9/0017* (2013.01); *A61K 9/0048* (2013.01); *A61K 9/0051* (2013.01); *A61K 31/57* (2013.01); *A61K 31/573* (2013.01); *Y10T 29/49826* (2015.01)

(58) Field of Classification Search
None
See application file for complete search history.

(56) References Cited

U.S. PATENT DOCUMENTS

| 2,564,977 | A | 8/1951 | Hu et al. |
|---|---|---|---|
| 2,585,815 | A | 2/1952 | McLintock |
| 2,886,497 | A | 5/1959 | Butler |
| 3,232,117 | A | 2/1966 | Gilmont |
| 3,416,530 | A | 12/1968 | Ness |
| 3,618,604 | A | 11/1971 | Ness |
| 3,641,237 | A | 2/1972 | Gould et al. |
| 3,828,777 | A | 8/1974 | Ness |
| 3,831,583 | A | 8/1974 | Edmunds, Jr. et al. |
| 3,845,201 | A | 10/1974 | Haddad et al. |
| 3,902,495 | A | 9/1975 | Weiss et al. |
| 3,914,402 | A | 10/1975 | Shell |
| 3,916,899 | A | 11/1975 | Theeuwes et al. |
| 3,926,188 | A | 12/1975 | Baker et al. |
| 3,949,748 | A | 4/1976 | Malmin |
| 3,949,750 | A | 4/1976 | Freeman |
| 3,961,628 | A | 6/1976 | Arnold |
| 3,977,404 | A | 8/1976 | Theeuwes |
| 3,995,635 | A | 12/1976 | Higuchi et al. |
| 4,008,719 | A | 2/1977 | Theeuwes et al. |
| 4,014,333 | A | 3/1977 | McIntyre |
| 4,014,334 | A | 3/1977 | Theeuwes et al. |
| 4,014,335 | A | 3/1977 | Arnold |
| 4,034,756 | A | 7/1977 | Higuchi et al. |
| 4,034,758 | A | 7/1977 | Theeuwes |
| 4,077,407 | A | 3/1978 | Theeuwes et al. |

(Continued)

FOREIGN PATENT DOCUMENTS

| CN | 101327356 A | 12/2008 |
|---|---|---|
| CN | 101600476 A | 12/2009 |

(Continued)

OTHER PUBLICATIONS

Carbonaro et al. Nano-pore silicon membrane characterization by diffusion and electrical resistance, Journal of Membrane Science, Apr. 2004.*
Jornitz et al., Filter Integrity Testing in Liquid Applications, Revisited; Part I; Pharmaceutical Technology, Oct. 2001, p. 34-50.*
Millipore, Filter Integrity Test Methods; Millipore Corporation, 1999.*
ASTM Designation: E 128-99, published Aug. 1999.*
Andrews, "Effect of nonsteroidal anti-inflammatory drugs on LFA-1 and ICAM-1 expression in gastric mucosa," Am J Physiol. Apr. 1994;266(4 Pt 1):G657-664.
Arvo, Agenda for the Summer Eye Research Conference, (Jul. 2009).
Avery et al., "Intravitreal bevacizumab (Avastin) in the treatment of proliferative diabetic retinopathy," Ophthalmology. Oct. 2006, 113(10):1695-1705.e6.

(Continued)

*Primary Examiner* — Michael G Hartley
*Assistant Examiner* — Nabila Ebrahim
(74) *Attorney, Agent, or Firm* — Fred C. Hernandez; Mintz Levin Cohn Ferris Glovsky and Popeo, P.C.

(57) ABSTRACT

A therapeutic device to release a therapeutic agent comprises a porous structure coupled to a container comprising a reservoir. The reservoir comprises a volume sized to release therapeutic amounts of the therapeutic agent for an extended time when coupled to the porous structure and implanted in the patient. The porous structure may comprise a first side coupled to the reservoir and a second side to couple to the patient to release the therapeutic agent. A plurality of interconnecting channels can extend from the first side to the second side so as to connect a first a plurality of openings on the first side with a second plurality of openings on the second side.

18 Claims, 62 Drawing Sheets

(56) References Cited

U.S. PATENT DOCUMENTS

| | | |
|---|---|---|
| 4,111,201 A | 9/1978 | Theeuwes |
| 4,111,203 A | 9/1978 | Theeuwes |
| 4,135,514 A | 1/1979 | Zaffaroni et al. |
| 4,160,452 A | 7/1979 | Theeuwes |
| 4,164,559 A | 8/1979 | Miyata et al. |
| 4,179,497 A | 12/1979 | Cohen et al. |
| 4,186,184 A | 1/1980 | Zaffaroni |
| 4,200,098 A | 4/1980 | Ayer et al. |
| 4,220,152 A | 9/1980 | Dresback |
| 4,220,153 A | 9/1980 | Dresback |
| 4,256,108 A | 3/1981 | Theeuwes |
| 4,298,000 A | 11/1981 | Thill et al. |
| 4,300,557 A | 11/1981 | Refojo et al. |
| 4,309,776 A | 1/1982 | Berguer |
| 4,326,525 A | 4/1982 | Swanson et al. |
| 4,327,725 A | 5/1982 | Cortese et al. |
| 4,343,787 A | 8/1982 | Katz |
| 4,439,196 A | 3/1984 | Higuchi |
| 4,439,198 A | 3/1984 | Brightman, II et al. |
| 4,475,916 A | 10/1984 | Himmelstein |
| 4,484,922 A | 11/1984 | Rosenwald |
| 4,519,801 A | 5/1985 | Edgren |
| 4,609,374 A | 9/1986 | Ayer |
| 4,627,850 A | 12/1986 | Deters et al. |
| 4,634,418 A | 1/1987 | Binder |
| 4,634,427 A | 1/1987 | Hannula et al. |
| 4,673,405 A | 6/1987 | Guittard et al. |
| 4,693,886 A | 9/1987 | Ayer |
| 4,712,550 A | 12/1987 | Sinnett |
| 4,730,013 A | 3/1988 | Bondi et al. |
| 4,737,150 A | 4/1988 | Baeumle et al. |
| 4,774,091 A | 9/1988 | Yamahira et al. |
| 4,777,049 A | 10/1988 | Magruder et al. |
| 4,781,675 A | 11/1988 | White |
| 4,851,228 A | 7/1989 | Zentner et al. |
| 4,853,229 A | 8/1989 | Theeuwes |
| 4,863,457 A | 9/1989 | Lee |
| 4,865,846 A | 9/1989 | Kaufman |
| 4,883,459 A | 11/1989 | Calderon |
| 4,959,217 A | 9/1990 | Sanders et al. |
| 4,979,938 A | 12/1990 | Stephen et al. |
| 5,049,142 A | 9/1991 | Herrick et al. |
| 5,053,030 A | 10/1991 | Herrick et al. |
| 5,084,021 A | 1/1992 | Baldwin |
| 5,098,443 A | 3/1992 | Parel et al. |
| 5,128,145 A | 7/1992 | Edgren et al. |
| 5,141,748 A | 8/1992 | Rizzo |
| 5,147,647 A | 9/1992 | Darougar |
| 5,164,188 A | 11/1992 | Wong |
| 5,171,270 A | 12/1992 | Herrick |
| 5,174,999 A | 12/1992 | Magruder et al. |
| 5,238,687 A | 8/1993 | Magruder et al. |
| 5,277,912 A | 1/1994 | Lowe et al. |
| 5,282,829 A | 2/1994 | Hermes |
| 5,300,114 A | 4/1994 | Gwon et al. |
| 5,322,691 A | 6/1994 | Darougar et al. |
| 5,334,189 A | 8/1994 | Wade |
| 5,336,175 A | 8/1994 | Mames |
| 5,378,475 A | 1/1995 | Smith et al. |
| 5,413,572 A | 5/1995 | Wong et al. |
| 5,443,505 A | 8/1995 | Wong et al. |
| 5,466,233 A | 11/1995 | Weiner et al. |
| 5,476,511 A | 12/1995 | Gwon et al. |
| 5,516,522 A | 5/1996 | Peyman et al. |
| 5,554,132 A | 9/1996 | Straits et al. |
| 5,562,915 A | 10/1996 | Lowe et al. |
| 5,576,480 A * | 11/1996 | Hopkins et al. .................. 73/38 |
| 5,578,042 A | 11/1996 | Cumming |
| 5,681,572 A | 10/1997 | Seare, Jr. |
| 5,725,493 A | 3/1998 | Avery et al. |
| 5,766,242 A | 6/1998 | Wong et al. |
| 5,770,076 A | 6/1998 | Chu et al. |
| 5,773,019 A | 6/1998 | Ashton et al. |
| 5,797,898 A | 8/1998 | Santini, Jr. et al. |
| 5,807,581 A | 9/1998 | Rosenblatt et al. |
| 5,824,072 A | 10/1998 | Wong |
| 5,830,173 A | 11/1998 | Avery et al. |
| 5,830,492 A * | 11/1998 | Usala .............................. 424/424 |
| 5,830,546 A | 11/1998 | Ehret et al. |
| 5,836,935 A | 11/1998 | Ashton et al. |
| 5,868,697 A | 2/1999 | Richter et al. |
| 5,902,598 A | 5/1999 | Chen et al. |
| 5,916,584 A | 6/1999 | O'Donoghue et al. |
| 5,928,662 A | 7/1999 | Phillips |
| 5,951,512 A | 9/1999 | Dalton |
| 5,968,008 A | 10/1999 | Grams |
| 5,972,369 A | 10/1999 | Roorda et al. |
| 5,985,328 A | 11/1999 | Chu et al. |
| 6,001,386 A | 12/1999 | Ashton et al. |
| 6,096,070 A | 8/2000 | Ragheb et al. |
| 6,123,861 A | 9/2000 | Santini, Jr. et al. |
| 6,196,993 B1 | 3/2001 | Cohan et al. |
| 6,251,090 B1 | 6/2001 | Avery et al. |
| 6,303,290 B1 | 10/2001 | Liu et al. |
| 6,331,313 B1 | 12/2001 | Wong et al. |
| 6,331,523 B1 | 12/2001 | Kljavin et al. |
| 6,375,972 B1 | 4/2002 | Guo et al. |
| 6,395,300 B1 | 5/2002 | Straub et al. |
| 6,413,540 B1 | 7/2002 | Yaacobi |
| 6,416,777 B1 | 7/2002 | Yaacobi |
| 6,420,399 B1 | 7/2002 | Graff et al. |
| 6,472,162 B1 | 10/2002 | Coelho et al. |
| 6,551,291 B1 | 4/2003 | de Juan, Jr. et al. |
| 6,605,066 B1 | 8/2003 | Gravagna et al. |
| 6,663,668 B1 | 12/2003 | Chaouk et al. |
| 6,669,950 B2 | 12/2003 | Yaacobi |
| 6,685,940 B2 | 2/2004 | Andya et al. |
| 6,713,081 B2 | 3/2004 | Robinson et al. |
| 6,719,750 B2 | 4/2004 | Varner et al. |
| 6,740,077 B1 | 5/2004 | Brandau et al. |
| 6,756,049 B2 | 6/2004 | Brubaker et al. |
| 6,756,058 B2 | 6/2004 | Brubaker et al. |
| 6,932,983 B1 | 8/2005 | Straub et al. |
| 6,976,982 B2 | 12/2005 | Santini, Jr. et al. |
| 6,986,900 B2 | 1/2006 | Yaacobi |
| 7,026,329 B2 | 4/2006 | Crain et al. |
| 7,074,426 B2 | 7/2006 | Kochinke |
| 7,077,848 B1 | 7/2006 | de Juan, Jr. et al. |
| 7,090,681 B2 | 8/2006 | Weber et al. |
| 7,094,222 B1 | 8/2006 | Siekas et al. |
| 7,094,226 B2 | 8/2006 | Yaacobi |
| 7,117,870 B2 | 10/2006 | Prescott |
| 7,141,023 B2 | 11/2006 | Diermann et al. |
| 7,141,152 B2 | 11/2006 | Le Febre |
| 7,181,287 B2 | 2/2007 | Greenberg |
| 7,195,774 B2 | 3/2007 | Carvalho et al. |
| 7,195,778 B2 | 3/2007 | Fleshner-Barak et al. |
| 7,211,272 B2 | 5/2007 | Renner et al. |
| 7,276,050 B2 | 10/2007 | Franklin |
| 7,468,065 B2 | 12/2008 | Weber et al. |
| 7,476,510 B2 | 1/2009 | Kapur et al. |
| 7,585,517 B2 | 9/2009 | Cooper et al. |
| 7,615,141 B2 | 11/2009 | Schwartz et al. |
| 7,621,907 B2 | 11/2009 | Rodstrom |
| 7,625,927 B2 | 12/2009 | Klimko et al. |
| 7,678,078 B1 | 3/2010 | Peyman et al. |
| 7,686,016 B2 | 3/2010 | Wharton et al. |
| 7,709,049 B2 | 5/2010 | Chappa |
| 7,883,717 B2 | 2/2011 | Varner et al. |
| 7,893,040 B2 | 2/2011 | Loftsson et al. |
| 7,906,136 B2 | 3/2011 | Wong et al. |
| 7,909,800 B2 | 3/2011 | Cazzini |
| 7,914,442 B1 | 3/2011 | Gazdzinski |
| 7,939,094 B2 | 5/2011 | Schwarz et al. |
| 7,973,068 B2 | 7/2011 | Demopulos et al. |
| 8,486,052 B2 | 7/2013 | Varner et al. |
| 8,623,395 B2 | 1/2014 | de Juan, Jr. et al. |
| 8,795,712 B2 | 8/2014 | de Juan, Jr. et al. |
| 8,808,727 B2 | 8/2014 | de Juan, Jr. et al. |
| 2002/0026176 A1 | 2/2002 | Varner et al. |
| 2002/0086051 A1 | 7/2002 | Viscasillas |
| 2002/0106395 A1 | 8/2002 | Brubaker |
| 2002/0110591 A1 | 8/2002 | Brubaker et al. |
| 2002/0110592 A1 | 8/2002 | Brubaker et al. |

(56) References Cited

U.S. PATENT DOCUMENTS

| | | |
|---|---|---|
| 2002/0110635 A1 | 8/2002 | Brubaker et al. |
| 2003/0003129 A1 | 1/2003 | Yaacobi |
| 2003/0005945 A1 | 1/2003 | Onishi et al. |
| 2003/0014036 A1 | 1/2003 | Varner et al. |
| 2003/0118649 A1 | 6/2003 | Gao et al. |
| 2003/0119177 A1 | 6/2003 | Gruber et al. |
| 2003/0176854 A1 | 9/2003 | Rodstrom |
| 2003/0185872 A1 | 10/2003 | Kochinke |
| 2003/0212383 A1 | 11/2003 | Cote et al. |
| 2003/0235603 A1 | 12/2003 | Schwarz et al. |
| 2004/0011651 A1 | 1/2004 | Becker et al. |
| 2004/0019325 A1 | 1/2004 | Shekalim |
| 2004/0024371 A1 | 2/2004 | Plicchi et al. |
| 2004/0029832 A1 | 2/2004 | Zeldis |
| 2004/0092911 A1 | 5/2004 | Yaacobi |
| 2004/0106906 A1 | 6/2004 | Yaacobi |
| 2004/0131654 A1 | 7/2004 | Yaacobi |
| 2004/0131655 A1 | 7/2004 | Yaacobi |
| 2004/0171997 A1 | 9/2004 | Wilson et al. |
| 2004/0208910 A1 | 10/2004 | Ashton et al. |
| 2004/0209359 A1 | 10/2004 | Yayon et al. |
| 2004/0230183 A1 | 11/2004 | Breegi et al. |
| 2004/0247487 A1 | 12/2004 | Commercon et al. |
| 2004/0260380 A1 | 12/2004 | Marco et al. |
| 2004/0260381 A1 | 12/2004 | Marco et al. |
| 2005/0064010 A1 | 3/2005 | Cooper et al. |
| 2005/0074497 A1 | 4/2005 | Schultz |
| 2005/0112175 A1 | 5/2005 | Yaacobi |
| 2005/0112759 A1 | 5/2005 | Radisic et al. |
| 2005/0113806 A1 | 5/2005 | De Carvalho et al. |
| 2005/0119737 A1* | 6/2005 | Bene et al. .............. 623/4.1 |
| 2005/0143363 A1 | 6/2005 | De Juan et al. |
| 2005/0154399 A1 | 7/2005 | Weber et al. |
| 2005/0163711 A1 | 7/2005 | Nycz et al. |
| 2005/0181018 A1 | 8/2005 | Peyman |
| 2005/0244467 A1 | 11/2005 | Nivaggioli et al. |
| 2005/0244469 A1 | 11/2005 | Whitcup et al. |
| 2005/0244472 A1 | 11/2005 | Hughes et al. |
| 2005/0255144 A1 | 11/2005 | Schultz |
| 2005/0256499 A1 | 11/2005 | Pettis et al. |
| 2005/0271703 A1* | 12/2005 | Anderson ............ A61K 31/58 424/426 |
| 2005/0271706 A1 | 12/2005 | Anderson et al. |
| 2005/0276837 A1 | 12/2005 | Anderson et al. |
| 2005/0277802 A1 | 12/2005 | Larsen et al. |
| 2005/0281861 A1 | 12/2005 | Hughes et al. |
| 2005/0281863 A1 | 12/2005 | Anderson et al. |
| 2005/0287188 A1 | 12/2005 | Anderson et al. |
| 2006/0013835 A1 | 1/2006 | Anderson et al. |
| 2006/0020253 A1 | 1/2006 | Prescott |
| 2006/0039952 A1 | 2/2006 | Yaacobi |
| 2006/0052754 A1 | 3/2006 | Fields |
| 2006/0057277 A1 | 3/2006 | Chappa |
| 2006/0073182 A1 | 4/2006 | Wong et al. |
| 2006/0104969 A1 | 5/2006 | Oray et al. |
| 2006/0110428 A1 | 5/2006 | deJuan et al. |
| 2006/0129215 A1 | 6/2006 | Helmus et al. |
| 2006/0154981 A1 | 7/2006 | Klimko et al. |
| 2006/0172941 A1 | 8/2006 | Rastelli et al. |
| 2006/0182783 A1 | 8/2006 | Hughes et al. |
| 2006/0189608 A1 | 8/2006 | Bingaman |
| 2006/0200097 A1 | 9/2006 | Humayun et al. |
| 2006/0233858 A1 | 10/2006 | Tzekov et al. |
| 2006/0246112 A1 | 11/2006 | Snyder et al. |
| 2006/0257450 A1 | 11/2006 | Mudumba et al. |
| 2006/0258000 A1 | 11/2006 | Allen et al. |
| 2006/0258994 A1 | 11/2006 | Avery |
| 2007/0020336 A1 | 1/2007 | Loftsson et al. |
| 2007/0021357 A1 | 1/2007 | Tobia et al. |
| 2007/0026037 A1 | 2/2007 | Kloke et al. |
| 2007/0059336 A1 | 3/2007 | Hughes et al. |
| 2007/0071756 A1 | 3/2007 | Peyman |
| 2007/0072933 A1 | 3/2007 | Peyman |
| 2007/0077270 A1 | 4/2007 | Wen |
| 2007/0078359 A1 | 4/2007 | Luloh et al. |
| 2007/0088414 A1 | 4/2007 | Campbell et al. |
| 2007/0119450 A1 | 5/2007 | Wharton et al. |
| 2007/0128644 A1 | 6/2007 | Munenaka |
| 2007/0131610 A1 | 6/2007 | Peng et al. |
| 2007/0131611 A1 | 6/2007 | Peng et al. |
| 2007/0134305 A1 | 6/2007 | Zilberman |
| 2007/0141111 A1 | 6/2007 | Suokas et al. |
| 2007/0191863 A1 | 8/2007 | De Juan et al. |
| 2007/0197491 A1 | 8/2007 | Robin et al. |
| 2007/0203174 A1 | 8/2007 | Klimko et al. |
| 2007/0212388 A1 | 9/2007 | Patravale et al. |
| 2007/0212397 A1 | 9/2007 | Roth |
| 2007/0219632 A1 | 9/2007 | Castillejos |
| 2007/0233037 A1 | 10/2007 | Gifford, et al. |
| 2007/0235331 A1 | 10/2007 | Simpson et al. |
| 2007/0243230 A1 | 10/2007 | de Juan et al. |
| 2007/0260201 A1 | 11/2007 | Prausnitz et al. |
| 2007/0265599 A1 | 11/2007 | Castillejos |
| 2007/0269487 A1 | 11/2007 | de Juan et al. |
| 2008/0003219 A1 | 1/2008 | Peyman |
| 2008/0004329 A1 | 1/2008 | Jamieson et al. |
| 2008/0015545 A1 | 1/2008 | Sanchez et al. |
| 2008/0020045 A1 | 1/2008 | Chappa et al. |
| 2008/0038316 A1 | 2/2008 | Wong et al. |
| 2008/0057561 A1 | 3/2008 | Takahashi et al. |
| 2008/0066739 A1 | 3/2008 | LeMahieu et al. |
| 2008/0066741 A1 | 3/2008 | LeMahieu et al. |
| 2008/0069854 A1 | 3/2008 | Xiao et al. |
| 2008/0089923 A1 | 4/2008 | Burkstrand et al. |
| 2008/0111282 A1 | 5/2008 | Xie et al. |
| 2008/0124372 A1 | 5/2008 | Hossainy et al. |
| 2008/0139674 A1 | 6/2008 | Archambeau et al. |
| 2008/0145406 A1 | 6/2008 | Asgharian et al. |
| 2008/0146679 A1 | 6/2008 | Archambeau et al. |
| 2008/0147021 A1 | 6/2008 | Jani |
| 2008/0152694 A1 | 6/2008 | Lobl et al. |
| 2008/0154241 A1 | 6/2008 | Burkstrand et al. |
| 2008/0161741 A1 | 7/2008 | Bene et al. |
| 2008/0167600 A1 | 7/2008 | Peyman |
| 2008/0172014 A1 | 7/2008 | Whitcup et al. |
| 2008/0181930 A1 | 7/2008 | Rodstrom et al. |
| 2008/0195218 A1 | 8/2008 | Jones |
| 2008/0207502 A1 | 8/2008 | Rastelli et al. |
| 2008/0213611 A1 | 9/2008 | Asgari |
| 2008/0216736 A1 | 9/2008 | David |
| 2008/0228127 A1 | 9/2008 | Burns et al. |
| 2008/0233053 A1 | 9/2008 | Gross et al. |
| 2008/0233171 A1 | 9/2008 | Whitcup et al. |
| 2008/0233172 A1 | 9/2008 | Whitcup et al. |
| 2008/0233173 A1 | 9/2008 | Whitcup et al. |
| 2008/0241219 A1 | 10/2008 | Whitcup et al. |
| 2008/0241220 A1 | 10/2008 | Whitcup et al. |
| 2008/0241221 A1 | 10/2008 | Whitcup et al. |
| 2008/0241222 A1 | 10/2008 | Whitcup et al. |
| 2008/0241223 A1 | 10/2008 | Nivaggioli et al. |
| 2008/0249501 A1 | 10/2008 | Yamasaki |
| 2008/0269318 A1 | 10/2008 | Romano |
| 2008/0286338 A1 | 11/2008 | Rosenthal et al. |
| 2008/0292679 A1 | 11/2008 | Lyons et al. |
| 2008/0293691 A1 | 11/2008 | Brigandi et al. |
| 2009/0005864 A1 | 1/2009 | Eggleston |
| 2009/0036827 A1 | 2/2009 | Cazzini |
| 2009/0043253 A1 | 2/2009 | Podaima |
| 2009/0047335 A1 | 2/2009 | Rastelli et al. |
| 2009/0061071 A1* | 3/2009 | McMorrow et al. ......... 427/2.14 |
| 2009/0074786 A1 | 3/2009 | Dor et al. |
| 2009/0081271 A1* | 3/2009 | Clarke ................ A61F 2/00 424/423 |
| 2009/0081272 A1 | 3/2009 | Clarke et al. |
| 2009/0082631 A1 | 3/2009 | Cronin et al. |
| 2009/0087494 A1 | 4/2009 | Kompella et al. |
| 2009/0092654 A1 | 4/2009 | de Juan, Jr. et al. |
| 2009/0093752 A1 | 4/2009 | Richard et al. |
| 2009/0099626 A1 | 4/2009 | de Juan, Jr. et al. |
| 2009/0104243 A1 | 4/2009 | Utkhede et al. |
| 2009/0105749 A1 | 4/2009 | de Juan et al. |
| 2009/0124997 A1 | 5/2009 | Pettis et al. |
| 2009/0192493 A1 | 7/2009 | Meng et al. |
| 2009/0196903 A1 | 8/2009 | Kliman |

(56) References Cited

U.S. PATENT DOCUMENTS

| | | |
|---|---|---|
| 2009/0214601 A1 | 8/2009 | Chappa et al. |
| 2009/0220572 A1 | 9/2009 | Deschatelets et al. |
| 2009/0224064 A1 | 9/2009 | Brodbeck et al. |
| 2009/0234449 A1 | 9/2009 | De Juan, Jr. et al. |
| 2009/0240208 A1 | 9/2009 | Cowan |
| 2009/0240215 A1 | 9/2009 | Humayun et al. |
| 2009/0247458 A1 | 10/2009 | Watson et al. |
| 2009/0258069 A1 | 10/2009 | Burnier et al. |
| 2009/0259212 A1 | 10/2009 | Sabbah |
| 2009/0263346 A1 | 10/2009 | Taft et al. |
| 2009/0263495 A1 | 10/2009 | Watson et al. |
| 2009/0274730 A1 | 11/2009 | Watson et al. |
| 2009/0274771 A1 | 11/2009 | Watson et al. |
| 2009/0280470 A1 | 11/2009 | Fare et al. |
| 2009/0306025 A1 | 12/2009 | Lane |
| 2009/0306595 A1 | 12/2009 | Shih et al. |
| 2009/0318545 A1 | 12/2009 | Silver et al. |
| 2009/0324686 A1 | 12/2009 | Cooper et al. |
| 2009/0324687 A1 | 12/2009 | Cooper et al. |
| 2009/0324688 A1 | 12/2009 | Cooper et al. |
| 2009/0324689 A1 | 12/2009 | Cooper et al. |
| 2009/0324690 A1 | 12/2009 | Cooper et al. |
| 2009/0326448 A1 | 12/2009 | Huo et al. |
| 2010/0003333 A1 | 1/2010 | Watson et al. |
| 2010/0004189 A1 | 1/2010 | Watson et al. |
| 2010/0008997 A1 | 1/2010 | Watson et al. |
| 2010/0009008 A1 | 1/2010 | Watson et al. |
| 2010/0010452 A1 | 1/2010 | Paques et al. |
| 2010/0011888 A1 | 1/2010 | Pawliszyn et al. |
| 2010/0015157 A1 | 1/2010 | Andya et al. |
| 2010/0015158 A1 | 1/2010 | Robinson et al. |
| 2010/0016786 A1 | 1/2010 | Drews et al. |
| 2010/0021464 A1 | 1/2010 | Archambeau et al. |
| 2010/0022943 A1 | 1/2010 | Mauch et al. |
| 2010/0022945 A1 | 1/2010 | Rodstrom |
| 2010/0023033 A1 | 1/2010 | Mauch et al. |
| 2010/0028442 A1 | 2/2010 | Archambeau et al. |
| 2010/0028443 A1 | 2/2010 | Watson et al. |
| 2010/0030136 A1 | 2/2010 | Dacquay et al. |
| 2010/0034870 A1 | 2/2010 | Sim et al. |
| 2010/0083963 A1 | 4/2010 | Wharton et al. |
| 2010/0100043 A1 | 4/2010 | Racenet |
| 2010/0100054 A1 | 4/2010 | Cormier et al. |
| 2010/0114017 A1 | 5/2010 | Lenker et al. |
| 2010/0114309 A1 | 5/2010 | de Juan, Jr. et al. |
| 2010/0158980 A1 | 6/2010 | Kopczynski et al. |
| 2010/0168535 A1 | 7/2010 | Robinson et al. |
| 2010/0174272 A1 | 7/2010 | Weiner |
| 2010/0185205 A1 | 7/2010 | Novakovic et al. |
| 2010/0189765 A1 | 7/2010 | Erickson et al. |
| 2010/0197512 A1 | 8/2010 | Trinkle et al. |
| 2010/0216702 A1 | 8/2010 | Szkudlinski et al. |
| 2010/0221309 A1 | 9/2010 | Myers et al. |
| 2010/0227904 A1 | 9/2010 | Kabra et al. |
| 2010/0255061 A1 | 10/2010 | de Juan, Jr. et al. |
| 2010/0256597 A1 | 10/2010 | Prausnitz et al. |
| 2010/0266664 A1 | 10/2010 | Asgharian et al. |
| 2010/0286121 A1 | 11/2010 | Rohrs et al. |
| 2010/0286791 A1 | 11/2010 | Goldsmith |
| 2010/0297046 A1 | 11/2010 | Schwartz et al. |
| 2010/0297120 A1 | 11/2010 | Beliveau et al. |
| 2010/0297193 A1 | 11/2010 | Archambeau et al. |
| 2010/0303917 A1 | 12/2010 | Watson et al. |
| 2010/0303918 A1 | 12/2010 | Watson et al. |
| 2010/0310664 A1 | 12/2010 | Watson et al. |
| 2010/0310665 A1 | 12/2010 | Watson et al. |
| 2010/0316723 A1 | 12/2010 | Watson et al. |
| 2010/0330146 A1 | 12/2010 | Chauhan et al. |
| 2011/0009571 A1 | 1/2011 | Taft et al. |
| 2011/0014264 A1 | 1/2011 | Helmus et al. |
| 2011/0033933 A1 | 2/2011 | Gharib et al. |
| 2011/0034448 A1 | 2/2011 | Chang et al. |
| 2011/0081384 A1 | 4/2011 | Archambeau et al. |
| 2011/0098686 A1 | 4/2011 | Varner et al. |
| 2011/0104155 A1 | 5/2011 | Rekik |
| 2011/0108025 A1 | 5/2011 | Fink et al. |
| 2011/0111006 A1 | 5/2011 | Wong et al. |
| 2011/0112188 A1 | 5/2011 | Tobia et al. |
| 2011/0117083 A1 | 5/2011 | Bais et al. |
| 2011/0125178 A1 | 5/2011 | Drews et al. |
| 2011/0159073 A1 | 6/2011 | deJuan et al. |
| 2011/0190723 A1 | 8/2011 | Fangrow |
| 2011/0206646 A1 | 8/2011 | Alfonso et al. |
| 2012/0029445 A1 | 2/2012 | de Juan, Jr. et al. |
| 2012/0029470 A1 | 2/2012 | Juan, Jr. et al. |
| 2012/0095439 A1 | 4/2012 | de Juan, Jr. et al. |
| 2013/0304031 A1 | 11/2013 | Varner et al. |
| 2013/0324942 A1 | 12/2013 | de Juan, Jr. et al. |
| 2014/0121609 A1 | 5/2014 | de Juan, Jr. et al. |
| 2014/0243795 A1 | 8/2014 | Varner et al. |

FOREIGN PATENT DOCUMENTS

| | | |
|---|---|---|
| CN | 102365109 A | 2/2012 |
| EP | 0033042 B1 | 8/1984 |
| EP | 0 228 185 A1 | 7/1990 |
| EP | 0498471 A2 | 8/1992 |
| EP | 0500143 A2 | 8/1992 |
| EP | 0671165 A2 | 9/1995 |
| EP | 0295248 B2 | 4/1999 |
| EP | 0944658 B1 | 6/2003 |
| EP | 1671624 A1 | 6/2006 |
| EP | 1385452 | 9/2006 |
| EP | 1409065 | 1/2007 |
| EP | 1337284 B1 | 12/2007 |
| EP | 1911481 | 4/2008 |
| EP | 1521572 B1 | 3/2009 |
| JP | 01-149716 | 6/1989 |
| JP | 01-197429 A | 8/1989 |
| JP | 2001-518880 A | 10/2001 |
| JP | 2004-516889 A | 6/2004 |
| JP | 2004-524866 A | 8/2004 |
| JP | 2006-526430 A | 11/2006 |
| JP | 2009-514888 A | 4/2009 |
| JP | 2009-523821 A | 6/2009 |
| JP | 2009-529968 A | 8/2009 |
| JP | 2010-521470 A | 6/2010 |
| WO | WO-8804573 A1 | 6/1988 |
| WO | WO-9007545 A2 | 7/1990 |
| WO | WO-9528984 | 11/1995 |
| WO | WO-9729850 | 8/1997 |
| WO | WO-9825982 | 6/1998 |
| WO | WO-9843611 A1 | 10/1998 |
| WO | WO-9911244 | 3/1999 |
| WO | WO-0048660 | 8/2000 |
| WO | WO-0126714 | 4/2001 |
| WO | WO-0150943 | 7/2001 |
| WO | WO-0168016 | 9/2001 |
| WO | WO-02/17831 A2 | 3/2002 |
| WO | WO-02053128 A2 | 7/2002 |
| WO | WO-02100318 | 12/2002 |
| WO | WO-03028765 | 4/2003 |
| WO | WO-03077972 | 9/2003 |
| WO | WO-03082188 | 10/2003 |
| WO | WO-2004000267 | 12/2003 |
| WO | WO-2004/073765 A2 | 9/2004 |
| WO | WO-2004112653 | 12/2004 |
| WO | WO-2005016401 | 2/2005 |
| WO | WO-2005027906 | 3/2005 |
| WO | WO-2005028006 | 3/2005 |
| WO | WO-2005091922 | 10/2005 |
| WO | WO-2005107705 | 11/2005 |
| WO | WO-2005110362 | 11/2005 |
| WO | WO-2005110436 | 11/2005 |
| WO | WO-2005110473 | 11/2005 |
| WO | WO-2005117780 | 12/2005 |
| WO | WO-2006014484 | 2/2006 |
| WO | WO-2006015385 | 2/2006 |
| WO | WO-2006023530 | 3/2006 |
| WO | WO-2006031358 | 3/2006 |
| WO | WO-2006031388 | 3/2006 |
| WO | WO-2006044614 | 4/2006 |
| WO | WO-2006050221 | 5/2006 |
| WO | WO-2006068838 | 6/2006 |

(56) References Cited

FOREIGN PATENT DOCUMENTS

| | | |
|---|---|---|
| WO | WO-2006071554 | 7/2006 |
| WO | WO-2006082588 | 8/2006 |
| WO | WO-2006108054 | 10/2006 |
| WO | WO-2006127962 | 11/2006 |
| WO | WO-2006138609 | 12/2006 |
| WO | WO-2007012974 | 2/2007 |
| WO | WO-2007035473 | 3/2007 |
| WO | WO-2007035620 | 3/2007 |
| WO | WO-2007038453 | 4/2007 |
| WO | WO-2007044534 | 4/2007 |
| WO | WO-2007047744 | 4/2007 |
| WO | WO-2007066339 | 6/2007 |
| WO | WO-2007084582 | 7/2007 |
| WO | WO-2007084765 | 7/2007 |
| WO | WO-2007101204 | 9/2007 |
| WO | WO-2007115259 | 10/2007 |
| WO | WO-2007117394 | 10/2007 |
| WO | WO-2007131050 | 11/2007 |
| WO | WO-2007133761 | 11/2007 |
| WO | WO-2007133762 | 11/2007 |
| WO | WO-2008003043 | 1/2008 |
| WO | WO-2008005240 | 1/2008 |
| WO | WO-2008011125 | 1/2008 |
| WO | WO-2008019265 | 2/2008 |
| WO | WO-2008033924 | 3/2008 |
| WO | WO-2008040062 | 4/2008 |
| WO | WO-2008045272 | 4/2008 |
| WO | WO-2008052145 | 5/2008 |
| WO | WO-2008060359 | 5/2008 |
| WO | WO-2008061043 | 5/2008 |
| WO | WO-2008076544 | 6/2008 |
| WO | WO-2008094989 | 8/2008 |
| WO | WO-2008115290 | 9/2008 |
| WO | WO-2008116165 | 9/2008 |
| WO | WO-2008144340 | 11/2008 |
| WO | WO-2008144919 | 12/2008 |
| WO | WO-2009012075 | 1/2009 |
| WO | WO-2009023615 | 2/2009 |
| WO | WO-2009046164 | 4/2009 |
| WO | WO-2009055620 | 4/2009 |
| WO | WO-2009055671 | 4/2009 |
| WO | WO-2009055729 | 4/2009 |
| WO | WO-2009055824 | 4/2009 |
| WO | WO-2009061607 | 5/2009 |
| WO | WO-2009073192 | 6/2009 |
| WO | WO-2009086112 | 7/2009 |
| WO | WO-2009089409 | 7/2009 |
| WO | WO-2009094466 | 7/2009 |
| WO | WO-2009112878 | 9/2009 |
| WO | WO-2009117112 | 9/2009 |
| WO | WO-2009124096 | 10/2009 |
| WO | WO-2009128932 | 10/2009 |
| WO | WO-2009134929 | 11/2009 |
| WO | WO-2009137777 | 11/2009 |
| WO | WO-2010008424 | 1/2010 |
| WO | WO-2010021993 | 2/2010 |
| WO | WO-2010047753 | 4/2010 |
| WO | WO-2010062628 | 6/2010 |
| WO | WO-2010066714 | 6/2010 |
| WO | WO-2010075565 | 7/2010 |
| WO | WO-2010078063 | 7/2010 |
| WO | WO-2010088548 | 8/2010 |
| WO | WO-2010093945 | 8/2010 |
| WO | WO-2010095940 | 8/2010 |
| WO | WO-2010125416 | 11/2010 |
| WO | WO-2010126908 | 11/2010 |
| WO | WO-2010135369 | 11/2010 |
| WO | WO-2010141729 | 12/2010 |
| WO | WO-2010147661 | 12/2010 |
| WO | WO-2011008896 | 1/2011 |
| WO | WO-2011008897 | 1/2011 |
| WO | WO-2011028850 | 3/2011 |
| WO | WO-2011034627 | 3/2011 |
| WO | WO-2011079232 | 6/2011 |
| WO | WO-2012019047 | 2/2012 |

OTHER PUBLICATIONS

Bakri et al., "The effect of intravitreal triamcinolone acetonide on intraocular pressure," Ophthalmic Surgery, Lasers and Imaging, Sep./Oct. 2003; 34(5): 386-390.

Bird et al., Transport Phenomena, John Wiley & Sons, Inc., New York, 1960, pp. 196-201.

Block et al., "Solubility and dissolution of triamcinolone acetonide," Journal of Pharmaceutical Sciences,Apr. 1973; 62(4):617-621.

Breslin, C.W., et al., "Chapter 7. Slow Release Artificial Tears", *Symposium on Ocular Therapy* pp. 77-83, 1977.

Castro et al., "Effect of COX inhibitors on VEGF-induced retinal vascular leakage and experimental corneal and choroidal neovascularization," Exp Eye Res. Aug. 2004;79(2):275-285.

Chirila et al., "The Vitreous Humor" in *Handbook of Biomaterial Properties*, eds. Black & Hastings. Chapman & Hall, London, 1998; pp. 125-131.

Cousins et al., "Program # 1251—Targeting Complement Factor 5 in Combination with Vascular Endothelial Growth Factor (VEGF) Inhibition for Neovascular Age Related Macular Degeneration (AMD): Results of a Phase 1 Study," [Presentation Abstract], AMD Clinical Trials Session # 220, May 3, 2010.

Deissler et al., "VEGF-induced effects on proliferation, migration and tight junctions are restored by ranibizumab (Lucentis) in microvascular retinal endothelial cells,"Br J Ophthalmol 2008;92:839-843.

Del Amo, et al., Current & future ophthalmic drug delivery systems . . . , *Drug Discovery Today*, vol. 13, Nos. 3/4, Feb. 2008.

Donoso et al., "The role of inflammation in the pathogenesis of age-related macular degeneration," Sury Ophthalmol. Mar.-Apr. 2006;51(2):137-52.

Duvvuri et al., Drug Delivery to the Retina: Challenges and Opportunities, *Expert Opinion on Biological Therapy*, 2003, vol. 3(1): 45-56.

European Medicine Agency, Scientific Discussion; retrieved from the Internet; <http://www.ema.europa.eu/docs/en_GB/document_library/EPAR_-_Scientific_Discussion/human/000715/WC500043550.pdf>, EMEA 2007, 54 pages total. 2007.

Funatsu et al. "Association of vitreous inflammatory factors with diabetic macular edema," Ophthalmology 2009;116:73-79.

Gaudana et al., Recent Perspectives in Ocular Drug Delivery, *Pharmaceutical Research*, 2008.

Gaudreault et al., "Preclinical Pharmacokinetics of Ranibizumab (rhuFabV2) after a Single Intravitreal Administration," Investigative Ophthalmology and Visual Science. 2005;46:726-733. Retrieved from the Internet: http://www.iovs.org/cgi/reprint/46/2/726.

Gillies et al., "Intravitreal triamcinolone for refractory diabetic macular edema: two-year results of a double-masked, placebo-controlled, randomized clinical trial," Ophthalmology. Sep. 2006;113(9):1533-1538.

Haller, An Overview of Sustained-release Drug Implants, Retinal Physician, Jan. 2008.

Hastedt & Wright, "Diffusion in porous materials above the percolation threshold," Pharm. Res. Sep. 1990; 7(9):893-901 (1990).

Heier et al, "Ketorolac versus prednisolone versus combination therapy in the treatment of acute pseudophakic cystoid macular edema," Ophthalmology. Nov. 2000;107(11):2034-2038 ;discussion 2039.

Janoria et al., Novel Approaches to Retinal Drug Delivery, *Expert Opinion Drug Delivery*, 2007.

Jena et al., "A Novel Technique for Surface Area and Particle Size Determination of Components of Fuel Cells and Batteries," Porous Materials, Inc., Dec. 2006, 3 pages total. Downloaded from the Internet: http://www.pmiapp.com/publications/docs/A_Novel_technique_for_surface_area.pdf>>.

"Juvederm", FDA, 2006, XP002670727, Retrieved from the Internet: URL:http://www.accessdata.fda.gov/cdrh_docs/pdf5/P050047b.pdf [retrieved on Mar. 1, 2012] p. 1, last paragraph.

Kang et al., "Inhibitory effects of anti-inflammatory drugs on interleukin-6 bioactivity," Biol Pharm Bull. Jun. 2001;24(6):701-703.

(56) References Cited

OTHER PUBLICATIONS

Katz, I.M., et al., "A Soluble Sustained-Release Ophthalmic Delivery Unit", 8:5 (May 1977) pp. 728-734.

Lamberts, D.W., M.D., et al., "A Clinical Study of Slow-Releasing Artificial Tears", *Ophthalmology* 85 (1978) pp. 794-800.

Lee, D.A., et al., "Glaucoma Filtration Surgery in Rabbits Using Bioerodible Polymers and 5-Fluorouracil", *Ophthalmology* 94:12 (1987) pp. 1523-1530.

Lee, D.A., et al., "The Use of Bioerodible Polymers and 5-Fluorouracil in Glaucoma Filtration Surgery", *Investigative Ophthalmology & Visual Science* 29-11 (1988) pp. 1692-1697.

Li, et al., An electrochemical introculardrug delivery device, *Science Direct, Sensors and Actuators*, www.sciencedirect.com, Jul. 4, 2007.

Lopez-Armada et al., "Modulation of cell recruitment by anti-inflammatory agents in antigen-induced arthritis," Ann Rheum Dis Nov. 2002;61(11):1027-1030.

Luncentis, INN-Ranibizumab, "Scientific Discussion," European Medicines Agency ; retrieved from the Internet<http://www.ema.europa.eu/docs/en_GB/document_library/EPAR_-_Assessment_Report_-_Variation/human/000715/WC500101009.pdf>. Oct. 21, 2010.

MAbPac SCX-10 Column for Monoclonal Antibody Variant Analysis, http://www.dionex.com/en-us/webdocs/87008-DS-MAbPac-SCX-10-Column-20Aug2010-LPN2567-03.pdf.

Metal Powder Industries Federation, Porous Metal Design Guidebook, 2007, 24 pages total. Downloaded from the Internet: http://www.mpif.org/DesignCenter/porous.pdf>>.

Miller, DP, et al., *Thermophysical Properties of Trehalose and Its Concentrated Aqueous Solutions*, Pharmaceutical Research, vol. 14, No. 5, 1997, pp. 578-590.

Molokhia et al, "Transscleral iontophoretic and intravitreal delivery of a macromolecule: Study of ocular distribution in vivo and postmortem with MRI", Experimental Eye Research 88 (2009) 418-425.

Moritera, T., et al., "Microspheres of Biodegradable Polymers as a Drug-Delivery System in the Vitreous", *Investigative Ophthalmology & Visual Science* 32-6 (1991) pp. 1785-1790.

MOTT Corporation, "Sintered Metal Powder Media," American Filtration & Separation Society 2007, 2 pages total. Downloaded from the Internet:http://www.afssociety.org/education/0907oneminute.htm.

Navarro, "The Optical Design of the Human Eye: a Critical Review," J Optom, Jan.-Mar. 2009 2(1): 3-18.

Nutan, MTH, et al., *General Principles of Suspensions, in Pharmaceutical Suspensions Fron Formulation Development to Manufacturing*, editors AK Kulshreshtha, et al., Spinger, 2010.

Okabe et al., "Intraocular tissue distribution of betamethasone after intrascleral administration using a non-biodegradable sustained drug delivery device," Investigative Ophthalmology and Visual Science. 2003;44:2702-2707. Downloaded from the Internet: http://www.iovs.org/cgi/reprint/44/6/2702.

Rosenfeld, "The Latest Research: Intravitreal Bevacizumab for Proliferative Diabetic Retinopathy," Review of Ophthalmology's Retina Online, Feb. 2006; retrieved from the Internet: http://www.revophth.com/archive/newsletter/0206_retina.htm.

Saline (medicine)—Wikipedia, the free encyclopedia. http://web.archive.org/web/20110205192937/http://en.wikipedia.org/wiki/Saline_(medicine). Apr. 27, 2012.

Sanborn G.E., et al., Sustained-Release Ganciclovir Therapy for Treatment of Cytomegalovirus Retinitis, Use of an Intravitreal Device, Arch. Ophthalmol, vol. 110, 188-195 (Feb. 1992).

Sheardown and Saltzman, Novel Drug Delivery Systems for Posterior Segment Ocular Disease, *Opthalmology: Ocular Angiogenesis: Diseases, Mechanisms and Therapeutics*, 2007, pp. 393-408.

Smith et al., "Spectrophotometric determination of pKa values for fluorescein using activity coefficient corrections," WaterSA 2002; 28(4):395-402.

Smith, T.J., et al., "Intravitreal Sustained-Release Ganciclovir", *Arch. Ophthamol* 110 (1992) pp. 255-258.

Soheilian et al., "Pilot Study of Intravitreal Injection of Diclofenac for Treatment of Macular Edema of Various Etiologies," Retina, Mar. 2010; 30(3): 509-515.

Stay et al. Computer Simulation of Convective and Diffusive Transport of Controlled-Release Drugs in the vitreous Humor, *Pharm Res* 2003,20(1), pp. 96-102.

Theodossiadis et al., "Intravitreal administration of the anti-tumor necrosis factor agent infliximab for neovascular age-related macular degeneration," Am J Ophthalmol. May 2009;147(5):825-830.

Weiner, A.L., "Chapter 13: Polymeric Drug Delivery Systems for the Eye", *Polymeric Site-Specific Pharmacotherapy*, pp. 315-346, Edited by A.J. Domb (1994) John Wiley & Sons Ltd.

Williams et al., "Treating Diabetic Macular Edema With Ocular NSAIDs," Retinal Physician, Nov. 2007; retrieved from the Internet Nov. 11, 2007. http://www.retinalphysician.com/article.aspx?article=101096>, 5 pages total.

Wright, P., et al. "Slow-Release Artificial Tear Inserts in the Treatment of Dry Eyes Resulting from the Oculomucocutaneous Syndrome", *British Journal of Ophthalmology* 67 (1983) pp. 393-397.

Yao et al. (Prevention of Laser Photocoagulation Induced Choroidal Neovascularization Lesions by Intravitreal Doses of Ranibizumab in Cynomolgus Monkeys, ARVO 2009 abstract D906).

AMD Preclinical Studies. Anti-Factor D Fab Specifically Inhibits the Alternative Pathway. The Association for Research in Vision and Ophthalmology, Inc. 2010.

\* cited by examiner

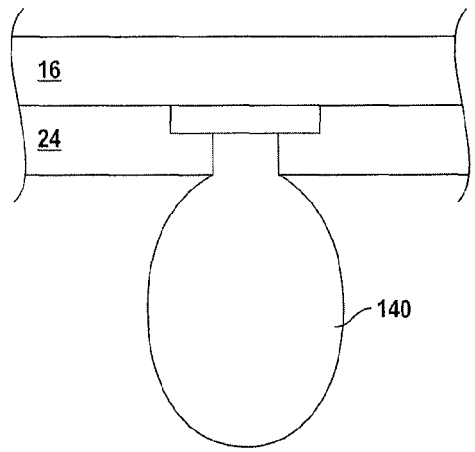
FIG. 1A-2-2
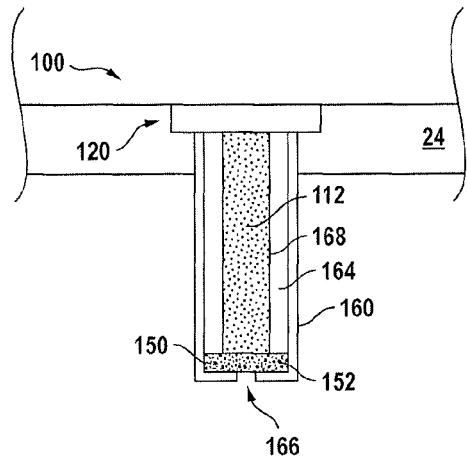
FIG. 1B
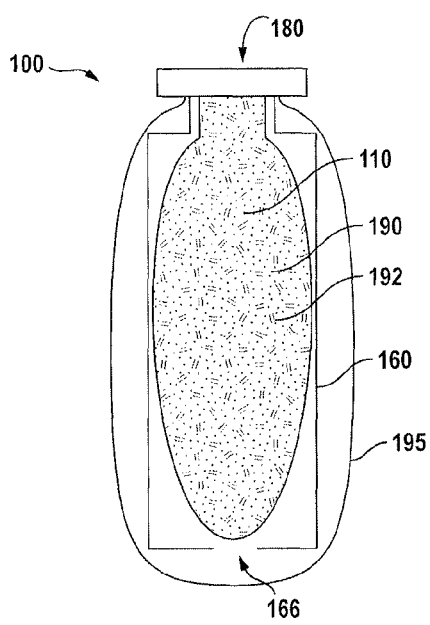
FIG. 1C
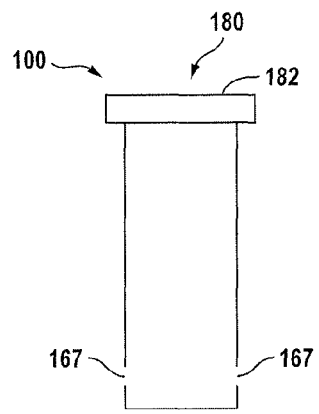
FIG. 1C-A

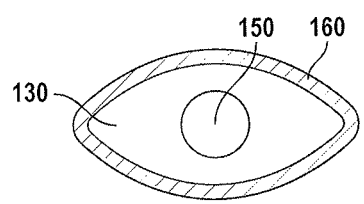
FIG. 7B-6A
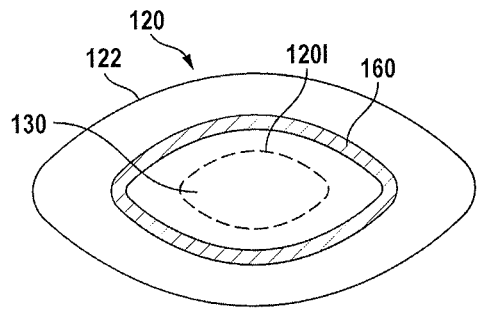
FIG. 7B-6B
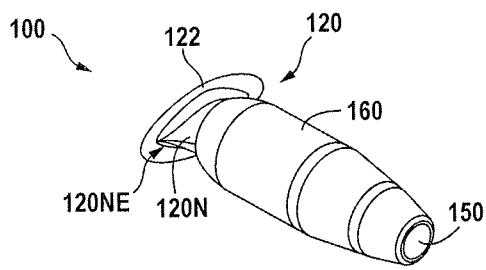
FIG. 7B-6C
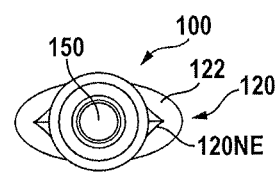
FIG. 7B-6D
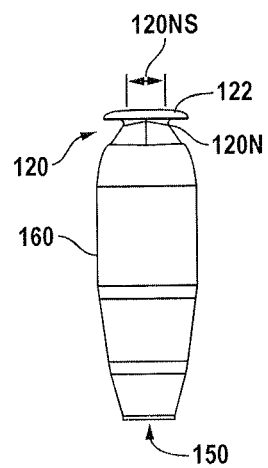
FIG. 7B-6E1
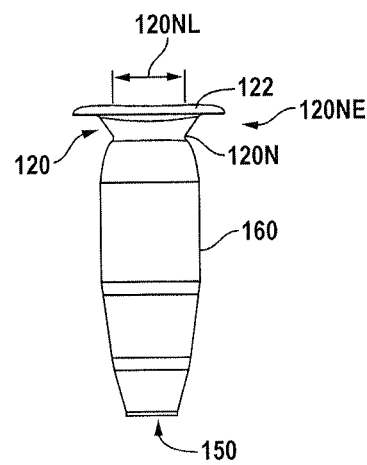
FIG. 7B-6E2
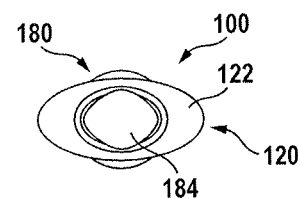
FIG. 7B-6F

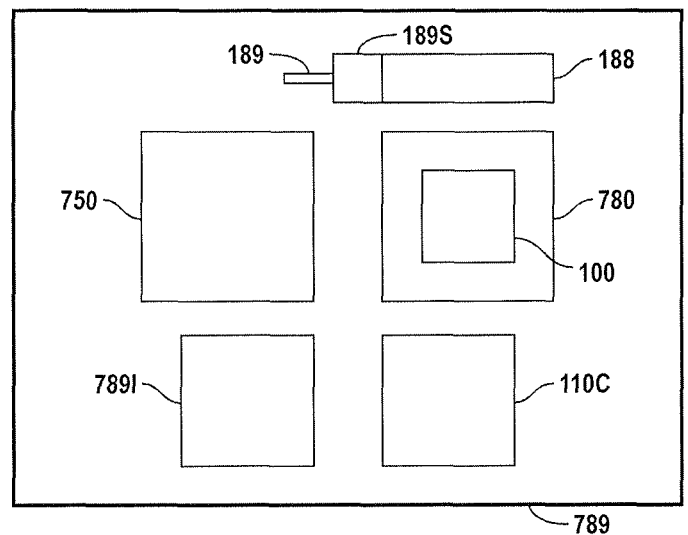
FIG. 7G
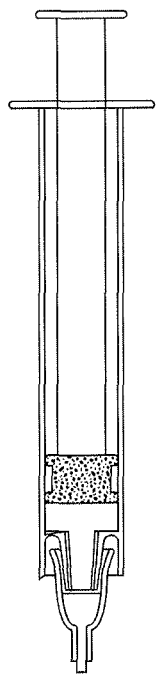 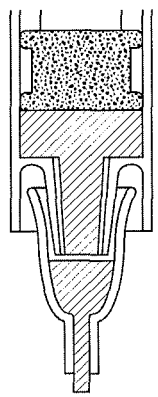 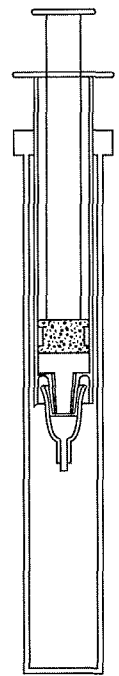
FIG. 8　　　FIG. 8-1　　　FIG. 8-2

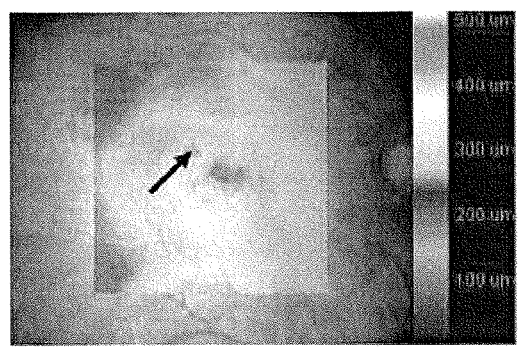
FIG. 30A-1
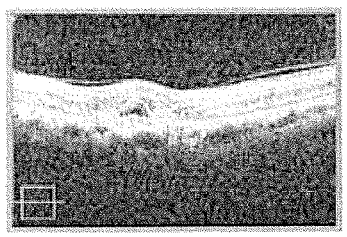 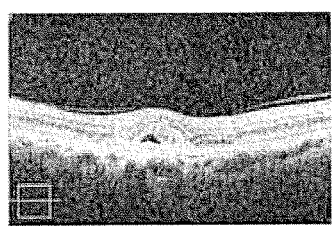 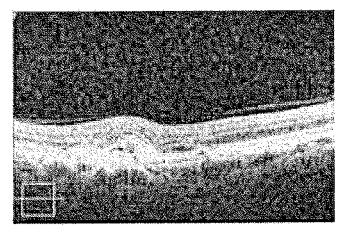
FIG. 30B-1  FIG. 30B-2  FIG. 30B-3

POSTERIOR SEGMENT DRUG DELIVERY

CROSS-REFERENCES TO RELATED APPLICATIONS

The present application is a continuation of copending U.S. patent application Ser. No. 13/831,695 filed Mar. 15, 2013, titled "POSTERIOR SEGMENT DRUG DELIVERY," which in turn is a continuation of U.S. patent application Ser. No. 12/696,678 filed Jan. 29, 2010, now U.S. Pat. No. 8,399,006, titled, "POSTERIOR SEGMENT DRUG DELIVERY," which in turn claims priority to U.S. Provisional Application Nos. U.S. 61/148,375 filed Jan. 29, 2009, entitled, "POSTERIOR SEGMENT DRUG DELIVERY;" 61/174,887 filed May 1, 2009, entitled "POSTERIOR SEGMENT DRUG DELIVERY;" 61/261,717 filed Nov. 16, 2009, entitled "POSTERIOR SEGMENT DRUG DELIVERY;" 61/284,832 filed on Dec. 24, 2009, entitled "POSTERIOR SEGMENT DRUG DELIVERY;" and 61/299,282 filed Jan. 28, 2010, entitled "POSTERIOR SEGMENT DRUG DELIVERY;" the full disclosures of which are incorporated herein by reference.

STATEMENT AS TO RIGHTS TO INVENTIONS MADE UNDER FEDERALLY SPONSORED RESEARCH AND DEVELOPMENT

Not Applicable

BACKGROUND OF THE INVENTION

The present invention relates to delivery of therapeutic agents to the posterior segment of the eye. Although specific reference is made to the delivery of macromolecules comprising antibodies or antibody fragments to the posterior segment of the eye, embodiments of the present invention can be used to deliver many therapeutic agents to many tissues of the body. For example, embodiments of the present invention can be used to deliver therapeutic agent to one or more of the following tissues: intravascular, intra-articular, intrathecal, pericardial, intraluminal and gut.

The eye is critical for vision. The eye has a cornea and a lens that form an image on the retina. The image formed on the retina is detected by rods and cones on the retina. The light detected by the rods and cones of the retina is transmitted to the occipital cortex brain via the optic nerve, such that the individual can see the image formed on the retina. Visual acuity is related to the density of rods and cones on the retina. The retina comprises a macula that has a high density of cones, such that the user can perceive color images with high visual acuity.

Unfortunately, diseases can affect vision. In some instances the disease affecting vision can cause damage to the retina, even blindness in at least some instances. One example of a disease that can affect vision is age-related macular degeneration (hereinafter AMD). Although therapeutic drugs are known that can be provided to minimize degradation of the retina, in at least some instances the delivery of these drugs can be less than ideal.

In some instances a drug is injected into the eye through the sclera. One promising class of drugs for the treatment of AMD is known as vascular endothelial growth factor VEGF inhibitors. Unfortunately, in at least some instances injection of drugs can be painful for the patient, involve at least some risk of infection and hemorrhage and retinal detachment, and can be time consuming for the physician and patient. Consequently, in at least some instances the drug may be delivered less often than would be ideal, such that at least some patients may receive less drug than would be ideal in at least some instances.

Work in relation to embodiments of the present invention also suggests that an injection of the drug with a needle results in a bolus delivery of the drug, which may be less than ideal in at least some instances. For example, with a bolus injection of drug, the concentration of drug in the vitreous humor of the patient may peak at several times the required therapeutic amount, and then decrease to below the therapeutic amount before the next injection.

Although some implant devices have been proposed, many of the known devices are deficient in at least some respects in at least some instances. At least some of the known implanted devices do not provide sustained release of a therapeutic drug for an extended period. For example, at least some of the known implanted devices may rely on polymer membranes or polymer matrices to control the rate of drug release, and many of the known membranes and matrices may be incompatible with at least some therapeutic agents such as ionic drugs and large molecular weight protein drugs in at least some instances. At least some of the known semi-permeable polymer membranes may have permeability that is less than ideal for the extended release of large molecular weight proteins such as antibodies or antibody fragments. Also, work in relation to embodiments of the present invention also suggests that at least some of the known semi-permeable membranes can have a permeability of large molecules that may vary over time and at least some of the known semi-permeable membranes can be somewhat fragile, such that drug release for extended periods can be less than ideal in at least some instances. Although capillary tubes have been suggested for drug release, work in relation to embodiments of the present invention suggests that flow through capillary tubes can be less than ideal in at least some instances, for example possibly due to bubble formation and partial clogging.

At least some of the known implantable devices can result in patient side effects in at least some instances when a sufficient amount of drug is delivered to treat a condition of the eye. For example, at least some of the commercially available small molecule drug delivery devices may result in patient side effects such as cataracts, elevated intraocular pressure, dizziness or blurred vision in at least some instances. Although corticosteroids and analogues thereof may be delivered with an implanted device to treat inflammation, the drug delivery profile can be less than ideal such that the patient may develop a cataract in at least some instances.

Although at least some of the proposed implanted devices may permit an injection into the device, one potential problem is that an injection into an implanted device can cause at least some risk of infection for the patient in at least some instances. Also, in at least some instances the drug release rate of an implanted device can change over time, such that the release rate of the drug can be less than ideal after injection in at least some instance. At least some of the proposed implanted devices may not be implanted so as to minimize the risk of infection to the patient. For example, at least some of the proposed devices that rely on pores and capillaries may allow microbes such as bacteria to pass through the capillary and/or pore, such that infection may be spread in at least some instances. Also, work in relation to embodiments of the present invention suggests that at least some of the proposed implanted devices do not provide adequate protection from the patient's immune system, such as from macrophages and antibodies, thereby limiting the therapeutic effect in at least some instances.

In light of the above, it would be desirable to provide improved therapeutic devices and methods that overcome at least some of the above deficiencies of the known therapies, for example with improved drug release that can be maintained when implanted over an extended time.

SUMMARY OF THE INVENTION

Embodiments of the present invention provide therapeutic devices that deliver therapeutic amounts of a therapeutic agent for an extended time to the posterior segment of the eye, for example an extended time of at least about 1 month. The therapeutic device may reduce the frequency of negative side effects associated with direct intraocular injection such as pain, retinal detachment, hemorrhaging and infection because injections can be made less frequently and can be made into the reservoir of the device rather than into the eye. The therapeutic device can be configured to replace the therapeutic agent when the device is implanted at least partially within the eye of the patient. The therapeutic device may be implanted in the eye so as to extend through the sclera of the eye, and the therapeutic device may comprise a container and a port or penetrable barrier configured to receive a quantity of therapeutic agent. The therapeutic agent can be placed in the container in many ways, for example by placing a solid insert through the port to the inside of the container or by injecting a formulation of the therapeutic agent through the penetrable barrier into the container. The therapeutic device may comprise a binding agent that reversibly or releasably couples to the therapeutic agent such that the therapeutic agent is released from the device for the extended time.

In many embodiments, the therapeutic device is configured to provide continuous release of therapeutic quantities of at least one therapeutic agent for an extended time of at least 3 months, for example 6 months, such that the frequency of injections into the therapeutic device and risk of infection can be substantially decreased. In additional embodiments, the therapeutic device is configured to provide continuous release of therapeutic quantities of at least one therapeutic agent for an extended time of at least 12 months, or at least 2 years or at least 3 years.

The therapeutic device can be configured in many ways to release the therapeutic agent for the extended time and may comprise at least one of an opening, an elongate structure, a porous structure, or a porous surface sized to release the therapeutic agent for the extended time. For example, the therapeutic device may comprise the porous structure to release the therapeutic agent through the porous structure for the extended period. The porous structure may comprise a sintered material having many channels, for example interconnecting channels, extending around many particles adhered to each other. The porous structure may comprise a first side comprising a first plurality of openings coupled to the reservoir and a second side comprising a second plurality of openings to couple to the vitreous humor. The interconnecting channels may extend between each of the first plurality of openings of the first side and each of the second plurality of openings of the second side so as to maintain release of the therapeutic agent through the porous structure, for example when at least some the openings are blocked. The porous structure can be rigid and maintain release of the therapeutic agent through the interconnecting channels when tissue or cells cover at least a portion of the openings, for example when the porous structure is implanted for an extended time and the drug reservoir refilled.

The therapeutic device may comprise a retention structure configured to couple to the sclera to position the container for delivery of the therapeutic agent into the vitreous humor of the eye, such that the conjunctiva may extend over the retention structure when the device is implanted so as to inhibit the risk of infection to the patient and allow access to the device with decreased risk of infection. For example, the retention structure may comprise a flange extending outward for placement between the conjunctiva and sclera and a narrow portion to fit within the incision through the sclera. The narrow portion to fit the incision may comprise an elongate cross sectional profile sized to fit the incision. The elongate cross-sectional profile sized to fit the incision can improve the fit of the implanted device to the scleral incision, and may seal the implant against the sclera along the incision. The elongate cross sectional profile of the narrow portion can be sized in many ways to fit the incision. For example, the elongate cross section may comprises a first dimension longer than a second dimension and may comprise one or more of many shapes such as dilated slit, dilated slot, lentoid, oval, ovoid, or elliptical. The dilated slit shape and dilated slot shape may correspond to the shape sclera tissue assumes when cut and dilated. The lentoid shape may correspond to a biconvex lens shape. The elongate cross-section of the narrow portion may comprise a first curve along a first axis and a second curve along a second axis different than the first curve.

In many embodiments, the reservoir of the therapeutic device is flushable and/or refillable. This provides the added benefit that the physician may remove the therapeutic agent from the patient by flushing the agent from the reservoir of the therapeutic device rather than waiting for the therapeutic agent to be eliminated from the patient. This removal can be advantageous in cases where the patient has an adverse drug reaction or benefit from a pause in therapy sometimes referred to as a drug holiday. The volume of the reservoir and release rate of the porous structure can be tuned to receive a volume of a commercially available formulation, such that the therapeutic agent can be released for an extended time. For example, the volume of commercially available therapeutic agent may correspond to a bolus injection having a treatment duration, for example one month, and the reservoir volume and release rate tuned to receive the formulation volume can extend the treatment duration of the injected volume by a factor of at least about two, for example from one month to two or more months.

The therapeutic device may comprise a first narrow profile configuration for placement, and a second expanded profile to deliver the drug with the reservoir when positioned in the eye. For example, the therapeutic device may comprise a flexible barrier material coupled to a support, such that the barrier material and support can be expanded from a first narrow profile configuration to the second expanded profile configuration. The support can provide a substantially constant reservoir volume in the expanded configuration, such that the device can be tuned with the porous structure and expandable reservoir to receive the volume of therapeutic agent formulation and so as to release therapeutic amounts for the extended time. The therapeutic device may comprise a porous barrier extending around the container with channels sized to pass the therapeutic agent from the container therethrough and to inhibit migration of at least one of a bacterial cell out of the container or a macrophage or other immune cell into the container.

In a first aspect, embodiments provide a therapeutic device to deliver a therapeutic agent to an eye having a sclera and a vitreous humor. A container is configured to hold the therapeutic agent. The container is configured to release the therapeutic agent into the vitreous humor at therapeutic amounts for an extended time.

In many embodiments, the therapeutic agent comprises molecules having a molecular weight from about 100 Daltons to about 1,000,000 Daltons.

In many embodiments, the therapeutic agent comprises molecules having a molecular weight from about 200 Daltons to about 1000 Daltons.

In many embodiments, the therapeutic agent comprises a corticosteroid or an analogue thereof. The corticosteroid or the analogue thereof may comprise one or more of trimacinalone, trimacinalone acetonide, dexamethasone, dexamethasone acetate, fluocinolone, fluocinolone acetate, or analogues thereof.

In many embodiments, the therapeutic agent comprises a VEGF inhibitor.

In many embodiments, the therapeutic agent comprises a macromolecule having a molecular weight from about 10 k Daltons to about 400 k Daltons.

In many embodiments, the macromolecule may comprise a VEGF inhibitor. The macromolecule may comprise one or more of antibodies or antibody fragments. The one or more of the antibodies or the antibody fragments comprise a VEGF inhibitor. The VEGF inhibitor may comprise Ranibizumab. The VEGF inhibitor may comprise Bevacizumab. The VEGF inhibitor may comprise VEGF trap, for example Aflibercept™.

In many embodiments, the macromolecule comprise complement factor.

In many embodiments, the therapeutic agent comprises a complement factor inhibitor.

In many embodiments, container comprises a reservoir volume sized to contain a liquid formulation of the therapeutic agent.

In many embodiments, the volume to contain the liquid formulation is within a range from 10 uL to about 100 uL.

In many embodiments, the container is sized to contain from about 0.001 mg to about 50 mg of therapeutic agent, for example sized to contain from about 0.1 mg to about 10 mg of therapeutic agent. The container may be sized to contain from about 0.5 mg to about 1 mg of therapeutic agent. The container can be sized to contain from about 0.05 mg to about 1 mg of therapeutic agent.

In many embodiments, the container and the therapeutic agent are configured to release the therapeutic agent to sustain from about 0.1 ug/mL to about 10 ug/mL of therapeutic agent in the vitreous humor for the extended time. The container and the therapeutic agent can be configured to release the therapeutic agent to sustain from about 0.1 ug/mL to about 4 ug/mL of the therapeutic agent in the vitreous humor for the extended time. The container and the therapeutic agent can be configured to release the therapeutic agent to sustain from about 0.2 ug/mL to about 5 ug/mL of the therapeutic agent in the vitreous humor for the extended time.

In many embodiments, the extended time comprises at least about 1 month. For example, the extended time may comprise at least about 3 months. The extended time may comprise at least about 6 months. The extended time may comprise at least about 12 months. The extended time may comprise at least about 18 months. The extended time may comprise at least about 24 months.

In many embodiments, the therapeutic device further comprises a binding agent to couple to the therapeutic agent such that the therapeutic agent is released from the container for the extended time. The binding agent may comprise particles of material. The binding agent may comprise a pH sensitive binding agent. The binding agent may comprise a salt sensitive binding agent. The binding agent may comprise a pH sensitive binding agent configured to reversibly couple to the therapeutic agent at a non-physiologic pH below 6.5 or above 8 and to release the therapeutic agent at a physiologic pH of about 7. The pH sensitive binding agent can be configured to reversibly couple to the therapeutic agent at a pH of about 5 to about 6.5 and to release the therapeutic agent at a physiologic pH of about 7.

A stabilizer may extend release of the therapeutic agent. The stabilizer may comprise a buffer disposed within the container to decrease the pH within the container when the device is placed in the eye. The buffer may comprise a macromolecule having a molecular weight of at least about 2 k Daltons. The stabilizer may comprise an erodible material. The erodible material may decrease the pH when the material erodes.

In many embodiments, the container comprises a reservoir having a capacity from about 0.005 cc to about 2 cc to deliver therapeutic amounts of the therapeutic agent for the extended time and wherein the device comprises a volume of no more than about 0.25 cc to minimize distension of the eye when the device is inserted.

In many embodiments, the reservoir has a capacity from about 0.005 cc to about 0.6 cc to deliver therapeutic amounts of the therapeutic agent for the extended time and wherein the device comprises a volume of no more than about 0.6 cc to minimize distension of the eye when the device is inserted.

In many embodiments, the therapeutic device comprising a length extending through the sclera and into the vitreous humor and the length is within a range from about 2 to 12 mm. The length can be within a range from about 4 to 6 mm.

In many embodiments, the device further comprises a retention structure coupled to the container and configured to couple to the sclera to retain the container at least partially within the eye. The retention structure may comprise an extension coupled to the container and extending outward from the container to extend between the sclera and the conjunctiva to retain the container. The retention structure may comprise a collar. The collar may comprise an expandable collar.

In many embodiments, the device further comprises an injection port extending to the container and having a channel extending through the sclera to receive an injection of therapeutic agent to refill the container when the container is implanted at least partially within the vitreous humor. The device may further comprise a needle stop to limit penetration of the needle when the therapeutic agent is injected into the container. The needle stop can be disposed on a distal end of the container opposite the injection port. The injection port may comprise a smooth upper surface configured for placement under the conjunctiva.

In many embodiments, the device further comprises a bactericidal agent around at least a portion of an outer surface of the device to inhibit bacterial growth along the outer surface.

In many embodiments, the device further comprises a sponge to encourage tissue ingrowth. The sponge may comprise a bactericidal agent. Alternatively, the sponge may not comprise a bactericidal agent.

In many embodiments, the device further comprises a sponge material impregnated with the bactericidal agent around the portion of the outer surface. The sponge material may comprise collagen and the bactericidal agent may comprise sliver, the collagen impregnated with the silver.

In many embodiments, the container comprises a plurality of chambers connected with a plurality of channels to linearize a rate of release of the therapeutic agent.

In another aspect embodiments provide therapeutic device to treat an eye comprising a vitreous humor. The device comprises a therapeutic agent and a binding agent. The therapeutic agent is reversibly coupled to the binding agent such that the binding agent releases therapeutic amounts of the therapeutic agent into the vitreous humor of the eye for an extended time.

In many embodiments, the binding agent and the therapeutic agent are sized for injection into a vitreous humor of the eye when the therapeutic agent is reversibly coupled to the binding agent and wherein the binding agent is configured to release therapeutic amounts of the therapeutic agent for at least about 3 months. The binding agent may comprise a size of no more than about 1000 nm to minimize light scatter and at least about 5 nm such that the therapeutic agent coupled to the binding agent is retained in the vitreous humor for the extended time. The binding agent may comprise particles having a size of no more than about 100 nm to minimize light scatter and at least about 5 nm such that the therapeutic agent coupled to the binding agent is retained in the vitreous humor for the extended time.

In another aspect embodiments provide a therapeutic device to deliver a therapeutic agent to an eye having a sclera and a vitreous humor. The device comprises a retention structure configured to couple to the sclera. A container is coupled to the retention structure and configured to hold the therapeutic agent. The container comprises a chamber to hold the therapeutic agent, and a barrier to inhibit flow of the therapeutic agent from the container. The barrier comprises at least one opening to release the therapeutic agent to the vitreous humor. A porous structure is disposed between the barrier and the chamber to release the therapeutic agent into the vitreous humor through the at least one opening at therapeutic amounts for an extended time.

In many embodiments, the porous structure comprises a glass frit.

In many embodiments, the porous structure may comprise a porous annular portion and a porous circular end.

In many embodiments, the barrier comprises a material to inhibit substantially the release of the therapeutic agent from the container and the material is shaped so as to define the at least one opening to release the therapeutic agent.

In many embodiments, the barrier comprises a substantially non-porous material to inhibit substantially the release of the therapeutic agent from the container.

In many embodiments, the barrier comprises a tube and the porous structure comprises a circular disk disposed near the end of the tube.

In many embodiments, porous structure comprises a removable cartridge configured for placement and removal when the barrier is positioned in the eye and the retention structure is coupled to the sclera to retain the barrier.

In another aspect embodiments provide a therapeutic device to deliver a therapeutic agent to an eye having a sclera and a vitreous humor. A retention structure is configured to couple to the sclera. A container is coupled to the retention structure and configured to hold the therapeutic agent and a binding agent. A porous barrier is coupled to the retention structure and the rigid container. The porous barrier extends substantially around the container.

In many embodiments, the therapeutic agent and the binding agent are configured to release the therapeutic agent at therapeutic amounts for a sustained time.

In many embodiments, the device further comprises at least one opening formed in the container, and the opening is sized such that the therapeutic agent and the binding agent are configured to release the therapeutic agent through the at least one opening at therapeutic amounts for the sustained time.

In many embodiments, the porous barrier is configured to inhibit at least one of bacterial migration into the container, macrophage migration into the container or antibody migration into the container.

In many embodiments, the porous barrier comprises pores sized to pass the therapeutic agent from the container to the vitreous humor.

In many embodiments, the porous barrier comprises a pore size of at least about 10 nm to release the therapeutic agent and no more than about 200 nm to inhibit at least one of bacterial migration out of the container, macrophage migration or antibody migration into the container.

In many embodiments, the porous barrier comprises a flexible material.

In many embodiments, the porous barrier comprises an inflatable balloon configured to inflate when the therapeutic agent is injected into the container.

In many embodiments, the container comprises a rigid material to retain the therapeutic agent and the binding agent.

In many embodiments, the container comprises a material substantially impermeable to the therapeutic agent and at least one opening sized to release the therapeutic agent.

In many embodiments, therapeutic device further comprises an injection port sized to receive a needle.

In another aspect embodiments provide a therapeutic device to deliver a therapeutic agent to an eye having a sclera and a vitreous humor. A retention structure is configured to couple to the sclera. A container is coupled to the retention structure and configured to hold a therapeutic quantity of the therapeutic agent. The container comprises a first chamber to hold the therapeutic agent, and a barrier to inhibit flow of the therapeutic agent from the container. The barrier comprises at least one opening sized to release the therapeutic agent. A second chamber is coupled to the container through the at least one opening. The second chamber is configured to couple to the vitreous humor through a second at least one opening. The first at least one opening and the second at least one opening are sized to release the therapeutic agent into the vitreous humor through the second at least one opening at therapeutic amounts for an extended time.

In many embodiments, the second chamber comprises a volume sized to linearize a release rate of the therapeutic agent through the second at least one opening.

In another aspect, embodiments provide a method of sustained drug delivery to a posterior segment of an eye having a sclera and a vitreous humor. A container is inserted at least partially into the vitreous humor of the eye such that the container is retained with the sclera. The container comprises a first portion of therapeutic agent reversibly coupled to a first binding medium. The first portion of therapeutic agent is released from the first binding medium and through container to the vitreous at therapeutic amounts for an extended time. The binding medium is removed from the container. The binding medium is replaced with a second binding medium and a second portion of the therapeutic agent, wherein second portion of the therapeutic agent is released from the container for a second extended time.

In many embodiments, a protective barrier is inserted with the container and the protective barrier is disposed substantially around the container to inhibit at least one of a bacterial migration, a macrophage migration or an antibody migration into the container.

In many embodiments, first binding medium comprises at least one of a first insert, a first fibrous structure, a first slurry, or a first liquid and wherein the second binding medium comprises at least one of a second insert, a second fibrous structure, a second slurry or a second liquid.

In many embodiments, the liquid first binding medium is removed when the second binding medium is replaced.

In many embodiments, the first binding medium is removed when the second liquid is replaced to minimize volume changes within the eye.

In many embodiments, the first binding medium is removed when the second liquid is replaced to decrease volume changes within the eye.

In many embodiments, the first binding medium is removed when the second liquid is replaced to inhibit distension of the eye.

In many embodiments, the binding medium comprises an insert and wherein the insert is removed before a second insert is inserted.

In another aspect, embodiments provide a device to deliver a therapeutic agent to a container implanted at least partially in the eye. The device comprises a first chamber configured to store the therapeutic agent, and a second chamber configured to receive a liquid from the container. An elongate structure extends distally and comprising at least one channel coupled to the first chamber and the second chamber.

In many embodiments, the device further comprises a first one way valve coupled to the first chamber and the at least one channel. The first one way valve is configured to pass the therapeutic agent when a size of the first chamber decreases and inhibit flow into the first chamber from the channel when the size of the first chamber increases. A second one way valve can be coupled to the second chamber and the at least one channel. The second one way valve can be configured to inhibit flow of the therapeutic agent into the second chamber when a size of the first chamber decreases and to permit flow into the second chamber from the channel when the size of the first chamber increases.

In many embodiments, the first at least one channel comprises a first channel and a second channel. The first channel is coupled to the first chamber to inject the therapeutic agent and the second channel is coupled to the second chamber to draw fluid into the second chamber when the therapeutic agent is injected.

In another aspect embodiments provide therapeutic device to deliver a therapeutic agent to an eye having a sclera and a vitreous humor. A retention structure is configured to couple to the sclera. A container is coupled to the retention structure and configured to hold the therapeutic agent. A stop is disposed inside the container.

In many embodiments, the retention structure is configured to receive a needle.

In many embodiments, the stop comprises a concave surface directed toward the retention structure such that fluid is mixed within the container when a substance is injected with the needle.

In many embodiments, the container comprises at least one exit port to pass material from the container when the substance is injected with the needle, and the at least one exit is located distal to the concave surface such that the concave surface directs the injected substance away from the at least one exit port.

In another aspect embodiments provide a therapeutic device to release at least one therapeutic agent into a patient. The therapeutic device comprises a container to contain a therapeutic amount of the at least one therapeutic agent. The container comprises a reservoir with a volume sized to contain a therapeutic quantity of the at least one therapeutic agent for release over the extended time. The container comprises a rigid porous structure comprising a thickness and a surface area coupled to the reservoir and configured to release therapeutic amounts of the at least one therapeutic agent for the extended time.

In many embodiments, the container comprises a penetrable barrier configured to receive an injection of a therapeutic quantity of the at least one therapeutic agent, and the container comprises a barrier coupled to the penetrable barrier and the rigid porous structure to contain the at least one therapeutic agent.

In many embodiments, the barrier is coupled to the penetrable barrier comprises a tube.

In many embodiments, the rigid porous structure comprises a needle stop.

In many embodiments, the penetrable barrier comprises a septum configured to receive and pass a needle, and the septum is configured to seal when the needle is removed.

In many embodiments, the channels of the rigid porous structure comprises interconnected substantially fixed channels. The rigid porous structure can remain rigid and the channels can remain substantially fixed when the therapeutic agent is injected into the reservoir with at least some pressure.

In many embodiments, the rigid porous structure comprises a thickness within a range from about 0.1 mm to about 6 mm.

In many embodiments, the rigid porous structure comprises a thickness within a range from about 0.5 mm to about 6 mm.

In many embodiments, the rigid porous structure comprises a hardness parameter within a range from about 160 Vickers to about 500 Vickers. The rigid porous structure may comprise a hardness parameter within a range from about 200 Vickers to about 240 Vickers.

In many embodiments, the rigid porous structure comprises a surface area within a range from about 2 mm($^2$) to 0.2 mm($^2$).

In many embodiments, the rigid porous structure comprises a low resistance to flow. The porous structure may comprise a porosity to maintain the low resistance to flow. The porous structure may comprise a plurality of interconnecting channels extending between openings of a first side of the porous structure and openings of a second side of the porous structure to maintain the low resistance to flow. Interconnections among the plurality of interconnecting channels can maintain the low resistance to flow when at least some of the channels are blocked.

In many embodiments, the low resistance to flow corresponds to a resistance no more than a resistance of a needle sized to inject the therapeutic agent into the reservoir.

In many embodiments, the low resistance to flow corresponds to a pressure drop across the porous structure of no more than about 30 mm Hg when the therapeutic agent is injected. The pressure drop across the porous structure may comprise no more than about 20 mm Hg when the therapeutic agent is injected such that a physician can determine the presence of blockage of the interconnecting channels when the therapeutic agent is injected.

In many embodiments, the pressure drop across the porous structure corresponds to no more than a pressure drop of 35 Gauge needle to inject the therapeutic agent.

In many embodiments, the pressure drop across the porous structure corresponds to no more than a pressure drop of 35 Gauge needle having a length sized to inject the therapeutic agent into the reservoir.

In many embodiments, the rigid porous structure comprises a resistance to flow of an injected solution or suspension through a thirty gauge needle such that ejection of said solution or suspension through the rigid porous structure is substantially inhibited when said solution or suspension is injected into the reservoir. The reservoir may comprise a vent.

In many embodiments, the volume of the reservoir comprises from about 5 uL to about 2000 uL of a solution or suspension of the at least one therapeutic agent to release the at least one therapeutic agent for the extended period.

In many embodiments, the volume of the reservoir comprises from about 10 uL to about 200 uL of a solution or suspension of the at least one therapeutic agent to release the at least one therapeutic agent for the extended period.

In many embodiments, therapeutic device further comprises a retention structure affixed to the container and configured to couple to at least one tissue structure of the patient for the extended period. The at least one tissue structure may comprise a sclera of an eye of the patient and wherein the rigid porous structure is disposed on at least a portion of the container to release the at least one therapeutic agent into the eye for the extended period. The rigid porous structure can be disposed on at least a portion of the container to release the at least one therapeutic agent into at least one of the vitreous humor, the aqueous humor, the choroid, the sclera or the retina of the eye for the extended period.

In many embodiments, the rigid porous structure is disposed on a distal portion of the container to release the at least one therapeutic agent into the vitreous humor for convective transport to the retina of the eye for the extended period.

In many embodiments, the rigid porous structure is disposed on a proximal portion of the container to release the at least one therapeutic agent into the vitreous humor to couple to one or more of a ciliary body or a trabecular meshwork of the eye.

In many embodiments, the rigid porous structure comprises a surface oriented toward a target tissue of the eye when positioned in the eye.

In many embodiments, the rigid porous structure comprises a surface oriented away from a lens of the eye and toward a retina of the eye when positioned in the eye.

In many embodiments, the rigid porous structure comprises a surface oriented away from a lens of the eye and toward a retina of the eye to inhibit a cataract when positioned in the eye.

In many embodiments, the at least one tissue structure comprises a conjunctiva of the eye and the retention structure is configured to extend outward from the container between the sclera and the conjunctiva to retain the container for the extended period. The container may comprise a penetrable barrier and wherein the penetrable barrier and the retention structure are each configured to minimize erosion of surrounding tissues when positioned in an eye. The retention structure can inhibit or prevent the device from moving into the eye during refilling. The retention structure may extend outward from the container and comprise at least one of a suture hole for attachment to the sclera via a standard suture.

In many embodiments, the rigid porous structure comprises a plurality of rigid porous structures coupled to the reservoir and configured to release the at least one therapeutic agent for the extended period.

In many embodiments, the rigid porous structure comprises a molded rigid porous structure. The molded rigid porous structure may comprise at least one of a disk, a helix or a tube coupled to the reservoir and configured to release the at least one therapeutic agent for the extended period.

In many embodiments, the reservoir and the porous structure are configured to release therapeutic amounts of the at least one therapeutic agent corresponding to a concentration of at least about 0.001 μg per ml of vitreous humor for an extended period of at least about three months.

In many embodiments, the reservoir and the porous structure are configured to release therapeutic amounts of the at least one therapeutic agent corresponding to a concentration of at least about 0.01 μg per ml of vitreous humor and no more than about 300 μg per ml for an extended period of at least about three months. The reservoir and the porous structure can be configured to release therapeutic amounts of the at least one therapeutic agent corresponding to a concentration of at least about 0.1 μg per ml of vitreous humor. The reservoir and the porous structure can be configured to release no more than about 10 μg per ml for the extended period of at least about three months.

In many embodiments, the at least one therapeutic agent comprises a protein or peptide and a molecular weight of at least about 10 k Daltons.

In many embodiments, the at least one therapeutic agent comprises a VEGF inhibitor.

In many embodiments, the at least one therapeutic agent comprises at least a fragment of an antibody and a molecular weight of at least about 10 k Daltons. The at least one therapeutic agent may comprise ranibizumab. The at least one therapeutic agent may comprise bevacizumab. The at least one therapeutic agent may comprise Aflibercept™.

In many embodiments, the reservoir and the porous structure are configured to release therapeutic amounts of the at least one therapeutic agent corresponding to a concentration of at least about 0.1 ug per ml of vitreous humor. The reservoir and the porous structure can be configured to release no more than about 10 ug per ml for an extended period of at least about 6 months.

In many embodiments, the reservoir and the porous structure are configured to release therapeutic amounts of the at least one therapeutic agent corresponding to a concentration of at least about 0.1 ug per ml of vitreous humor and no more than about 10 ug per ml for an extended period of at least about twelve months. The reservoir and the porous structure can be configured to release therapeutic amounts of the at least one therapeutic agent corresponding to a concentration of at least about 0.1 ug per ml of vitreous humor and no more than about 10 ug per ml for an extended period of at least about twelve months.

In many embodiments, the interconnecting channels of the rigid porous structure are sized to limit a size of molecules passed through the channels of the rigid porous structure.

In many embodiments, the channels of the rigid porous structure comprise a hydrogel configured to limit a size of molecules passed through the channels of the rigid porous structure. The hydrogel can be configured to pass the at least one therapeutic agent comprising molecules comprising a cross-sectional size of no more than about 10 nm. The hydrogel may comprise a water content of at least about 70%. The hydrogel may comprise a water content of no more than about 90% to limit molecular weight of the at least one therapeutic agent to about 30 k Daltons. The hydrogel may comprise a water content of no more than about 95% to limit molecular weight of the at least one therapeutic agent to about 100 k Daltons. The hydrogel may comprise a water content within a range from about 90% to about 95% such that the channels of the porous material are configured to pass Ranibizumab and substantially not pass Bevacizumab.

In many embodiments, the Ranibizumab comprises ranibizumab comprising a recombinant humanized IgG1 kappa monoclonal antibody Fab fragment designed for intraocular use and wherein the ranibizumab is configured to bind to and inhibit the biologic activity of human vascular endothelial growth factor A (VEGF-A) and wherein the Ranibizumab has a molecular weight of approximately 48 k Daltons.

In many embodiments, the bevacizumab comprises a recombinant humanized monoclonal IgG1 antibody configured to bind to and inhibits the biologic activity of human vascular endothelial growth factor (VEGF) and wherein bevacizumab comprises human framework regions and the complementarity-determining regions of a murine antibody configured to bind to VEGF and wherein the bevacizumab has a molecular weight of approximately 149 k Daltons.

In many embodiments, the porous structure comprises a porosity, a thickness, a channel parameter and a surface area configured to release therapeutic amounts for the extended period. The porosity may comprise a value within a range from about 3% to about 70%. The porosity may comprise a value within a range from about 3% to about 30%. The porosity may comprise a value within a range from about 5% to about 10%. The porosity may comprise a value within a range is from about 10% to about 25%. The porosity may comprise a value within a range is from about 10% to about 20%.

In many embodiments, the channel parameter comprises a fit parameter corresponding to the tortuosity of the channels.

In many embodiments, the channel parameter comprises a fit parameter corresponding to an effective length of interconnecting channels extending from a first side of the porous structure to a second side of the porous structure. The effective length of the interconnecting channels may correspond to at least about 2 times a thickness of the porous structure. The effective length of the interconnecting channels may correspond to at least about 5 times a thickness of the porous structure.

In many embodiments, the rate of release of the at least one therapeutic agent corresponds to a ratio of the porosity to the channel parameter, and the ratio of the porosity to the channel parameter is less than about 0.5 such that the porous structure releases the at least one therapeutic agent for the extended period. The ratio of the porosity to the channel parameter can be less than about 0.2 such that the porous structure releases the at least one therapeutic agent for the extended period. The ratio of the porosity to the channel parameter can be less than about 0.1 such that the porous structure releases the at least one therapeutic agent for the extended period. The ratio of the porosity to the channel parameter can be less than about 0.05 such that the porous structure releases the at least one therapeutic agent for the extended period.

In many embodiments, the channel parameter comprises a value of at least about 1. The value of the channel parameter may comprise at least about 2. The channel parameter may comprise a value of at least about 5.

In many embodiments, porous structure comprises a release rate index determined with a ratio of the porosity times a cross-sectional area of the porous structure divided by the channel parameter times a thickness of the porous structure, the thickness extending across the cross sectional area. The porous structure may comprise a release rate index of no more than about 5.0 mm. The porous structure may comprise a release rate index of no more than about 2 mm. The porous structure may comprise a release rate index of no more than about 1.2 mm. The porous structure may comprise a release rate index of no more than about 0.2 mm. The porous structure may comprise a release rate index of no more than about 0.1 mm. The porous structure may comprise a release rate index of no more than about 0.05 mm.

In many embodiments, the channels of the rigid porous structure are sized to pass the at least one therapeutic agent comprising molecules having a molecular weight of at least about 100 Daltons.

In many embodiments, the channels of the rigid porous structure are sized to pass the at least one therapeutic agent comprising molecules having a molecular weight of at least about 50 k Daltons.

In many embodiments, the channels of the rigid porous structure comprises interconnecting channels configured to pass the at least one therapeutic agent among the interconnecting channels. The rigid porous structure may comprise grains of rigid material and wherein the interconnecting channels extend at least partially around the grains of rigid material to pass the at least one therapeutic agent through the porous material. The grains of rigid material can be coupled together at loci of attachment, and the interconnecting channels can extend at least partially around the loci of attachment.

In many embodiments, the porous structure comprises a sintered material. The sintered material may comprise grains of material in which the grains comprise an average size of no more than about 20 um. The sintered material may comprise grains of material in which the grains comprise an average size of no more than about 10 um. The sintered material may comprise grains of material in which the grains comprise an average size of no more than about 5 um. The sintered material may comprise grains of material in which the grains comprise an average size of no more than about 1 um.

In many embodiments, the sintered material comprises grains of material corresponding to a media grade of no more than about 0.1. The sintered material comprises grains of material corresponding to a media grade of no more than about 0.2. The sintered material may comprise grains of material corresponding to a media grade of no more than about 0.3. The sintered material may comprise grains of material corresponding to a media grade of no more than about 0.5.

In many embodiments, the channels are sized to pass therapeutic quantities of the at least one therapeutic agent through the sintered material for the extended time.

In many embodiments, the channels are sized to inhibit penetration of microbes through the sintered material. The channels are sized to inhibit penetration of bacteria through the sintered material.

In many embodiments, the sintered material comprises a wettable material. The sintered material may comprise a wettable material to inhibit bubbles within the channels of the material.

In many embodiments, the sintered material comprises at least one of a metal, a ceramic, a glass or a plastic. The sintered material may comprises a sintered composite material and the composite material may comprises two or more of the metal, the ceramic, the glass or the plastic. The sintered material may comprise the metal and the metal may comprise at least one of Ni, Ti, nitinol, stainless steel, cobalt chrome, elgiloy, hastealloy, c-276 alloy or Nickel 200 alloy. The sintered material may comprise the metal and the metal may comprise at least one of stainless steel 304, 304L, 316 or 316L. The sintered material comprises a ceramic. The sintered material comprises the glass. The sintered material comprises the plastic, the plastic comprising a wettable coating to inhibit bubble formation in the channels and wherein the plastic comprises at least one of PEEK, polyethylene, polypropylene, polyimide, polystyrene, polyacrylate, polymethacrylate, or polyamide.

In many embodiments, the at least one therapeutic agent stored in the reservoir of the container comprises at least one of a solid comprising the at least one therapeutic agent, a solution comprising the at least one therapeutic agent, a suspension comprising the at least one therapeutic agent, particles comprising the at least one therapeutic agent adsorbed thereon, or particles reversibly bound to the at least one therapeutic agent.

In many embodiments, the device is sized to pass through a lumen of a cannula.

In another aspect embodiments provide therapeutic device to release at least one therapeutic agent into a patient having a retina. The therapeutic device comprises a container to contain a therapeutic amount of the at least one therapeutic agent. The container comprises a reservoir with a volume sized to contain a therapeutic quantity of the at least one therapeutic agent for release over the extended time. The container comprises a porous structure comprising a thickness and a surface area coupled to the reservoir and configured to release therapeutic amounts of the at least one therapeutic agent for the extended time. The porous structure is disposed on a distal portion of the container. A retention structure is coupled to the container to couple to a sclera of the eye and position the porous structure at a location of the eye to deliver the therapeutic agent toward a target region of the retina with convective flow of the vitreous humor.

In many embodiments, the target location of the retina corresponds to neovascularization of a lesion coupled to the target region of the retina.

In many embodiments, the therapeutic agent comprises a macromolecule and wherein the porous structure comprises interconnecting channels sized to pass the macromolecule.

In many embodiments, the therapeutic agent comprises a steroid and wherein the porous structure comprises a surface oriented away from a lens of the eye to inhibit formation of a cataract when the steroid is released.

In another aspect embodiments provide therapeutic device to release at least one therapeutic agent into a patient having a retina. The therapeutic device comprises a container to contain a therapeutic amount of the at least one therapeutic agent. The container comprises a reservoir with a volume sized to contain a therapeutic quantity of the at least one therapeutic agent for release over the extended time. The container comprises a porous structure comprising a thickness and a surface area coupled to the reservoir and configured to release therapeutic amounts of the at least one therapeutic agent for the extended time. The porous structure is disposed on a proximal portion of the container. A retention structure is coupled to the container to couple to a sclera of the eye and position the porous structure at a location of the eye to deliver the therapeutic agent to one or more of the ciliary body or a trabecular meshwork of the eye to treat glaucoma.

In many embodiments, the therapeutic agent comprises a prostaglandin or a prostaglandin analog.

In another aspect embodiments provide a method of treating an eye of a having a vitreous humor and a retina. A target location of the retina is identified for treatment. A container is positioned, and the container has a therapeutic amount of a therapeutic agent. The container comprises a porous structure to release therapeutic amounts of the at least one therapeutic agent for the extended time. The porous structure is positioned in the vitreous humor at a location away from the retina to deliver the therapeutic agent to the target location with convective flow of the vitreous humor.

In many embodiments, the target location comprises choroidal neovascularization of a choroid of the eye coupled to the target location of the retina and wherein the therapeutic agent comprises a macromolecule to treat the choroidal neovascularization.

In many embodiments, the therapeutic agent comprises a macromolecule and wherein the container is coupled to the sclera and sized to position the porous structure along a flow path of the vitreous humor extending toward the target location.

In another aspect embodiments provide a therapeutic device to release at least one therapeutic agent into an eye of a patient. The therapeutic device comprises a container to contain a therapeutic amount of the at least one therapeutic agent. The container comprises a reservoir with a volume sized to contain a therapeutic quantity of the at least one therapeutic agent for release over the extended time. The container comprises a rigid porous structure comprising a thickness, a surface area and interconnecting channels coupled to the reservoir and configured to release therapeutic amounts of the at least one therapeutic agent for the extended time, the rigid porous structure disposed on a distal portion of the container to release the at least one therapeutic agent into the eye. A penetrable barrier is coupled to the reservoir and disposed on a proximal portion of the container to receive an injection of the at least one therapeutic agent. A retention structure is affixed to the container and configured to couple to a tissue of the eye of the patient for the extended period.

In another aspect embodiments provide a method of treating an eye. A container comprising a reservoir and a penetrable barrier is placed at least partially through a sclera of the eye, wherein the reservoir comprises a fluid. At least one needle is passed through the penetrable barrier and the conjunctiva disposed over the penetrable barrier. A therapeutic amount of at least one therapeutic agent is injected into the container. The fluid in the reservoir is substantially removed from the container when the therapeutic amount is injected.

In many embodiments, the fluid comprises a buffer.

In many embodiments, the fluid comprises at least one therapeutic agent.

In many embodiments, the at least one needle penetrates the penetrable barrier at a locus of penetration, the method further comprising removing the at least one needle from the penetrable barrier.

In many embodiments, the container comprises a rigid porous sintered material configured to release the at least one therapeutic agent from the container for an extended period of at least about three months, and the rigid porous sintered material comprises a needle stop disposed opposite the penetrable barrier.

In many embodiments, the at least one therapeutic agent is removed from the container with an injection of a solution in response to a patient reaction to the at least one therapeutic agent. An additional amount of the at least one therapeutic agent may be injected into the container to resume treatment of the patient with the at least one therapeutic agent.

In many embodiments, the at least one therapeutic agent injected into the container comprises at least one of a suspension of solid particles of the at least one therapeutic agent, a solution of the at least one therapeutic agent, at least one therapeutic agent adsorbed on particles or at least one therapeutic agent reversibly bound on particles.

In another aspect, embodiments provide a device to inject at least one therapeutic agent into a container positioned at least partially within the eye. The device comprises a chamber to hold a therapeutic quantity of at least one therapeutic agent. At least one needle is coupled to the chamber and comprising a first lumen sized to inject the at least one therapeutic agent into the container and a second lumen sized to receive liquid from the container when a quantity of at least one therapeutic agent is injected.

In many embodiments, the at least one needle comprises a first needle coupled to the chamber and a second needle coupled to a receptacle to receive the liquid ejected from the container when the at least one therapeutic agent is injected.

In many embodiments, the at least one needle comprises a first needle coupled to the chamber and a second needle coupled to a receptacle under vacuum to receive the liquid ejected from the container when the at least one therapeutic agent is injected.

In many embodiments, the first lumen extends to a first opening and the second lumen extends to a second opening, the first opening spaced apart from the second opening such that the liquid of the container is substantially replaced when the quantity of the at least one therapeutic agent is injected.

In another aspect, embodiments provide a therapeutic device to release at least one therapeutic agent into a vitreous humor of an eye of a patient. The therapeutic device comprises a container to contain a therapeutic amount of the at least one therapeutic agent, the container comprising a reservoir with a volume sized to contain a therapeutic quantity of at least one therapeutic agent for release over an extended time of at least one year. The reservoir comprises a volume of at least about 10 uL. The container comprises a barrier coupled to the reservoir and disposed along at least a portion of the reservoir container to contain therapeutic agent within the reservoir. A porous structure comprising a thickness, a surface area and channels is coupled to the reservoir and configured to release therapeutic amounts of the at least one therapeutic agent for the extended time of at least one year, the porous structure is coupled to the container to release the at least one therapeutic agent into the eye. A retention structure is affixed to the container and configured to couple to a sclera of the eye of the patient for the extended period.

In many embodiments, the at least one therapeutic agent comprises ranibizumab.

In many embodiments, the at least one therapeutic agent comprises bevacizumab.

In many embodiments, the at least one therapeutic agent comprises steroids, nonsteroidals, anti-inflammatories, antibiotics, glaucoma treatments or neuroprotectives.

In many embodiments, the quantity comprises at least about 20 uL and wherein the extended time comprises at least about two years and a molecular weight of the at least one therapeutic agent comprises at least about 100 Daltons.

In many embodiments, the quantity comprises at least about 20 uL and wherein the extended time comprises at least about two years and a molecular weight of the at least one therapeutic agent comprises at least about 10 k Daltons.

In many embodiments, the quantity comprises at least about 30 uL and wherein the extended time comprises at least about three years and a molecular weight of the at least one therapeutic agent comprises at least about 100 Daltons.

In many embodiments, the quantity comprises at least about 30 uL and wherein the extended time comprises at least about three years and a molecular weight of the at least one therapeutic agent comprises at least about 10 k Daltons.

In another aspect, embodiments provide a therapeutic device to release at least one therapeutic agent into a vitreous humor of an eye of a patient. The therapeutic device comprises a container to contain a therapeutic amount of the at least one therapeutic agent. The container comprises a reservoir with a volume sized to contain a therapeutic quantity of at least one therapeutic agent for release over an extended time. The container comprises a barrier coupled to the reservoir and disposed along at least a portion of the reservoir container to contain therapeutic agent within the reservoir. A porous structure comprising a first side having comprising a first plurality of openings is coupled to the reservoir and a second side comprises a second plurality of openings to couple to the vitreous humor. The interconnecting channels extend between each of the first plurality of openings of the first side and each of the second plurality of openings of the second side to maintain release of the therapeutic agent through the porous structure when partially blocked. A retention structure is affixed to the container to couple to a sclera of the eye of the patient for the extended period.

In many embodiments, the release of the therapeutic agent through the porous structure is maintained when partially blocked with particles.

In many embodiments, the release of the therapeutic agent through the porous structure is maintained when partially blocked with particles.

In many embodiments, the release of the therapeutic agent through the porous structure is maintained when partially blocked with particles comprising one or more of degraded therapeutic agent or aggregated therapeutic agent. The particles may comprise the degraded therapeutic agent, and the degraded therapeutic agent may comprise a conformational change of a molecular structure of the therapeutic agent such that efficacy of the degraded therapeutic agent is less than the therapeutic agent. The particles may comprise the degraded therapeutic agent and the degraded therapeutic agent may comprise at least one altered chemical bond such that the molecules of the therapeutic agent such that efficacy of the degraded therapeutic agent is less than the therapeutic agent. The particles may comprise the aggregated therapeutic agent and wherein the aggregated therapeutic agent comprises a plurality of molecules of the therapeutic agent.

In many embodiments, the release of the therapeutic agent through the porous structure is maintained when a portion of the first side or the second side is blocked with a covering material.

In another aspect, embodiments provide a therapeutic device to release at least one therapeutic agent into a vitreous humor of an eye of a patient. The therapeutic device comprises a container to contain a therapeutic amount of the at least one therapeutic agent, the container comprising a reservoir with a volume sized to contain a therapeutic quantity of at least one therapeutic agent for release over an extended time. The container comprises a barrier coupled to the reservoir and disposed along at least a portion of the reservoir container to contain therapeutic agent within the reservoir. A porous structure comprises a first side having comprising a first area coupled to the reservoir and a second side having a second area to couple to the vitreous humor. A flow rate of the therapeutic agent through the porous structure decreases less than a percent amount when the first area or the second area are decreased by the percent amount. A retention structure is affixed to the container to couple to a sclera of the eye of the patient for the extended period.

In many embodiments, the flow rate of the therapeutic agent through the porous structure decreases less than the percent amount when the first area and the second area are decreased by the percent amount.

In many embodiments, a flow rate of the therapeutic agent through the porous structure decreases less than five percent amount when the first area or the second area are decreased by the five percent.

In another aspect, embodiments provide a therapeutic device to release at least one therapeutic agent into a vitreous humor of an eye of a patient. The therapeutic device comprises a container to contain a therapeutic amount of the at least one therapeutic agent. The container comprises a reservoir with a volume sized to contain a therapeutic quantity of at least one therapeutic agent for release over an extended time. The container comprises a barrier coupled to the reservoir and disposed along at least a portion of the reservoir container to contain therapeutic agent within the reservoir. A porous structure comprises a first side having a first plurality of openings coupled to the reservoir and a second side having a second plurality of openings to couple to the vitreous humor. Interconnecting channels extend from the first plurality of openings on the first side to the second plurality of openings on the second side to connect each of the plurality of openings on the first side with each of the plurality of openings on the second side. A retention structure is affixed to the container and configured to couple to a sclera of the eye of the patient for the extended period.

In many embodiments, the first plurality comprises at least about 10 openings on the first side and the second plurality comprises at least about 10 openings on the second side and each of the at least about 10 openings of the first side is connected to each of the at least about 10 openings on the second side with the interconnecting channels.

In many embodiments, the first plurality comprises at least about 20 openings on the first side and the second plurality comprises at least about 20 openings on the second side and each of the at least about 20 openings of the first side is connected to each of the at least about 20 openings on the second side with the interconnecting channels.

In many embodiments, the first plurality comprises at least about 40 openings on the first side and the second plurality comprises at least about 40 openings on the second side and each of the at least about 40 openings of the first side is connected to each of the at least about 40 openings on the second side with the interconnecting channels.

In another aspect, embodiments provide a therapeutic device to release at least one therapeutic agent into a vitreous humor of an eye of a patient. The therapeutic device comprises a container to contain a therapeutic amount of the at least one therapeutic agent. The container comprises a reservoir with a volume sized to contain a therapeutic quantity of at least one therapeutic agent for release over an extended time. The container comprises a barrier coupled to the reservoir and disposed along at least a portion of the reservoir container to contain therapeutic agent within the reservoir. A porous structure comprises a first side having a first plurality of openings coupled to the reservoir and a second side comprising a second plurality of openings to couple to the vitreous humor. The porous material comprises particles sintered to form interconnecting channels extending between each of the first plurality of openings of the first side and each of the second plurality of openings of the second side. Release of the therapeutic agent through the porous structure corresponds substantially to a distribution of sizes of the sintered material and a porosity of the sintered material above a percolation threshold. A retention structure is affixed to the container to couple to a sclera of the eye of the patient for the extended period.

In many embodiments, the distribution corresponds to at least about ten sintered particles disposed between the first plurality of openings and the second plurality of openings to maintain release of the therapeutic agent when one or more of the first openings or the second openings is partially blocked.

In another aspect, embodiments provide a therapeutic device to release at least one therapeutic agent into a vitreous humor of an eye of a patient. The therapeutic device comprises a container to contain a therapeutic amount of the at least one therapeutic agent. The container comprises a reservoir with a volume sized to contain a therapeutic quantity of at least one therapeutic agent for release over an extended time. The volume corresponds to a cross-sectional dimension of the container and a height of the container. The container comprises a barrier coupled to the reservoir and disposed along at least a portion of the reservoir to contain therapeutic agent within the reservoir. A porous structure comprises a first side coupled to the reservoir and a second side to couple to the vitreous humor. The porous structure comprises a thickness extending between the first side and the second side and a cross-sectional dimension corresponding to an area of the first side and an area of the second side. The cross-sectional dimension of the porous structure comprises at least about ten percent of the cross-sectional dimension of the container to release the therapeutic agent for the extended time. A retention structure is affixed to the container to couple to a sclera of the eye of the patient for the extended time.

In many embodiments, the cross-sectional dimension of the porous structure comprises at least about twenty percent of the cross-sectional dimension of the container to release the therapeutic agent for the extended time.

In many embodiments, the cross-sectional dimension of the porous structure comprises at least about thirty percent of the cross-sectional dimension of the container to release the therapeutic agent for the extended time.

In another aspect, embodiments provide a therapeutic device to release at least one therapeutic agent into a vitreous humor of an eye of a patient. The therapeutic device comprises an expandable container to contain a therapeutic amount of the at least one therapeutic agent. The expandable container comprises a first narrow profile configuration for insertion into the eye and a second expanded profile configuration having a reservoir sized to contain a therapeutic amount of the at least one therapeutic agent. The expandable container comprises a porous structure coupled to the reservoir to release the at least one therapeutic agent. An expandable retention structure comprises a first narrow profile configuration for insertion at least partially into a sclera of the eye and a second expanded profile configuration to couple to the sclera of the eye. The expandable retention structure is affixed to the expandable container to couple the expandable container to the vitreous humor for the extended time.

In many embodiments, the expandable retention structure comprises a resilient material comprising one or more of metal, thermoplastic, shape memory material or Nitinol.

In many embodiments, the expandable retention structure comprises a first extension to couple to a lower side of the sclera and a second extension to couple to an upper side of the sclera.

In many embodiments, the first extension comprises a flange extending distally in the first configuration to pass through the sclera and wherein the flange extends laterally in the second configuration to couple to the sclera.

In many embodiments, the second extension comprises a flange extending proximally in the first configuration to pass through a lumen of an insertion tool and wherein the flange extends laterally in the second configuration to couple to the sclera.

In another aspect, embodiments provide a therapeutic device to release at least one therapeutic agent into a vitreous humor of an eye of a patient. The therapeutic device comprises an expandable container comprising a first narrow profile configuration for insertion into the eye and a second expanded configuration comprising a reservoir to contain a therapeutic amount of the at least one therapeutic agent. The expandable container comprises a rigid porous structure to release the at least one therapeutic agent and an expandable barrier to inhibit release of the at least one therapeutic agent. An expandable support is affixed to the porous structure and the expandable barrier to couple the porous structure to the reservoir when the container has the expanded configuration.

An expandable retention structure comprises a first narrow profile configuration for insertion at least partially into a sclera of the eye and a second expanded profile configuration to couple to the sclera of the eye. The expandable retention structure is affixed to the expandable container to couple the expandable container to the vitreous humor for the extended time.

In many embodiments, the expandable support comprises a resilient material comprising one or more of metal, thermoplastic, shape memory material or Nitinol.

In many embodiments, the expandable support comprises a proximal annular portion and a distal annular portion, wherein a plurality of members extend between the proximal annular portion and the distal annular portion.

In many embodiments, the plurality of expandable members separate between the proximal annular portion and the distal annular portion when the container comprises the expanded configuration.

In many embodiments, the therapeutic device further comprises a penetrable barrier supported with the proximal annular portion.

In many embodiments, the rigid porous structure is supported with the distal annular portion.

In another aspect, embodiments provide a therapeutic device to release at least one therapeutic agent into a vitreous humor of an eye of a patient. The therapeutic device comprises a container to contain a therapeutic amount of the at least one therapeutic agent. The container comprises a reservoir with a volume sized to contain a therapeutic quantity of at least one therapeutic agent for release over an extended time. A retention structure is affixed to the container to couple to a sclera of the eye of the patient for the extended time. The retention structure comprises an extension to couple to an upper side of the sclera. The retention structure comprises a portion to receive the sclera under the extension. The portion comprises a first width extending in a first direction and a second width extending in a second direction. The first width is greater than the second width.

In many embodiments, the portion comprises an elongate cross-sectional profile having the first width extending along a first axis and the second width extending along a second axis.

In many embodiments, the portion comprises an elliptical cross-sectional profile having the first width extending along a first axis of the elliptical profile and the second width extending along a second axis of the elliptical profile.

In many embodiments, portion comprises a narrow portion having the first width sized larger than a cross-sectional dimension of the container and having the second width sized smaller than a cross-sectional dimension of the container to seal an incision of the sclera with the cross-sectional profile.

In many embodiments, the narrow portion comprises a recess extending substantially around the narrow portion and wherein the recess comprises a thickness sized to receive the sclera.

In many embodiments, the extension comprises a first extension width extending in the first direction and a second extension width extending in the second direction, the first extension width greater than the second extension width.

In many embodiments, the extension comprises an elliptical profile having the first extension width extending along a first axis of the elliptical profile and the second extension width extending along a second axis of the elliptical profile.

In many embodiments, the container comprises a cross-sectional profile having a first distance across and a second distance across greater than the first distance across.

In many embodiments, the container comprises a cross-sectional profile having a first distance across and a second distance across greater than the first distance across and wherein the first distance is aligned substantially with the first width and the second dimension across is aligned substantially with the second width to decrease visual interference.

In many embodiments, the cross-sectional profile of the container comprises an elliptical profile.

In another aspect, embodiments provide a method of treating an eye having a vitreous humor and a sclera. A therapeutic device is provided to release at least one therapeutic agent into the vitreous humor of an eye of a patient. The therapeutic device comprises a container and a retention structure affixed to the container. The retention structure comprises a narrow portion having a first longer distance across extending in a first direction and a second shorter distance across extending in a second direction. The first longer distance is greater than the second shorter distance. An elongate incision is formed in the sclera, the incision comprising a length extending along a pars plana of the eye and a width, the length greater than the width. The container is positioned in the eye to release the therapeutic agent. The narrow portion of the retention structure is aligned with the elongate incision such that the first longer distance across extends substantially along the elongate incision and the second shorter distance across extends substantially across the width of the incision.

In many embodiments, the pars plana extends circumferentially along the eye between a choroid of the eye and a pars plicata of the eye and wherein the length of the incision is greater than a distance across the pars plana between the choroid of the eye and the pars plicata of the eye and wherein the length of the incision is oriented to fit the incision within the pars plana of the eye.

In many embodiments, the eye comprises a conjunctiva and wherein the retention structure comprises an extension having a distance across greater than the longer distance of the narrow portion and wherein the extension is positioned between the sclera and the conjunctiva.

In another aspect, embodiments provide a method of treating an eye of a patient. A therapeutic device is provided comprising a reservoir and a therapeutic agent disposed therein. The container is positioned in the eye to release the therapeutic agent. The narrow portion of the retention structure is aligned with the elongate incision such that the first longer distance across extends substantially along the elongate incision and the second shorter distance across extends substantially across the width of the incision.

In another aspect, embodiments provide a method of treating an eye of a patient. A therapeutic device is provided comprising a container and a therapeutic agent disposed within the container. The therapeutic agent comprises a half-life within the container of at least about 20 days when implanted. The container is positioned in the eye to release the therapeutic agent, wherein the eye is treated with the therapeutic agent for at least about 90 days.

In another aspect, embodiments provide a method of treating an eye of a patient. A therapeutic device is provided comprising a reservoir and a therapeutic agent disposed within the reservoir. The therapeutic agent comprises a half-life within the reservoir of no more than about 30 days when implanted. The container is positioned in the eye to release the therapeutic agent, the eye is treated with the therapeutic agent for at least about 180 days.

In another aspect, embodiments provide a method of treating an eye of a patient. A therapeutic device is provided comprising a reservoir and a therapeutic agent disposed within the reservoir, and the therapeutic agent comprises a half-life within the reservoir when implanted. The half life within the reservoir is substantially greater than a corresponding half-life of the therapeutic agent when injected directly into the vitreous. The container is positioned in the eye to release the therapeutic agent, and the eye is treated with the therapeutic agent for at least about 180 days.

In many embodiments, the therapeutic agent comprises ranibizumab.

In another aspect, embodiments provide a method of manufacturing a therapeutic device to release a therapeutic agent. A gas is measured coupled to a porous structure. A container is provided to contain the therapeutic agent. The porous structure is coupled to the container.

In many embodiments, the gas is measured to determine a release rate of the therapeutic agent through the porous structure.

In many embodiments, the gas is measured to determine a resistance to flow of the porous structure.

In many embodiments, the gas is measured with a first pressure at a first time and a second pressure at a second time.

In many embodiments, the gas is measured with a pressure drop across the porous structure.

In many embodiments, the gas is measured with a volume of gas passed through the porous structure per unit time.

In many embodiments, the gas is measured before the porous structure is coupled to the container.

In many embodiments, the therapeutic device comprises a support structure and the gas flow is measured when the porous structure is affixed to the support structure.

In many embodiments, the gas flow is measured a first time before the porous structure is coupled to the container and the device therapeutic comprises a support and wherein the gas flow is measured a second time when the porous structure is affixed to the support.

In another aspect, embodiments provide a method of treating an eye having a vitreous humor. A quantity of a formulation of therapeutic agent is injected into a therapeutic device, and the therapeutic device is tuned to receive the quantity.

In another aspect, embodiments provide a method of treating an eye having a vitreous humor. A formulation of a therapeutic agent is provided. The therapeutic agent is capable of treating the eye with bolus injections. The formulation has a corresponding period between each of the bolus injections to treat the eye and each of the bolus injections comprises a volume of the formulation such that each of the bolus injections corresponds to a range of therapeutic concentrations of the agent in the vitreous humor to treat the eye. A therapeutic device is provided to treat the eye with an injection of the volume of the formulation into the device, and the device comprises a container having a chamber to contain a volume of the therapeutic agent and a mechanism to release the therapeutic agent from the chamber to the vitreous humor. The volume of the container and the release mechanism are tuned to treat the eye with concentrations of the therapeutic agent in the vitreous humor within the range for an extended time with each injection of the quantity, and the extended time comprises at least about twice the period.

In many embodiments, the chamber comprises a substantially fixed volume and the release rate mechanism comprises a substantially rigid structure to maintain release of the therapeutic agent above the minimum inhibitory concentration for the extended time with each injection of a plurality of injections.

In many embodiments, the release mechanism comprises one or more of a porous frit, a permeable membrane, a semi-permeable membrane, a capillary tube or a tortuous channel, nano-structures, nano-channels or sintered nano-particles.

In many embodiments, the release mechanism comprises the porous frit and wherein the porous frit comprises a porosity, cross sectional area, and a thickness to release the therapeutic agent for the extended time.

In many embodiments, the volume of the container comprises no more than about twice the volume of the formulation.

In many embodiments, the volume of the container comprises no more than the volume of the formulation.

In many embodiments, a first portion of the injection passes through the release mechanism and treats the patient when the formulation is injected and a second portion of the formulation is contained in the chamber when the formulation is injected and the concentration of therapeutic agent in the vitreous humor is within the range of the therapeutic concentrations for the extended time comprising at least about twice the period.

In many embodiments, the volume of the container comprises less than the volume of the injected formulation and wherein a first portion of the injection passes through the release mechanism when the formulation is injected and a second portion of the formulation is contained in the chamber when the formulation is injected.

In many embodiments, a vent is opened to exchange material disposed within the chamber with the injected formulation and wherein the vent is closed to pass the first portion through the release mechanism.

In many embodiments, the volume and the mechanism are tuned to release the therapeutic concentration within the range for the extended time based on a half life of the therapeutic agent in the vitreous humor of the eye. The eye may comprise a human eye and the half life can be determined based on the half life of the therapeutic agent in the human eye. The half life of the therapeutic agent may comprise at least about one hour, for example for a therapeutic agent comprising a small molecule. The half life of the therapeutic agent may comprise at least about four days, for example for a therapeutic agent comprising a large molecule.

In another aspect, embodiments provide a method of treating an eye having a vitreous humor. A therapeutic device is provided having a chamber sized to contain a volume of a therapeutic agent and a porous structure coupled to the chamber. An injector is provided comprising at least one lumen to inject a formulation of a therapeutic agent, the injector comprising a valve coupled to the at least one lumen. The therapeutic device is coupled to the injector with the at least one lumen extending at least partially into the therapeutic device. A first portion of the formulation is injected into the chamber when the valve is open to exchange material disposed within the chamber with the first portion formulation. A second portion of the formulation is injected when the valve is closed to pass formulation through the porous structure.

In many embodiments, a part of the first portion passes through the porous structure when the valve is closed and the second portion is injected.

In many embodiments, a part of the second portion passes through the porous structure when the valve is closed and the second portion is injected.

In another aspect, embodiments provide a therapeutic device for treating an eye having a vitreous humor. The therapeutic device comprises a reservoir and porous structure tuned to release for an extended time therapeutic amounts of a therapeutic agent injected into the reservoir.

In many embodiments, the porous structure comprises a release mechanism, and the reservoir volume and the release mechanism are tuned to release the therapeutic amounts of the therapeutic agent for the extended time based on a half life of the therapeutic agent in the vitreous humor of the human eye. The half life of the therapeutic agent may comprise at least about one hour, for example for a therapeutic agent comprising a small molecule. The half life of the therapeutic agent may comprise at least about four days, for example for a therapeutic agent comprising a large molecule.

In another aspect, embodiments provide a method of treating an eye having a vitreous humor. The therapeutic device is provided comprising a reservoir and porous structure tuned to release therapeutic amounts of a therapeutic agent for an extended time. A quantity of therapeutic agent is injected into the reservoir, and the therapeutic agent is released from the tuned reservoir and porous structure for the extended time.

In another aspect, embodiments provide an apparatus to treat an eye having a vitreous humor. The apparatus comprises a therapeutic device comprising reservoir to contain a therapeutic agent and a porous structure. An injector has a first chamber and a second chamber and at least one needle comprising a first lumen and a second lumen, and the first chamber coupled to the first lumen to inject the therapeutic agent from the first chamber into the reservoir. The second chamber is coupled to the second lumen with a valve disposed therebetween to receive material from the reservoir when the valve is open and pass therapeutic agent through the porous structure when the valve is closed.

In another aspect, embodiments provide a method of treating an eye having a vitreous humor. A volume of a formulation of Ranibizumab is injected into a therapeutic device, the volume is within a range from about 40 to 60 uL. The concentration of Ranibizumab of the formulation is within a range from about 8 to 12 mg/mL, such that the injection comprises a weight Ranibizumab within a range from about 0.4 to about 0.6 mg of Ranibizumab. The Ranibizumab is released in therapeutic amounts for an extended time of at least about 4 months.

In many embodiments, the formulation comprises a commercially available formulation of Lucentis™ and the volume corresponds to a monthly bolus injection of about 50 uL of Lucentis™ and a concentration of the Ranibizumab in the vitreous humor remains at least about 4 ug/mL for the extended time.

In another aspect, embodiments provide a method of treating an eye. The method comprises placing a container comprising a reservoir and a penetrable barrier at least partially through a sclera of the eye, wherein the reservoir comprises a fluid. A therapeutic amount of at least one therapeutic agent is injected into the container. The therapeutic amount corresponds to a bolus injection to treat the eye for about one month and therapeutic quantities of the therapeutic agent are released from the container for at least about two months to treat the eye.

In another aspect, embodiments provide a method of treating an eye, the eye having a sclera and a pars plana. A therapeutic device is provided comprising a drug reservoir, a porous structure and a retention structure, the retention structure comprising an elongate cross-sectional profile. An incision is formed through the sclera and extending along the pars plana region. The therapeutic device is advanced into the sclera with the elongate cross-sectional profile aligned with the incision along the pars plana, and the elongate cross-sectional profile seals the incision when the elongate cross-sectional profile contacts the sclera.

In many embodiments, the alignment structure comprises a conformable flange disposed over the elongate cross-sectional profile and wherein the conformable flange contacts and upper surface of the sclera when the elongate cross-sectional profile contacts the sclera.

In many embodiments, the eye comprises a conjunctiva and the method further comprises forming a first incision through the conjunctiva at a first location. The conjunctive is moved to expose the sclera at a second location. The incision through the sclera is formed at the second location, and the incision through conjunctiva is slid to the first location to cover the implant at the second location and seal the incision.

In another aspect, embodiments provide an apparatus. The apparatus comprises a therapeutic device comprising a shape changing drug reservoir, a porous structure and a retention structure, and cannula. The therapeutic device is positioned within the cannula.

In many embodiments, the therapeutic device comprises an elongate narrow shape for insertion into the sclera and wherein the device is configured to expand to a second elongate wide shape for retention in the sclera In many embodiments, the reservoir comprises a thin elongated shape when inserted through the sclera and comprises an extended, ballooned shape, when filled with therapeutic agent.

In another aspect, embodiments provide a therapeutic device to treat a patient. The device comprising means for releasing therapeutic amounts of a therapeutic agent for an extended period.

BRIEF DESCRIPTION OF THE DRAWINGS

FIG. 1A-1 shows a therapeutic device implanted at least partially within the sclera of the eye as in FIG. 1;

FIG. 1A-1-1 and 1A-1-2 show a therapeutic device implanted under the conjunctiva and extending through the sclera to release a therapeutic agent into vitreous humor of the eye so as to treat the retina of the, in accordance with embodiments of the present invention;

FIG. 1A-2 shows structures of a therapeutic device configured for placement in an eye as in FIGS. 1A-1 and 1A-1-1, according to embodiments of the present invention;

FIG. 1A-2-1 shows a therapeutic device loaded into an insertion cannula, in which the device comprises an elongate narrow shape for insertion into the sclera, and in which the device is configured to expand to a second elongate wide shape for retention at least partially in the sclera;

FIG. 1A-2-2 shows a therapeutic device comprising a reservoir suitable for loading in a cannula;

FIG. 1B shows a therapeutic device configured for placement in an eye as in FIG. 1A-1 and 1A-1-1, in accordance with embodiments of the present invention;

FIG. 1C-A shows at least one exit port, according to embodiments of the present invention;

FIG. 1C-1 shows a method of removing a binding material, according to embodiments of the present invention;

FIG. 1C-2 and inserting the therapeutic agent with a second insert having the TA bound thereon;

FIG. 1C-3 shows syringe being filled with a commercially available formulation of therapeutic agent for injection into the therapeutic device, in accordance with embodiments;

FIG. 1E-1 shows a therapeutic device configured for placement in an eye as in FIGS. 1A-1 and 1A-1-1, in which the device comprises a needle stop located at the bottom of the therapeutic device and the shape of the device encourages the movement of the therapeutic agent within the chamber of the therapeutic device;

FIG. 1E-2 shows a therapeutic device configured for placement in an eye as in FIGS. 1A-1 and 1A-1-1, in which the device comprises a needle stop located in the middle of the therapeutic device;

FIG. 1E-3 shows a therapeutic device configured for placement in an eye as in FIGS. 1A-1 and 1A-1-1, in which the device comprises a needle stop located in the middle of the therapeutic device and the shape of the device encourages the movement of the therapeutic agent within the chamber of the therapeutic device;

FIG. 1E-3-1 shows a top view of the therapeutic device configured for placement in an eye as in FIGS. 1E-3;

FIG. 2 shows an access port suitable for incorporation with the therapeutic device, in accordance with embodiments of the present invention;

FIG. 5A-1 shows a therapeutic device coupled to an injector to simultaneously inject and remove material from the device;

FIG. 5C1 shows a therapeutic device comprising a tortuous channel;

FIG. 5C2 shows a therapeutic device comprising a coiled channel;

FIG. 6A-1 shows a therapeutic device comprising a container having a penetrable barrier disposed on a first end, a porous structure disposed on a second end to release therapeutic agent for an extended period, and a retention structure comprising an extension protruding outward from the container to couple to the sclera and the conjunctiva;

FIG. 6A-2 shows a therapeutic device as in FIG. 6A-1 comprising a rounded distal end;

FIG. 6B-1 shows interconnecting channels extending from a first side to a second side of the porous structure as in FIG. 6B;

FIG. 6B-2 shows a plurality of paths of the therapeutic agent along the interconnecting channels extending from a first side to a second side of the porous structure as in FIGS. 6B and 6B-1;

FIG. 6B-3 shows blockage of the openings with a covering and the plurality of paths of the therapeutic agent along the interconnecting channels extending from a first side to a second side of the porous structure as in FIGS. 6B and 6B-1;

FIG. 6B-4 shows blockage of the openings with particles and the plurality of paths of the therapeutic agent along the interconnecting channels extending from a first side to a second side of the porous structure as in FIGS. 6B and 6B-1;

FIG. 6B-5 shows an effective cross-sectional size and area corresponding to the plurality of paths of the therapeutic agent along the interconnecting channels extending from a first side to a second side of the porous structure as in FIGS. 6B and 6B-1;

FIG. 7A-1 shows a therapeutic device coupled to an injector needle comprising a stop that positions the distal end of the needle near the proximal end of the device to flush the reservoir with ejection of liquid formulation through the porous frit structure, in accordance with embodiments;

FIG. 7A2 shows a therapeutic device comprising a penetrable barrier coupled to an injector to inject and remove material from the device such that the liquid in the reservoir is exchanged with the injected formulation, in accordance with embodiments;

FIG. 7B-1 shows a side cross-sectional view of a therapeutic device comprising a retention structure having a cross-section sized to fit in an elongate incision, in accordance with embodiments;

FIG. 7B-2 shows an isometric view of the therapeutic device as in FIG. 7B-1;

FIG. 7B-3 shows a top view of the therapeutic device as in FIG. 7B-1;

FIG. 7B-4 shows a side cross sectional view along the short side of the retention structure of the therapeutic device as in FIG. 7B-1;

FIG. 7B-5 shows a bottom view of the therapeutic device as in FIG. 7B-1 implanted in the sclera;

FIG. 7B-5A shows a cutting tool comprising a blade having a width corresponding to the perimeter of the barrier and the perimeter of the narrow retention structure portion;

FIGS. 7B-6A and 7B-6B show distal cross-sectional view and a proximal cross-sectional view, respectively, of a therapeutic device comprising an elongate and non-circular cross-sectional size, in accordance with embodiments;

FIG. 7B-6C shows an isometric view of the therapeutic device having a retention structure with an elongate cross-sectional size, in accordance with embodiments;

FIG. 7B-6D shows a distal end view of the therapeutic device as in FIG. 7B-6C;

FIG. 7B-6E1 shows a side view of the short axis of the narrow neck portion of the therapeutic device as in FIG. 7B-6C;

FIG. 7B-6E2 shows a side view of the long axis of the narrow neck portion of the therapeutic device as in FIG. 7B-6C;

FIG. 7B-6F shows a proximal view of the therapeutic device as in FIGS. 7B-6C;

FIG. 7B-6G to FIG. 7B-6I show exploded assembly drawings for the therapeutic device as in FIGS. 7B-6C to 7B-6F;

FIG. 7C-1 shows an expandable therapeutic device comprising an expandable barrier material and support in an expanded configuration for extended release of the therapeutic agent, in accordance with embodiments;

FIG. 7C-1A shows the distal end portion of the support 160S as in FIG. 7C-1;

FIG. 7C-1B shows the support 160S disposed inside the barrier 160, in accordance with embodiments;

FIG. 7C-1C shows the support 160S disposed along the inner surface of the barrier 160, in accordance with embodiments;

FIG. 7C-2 shows the expandable therapeutic device as in FIG. 7C1 in a narrow profile configuration;

FIG. 7C-3 shows the expandable therapeutic device as in FIG. 7C1 in an expanded profile configuration;

FIGS. 7C-4A and 7C-4B show an expandable retention structure, in accordance with embodiments;

FIG. 7G shows a kit comprising a placement instrument, a container, and a therapeutic device within the container, in accordance with embodiments;

FIG. 8 show reservoirs with exit ports of defined diameters fabricated from 1 mL syringes with Luer-Lok™ tips and needles of varying diameter, in accordance with embodiments;

FIG. 8-1 shows the needles attached to syringes as in FIG. 8;

FIG. 8-2 shows the reservoirs placed into vials;

FIG. 11-1 shows the delivery rates from two replicates of a reservoir as in FIG. 11;

FIG. 13-1 shows the measured cumulative release of BSA of FIG. 13 measured to 180 days;

FIG. 22B-1 shows cumulative release for Avastin™ with porous frit structures having a thickness of 0.029";

FIG. 22B-2 shows rate of release for Avastin™ with porous frit structures having a thickness of 0.029" as in FIG. 22B-1;

FIG. 23A-1 shows cumulative release to about 90 days for Avastin™ with a reservoir volume of 20 uL as in FIG. 23A;

FIG. 23B-1 shows rate of release as in FIG. 23A-1;

FIG. 24A-1 shows cumulative release to about 90 days release for Avastin™ with a 0.1 media grade porous frit structure as in FIG. 24A;

FIG. 24B-1 shows rates of release of the devices as in FIG. 24A-1;

FIG. 25A shows cumulative release for fluorescein through a 0.2 media grade porous frit structure;

FIG. 25A-1 shows cumulative release to about 90 days for fluorescein through a 0.2 media grade porous frit structure as in FIG. 25A;

FIG. 25B shows rates of release of the devices as in FIG. 25A;

FIG. 25B-1 shows rates of release of the devices as in FIG. 25A-1;

FIG. 25C shows cumulative release to about thirty days for Lucentis™ through a 0.2 media grade porous frit structure having a diameter of 0.038 in and a length (thickness) of 0.029 in.;

FIG. 25D shows rates of release of the devices as in FIG. 25C;

Figure 1:
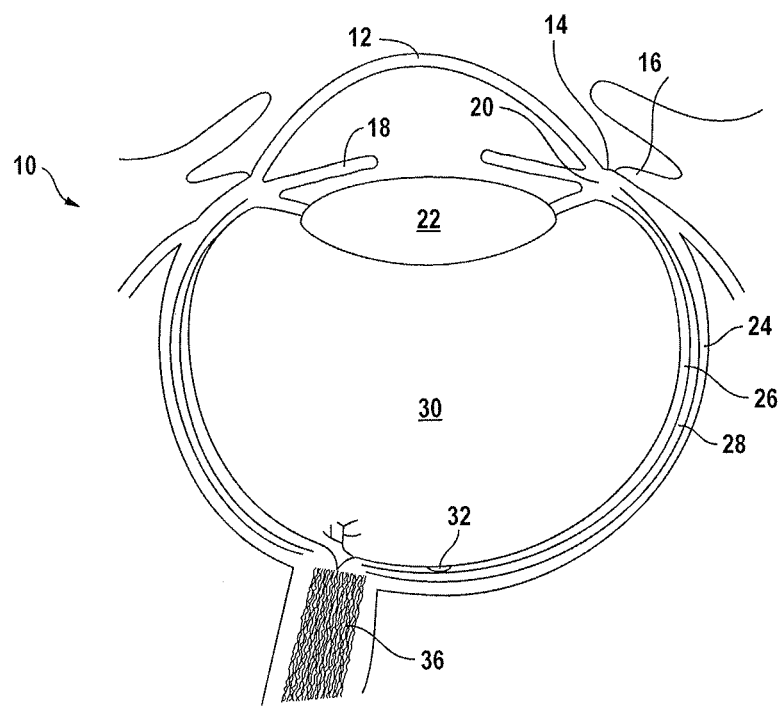
FIG. 1 shows an eye suitable for incorporation of the therapeutic device, in accordance with embodiments of the present invention.
Figure 25A:
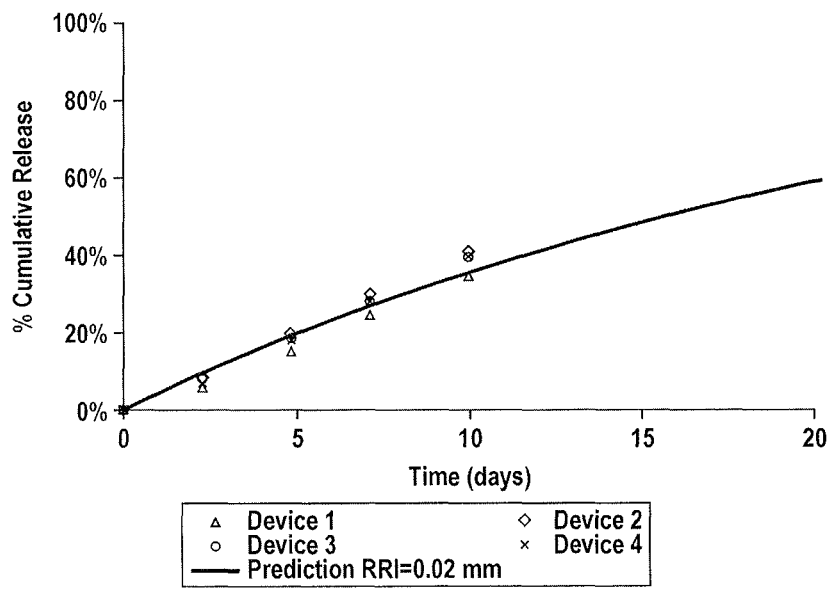
Figures 1, 25A:
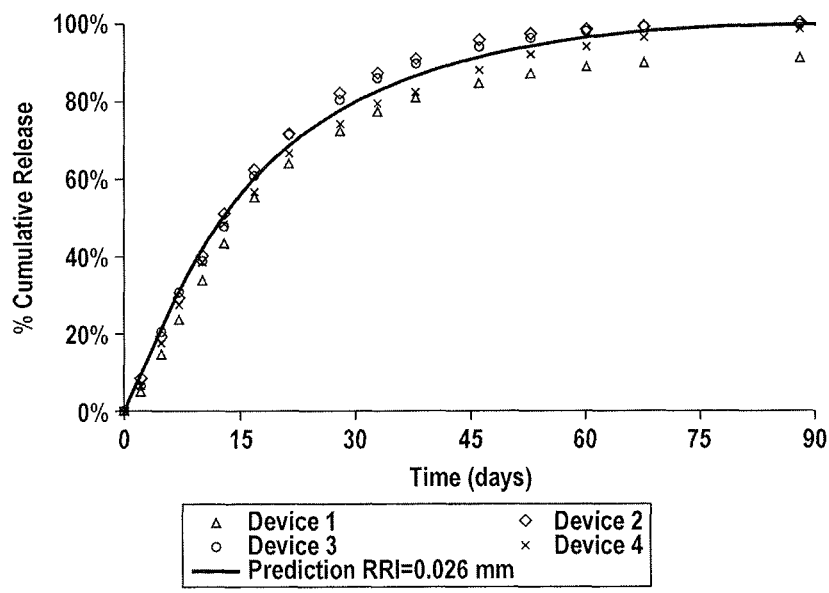
Figure 25B:
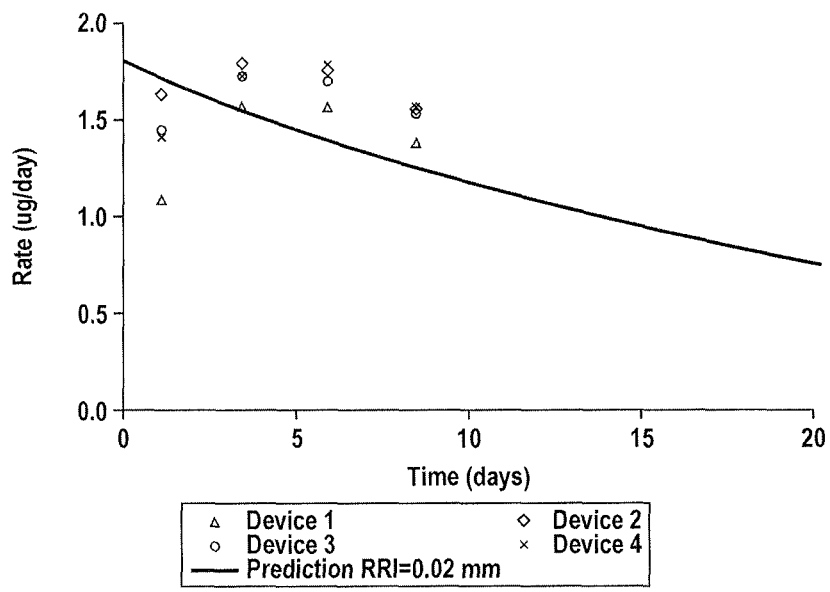
Figures 1, 25B:
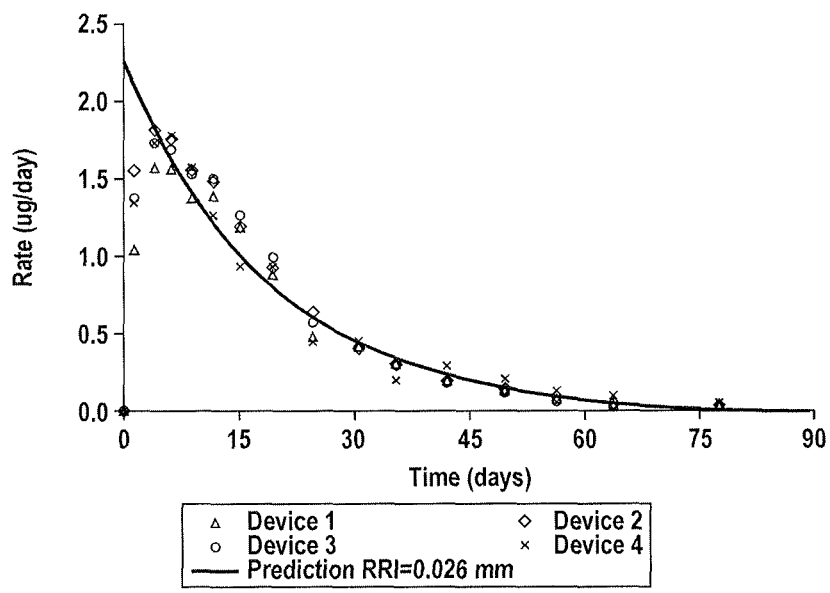
Figure 25C:
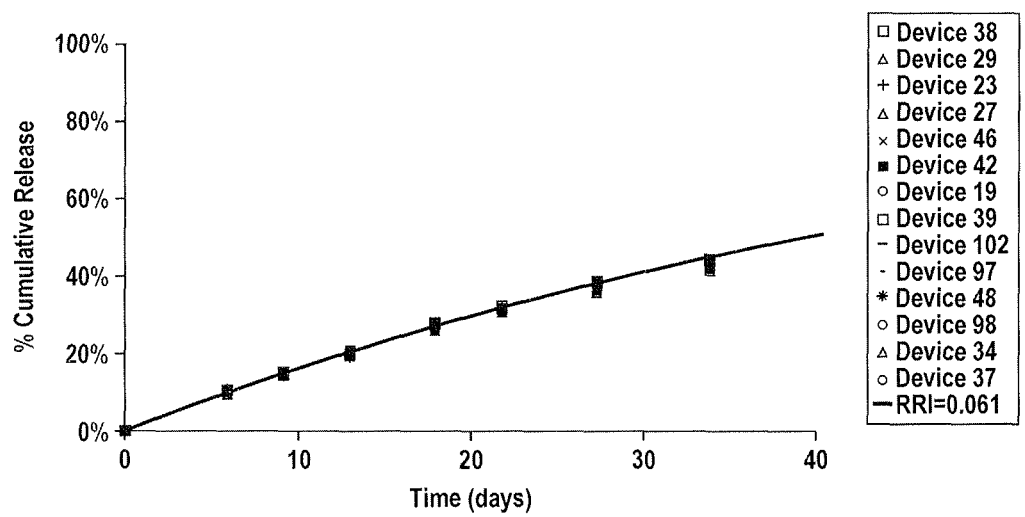
Figure 25D:
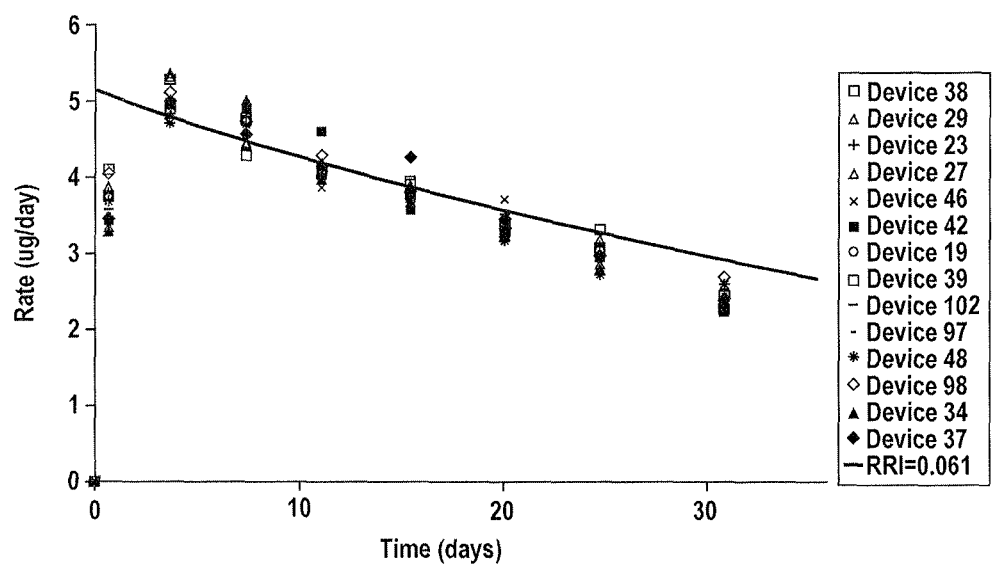
Figure 25E:
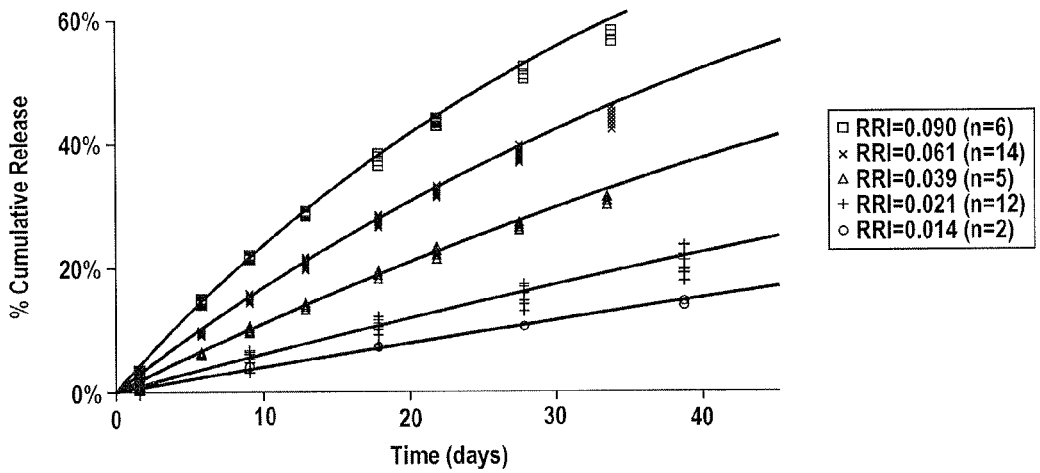
Figure 25F:
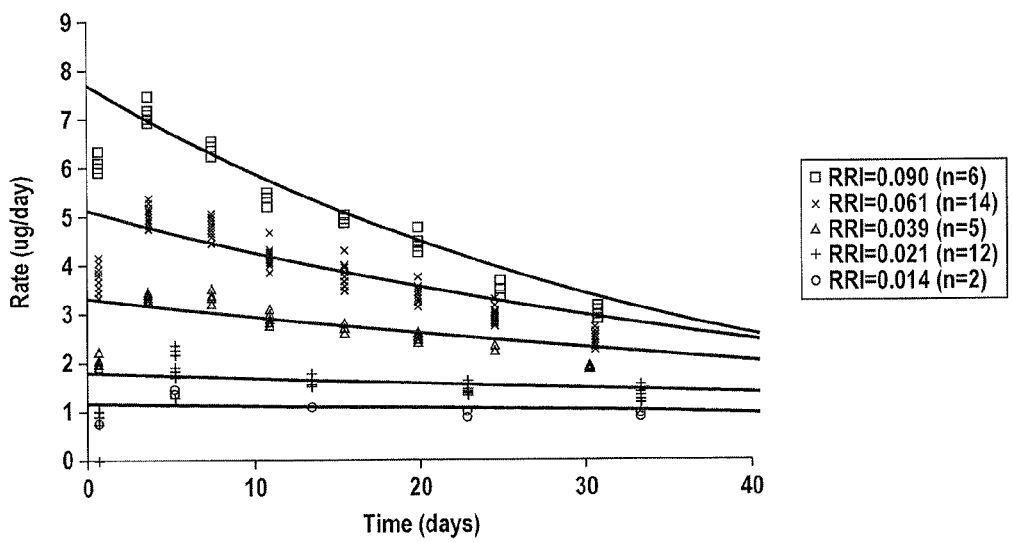
Figure 26A:
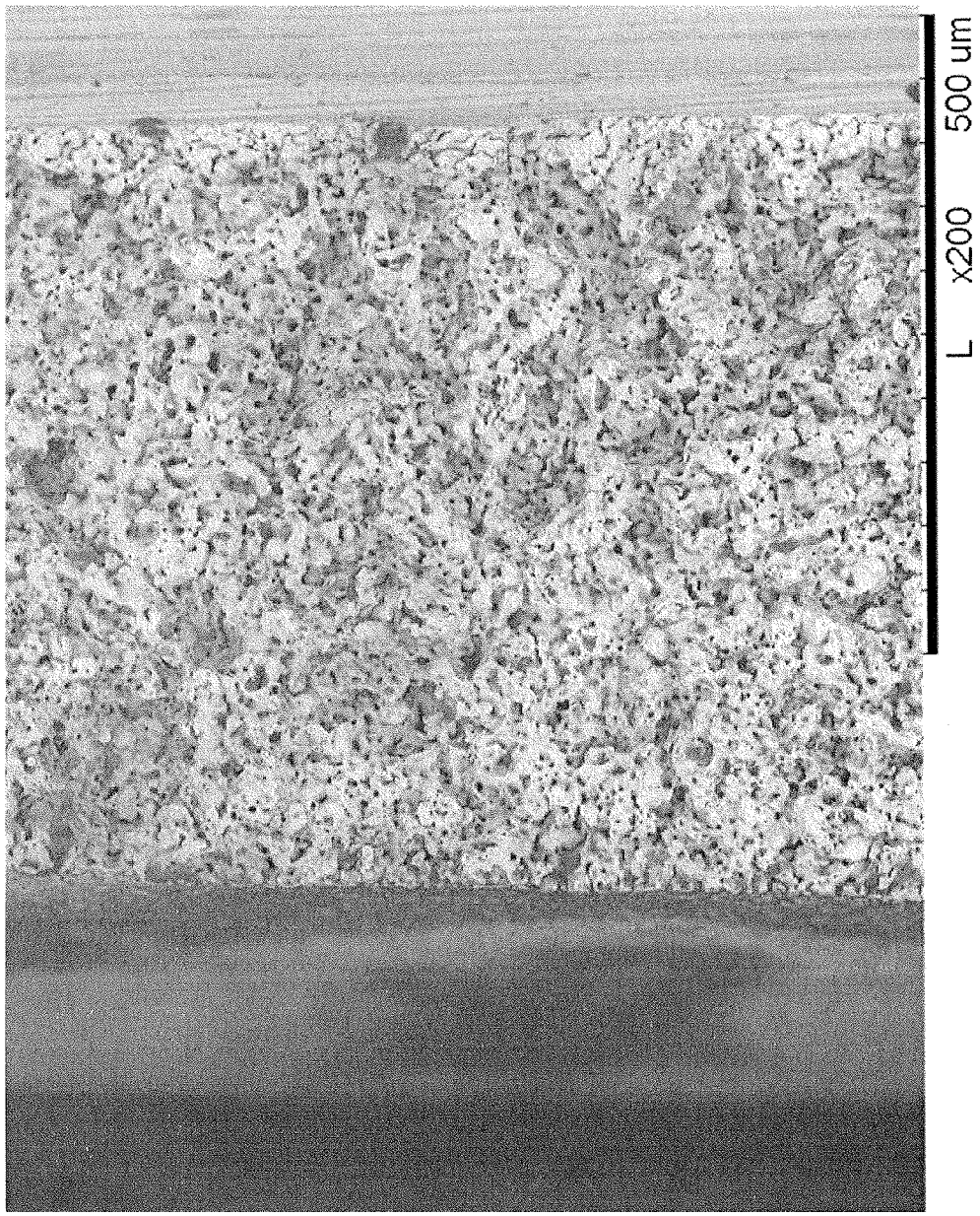
Figure 26B:
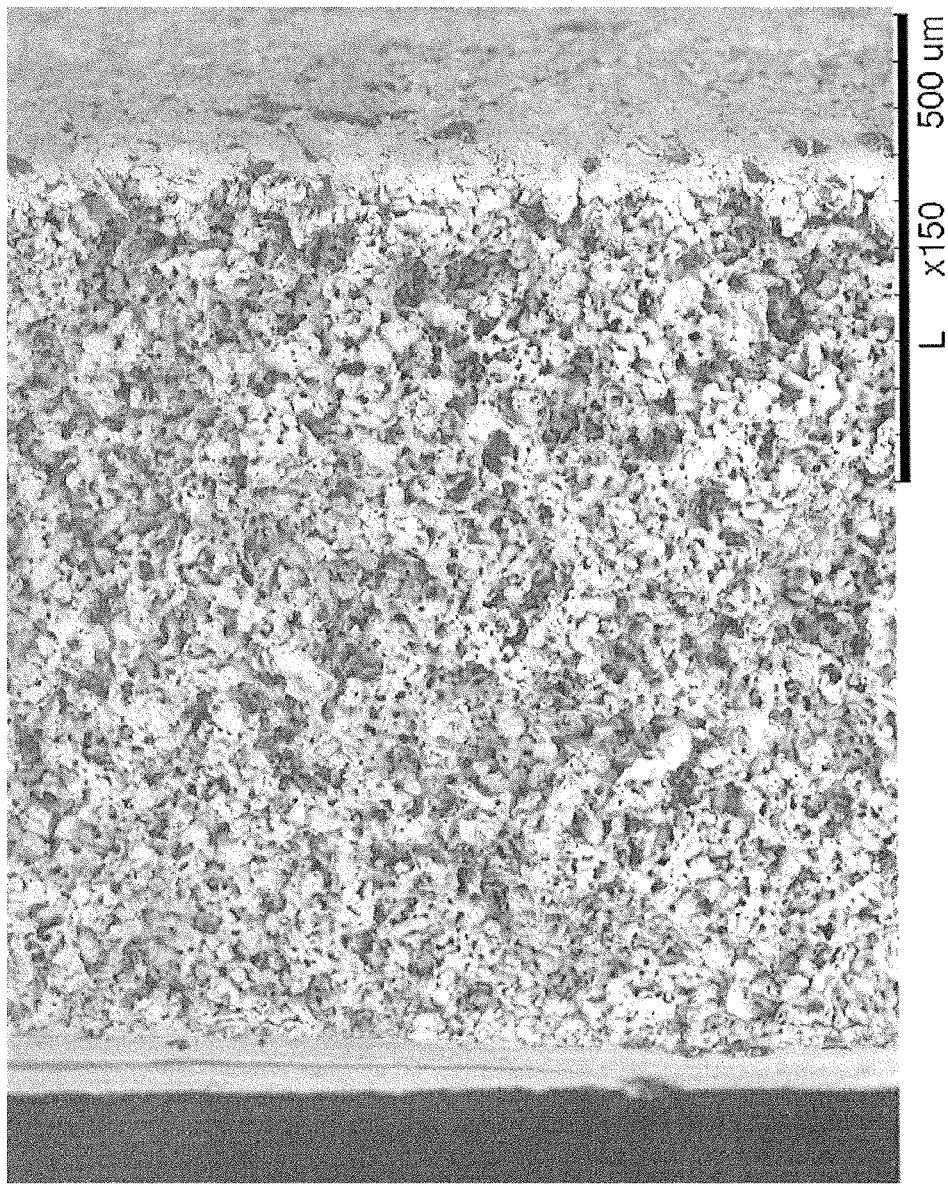
Figure 27A:
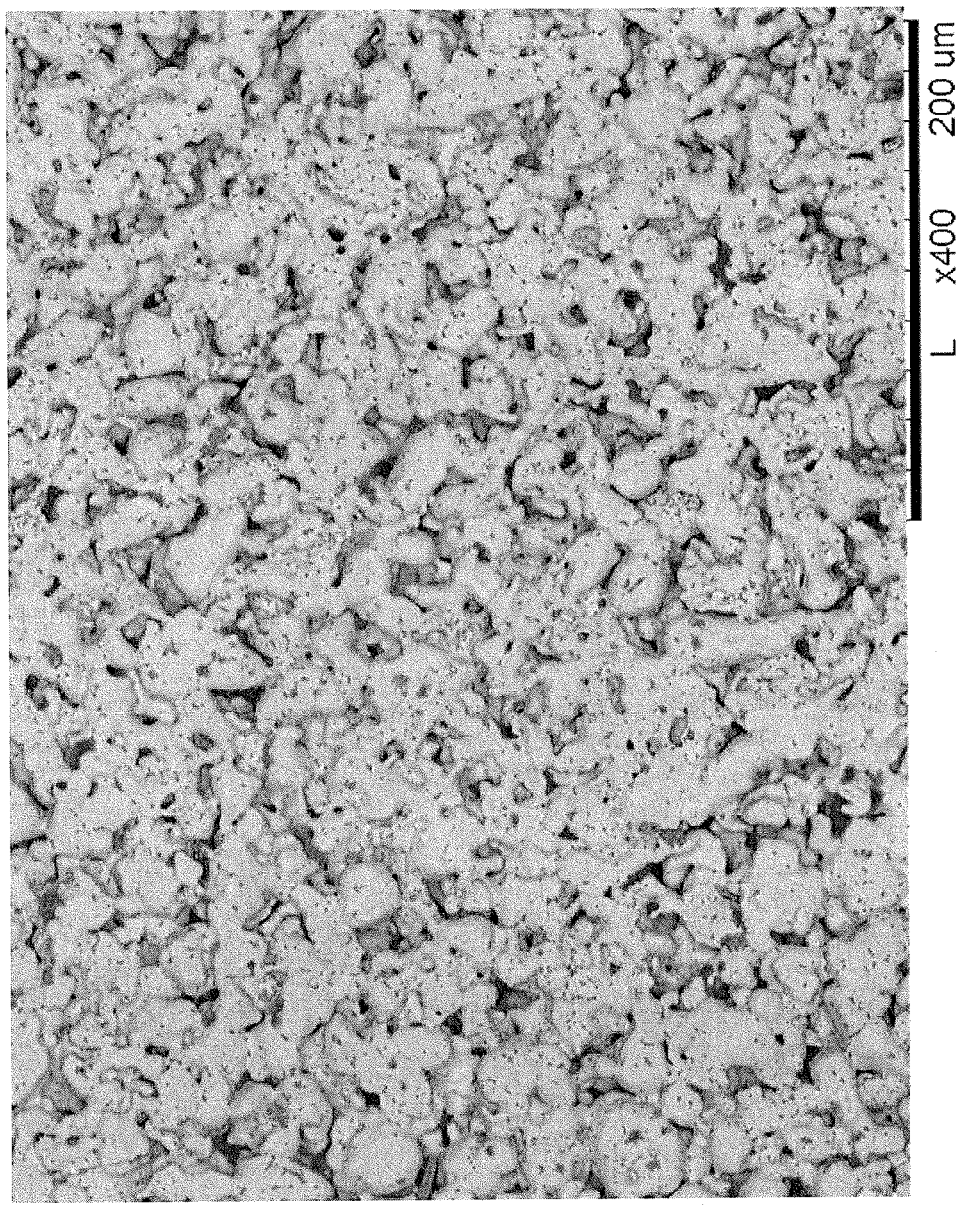
Figure 27B:
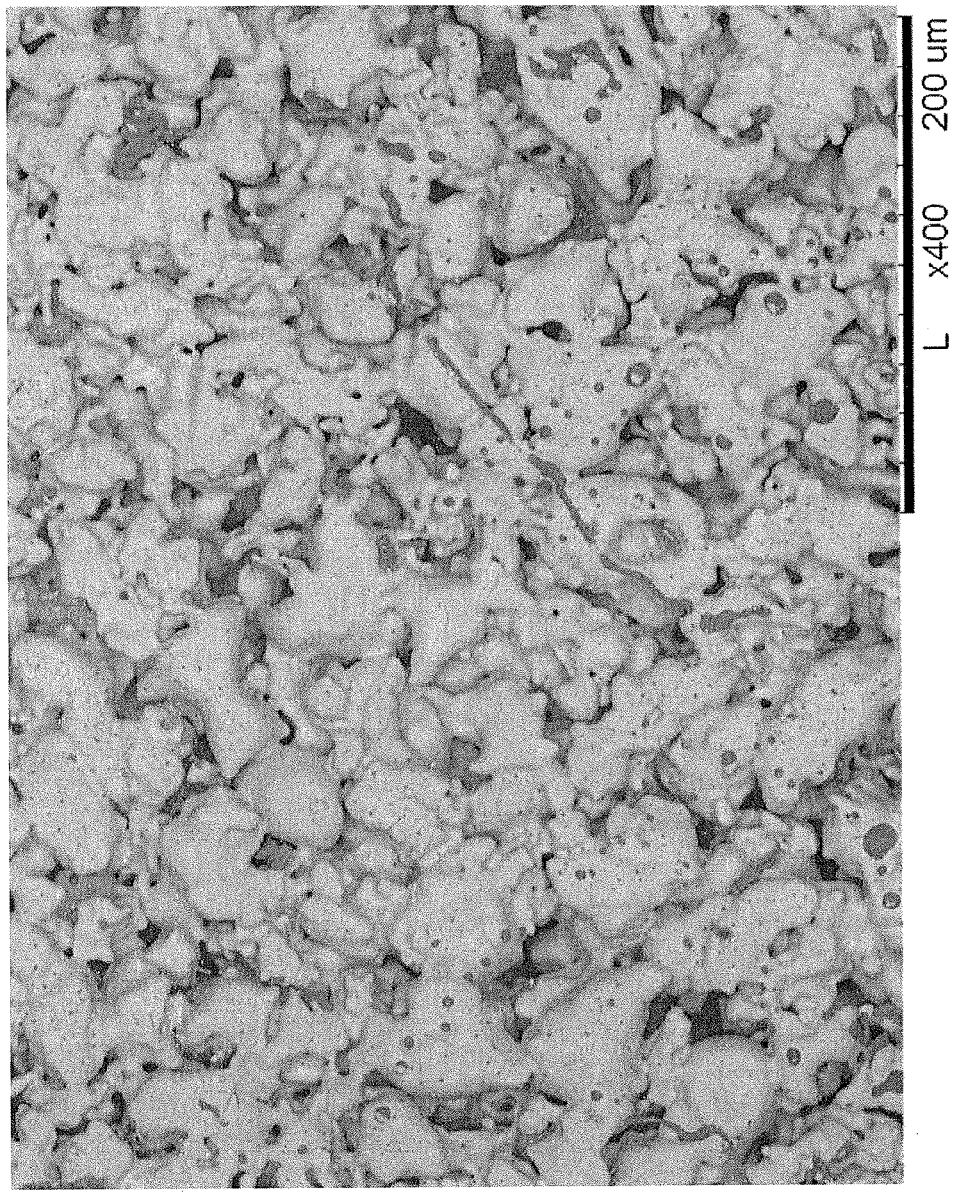
Figure 28:
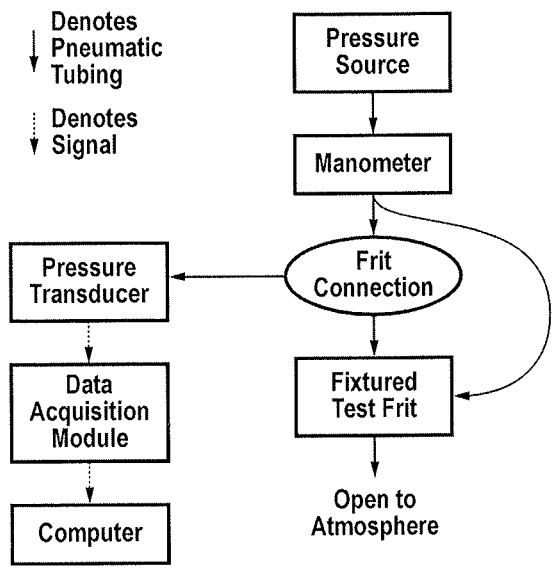
Figure 29:
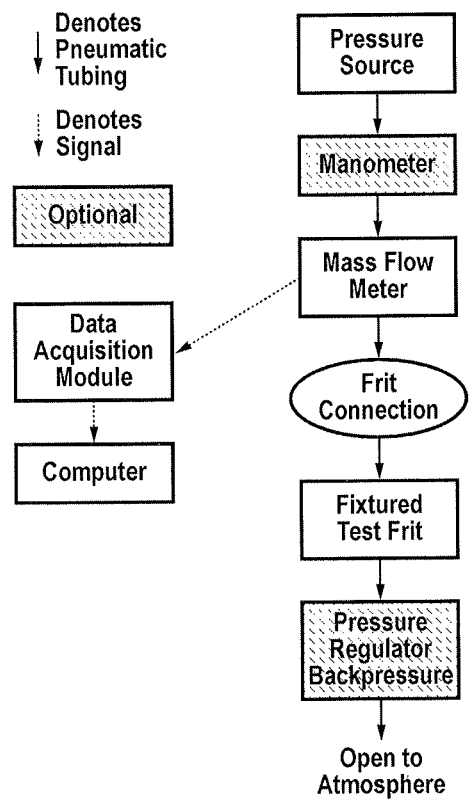
Figure 31A:
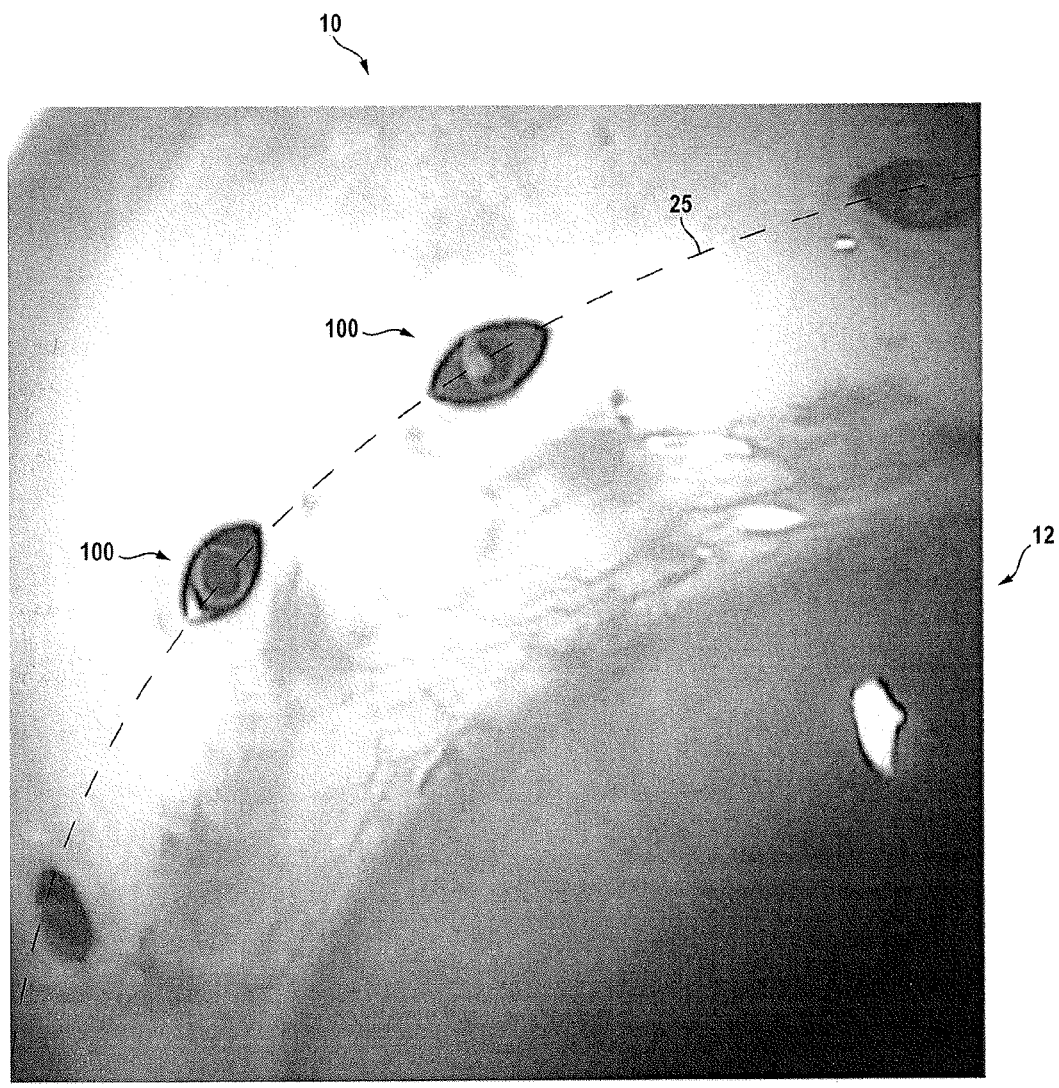
Figure 31B:
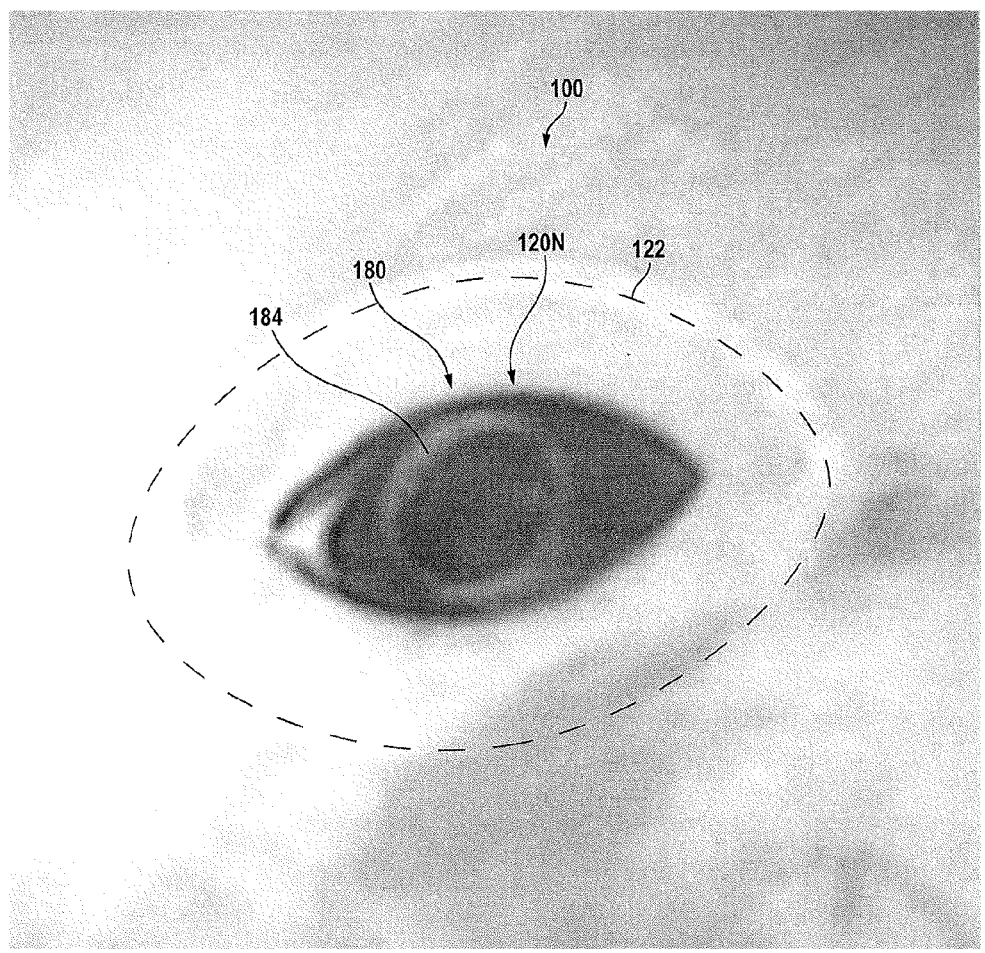

FIG. 25E shows cumulative release to about thirty days for Lucentis™ for 30 uL devices having a RRI's from about 0.015 to about 0.090;

FIG. 25F shows rates of release of the devices as in FIG. 25E;

FIGS. 26A and 26B show scanning electron microscope images from fractured edges of porous frit structures so as to show the structure of the porous structure to release the therapeutic agent, in accordance with embodiments;

FIGS. 27A and 27B show scanning electron microscope images from surfaces of porous frit structures, in accordance with embodiments;

FIG. 28 shows a pressure decay test and test apparatus for use with a porous structure so as to identify porous frit structures suitable for use with therapeutic devices, in accordance with embodiments described herein;

FIG. 29 shows a pressure flow test and test apparatus suitable for use with a porous structure so as to identify porous frit structures suitable for use with therapeutic devices, in accordance with embodiments described herein;

FIG. 30A-1 shows an example of an OCT macular cube OCT image used to identify a region of interest (black arrow) and determine the response to treatment;

FIGS. 30B-1, 30B-2 and 30B-3 show an example of a series of OCT scan images measured at pre-injection, one day post-injection and one week post-injection, respectively, of sections of the region of interest; and FIGS. 31A and 31B shows experimental implantation of therapeutic device into the pars plana region 25 of a rabbit eye with visualization of the device sealing the elongate incision under the flange and dark field visualization of the implanted therapeutic device.

DETAILED DESCRIPTION OF THE INVENTION

Although specific reference is made to the delivery of macromolecules comprising antibodies or antibody fragments to the posterior segment of the eye, embodiments of the present invention can be used to deliver many therapeutic agents to many tissues of the body. For example, embodiments of the present invention can be used to deliver therapeutic agent for an extended period to one or more of the following tissues: intravascular, intra articular, intrathecal, pericardial, intraluminal and gut.

Embodiments of the present invention provide sustained release of a therapeutic agent to the posterior segment of the eye or the anterior segment of the eye, or combinations thereof. Therapeutic amounts of a therapeutic agent can be released into the vitreous humor of the eye, such that the therapeutic agent can be transported by at least one of diffusion or convection to the retina or other ocular tissue, such as the choroid or ciliary body, for therapeutic effect.

As used herein the release rate index encompasses (PA/FL) where P comprises the porosity, A comprises an effective area, F comprises a curve fit parameter corresponding to an effective length and L comprises a length or thickness of the porous structure. The units of the release rate index (RRI) comprise units of mm unless indicated otherwise and can be determine by a person of ordinary skill in the art in accordance with the teachings described hereon.

As used herein, sustained release encompasses release of therapeutic amounts of an active ingredient of a therapeutic agent for an extended period of time. The sustained release may encompass first order release of the active ingredient, zero order release of the active ingredient, or other kinetics of release such as intermediate to zero order and first order, or combinations thereof.

As used herein a therapeutic agent referred to with a trade name encompasses one or more of the formulation of the therapeutic agent commercially available under the tradename, the active ingredient of the commercially available formulation, the generic name of the active ingredient, or the molecule comprising the active ingredient.

As used herein, similar numerals indicate similar structures and/or similar steps.

The therapeutic agent may be contained within a chamber of a container, for example within a reservoir comprising the container and chamber. The therapeutic agent may comprise a formulation such as solution of therapeutic agent, a suspension of a therapeutic agent or a dispersion of a therapeutic agent, for example. Examples of therapeutic agents suitable for use in accordance with embodiments of the therapeutic device are described herein, for example with reference to Table 1A below and elsewhere.

The therapeutic agent may comprise a macromolecule, for example an antibody or antibody fragment. The therapeutic macromolecule may comprise a VEGF inhibitor, for example commercially available Lucentis™. The VEGF (Vascular Endothelial Growth Factor) inhibitor can cause regression of the abnormal blood vessels and improvement of vision when released into the vitreous humor of the eye. Examples of VEGF inhibitors include Lucentis™, Avastin™, Macugen™, and VEGF Trap.

The therapeutic agent may comprise small molecules such as of a corticosteroid and analogues thereof. For example, the therapeutic corticosteroid may comprise one or more of trimacinalone, trimacinalone acetonide, dexamethasone, dexamethasone acetate, fluocinolone, fluocinolone acetate, or analogues thereof. Alternatively or in combination, he small molecules of therapeutic agent may comprise a tyrosine kinase inhibitor comprising one or more of axitinib, bosutinib, cediranib, dasatinib, erlotinib, gefitinib, imatinib, lapatinib, lestaurtinib, nilotinib, semaxanib, sunitinib, toceranib, vandetanib, or vatalanib, for example.

The therapeutic agent may comprise an anti-VEGF therapeutic agent. Anti-VEGF therapies and agents can be used in the treatment of certain cancers and in age-related macular degeneration. Examples of anti-VEGF therapeutic agents suitable for use in accordance with the embodiments described herein include one or more of monoclonal antibodies such as bevacizumab (Avastin™) or antibody derivatives such as ranibizumab (Lucentis™), or small molecules that inhibit the tyrosine kinases stimulated by VEGF such as lapatinib (Tykerb™), sunitinib (Sutent™), sorafenib (Nexavar™), axitinib, or pazopanib.

The therapeutic agent may comprise a therapeutic agent suitable for treatment of dry AMD such as one or more of Sirolimus™ (Rapamycin), Copaxone™ (Glatiramer Acetate), Othera™, Complement C5aR blocker, Ciliary Neurotrophic Factor, Fenretinide or Rheopheresis.

The therapeutic agent may comprise a therapeutic agent suitable for treatment of wet AMD such as one or more of REDD14NP (Quark), Sirolimus™ (Rapamycin), ATG003; Regeneron™ (VEGF Trap) or complement inhibitor (POT-4).

The therapeutic agent may comprise a kinase inhibitor such as one or more of bevacizumab (monoclonal antibody), BIBW 2992 (small molecule targeting EGFR/Erb2), cetuximab (monoclonal antibody), imatinib (small molecule), trastuzumab (monoclonal antibody), gefitinib (small molecule), ranibizumab (monoclonal antibody), pegaptanib (small molecule), sorafenib (small molecule), dasatinib (small molecule), sunitinib (small molecule), erlotinib (small molecule), nilotinib (small molecule), lapatinib (small molecule), panitumumab (monoclonal antibody), vandetanib (small molecule) or E7080 (targeting VEGFR2/VEGFR2, small molecule commercially available from Esai, Co.)

The amount of therapeutic agent within the therapeutic device may comprise from about 0.01 mg to about 1 mg, for example Lucentis™, so as to provide therapeutic amounts of the therapeutic agent for the extended time, for example at least 30 days. The extended time may comprise at least 90 days or more, for example at least 180 days or for example at least 1 year, at least 2 years or at least 3 years or more. The target threshold therapeutic concentration of a therapeutic agent such as Lucentis™ in the vitreous may comprise at least a therapeutic concentration of 0.1 ug/mL. For example the target threshold concentration may comprise from about 0.1 ug/mL to about 5 ug/mL for the extended time, where the upper value is based upon calculations shown in Example 9 using published data. The target threshold concentration is drug dependent and thus may vary for other therapeutic agents.

The delivery profile may be configured in many ways to obtain a therapeutic benefit from the sustained release device. For example, an amount of the therapeutic agent may be inserted into the container at monthly intervals so as to ensure that the concentration of therapeutic device is above a safety protocol or an efficacy protocol for the therapeutic agent, for example with monthly or less frequent injections into the container. The sustained release can result in an improved delivery profile and may result in improved results. For example, the concentration of therapeutic agent may remain consistently above a threshold amount, for example 0.1 ug/mL, for the extended time.

The insertion method may comprise inserting a dose into the container of the therapeutic device. For example, a single injection of Lucentis™ may be injected into the therapeutic device.

The duration of sustained delivery of the therapeutic agent may extend for twelve weeks or more, for example four to six months from a single insertion of therapeutic agent into the device when the device is inserted into the eye of the patient.

The therapeutic agent may be delivered in many ways so as to provide a sustained release for the extended time. For example, the therapeutic device may comprise a therapeutic agent and a binding agent. The binding agent may comprise small particles configured to couple releasably or reversibly to the therapeutic agent, such that the therapeutic agent is released for the extended time after injection into the vitreous humor. The particles can be sized such that the particles remain in the vitreous humor of the eye for the extended time.

The therapeutic agent may be delivered with a device implanted in the eye. For example, the drug delivery device can be implanted at least partially within the sclera of the eye, so as to couple the drug delivery device to the sclera of the eye for the extended period of time. The therapeutic device may comprise a drug and a binding agent. The drug and binding agent can be configured to provide the sustained release for the extended time. A membrane or other diffusion barrier or mechanism may be a component of the therapeutic device to release the drug for the extended time.

The lifetime of the therapeutic device and number of injections can be optimized for patient treatment. For example, the device may remain in place for a lifetime of 30 years, for example with AMD patients from about 10 to 15 years. For example, the device may be configured for an implantation duration of at least two years, with 8 injections (once every three months) for sustained release of the therapeutic agent over the two year duration. The device may be configured for implantation of at least 10 years with 40 injections (once every three months) for sustained release of the therapeutic agent.

The therapeutic device can be refilled in many ways. For example, the therapeutic agent can be refilled into the device in the physician's office.

The therapeutic device may comprise many configurations and physical attributes, for example the physical characteristics of the therapeutic device may comprise at least one of a drug delivery device with a suture, positioning and sizing such that vision is not impaired, and biocompatible material. The device may comprise a reservoir capacity from about 0.005 cc to about 0.2 cc, for example from about 0.01 cc to about 0.1 cc, and a device volume of no more than about 2 cc. A vitrectomy may be performed for device volumes larger than 0.1 cc. The length of the device may not interfere with the patient's vision and can be dependent on the shape of the device, as well as the location of the implanted device with respect to the eye. The length of the device may also depend on the angle in which the device is inserted. For example, a length of the device may comprise from about 4 to 6 mm. Since the diameter of the eye is about 24 mm, a device extending no more than about 6 mm from the sclera into the vitreous may have a minimal effect on patient vision.

Embodiments may comprise many combinations of implanted drug delivery devices. The therapeutic device may comprise a drug and binding agent. The device may also comprise at least one of a membrane, an opening, a diffusion barrier, a diffusion mechanism so as to release therapeutic amounts of therapeutic agent for the extended time.

FIG. 1 shows an eye 10 suitable for incorporation of the therapeutic device. The eye has a cornea 12 and a lens 22 configured to form an image on the retina 26. The cornea can extend to a limbus 14 of the eye, and the limbus can connect to a sclera 24 of the eye. A conjunctiva 16 of the eye can be disposed over the sclera. The lens can accommodate to focus on an object seen by the patient. The eye has an iris 18 that may expand and contract in response to light. The eye also comprises a choroid 28 disposed the between the sclera 24 and the retina 26. The retina comprises the macula 32. The eye comprises a pars plana 25, which comprises an example of a region of the eye suitable for placement and retention, for example anchoring, of the therapeutic device 100 as described herein. The pars plana region may comprise sclera and conjunctiva disposed between the retina and cornea. The therapeutic device can be positioned so as to extend from the pars plana region into the vitreous humor 30 to release the therapeutic agent. The therapeutic agent can be released into the vitreous humor 30, such that the therapeutic agent arrives at the retina and choroids for therapeutic effect on the macula. The vitreous humor of the eye comprises a liquid disposed between the lens and the retina. The vitreous humor may comprise convection currents to deliver the therapeutic agent to the macula.

Figures 1, 1A:
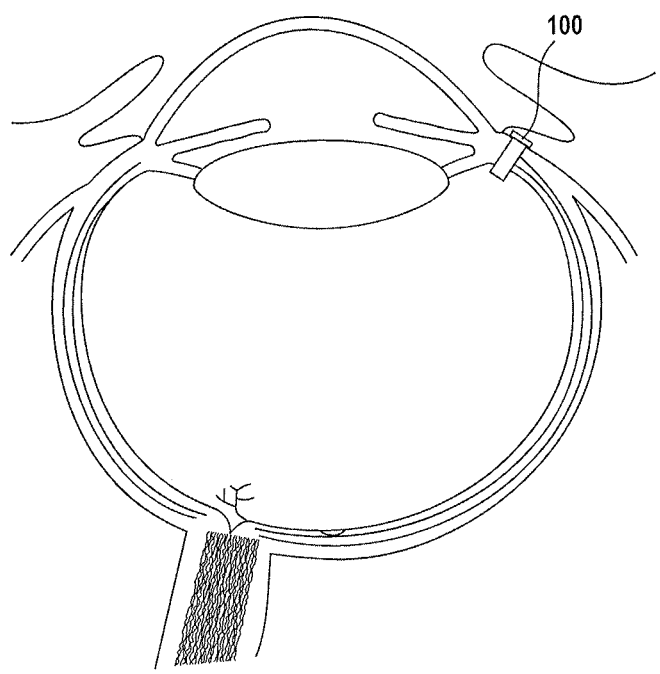
Figures 1, 1A:
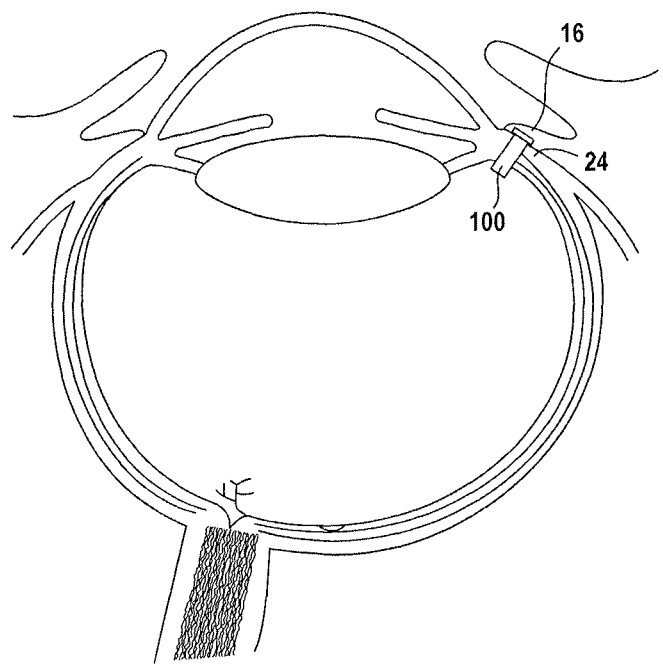

FIG. 1A-1 shows a therapeutic device 100 implanted at least partially within the sclera 24 of the eye 10 as in FIG. 1. The therapeutic device may comprise a retention structure, for example a protrusion, to couple the device to the sclera. The therapeutic device may extend through the sclera into vitreous humor 30, such that the therapeutic device can release the therapeutic agent into the vitreous humor.

Figures 1, 1A, 2:
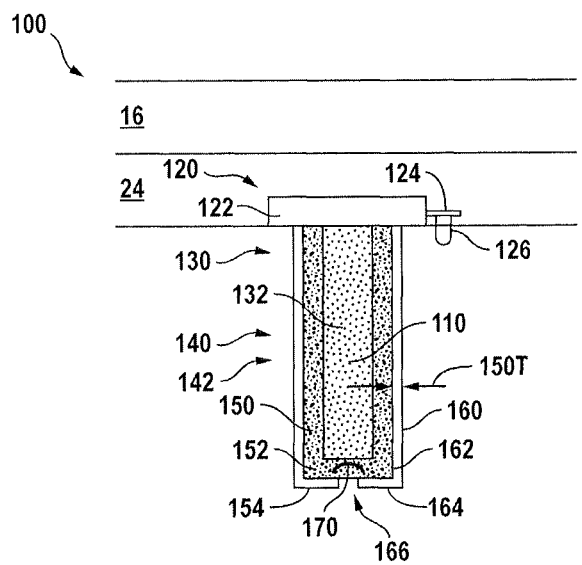
Figures 1, 1A, 2:
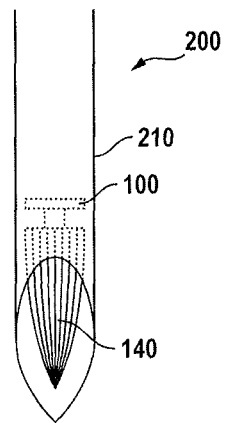
Figures 1, 1A, 2:
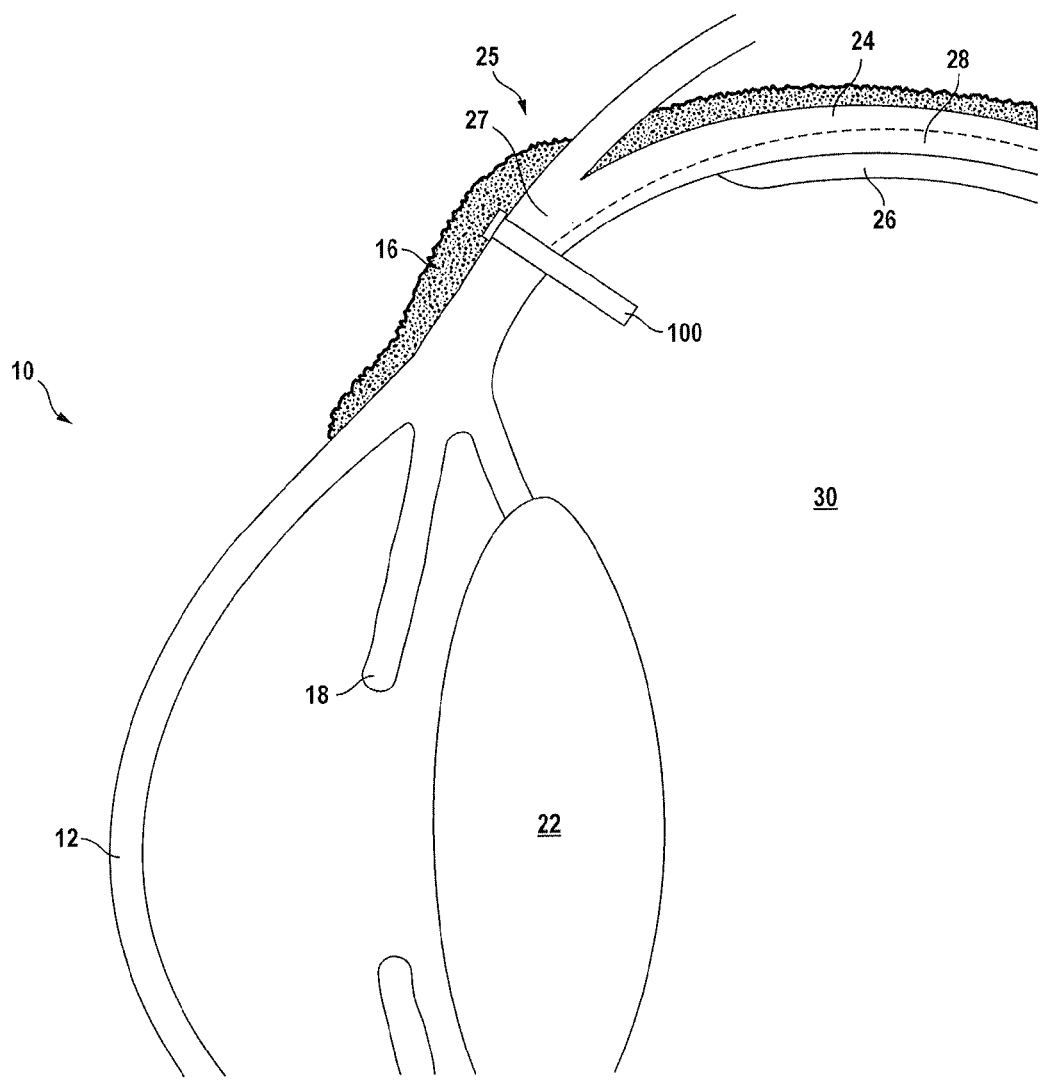

FIGS. 1A-1-1 and 1A-1-2 shows a therapeutic device 100 implanted under the conjunctiva 16 and extending through the sclera 24 to release a therapeutic agent 110 into vitreous humor 30 of the eye 10 so as to treat the retina of the eye. The therapeutic device 100 may comprise a retention structure 120 such as a smooth protrusion configured for placement along the sclera and under the conjunctiva, such that the conjunctiva can cover the therapeutic device and protect the therapeutic device 100. When the therapeutic agent 110 is inserted into the device 100, the conjunctiva may be lifted away, incised, or punctured with a needle to access the therapeutic device. The eye may comprise an insertion of the tendon 27 of the superior rectus muscle to couple the sclera of the eye to the superior rectus muscle. The device 100 may be positioned in many locations of the pars plana region, for example away from tendon 27 and one or more of posterior to the tendon, posterior to the tendon, under the tendon, or with nasal or temporal placement of the therapeutic device.

While the implant can be positioned in the eye in many ways, work in relation to embodiments suggests that placement in the pars plana region can release therapeutic agent into the vitreous to treat the retina, for example therapeutic agent comprising an active ingredient composed of large molecules.

Therapeutic agents 110 suitable for use with device 100 includes many therapeutic agents, for example as listed in Table 1A, herein below. The therapeutic agent 110 of device 100 may comprise one or more of an active ingredient of the therapeutic agent, a formulation of the therapeutic agent, a commercially available formulation of the therapeutic agent, a physician prepared formulation of therapeutic agent, a pharmacist prepared formulation of the therapeutic agent, or a commercially available formulation of therapeutic agent having an excipient. The therapeutic agent may be referred to with generic name or a trade name, for example as shown in Table 1A.

The therapeutic device 100 can be implanted in the eye to treat the eye for as long as is helpful and beneficial to the patient. For example the device can be implanted for at least about 5 years, such as permanently for the life of the patient. Alternatively or in combination, the device can be removed when no longer helpful or beneficial for treatment of the patient.

FIG. 1A-2 shows structures of therapeutic device 100 configured for placement in an eye as in FIGS. 1A-1, 1A-1-1 and 1A-1-2. The device may comprise retention structure 120 to couple the device 100 to the sclera, for example a protrusion disposed on a proximal end of the device. The device 100 may comprise a container 130 affixed to the retention structure 120. An active ingredient, for example therapeutic agent 110, can be contained within a reservoir 140, for example a chamber 132 defined by a container 130 of the device. The container 130 may comprise a porous structure 150 comprising a porous material 152, for example a porous glass frit 154, and a barrier 160 to inhibit release of the therapeutic agent, for example non-permeable membrane 162. The non-permeable membrane 162 may comprise a substantially non-permeable material 164. The non-permeable membrane 162 may comprise an opening 166 sized to release therapeutic amounts of the therapeutic agent 110 for the extended time. The porous structure 150 may comprise a thickness 150T and pore sizes configured in conjunction with the opening 166 so as to release therapeutic amounts of the therapeutic agent for the extended time. The container 130 may comprise reservoir 140 having a chamber with a volume 142 sized to contain a therapeutic quantity of the therapeutic agent 110 for release over the extended time. The device may comprise a needle stop 170. Proteins in the vitreous humor may enter the device and compete for adsorption sites on the porous structure and thereby may contribute to the release of therapeutic agent. The therapeutic agent 110 contained in the reservoir 140 can equilibrate with proteins in the vitreous humor, such that the system is driven towards equilibrium and the therapeutic agent 110 is released in therapeutic amounts.

The non-permeable membrane 162, the porous material 152, the reservoir 140, and the retention structure 120, may comprise many configurations to deliver the therapeutic agent 110. The non-permeable membrane 162 may comprise an annular tube joined by a disc having at least one opening formed thereon to release the therapeutic agent. The porous material 152 may comprise an annular porous glass frit 154 and a circular end disposed thereon. The reservoir 140 may be shape-changing for ease of insertion, i.e. it may assume a thin elongated shape during insertion through the sclera and then assume an extended, ballooned shape, once it is filled with therapeutic agent.

The porous structure 150 can be configured in many ways to release the therapeutic agent in accordance with an intended release profile. For example, the porous structure may comprise a porous structure having a plurality of openings on a first side facing the reservoir and a plurality of openings on a second side facing the vitreous humor, with a plurality of interconnecting channels disposed therebetween so as to couple the openings of the first side with the openings of the second side, for example a sintered rigid material. The porous structure 150 may comprise one or more of a permeable membrane, a semi-permeable membrane, a material having at least one hole disposed therein, nano-channels, nano-channels etched in a rigid material, laser etched nano-channels, a capillary channel, a plurality of capillary channels, one or more tortuous channels, tortuous microchannels, sintered nano-particles, an open cell foam or a hydrogel such as an open cell hydrogel.

FIG. 1A-2-1 shows therapeutic device 100 loaded into an insertion cannula 210 of an insertion apparatus 200, in which the device 100 comprises an elongate narrow shape for insertion into the sclera, and in which the device is configured to expand to a second elongate wide shape for retention at least partially in the sclera;

FIG. 1A-2-2 shows a therapeutic device 100 comprising reservoir 140 suitable for loading in a cannula, in which the reservoir 140 comprises an expanded configuration.

Figure 7:
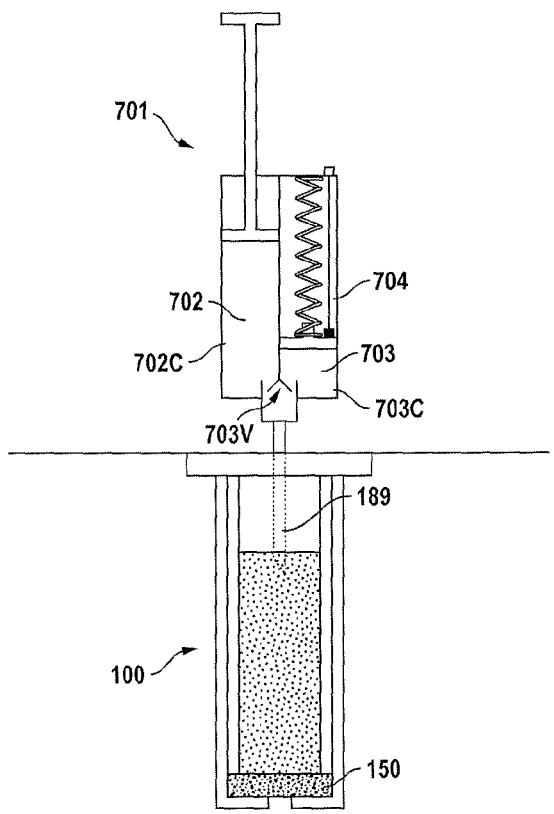
FIG. 7 shows a therapeutic device coupled to an injector that removes material from the device and injects therapeutic agent into the device, according to embodiments.
Figure 7A:
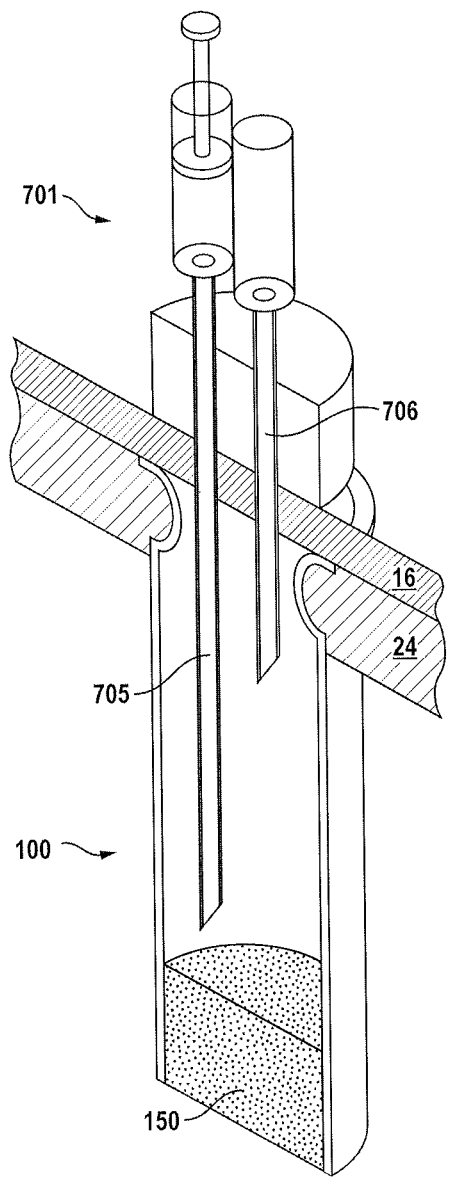
FIG. 7A shows a therapeutic device comprising a porous structure and a penetrable barrier as in FIG. 6E, with the penetrable barrier coupled to an injector to inject and remove material from the device, in accordance with embodiments.
Figures 1, 7A:
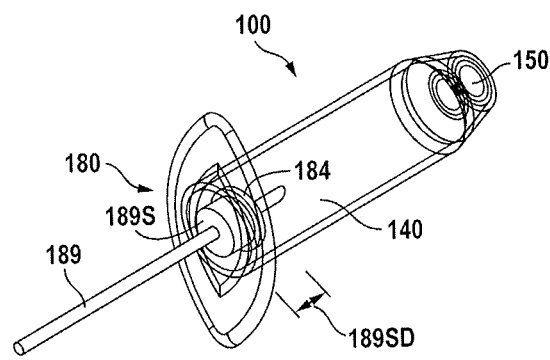
Figures 2, 7A:
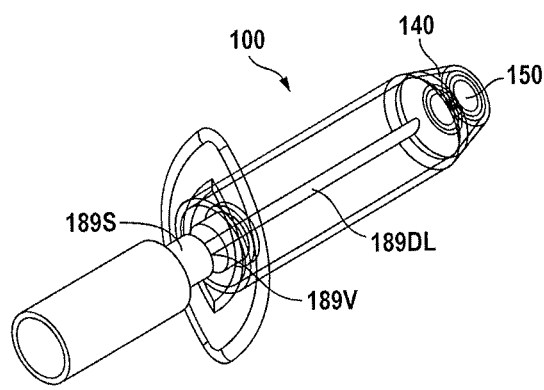
Figures 1, 7B:
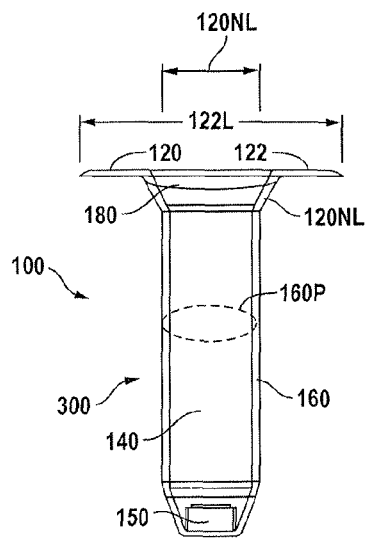
Figures 2, 7B:
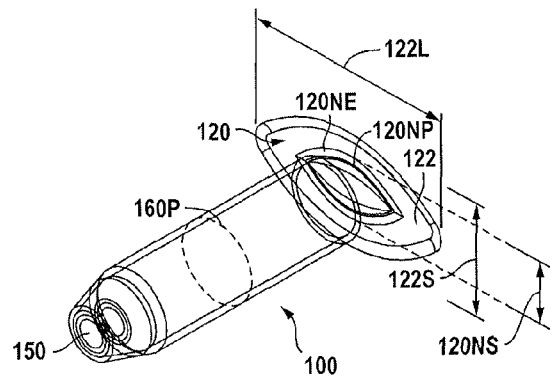
Figures 4, 7B:
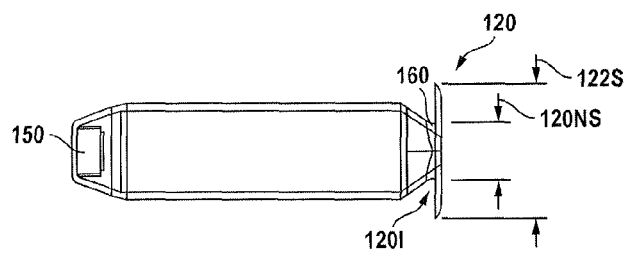
Figures 3, 7B:
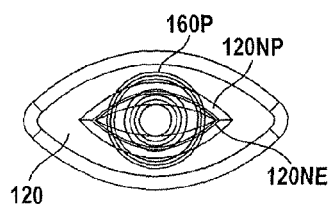
Figures 5A, 7B:
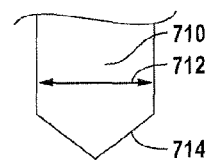
Figures 5, 7B:
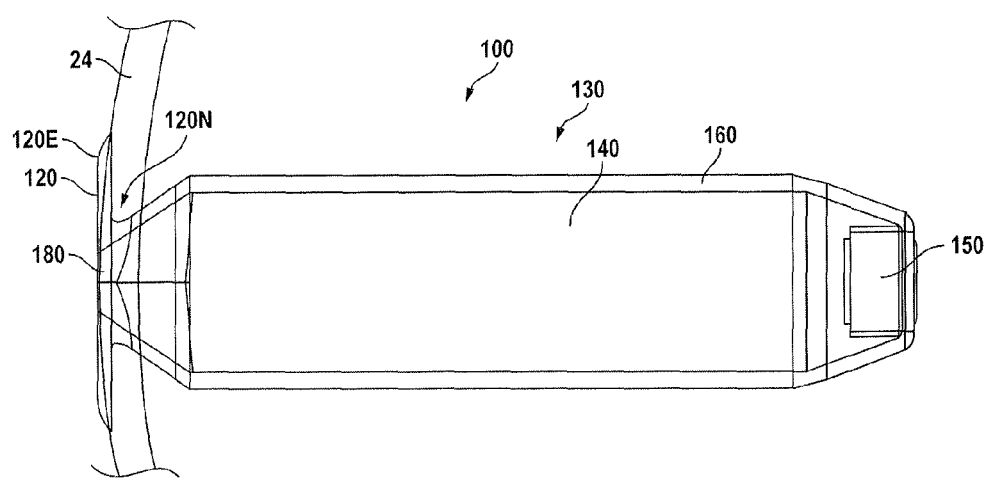
Figures 6G, 7B:
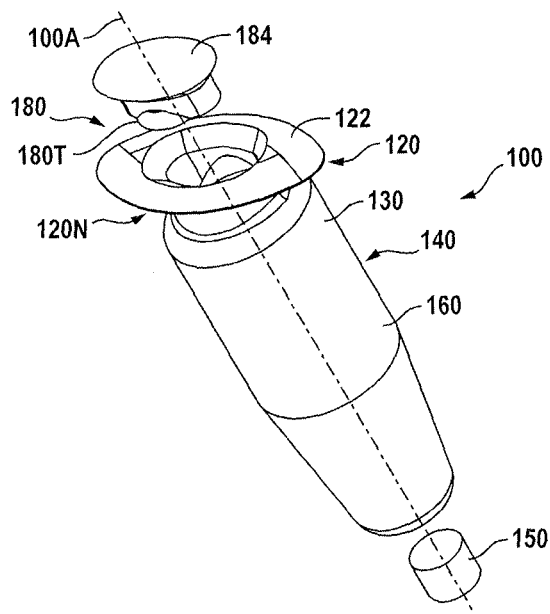
Figures 6H, 7B:
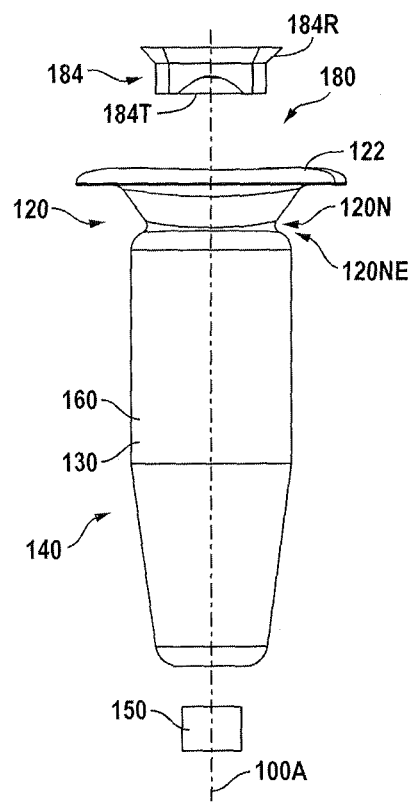
Figures 6I, 7B:
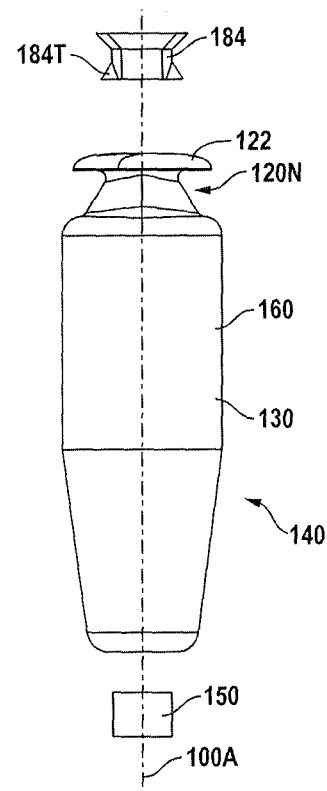
Figures 1, 7C:
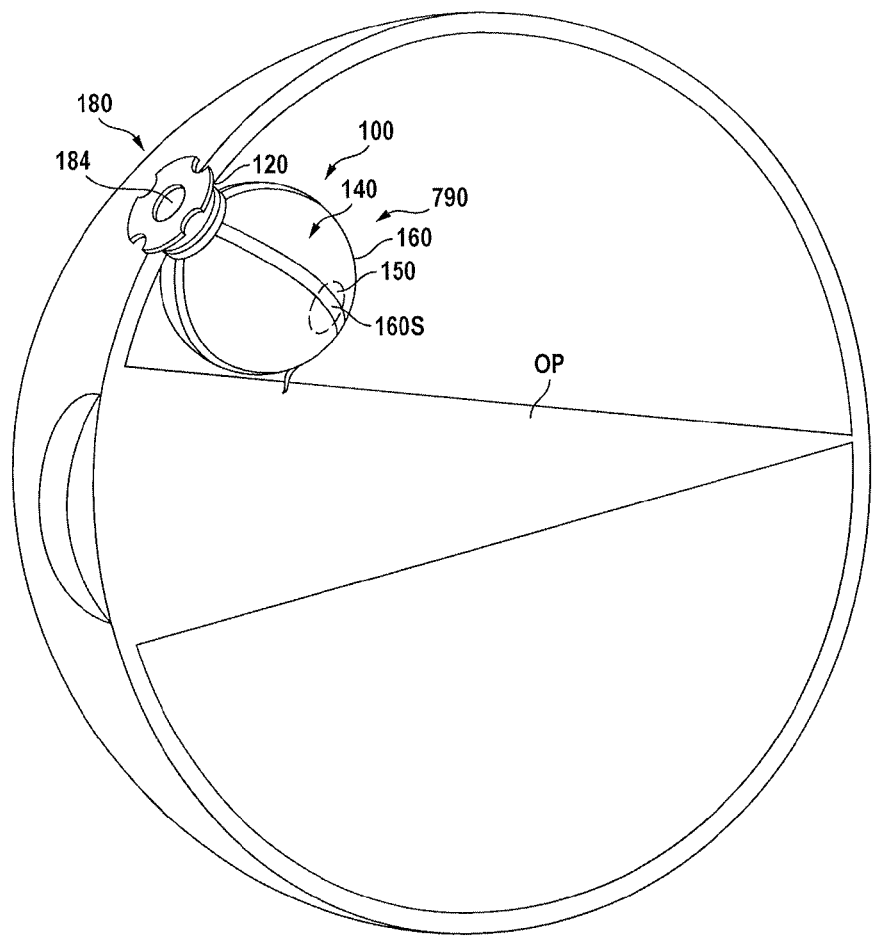
Figures 1A, 7C:
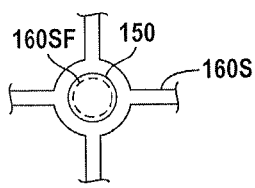
Figures 1B, 7C:
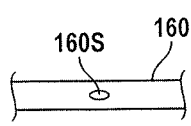
Figures 1C, 7C:
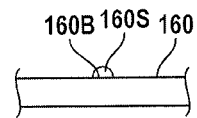
Figures 2, 7C:
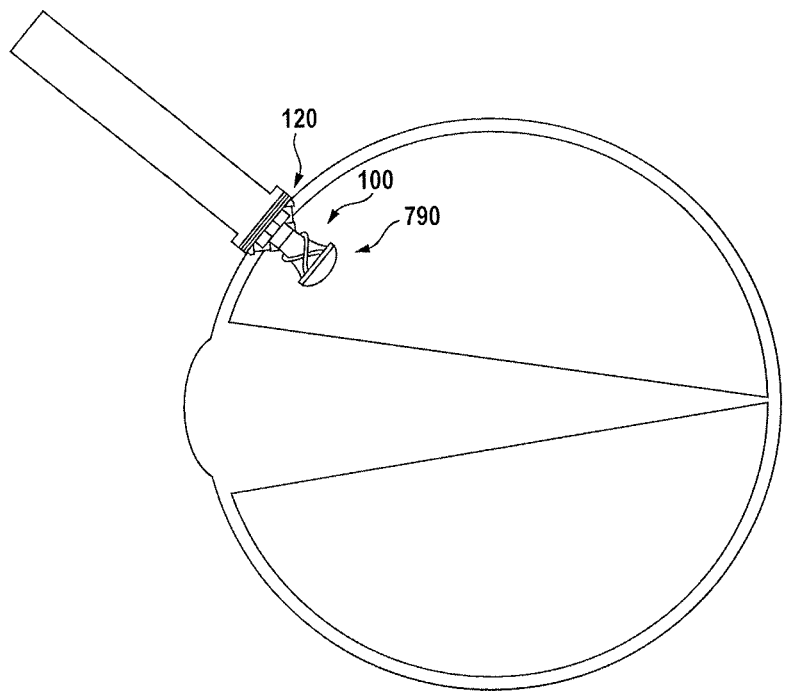
Figures 3, 7C:
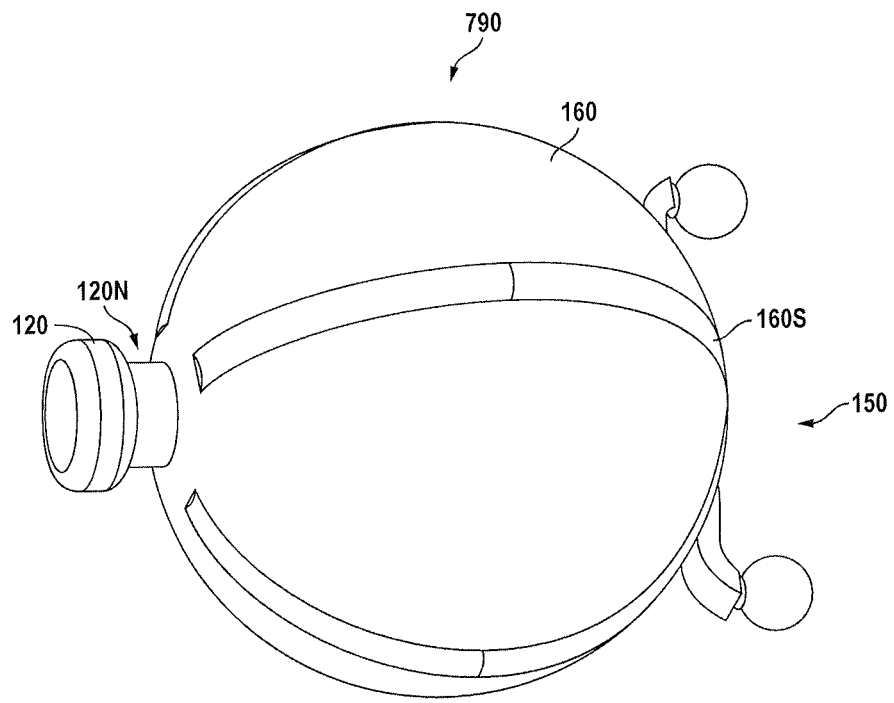
Figures 4A, 7C:
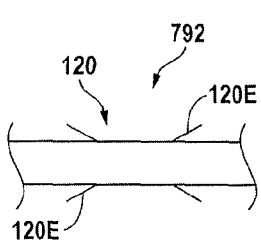
Figures 4B, 7C:
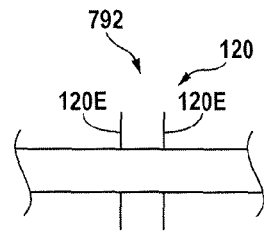

FIG. 1B shows therapeutic device 100 configured for placement in an eye as in FIG. 1A-1 and 1A-1-1. The device comprises retention structure 120 to couple to the sclera, for example flush with the sclera, and the barrier 160 comprises a tube 168. An active ingredient 112 comprising the therapeutic agent 110 is contained within tube 168 comprising non-permeable material 164. A porous material 152 is disposed at the distal end of the tube 168 to provide a sustained release of the therapeutic agent at therapeutic concentrations for the extended period. The non-permeable material 164 may extend distally around the porous material 152 so as to define an opening to couple the porous material 152 to the vitreous humor when the device is inserted into the eye.

The tube 168 and retention structure 120 may be configured to receive a glass rod, which is surface treated, and the glass rod can be injected with therapeutic agent. When the therapeutic agent has finished elution for the extended time, the rod can be replaced with a new rod.

The device 100 may comprise therapeutic agent and a carrier, for example a binding medium comprising a binding agent to deliver the therapeutic agent. The therapeutic agent can be surrounded with a column comprising a solid support that is eroded away.

Figures 1, 1C:
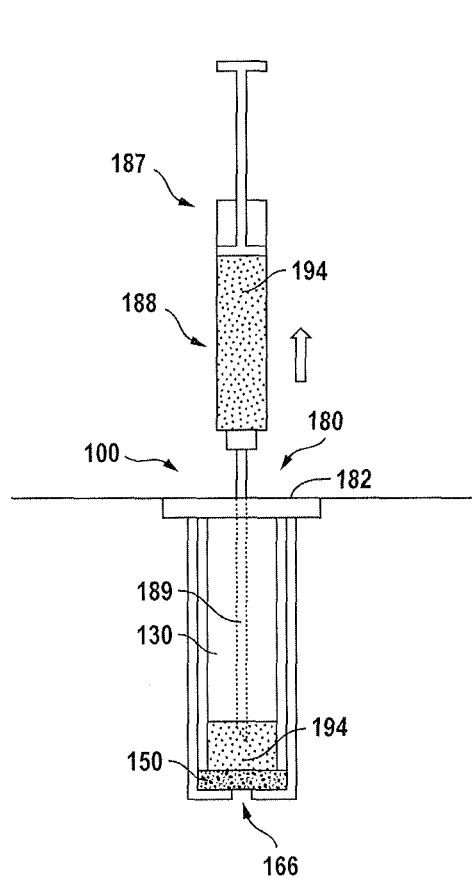
FIG. 1C shows a therapeutic device configured for placement in an eye as in FIG. 1A-1 and 1A-1-1, in accordance with embodiments of the present invention.
Figures 1, 1C, 2:
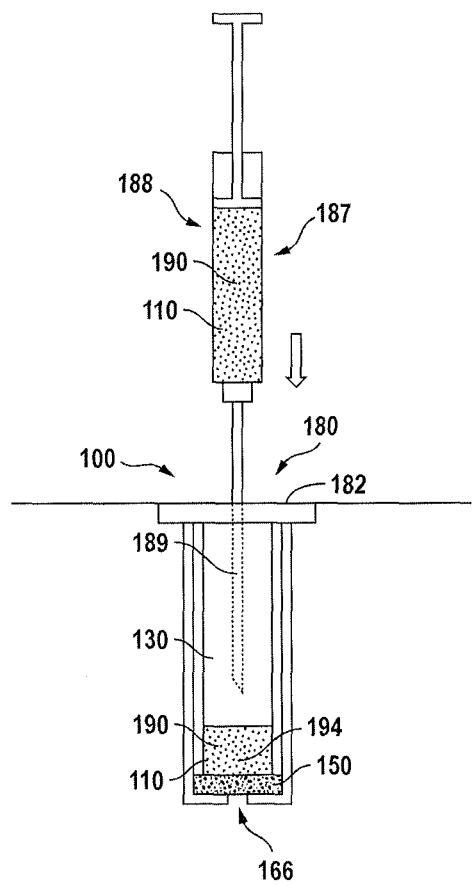

FIG. 1C shows a therapeutic device configured for placement in an eye as in FIG. 1A-1 and 1A-1-1. A binding medium 192 comprising a binding agent 190 such as glass wool may be loaded with therapeutic agent 110 prior to injection into the device through an access port 180. The device 100 may comprise binding, leak, and barrier functions to deliver the therapeutic agent for the extended time. The binding medium 192 and therapeutic agent 110 can be aspirated to replace the binding medium and therapeutic agent. The binding medium can be at least one of flushed or replaced when at least majority of the therapeutic agent has been released, such that additional therapeutic agent can be delivered from a second, injected binding medium comprising therapeutic agent. A membrane 195 can be disposed over the periphery of the therapeutic device 100. The membrane 195 may comprise methylcellulose, regenerated cellulose, cellulose acetate, nylon, polycarbonate, poly(tetrafluoroethylene) (PTFE), polyethersulfone, and polyvinylidene difluoride (PVDF). The therapeutic device may comprise barrier 160 shaped such that opening 166 comprises an exit port. The therapeutic agent may be released through at least one of a diffusion mechanism or convection mechanism. The number, size, and configuration of exit ports may determine the release rate of the therapeutic agent. The exit port may comprise a convection port, for example at least one of an osmotically driven convection port or a spring driven convection port. The exit port may also comprise a tubular path to which the therapeutic agent may temporarily attach, and then be released under certain physical or chemical conditions.

FIG. 1C-A shows at least one exit port 167, the exit port can be disposed on the device 100 to allow liquid to flow from inside the device outward, for example when fluid is injected into an injection port 182 of the device or when an insert such as a glass frit is inserted into the device. The therapeutic device may comprise an access port 180 for injection and/or removal, for example a septum. Additionally or in the alternative, when the therapeutic device is refilled, the contents of the device may be flushed into the vitreous of the eye.

FIG. 1C-1 shows a method of removing a binding agent 194. A needle 189 coupled to a syringe 188 of an injector 187 can be inserted into an access port 180 of the therapeutic device 100. The binding agent 194 can be aspirated with a needle.

FIG. 1C-2 shows a method of inserting the therapeutic agent 110 with a second binding agent 190 having the therapeutic agent 110 bound thereon. The therapeutic agent can be injected into a container 130 of the device for sustained release over the extended time.

FIG. 1C-3 shows syringe being filled with a formulation of therapeutic agent for injection into the therapeutic device. The needle 189 coupled to syringe 188 of injector 187 can be used to draw therapeutic agent 110 from a container 110C. The container 110C may comprise a commercially available container, such as a bottle with a septum, a single dose container, or a container suitable for mixing formulations. A quantity 110V of therapeutic agent 110 can be drawn into injector 187 for injection into the therapeutic device 100 positioned within the eye. The quantity 110V may comprise a predetermined quantity, for example based on the volume of the container of the therapeutic device 110 and an intended injection into the vitreous humor. The example the quantity 110V may exceed the volume of the container so as to inject a first portion of quantity 110V into the vitreous humor through the therapeutic device and to contain a second portion of quantity 110V within the container of the therapeutic device 110. Container 110C may comprise a formulation 110F of the therapeutic agent 110. The formulation 110F may comprise a commercially available formulations of therapeutic agent, for example therapeutic agents as described herein and with reference to Table 1A. Non-limiting examples of commercially available formulations that may be suitable for use in accordance with the embodiments described herein include Lucentis™ and Triamcinolone, for example. The formulation 110F may be a concentrated or diluted formulation of a commercially available therapeutic agent, for example Avastin™. The osmolarity and tonicity of the vitreous humor can be within a range from about 290 to about 320. For example, a commercially available formulation of Avastin™ may be diluted so as to comprise a formulation having an osmolarity and tonicity substantially similar to the osmolarity and tonicity of the vitreous humor, for example within a range from about 280 to about 340, for example about 300 mOsm. While the therapeutic agent 110 may comprise an osmolarity and tonicity substantially similar to the vitreous humor, the therapeutic agent 110 may comprise a hyper osmotic solution relative to the vitreous humor or a hypo osmotic solution relative to the vitreous humor. A person or ordinary skill in the art can conduct experiments based on the teachings described herein so as to determine empirically the formulation and osmolarity of the therapeutic agent to provide release of therapeutic agent for an extended time.

For example, in the United States of America, Lucentis™ (active ingredient ranibizumab) is supplied as a preservative-free, sterile solution in a single-use glass vial designed to deliver 0.05 mL of 10 mg/mL Lucentis™ aqueous solution with 10 mM histidine HCl, 10% α,α-trehalose dihydrate, 0.01% polysorbate 20, at pH 5.5. In Europe, the Lucentis™ formulation can be substantially similar to the formulation of the United States.

For example, the sustained release formulation of Lucentis™ in development by Genentech and/or Novartis, may comprise the therapeutic agent injected in to the device 100. The sustained release formulation may comprise particles comprising active ingredient.

For example, in the United States, Avastin™ (bevacizumab) is approved as an anticancer drug and in clinical trials are ongoing for AMD. For cancer, the commercial solution is a pH 6.2 solution for intravenous infusion. Avastin™ is supplied in 100 mg and 400 mg preservative-free, single-use vials to deliver 4 mL or 16 mL of Avastin™ (25 mg/mL). The 100 mg product is formulated in 240 mg α,α-trehalose dihydrate, 23.2 mg sodium phosphate (monobasic, monohydrate), 4.8 mg sodium phosphate (dibasic, anhydrous), 1.6 mg polysorbate 20, and Water for Injection, USP. The 400 mg product is formulated in 960 mg α,α-trehalose dihydrate, 92.8 mg sodium phosphate (monobasic, monohydrate), 19.2 mg sodium phosphate (dibasic, anhydrous), 6.4 mg polysorbate 20, and Water for Injection, USP. The commercial formulations are diluted in 100 mL of 0.9% sodium chloride before administration and the amount of the commercial formulation used varies by patient and indication. Based on the teachings described herein, a person of ordinary skill in the art can determine formulations of Avastin™ to inject into therapeutic device 100. In Europe, the Avastin™ formulation can be substantially similar to the formulation of the United States.

For example, in the United States, there are 2 forms of Triamcinolone used in injectable solutions, the acetonide and the hexacetonide. The acetamide is approved for intravitreal injections in the U.S. The acetamide is the active ingredient in TRIVARIS (Allergan), 8 mg triamcinolone acetonide in 0.1 mL (8% suspension) in a vehicle containing w/w percents of 2.3% sodium hyaluronate; 0.63% sodium chloride; 0.3% sodium phosphate, dibasic; 0.04% sodium phosphate, monobasic; and water, pH 7.0 to 7.4 for injection. The acetamide is also the active ingredient in Triesence™ (Alcon), a 40 mg/ml suspension.

A person of ordinary skill in the art can determine the osmolarity for these formulations. The degree of dissociation of the active ingredient in solution can be determined and used to determined differences of osmolarity from the molarity in these formulations. For example, considering at least some of the formulations may be concentrated (or suspensions), the molarity can differ from the osmolarity.

The formulation of therapeutic agent may injected into therapeutic device 100 may comprise many known formulations of therapeutic agents, and the formulation therapeutic agent comprises an osmolarity suitable for release for an extended time from device 100. Table 1B shows examples of osmolarity (Osm) of saline and some of the commercially formulations of Table 1A.

TABLE 1B

Summary of Calculations

| Description | Osm (M) |
| --- | --- |
| Saline (0.9%) | 0.308 |
| Phosphate Buffered Saline (PBS) | 0.313 |
| Lucentis ™ | 0.289 |
| Avastin ™ | 0.182 |
| Triamcinolone Acetonide (Trivaris-Allergan) | 0.342 |
| Triamcinolone Acetonide (Triessence - Alcon) | Isotonic* |
| Triamcinolone Acetonide (Kenalog - Apothecon) | Isotonic* |

*As described in package insert

The vitreous humor of the eye comprises an osmolarity of about 290 mOsm to about 320 mOsm. Formulations of therapeutic agent having an osmolarity from about 280 mOsm to about 340 mOsm are substantially isotonic and substantially iso-osmotic with respect to the vitreous humor of the eye. Although the formulations listed in Table 1B are substantially iso-osmotic and isotonic with respect to the vitreous of the eye and suitable for injection into the therapeutic device, the formulation of the therapeutic agent injected into the therapeutic device can be hypertonic (hyper-osmotic) or hypotonic (hypo-osmotic) with respect to the tonicity and osmolarity of the vitreous. Work in relation to embodiments suggests that a hyper-osmotic formulation may release the active ingredient of the therapeutic agent into the vitreous somewhat faster initially when the solutes of the injected formulation equilibrate with the osmolarity of the vitreous, and that a hypo-osmotic formulation such as Avastin™ may release the active ingredient of the therapeutic agent into the vitreous somewhat slower initially when the solutes of the injected formulation equilibrate with the eye. A person of ordinary skill in the art can conduct experiments based on the teaching described herein to determine empirically the appropriate reservoir chamber volume and porous structure for a formulation of therapeutic agent disposed in the reservoir chamber, so as to release therapeutic amounts of the therapeutic agent for an extended time and to provide therapeutic concentrations of therapeutic agent in the vitreous within a range of therapeutic concentrations that is above the minimum inhibitory concentration for the extended time.

Figures 1, 1C, 2, 3:
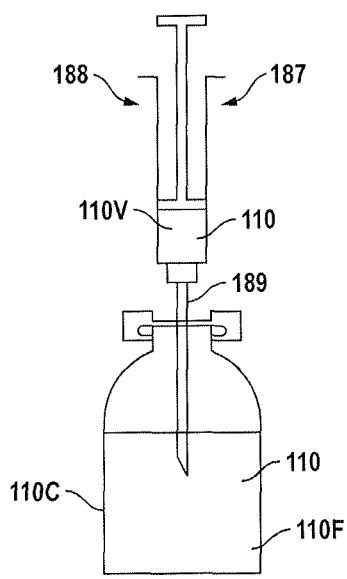
Figure 1D:
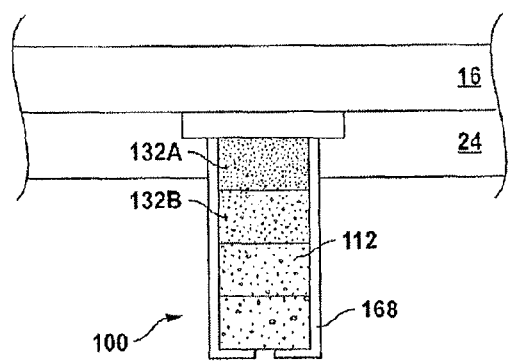
FIG. 1D shows a therapeutic device configured for placement in an eye as in FIG. 1A-1 and 1A-1-1, in which the device comprises a plurality of chambers and channels connecting the chambers so as to linearize the release of the therapeutic agent.

FIG. 1D shows a therapeutic device 100 configured for placement in an eye as in FIG. 1A-1 and 1A-1-1, in which the device comprises a plurality of chambers and channels connecting the chambers so as to linearize the release of the therapeutic agent. A first chamber 132A may comprise a reservoir having a first volume to contain the therapeutic quantity of the therapeutic agent. For example, the therapeutic agent comprises the active ingredient contained within the reservoir. A second chamber 132B can be disposed distally to the first chamber, with a first opening connecting the first chamber and the second chamber. The therapeutic agent can diffuse through the first opening into the second chamber. The second chamber comprises a second volume, such that therapeutic agent is temporarily stored in the second chamber so as to linearize, for example toward zero order, the delivery of the therapeutic agent. A second opening can extend from the second chamber toward the vitreous humor. The first opening, the second opening and the second volume can be sized so as to linearize the delivery of the therapeutic agent for the sustained release at therapeutic levels for the extended time. More than one therapeutic agent can be inserted into the therapeutic device. In such a case the two or more therapeutic agents may be mixed together or injected into separate chambers.

Additional chambers and openings can be disposed on the device to linearize the delivery of the drug. For example, a third chamber can be disposed distally to the second chamber. The second opening can couple the second chamber to the third chamber. For example, a fourth chamber can be disposed distally to the third chamber, a third opening can connect the third chamber and the fourth chamber.

Additionally or in the alternative, the therapeutic device may comprise at least one gate to provide for sustained drug delivery. The gate can be moved from "closed" to "open" position using magnetism or by applying electrical current. For example the gates can slide or twist. The gates can be spring-loaded, and may comprise a pump that can be reloaded. The gates may comprise an osmotic pump.

Figure 1E:
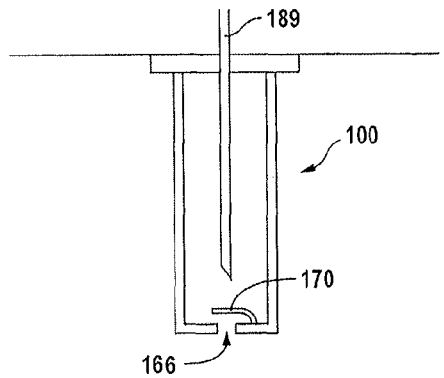
FIG. 1E shows a therapeutic device configured for placement in an eye as in FIGS. 1A-1 and 1A-1-1, in which the device comprises a needle stop located at the bottom of the therapeutic device.
Figures 1, 1E:
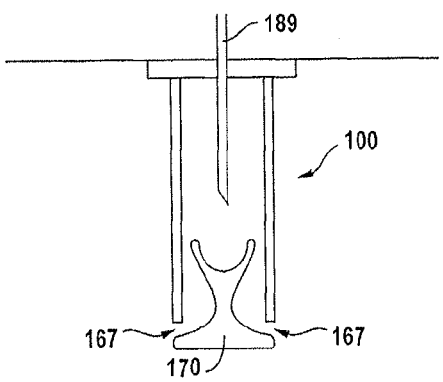
Figures 1, 1E, 2:
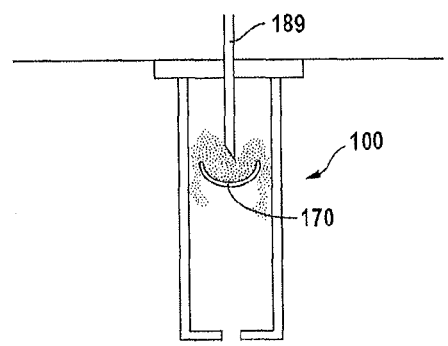
Figures 1, 1E, 2, 3:
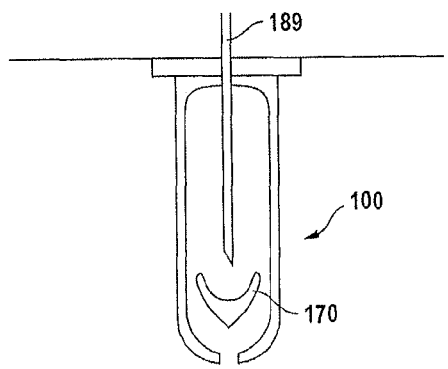
Figures 1, 1E, 2, 3:
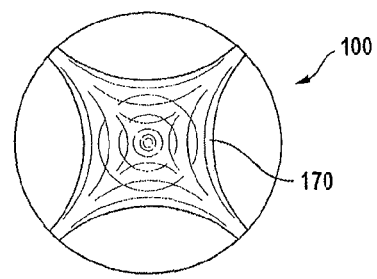
Figure 2:
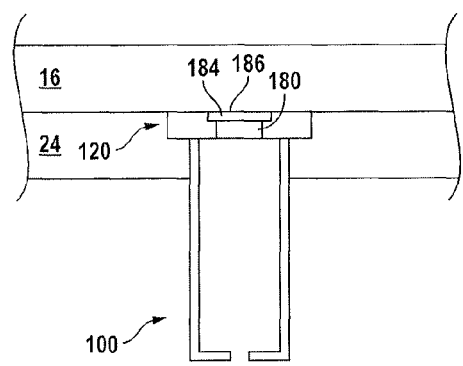

FIG. 1E shows a therapeutic device configured for placement in an eye as in FIGS. 1A-1 and 1A-1-1, in which the device comprises 100 needle stop 170 located at the bottom of the therapeutic device. The needle stop that may be included in the therapeutic device to keep the injection needle 189 from penetrating through and possibly damaging the exit port(s) 166 of the therapeutic device 100. The needle stop will desirably be made of a material of sufficient rigidity to prevent the advancement of the injection needle past a certain level in the therapeutic device. Additionally or in the alternative, the length of the injector's needle may be designed so that it may not penetrate through and possibly damage the exit port(s) of the therapeutic device.

As shown in FIGS. 1E and 1E-1, the needle stop 170 may be positioned at the posterior end of the therapeutic device. FIGS. 1E-2, 1E-3 and 1E-3-1 show other embodiments that may include needle stops placed in the middle of the device. The needle stop may be designed in such a manner as to function as a flow diverter for the therapeutic agent. The shape of the needle stop may encourage the mixing of the therapeutic agent with the rest of the fluids present in the inner chamber(s) of the therapeutic device.

FIG. 1E-1 shows a therapeutic device configured for placement in an eye as in FIGS. 1A-1 and 1A-1-1, in which the device comprises needle stop 170 located at the bottom of the therapeutic device and the shape of the device encourages the movement of the therapeutic agent within the chamber of the therapeutic device 100;

FIG. 1E-2 shows a therapeutic device configured for placement in an eye as in FIGS. 1A-1 and 1A-1-1, in which the device comprises needle stop 170 located in the middle of the therapeutic device;

FIG. 1E-3 shows a therapeutic device configured for placement in an eye as in FIGS. 1A-1 and 1A-1-1, in which the device comprises needle stop 170 located in the middle of the therapeutic device and the shape of the device encourages the movement of the therapeutic agent within the chamber of the therapeutic device;

FIG. 1E-3-1 shows a top view of the therapeutic device configured for placement in an eye as in FIGS. 1E-3;

FIG. 2 shows an access port 180 suitable for incorporation with the therapeutic device 100. The access port 180 may be combined with the therapeutic devices described herein, for example with reference to FIGS. 1A-1 to 1D. The access port may be disposed on a proximal end of the device. The access port 180 may comprise an opening formed in the retention structure 120 with a penetrable barrier 184 comprising a septum 186 disposed thereon. The access port may 180 be configured for placement under the conjunctiva 16 of the patient and above the sclera 24.

Figure 3A:
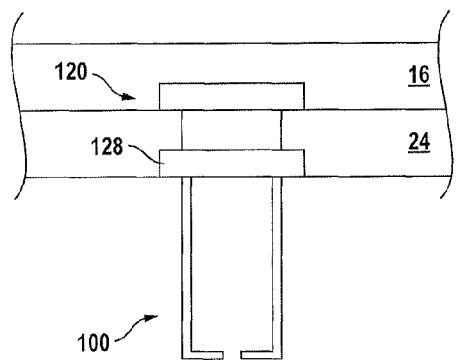
FIG. 3A shows a collar suitable for incorporation with the therapeutic device, in accordance with embodiments of the present invention.

FIG. 3A shows a collar 128 suitable for incorporation with the therapeutic device 100. The retention structure 120 configured to couple to the sclera 24 may comprise the collar 128. The collar may comprise an expandable collar.

Figure 3B:
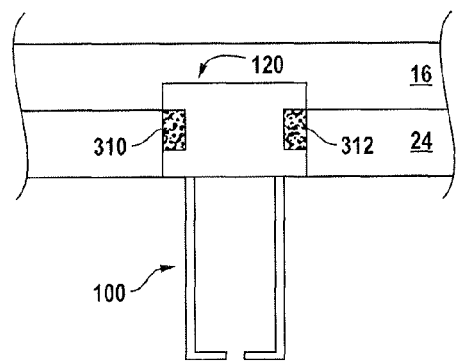
FIG. 3B shows biocompatible material impregnated with an anti-bacterial agent on the therapeutic device to inhibit bacterial growth along the device from the sclera to the vitreous humor.

FIG. 3B shows biocompatible material impregnated with an anti-bacterial agent 310 on the therapeutic device 100 to inhibit bacterial growth along the device from the sclera to the vitreous humor. The biocompatible material may comprise collagen, for example a collagen sponge 312, and the anti-bacterial agent may comprise silver impregnated in the collagen. The biocompatible material impregnated with the bactericide agent may extend around at least a portion of the outer surface of the device. The anti-bacterial agent may comprise a portion of the retention structure 120, such that the anti-bacterial agent is disposed at least partially within the sclera when the device is inserted into the eye.

Figure 4A:
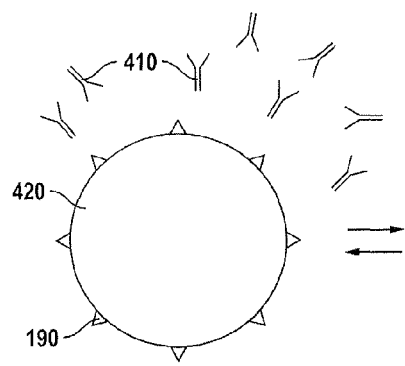
FIG. 4A shows released fragments of antibodies.
Figure 4B:
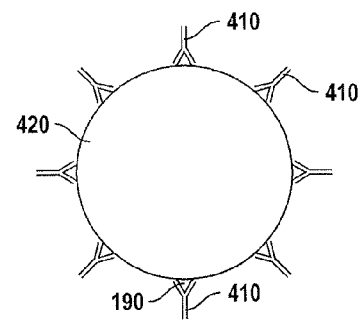
FIG. 4B shows antibody fragments reversibly bound to a substrate, in accordance with embodiments of the present invention.

FIG. 4A shows released antibodies comprising antibody fragments 410 and a substrate 420 comprising binding agent 190, and FIG. 4B shows an antibody fragments 410 reversibly bound to a substrate 420 with binding agent 190, in accordance with embodiments of the present invention. The antibody fragments can be reversibly bound to the substrate comprising the binding agent, such that the bound antibody fragments are in equilibrium with the unbound antibody fragments. One of ordinary skill in the art will recognize many substrates comprising binding agent to reversibly bind at least a portion of an antibody based on the teachings described herein. Examples of binding media may include particulates used in chromatography, such as: Macro-Prep t-Butyl HIC Support, Macro-Prep DEAE Support, CHT Ceramic, Hydroxyapatite Type I, Macro-Prep CM Support, Macro-Prep Methyl HIC Support, Macro-Prep Ceramic Hydroxyapatite Type II, UNOsphere S Cation Exchange Support, UNOsphere Q Strong Anion Exchange Support, Macro-Prep High-S Support, and Macro-Prep High-Q Support. Additional media to test for binding include ion exchange and bioaffinity chromatography media based on a hydrophilic polymeric support (GE Healthcare) that bind proteins with high capacity, and a hydrophilic packing material from Harvard Apparatus made from poly(vinyl alcohol) that binds more protein than silica. Other candidates would be known to those knowledgeable in the art.

Figure 5A:
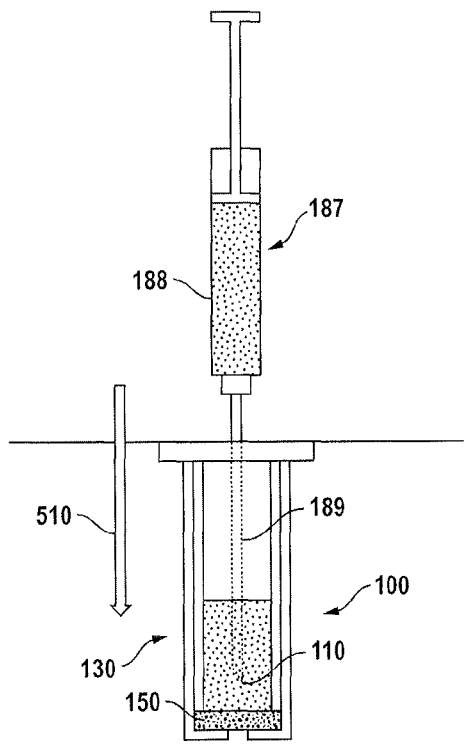
FIG. 5A shows a therapeutic device coupled to an injector to insert therapeutic agent into the device.
Figures 1, 5A:
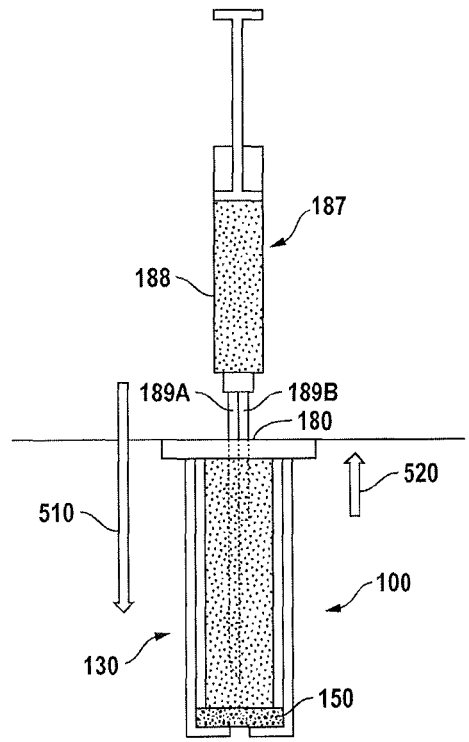

FIG. 5A shows therapeutic device 100 coupled to injector 187 to insert therapeutic agent 110 into container 130 of the device. The injector 187 may comprise needle 189 coupled to a syringe 188.

FIG. 5A-1 shows a therapeutic device 100 coupled to an injector 187 to inject and remove material from the device. The injector may comprise needle 189 having a first lumen 189A and a second lumen 189B configured to insert into a container of the device. The injector may simultaneously inject 510 therapeutic agent into and withdraw 520 liquid from the device. The injector may comprise a first one way valve and a second one way valve coupled to the first lumen and the second lumen, respectively.

Figure 5B:
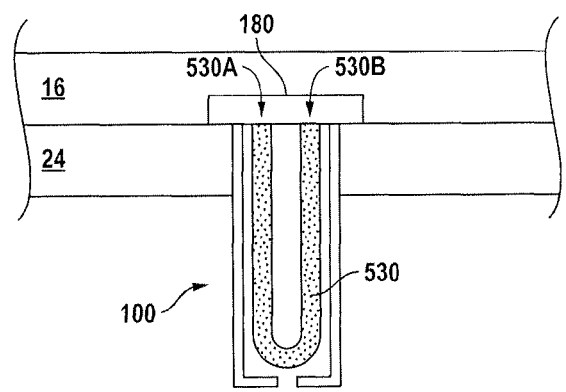
FIG. 5B shows a therapeutic device comprising a micro loop channel.

FIG. 5B shows a therapeutic device comprising a microloop channel 530. The microloop channel may extend to a first port 530A and a second port 530B, such the therapeutic agent can be injected into the first port, for example with a binding agent, and flowable material, for example liquid comprising binding agent, can be drawn from the microloop channel 530.

Figures 1, 5C:
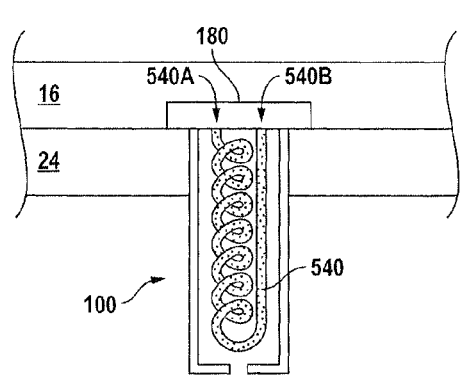
Figures 2, 5C:
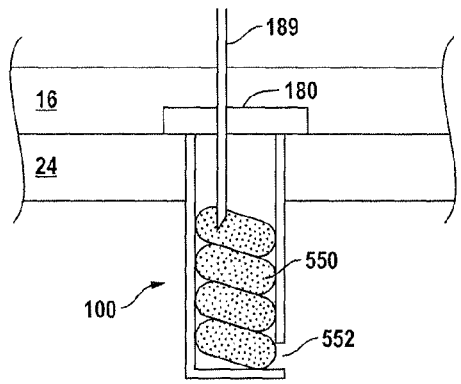

FIG. 5C-1 shows therapeutic device 100 comprising a tortuous channel 540. The tortuous channel may comprise extend from a first port 540A to a second port 540B, such that the therapeutic agent can be injected into the first port and flowable material, for example liquid comprising the binding agent, can be drawn from the second channel.

FIG. 5C-2 shows a therapeutic device comprising a tortuous coiled channel 550. The coiled channel 550 can extend to an exit port 552. A needle 189 can be inserted into the port 180 to inject therapeutic agent into device 100.

Figure 5D:
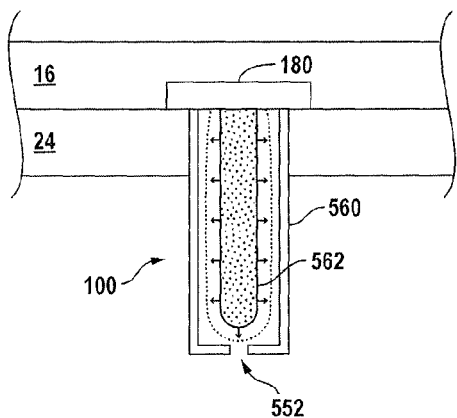
FIG. 5D shows an expandable and contractible structure to retain the therapeutic agent and an outer rigid casing to couple to the sclera.

FIG. 5D shows an expandable and contractible structure 562 to retain the therapeutic agent and an outer rigid casing 560 to couple to the sclera. The expandable structure 562 may comprise a membrane, such as at least one of a bag, a balloon, a flexible reservoir, a diaphragm, or a bag. The outer rigid casing may extend substantially around the structure 562 and may comprise an opening to release liquid into the vitreous humor when the structure is expanded and to draw vitreous humor inside a chamber of the casing when material is drawn from the structure and the structure contacts.

Figure 5E:
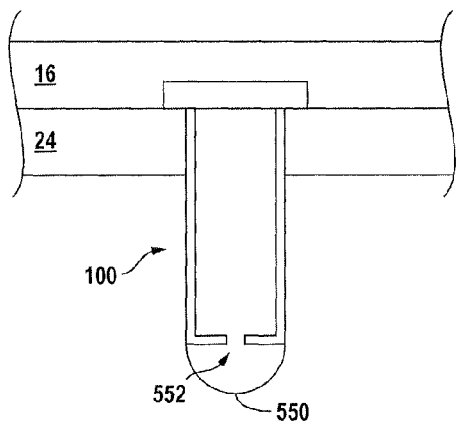
FIG. 5E shows a membrane disposed over an exit port of a therapeutic device.

FIG. 5E shows a membrane 550 disposed over an exit port 552 of therapeutic device 100.

Figure 5F:
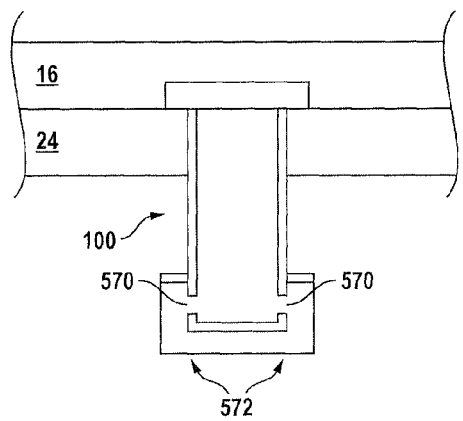
FIG. 5F shows a therapeutic device comprising a tubular membrane clamped onto the therapeutic device.

FIG. 5F shows therapeutic device 100 comprising a tubular membrane 572 clamped onto the therapeutic device over side ports 570 of device 100.

When the protective membranes have pores of 0.2 um diameter, they are 20 or more times larger than the proteins of interest, which may comprise a model for delivery of the therapeutic agent. For example, molecular weights and diameters of models of proteins of therapeutic interest are

| (a) | IgG | 150 kDa | 10.5 nm |
|---|---|---|---|
| (b) | BSA | 69 kDa | 7.2 nm |
| (c) | Fab fragment of IgG | 49 kDa | hydrodynamic diameter not reported |

Therefore, solutions of therapeutic compounds in the size range of IgG and BSA should flow relatively easily through 0.2 um pore size protective membranes used to stop passage of bacterial and other cells.

Binding Materials/Agents may comprise at least one of a chemical binding agent/material, a structural binding agent or material, or an electrostatic binding agent or material. The types of binding agent may comprise a classification composed of non-biodegradable material, for example at glass beads, glass wool or a glass rod. A surface can be derivatized with at least one functional group so as to impart the binding agent or material with the potential for at least one of ionic, hydrophobic, or bioaffinity binding to at least one therapeutic compound.

The binding agent may comprise a biodegradable material. For example, the biodegradation, binding, or a combination of the previous processes may control the diffusion rate.

The binding agent may comprise ion exchange, and the ion exchange may comprise at least one of a functional group, a pH sensitive binding or a positive or negative charge. For example, ion exchange with at least one of diethylaminoethyl or carboxymethyl functional groups.

The binding agent may comprise a pH sensitive binding agent. For example the binding agent can be configured to elute therapeutic agent at a pH of 7, and to bind the therapeutic agent at a pH from about 4 to about 6.5. A cation exchange binding agent can be configured, for example, such that at a pH of 7, the net negative charge of the binding agent decreases causing a decrease in binding of the positively charged drug and release of the therapeutic agent. A target buffer can be provided with the binding agent to reversibly couple the binding agent to the therapeutic agent. The rate of release can be controlled, for example slowed down, by using insolubility of the buffer in the vitreous. Alternatively or in combination the elution can be limited by using a porous membrane or a physical property such as a size of an opening.

The ion exchange may comprise positive or negative ion exchange.

The binding agent may comprise hydrophobic interaction. For example, the binding agent may comprise at least one binding to hydrophobic pockets, for example at least one of methyl, ethyl, propyl, butyl, t-butyl or phenyl functional groups.

The binding agent may comprise affinity, for example at least one of a macromolecular affinity or a metal chelation affinity. Examples can include a hydroxyapatite, or chelated metal, for example zinc. Iminodiacetic acid can be chelated with zinc.

The binding agent may comprise at least one of the following functions: charging, recharging or elution. The charging may comprise a porous material injected therein so as to release the active ingredient. The porous matter may have an extremely large inert surface area, which surface area is available for binding. The recharging may comprise removing carrier+therapeutic agent; and adding freshly "charged" carrier+therapeutic agent.

The elution may comprise a byproduct, for example unbound binding agent that can be removed. For example, diffusion (plug flow) of vitreous to change conditions, e.g. pH to reduce interaction of therapeutic agent+carriers.

Additionally or in the alternative, a sustained drug delivery system of the therapeutic agent may comprise drug delivery packets, e.g. microspheres, that are activated. The packets can be activated with at least one of photochemical activation, thermal activation or biodegradation.

The therapeutic device may comprise at least one structure configured to provide safety precautions. The device may comprise at least one structure to prevent at least one of macrophage or other immune cell within the reservoir body; bacterial penetration; or retinal detachment.

The therapeutic device may be configured for other applications in the body. Other routes of administration of drugs may include at least one of intraocular, oral, subcutaneous, intramuscular, intraperitoneal, intranasal, dermal, intrathecal, intravascular, intra articular, pericardial, intraluminal in organs and gut or the like.

Conditions that may be treated and/or prevented using the drug delivery device and method described herein may include at least one of the following: hemophilia and other blood disorders, growth disorders, diabetes, leukemia, hepatitis, renal failure, HIV infection, hereditary diseases such as cerebrosidase deficiency and adenosine deaminase deficiency, hypertension, septic shock, autoimmune diseases such as multiple sclerosis, Graves disease, systemic lupus erythematosus and rheumatoid arthritis, shock and wasting disorders, cystic fibrosis, lactose intolerance, Crohn's disease, inflammatory bowel disease, gastrointestinal or other cancers, degenerative diseases, trauma, multiple systemic conditions such as anemia, and ocular diseases such as, for example, retinal detachment, proliferative retinopathy, proliferative diabetic retinopathy, degenerative disease, vascular diseases, occlusions, infection caused by penetrating traumatic injury, endophthalmitis such as endogenous/systemic infection, post-operative infections, inflammations such as posterior uveitis, retinitis or choroiditis and tumors such as neoplasms and retinoblastoma.

Examples of therapeutic agents 110 that may be delivered by the therapeutic device 100 are described in Table 1A and may include Triamcinolone acetonide, Bimatoprost (Lumigan), Ranibizumab (Lucentis™), Travoprost (Travatan, Alcon), Timolol (Timoptic, Merck), Levobunalol (Betagan, Allergan), Brimonidine (Alphagan, Allergan), Dorzolamide (Trusopt, Merck), Brinzolamide (Azopt, Alcon). Additional examples of therapeutic agents that may be delivered by the therapeutic device include antibiotics such as tetracycline, chlortetracycline, bacitracin, neomycin, polymyxin, gramicidin, cephalexin, oxytetracycline, chloramphenicol kanamycin, rifampicin, ciprofloxacin, tobramycin, gentamycin, erythromycin and penicillin; antifungals such as amphotericin B and miconazole; anti-bacterials such as sulfonamides, sulfadiazine, sulfacetamide, sulfamethizole and sulfisoxazole, nitrofurazone and sodium propionate; antivirals such as idoxuridine, trifluorotymidine, acyclovir, ganciclovir and interferon; antiallergenics such as sodium cromoglycate, antazoline, methapyriline, chlorpheniramine, pyrilamine, cetirizine and prophenpyridamine; anti-inflammatories such as hydrocortisone, hydrocortisone acetate, dexamethasone, dexamethasone 21-phosphate, fluocinolone, medrysone, prednisolone, prednisolone 21-phosphate, prednisolone acetate, fluorometholone, betamethasone, and triamcinolone; non-steroidal anti-inflammatories such as salicylate, indomethacin, ibuprofen, diclofenac, flurbiprofen and piroxicam; decongestants such as phenylephrine, naphazoline and tetrahydrozoline; miotics and anticholinesterases such as pilocarpine, salicylate, acetylcholine chloride, physostigmine, eserine, carbachol, diisopropyl fluorophosphate, phospholine iodide and demecarium bromide; mydriatics such as atropine sulfate, cyclopentolate, homatropine, scopolamine, tropicamide, eucatropine and hydroxyamphetamine; sypathomimetics such as epinephrine; antineoplastics such as carmustine, cisplatin and fluorouracil; immunological drugs such as vaccines and immune stimulants; hormonal agents such as estrogens, estradiol, progestational, progesterone, insulin, calcitonin, parathyroid hormone and peptide and vasopressin hypothalamus releasing factor; beta adrenergic blockers such as timolol maleate, levobunolol Hcl and betaxolol Hcl; growth factors such as epidermal growth factor, fibroblast growth factor, platelet derived growth factor, transforming growth factor beta, somatotropin and fibronectin; carbonic anhydrase inhibitors such as dichlorophenamide, acetazolamide and methazolamide and other drugs such as prostaglandins, antiprostaglandins and prostaglandin precursors. Other therapeutic agents known to those skilled in the art which are capable of controlled, sustained release into the eye in the manner described herein are also suitable for use in accordance with embodiments of the present invention.

The therapeutic agent 110 may comprise one or more of the following: Abarelix, Abatacept, Abciximab, Adalimumab, Aldesleukin, Alefacept, Alemtuzumab, Alpha-1-proteinase inhibitor, Alteplase, Anakinra, Anistreplase, Antihemophilic Factor, Antithymocyte globulin, Aprotinin, Arcitumomab, Asparaginase, Basiliximab, Becaplermin, Bevacizumab, Bivalirudin, Botulinum Toxin Type A, Botulinum Toxin Type B, Capromab, Cetrorelix, Cetuximab, Choriogonadotropin alfa, Coagulation Factor IX, Coagulation factor VIIa, Collagenase, Corticotropin, Cosyntropin, Cyclosporine, Daclizumab, Darbepoetin alfa, Defibrotide, Denileukin diftitox, Desmopressin, Dornase Alfa, Drotrecogin alfa, Eculizumab, Efalizumab, Enfuvirtide, Epoetin alfa, Eptifibatide, Etanercept, Exenatide, Felypressin, Filgrastim, Follitropin beta, Galsulfase, Gemtuzumab ozogamicin, Glatiramer Acetate, Glucagon recombinant, Goserelin, Human Serum Albumin, Hyaluronidase, Ibritumomab, Idursulfase, Immune globulin, Infliximab, Insulin Glargine recombinant, Insulin Lyspro recombinant, Insulin recombinant, Insulin, porcine, Interferon Alfa-2a, Recombinant, Interferon Alfa-2b, Recombinant, Interferon alfacon-1, Interferonalfa-n1, Interferon alfa-n3, Interferon beta-1b, Interferon gamma-1b, Lepirudin, Leuprolide, Lutropin alfa, Mecasermin, Menotropins, Muromonab, Natalizumab, Nesiritide, Octreotide, Omalizumab, Oprelvekin, OspA lipoprotein, Oxytocin, Palifermin, Palivizumab, Panitumumab, Pegademase bovine, Pegaptanib, Pegaspargase, Pegfilgrastim, Peginterferon alfa-2a, Peginterferon alfa-2b, Pegvisomant, Pramlintide, Ranibizumab, Rasburicase, Reteplase, Rituximab, Salmon Calcitonin, Sargramostim, Secretin, Sermorelin, Serum albumin iodonated, Somatropin recombinant, Streptokinase, Tenecteplase, Teriparatide, Thyrotropin Alfa, Tositumomab, Trastuzumab, Urofollitropin, Urokinase, or Vasopressin. The molecular weights of the molecules and indications of these therapeutic agents are set for below in Table 1A, below.

The therapeutic agent 110 may comprise one or more of compounds that act by binding members of the immunophilin family of cellular proteins. Such compounds are known as "immunophilin binding compounds." Immunophilin binding compounds include but are not limited to the "limus" family of compounds. Examples of limus compounds that may be used include but are not limited to cyclophilins and FK506-binding proteins (FKBP5), including sirolimus (rapamycin) and its water soluble analog SDZ-RAD, tacrolimus, everolimus, pimecrolimus, CCI-779 (Wyeth), AP23841 (Ariad), and ABT-578 (Abbott Laboratories).

The limus family of compounds may be used in the compositions, devices and methods for the treatment, prevention, inhibition, delaying the onset of, or causing the regression of angiogenesis-mediated diseases and conditions of the eye, including choroidal neovascularization. The limus family of compounds may be used to prevent, treat, inhibit, delay the onset of, or cause regression of AMD, including wet AMD. Rapamycin may be used to prevent, treat, inhibit, delay the onset of, or cause regression of angiogenesis-mediated diseases and conditions of the eye, including choroidal neovascularization. Rapamycin may be used to prevent, treat, inhibit, delay the onset of, or cause regression of AMD, including wet AMD.

The therapeutic agent 110 may comprise one or more of: pyrrolidine, dithiocarbamate (NF.kappa.B inhibitor); squalamine; TPN 470 analogue and fumagillin; PKC (protein kinase C) inhibitors; Tie-1 and Tie-2 kinase inhibitors; inhibitors of VEGF receptor kinase; proteosome inhibitors such as Velcade™ (bortezomib, for injection; ranibuzumab (Lucentis™) and other antibodies directed to the same target; pegaptanib (Macugen™); vitronectin receptor antagonists, such as cyclic peptide antagonists of vitronectin receptor-type integrins; .alpha.-v/.beta.-3 integrin antagonists; .alpha.-v/.beta.-1 integrin antagonists; thiazolidinediones such as rosiglitazone or troglitazone; interferon, including .gamma.-interferon or interferon targeted to CNV by use of dextran and metal coordination; pigment epithelium derived factor (PEDF); endostatin; angiostatin; tumistatin; canstatin; anecortave acetate; acetonide; triamcinolone; tetrathiomolybdate; RNA silencing or RNA interference (RNAi) of angiogenic factors, including ribozymes that target VEGF expression; Accutane™ (13-cis retinoic acid); ACE inhibitors, including but not limited to quinopril, captopril, and perindozril; inhibitors of mTOR (mammalian target of rapamycin); 3-aminothalidomide; pentoxifylline; 2-methoxyestradiol; colchicines; AMG-1470; cyclooxygenase inhibitors such as nepafenac, rofecoxib, diclofenac, rofecoxib, NS398, celecoxib, vioxx, and (E)-2-alkyl-2(4-methanesulfonylphenyl)-1-phenylethene; t-RNA synthase modulator; metalloprotease 13 inhibitor; acetylcholinesterase inhibitor; potassium channel blockers; endorepellin; purine analog of 6-thioguanine; cyclic peroxide ANO-2; (recombinant) arginine deiminase; epigallocatechin-3-gallate; cerivastatin; analogues of suramin; VEGF trap molecules; apoptosis inhibiting agents; Visudyne™, snET2 and other photo sensitizers, which may be used with photodynamic therapy (PDT); inhibitors of hepatocyte growth factor (antibodies to the growth factor or its receptors, small molecular inhibitors of the c-met tyrosine kinase, truncated versions of HGF e.g. NK4).

The therapeutic agent 110 may comprise a combination with other therapeutic agents and therapies, including but not limited to agents and therapies useful for the treatment of angiogenesis or neovascularization, particularly CNV. Non-limiting examples of such additional agents and therapies include pyrrolidine, dithiocarbamate (NF.kappa.B inhibitor); squalamine; TPN 470 analogue and fumagillin; PKC (protein kinase C) inhibitors; Tie-1 and Tie-2 kinase inhibitors; inhibitors of VEGF receptor kinase; proteosome inhibitors such as Velcade™ (bortezomib, for injection; ranibizumab (Lucentis™) and other antibodies directed to the same target; pegaptanib (Macugen™); vitronectin receptor antagonists, such as cyclic peptide antagonists of vitronectin receptor-type integrins; .alpha.-v/.beta.-3 integrin antagonists; .alpha.-v/.beta.-1 integrin antagonists; thiazolidinediones such as rosiglitazone or troglitazone; interferon, including .gamma.-interferon or interferon targeted to CNV by use of dextran and metal coordination; pigment epithelium derived factor (PEDF); endostatin; angiostatin; tumistatin; canstatin; anecortave acetate; acetonide; triamcinolone; tetrathiomolybdate; RNA silencing or RNA interference (RNAi) of angiogenic factors, including ribozymes that target VEGF expression; Accutane™ (13-cis retinoic acid); ACE inhibitors, including but not limited to quinopril, captopril, and perindozril; inhibitors of mTOR (mammalian target of rapamycin); 3-aminothalidomide; pentoxifylline; 2-methoxyestradiol; colchicines; AMG-1470; cyclooxygenase inhibitors such as nepafenac, rofecoxib, diclofenac, rofecoxib, NS398, celecoxib, vioxx, and (E)-2-alkyl-2(4-methanesulfonylphenyl)-1-phenylethene; t-RNA synthase modulator; metalloprotease 13 inhibitor; acetylcholinesterase inhibitor; potassium channel blockers; endorepellin; purine analog of 6-thioguanine; cyclic peroxide ANO-2; (recombinant) arginine deiminase; epigallocatechin-3-gallate; cerivastatin; analogues of suramin; VEGF trap molecules; inhibitors of hepatocyte growth factor (antibodies to the growth factor or its receptors, small molecular inhibitors of the c-met tyrosine kinase, truncated versions of HGF e.g. NK4); apoptosis inhibiting agents; Visudyne™, snET2 and other photo sensitizers with photodynamic therapy (PDT); and laser photocoagulation.

The therapeutic agents may be used in conjunction with a pharmaceutically acceptable carrier such as, for example, solids such as starch, gelatin, sugars, natural gums such as acacia, sodium alginate and carboxymethyl cellulose; polymers such as silicone rubber; liquids such as sterile water, saline, dextrose, dextrose in water or saline; condensation products of castor oil and ethylene oxide, liquid glyceryl triester of a lower molecular weight fatty acid; lower alkanols; oils such as corn oil, peanut oil, sesame oil, castor oil, and the like, with emulsifiers such as mono- or di-glyceride of a fatty acid, or a phosphatide such as lecithin, polysorbate 80, and the like; glycols and polyalkylene glycols; aqueous media in the presence of a suspending agent, for example, sodium carboxymethylcellulose, sodium hyaluronate, sodium alginate, poly(vinyl pyrrolidone) and similar compounds, either alone, or with suitable dispensing agents such as lecithin, polyoxyethylene stearate and the like. The carrier may also contain adjuvants such as preserving, stabilizing, wetting, emulsifying agents or other related materials.

The therapeutic device may comprise a container configured to hold at least one therapeutic agent, the container comprising a chamber to hold the at least one therapeutic agent with at least one opening to release the at least one therapeutic agent to the vitreous humor and porous structure 150 placed within the at least one opening. The porous structure 150 may comprise a fixed tortuous, porous material such as a sintered metal, a sintered glass or a sintered polymer with a defined porosity and tortuosity that controls the rate of delivery of the at least one therapeutic agent to the vitreous humor. The rigid porous structures provide certain advantages over capillary tubes, erodible polymers and membranes as a mechanism for controlling the release of a therapeutic agent or agents from the therapeutic device. These advantages include the ability of the rigid porous structure to comprise a needle stop, simpler and more cost effective manufacture, flushability for cleaning or declogging either prior to or after implantation, high efficiency depth filtration of microorganisms provided by the labyrinths of irregular paths within the structure and greater robustness due to greater hardness and thickness of the structure compared to a membrane or erodible polymer matrix. Additionally, when the rigid porous structure is manufactured from a sintered metal, ceramic, glass or certain plastics, it can be subjected to sterilization and cleaning procedures, such as heat or radiation based sterilization and depyrogenation, that might damage polymer and other membranes. In certain embodiments, as illustrated in example 9, the rigid porous structure may be configured to provide a therapeutically effective, concentration of the therapeutic agent in the vitreous for at least 6 months. This release profile provided by certain configurations of the rigid porous structures enables a smaller device which is preferred in a small organ such as the eye where larger devices may alter or impair vision.

Figures 1, 6A:
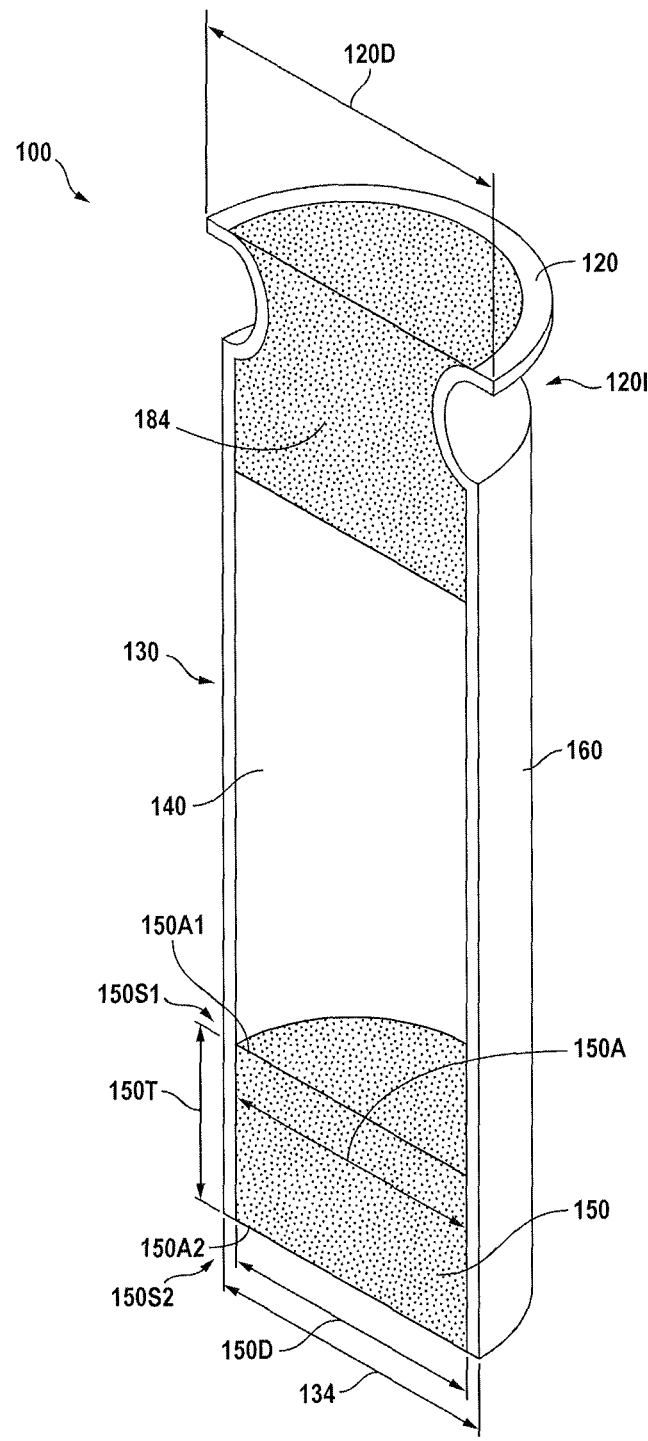
Figures 2, 6A:
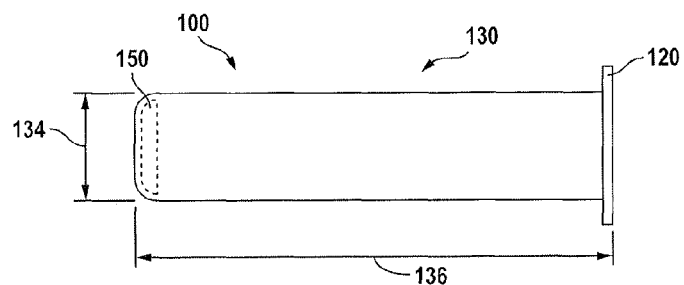

FIG. 6A-1 shows a therapeutic device 100 comprising a container 130 having a penetrable barrier 184 disposed on a first end, a porous structure 150 disposed on a second end to release therapeutic agent for an extended period, and a retention structure 120 comprising an extension protruding outward from the container to couple to the sclera and the conjunctiva. The extending protrusion of the retention structure may comprise a diameter 120D. The retention structure may comprise an indentation 120I sized to receive the sclera. The container may comprise a tubular barrier 160 that defines at least a portion of the reservoir, and the container may comprise a width, for example a diameter 134. The diameter 134 can be sized within a range, for example within a range from about 0.5 to about 4 mm, for example within a range from about 1 to 3 mm and can be about 2 mm, for example. The container may comprise a length 136, sized so as to extend from the conjunctive to the vitreous to release the therapeutic agent into the vitreous. The length 136 can be sized within a range, for example within a range from about 2 to about 14 mm, for example within a range from about 4 to 10 mm and can be about 7 mm, for example. The volume of the reservoir may be substantially determined by an inner cross sectional area of the tubular structure and distance from the porous structure to the penetrable barrier. The retention structure may comprise an annular extension having a retention structure diameter greater than a diameter of the container. The retention structure may comprise an indentation configured to receive the sclera when the extension extends between the sclera and the conjunctive. The penetrable barrier may comprise a septum disposed on a proximal end of the container, in which the septum comprises a barrier that can be penetrated with a sharp object such as a needle for injection of the therapeutic agent. The porous structure may comprise a cross sectional area 150A sized to release the therapeutic agent for the extended period.

The porous structure 150 may comprise a first side coupled to the reservoir 150 S1 and a second side to couple to the vitreous 150S2. The first side may comprise a first area 150A1 and the second side may comprise a second area 150A2. The porous structure may comprise a thickness 105T. The porous structure many comprise a diameter 150D.

The volume of the reservoir 140 may comprise from about 5 uL to about 2000 uL of therapeutic agent, or for example from about 10 uL to about 200 uL of therapeutic agent.

The therapeutic agent stored in the reservoir of the container comprises at least one of a solid comprising the therapeutic agent, a solution comprising the therapeutic agent, a suspension comprising the therapeutic agent, particles comprising the therapeutic agent adsorbed thereon, or particles reversibly bound to the therapeutic agent. For example, reservoir may comprise a suspension of a cortico-steroid such as triamcinolone acetonide to treat inflammation of the retina. The reservoir may comprise a buffer and a suspension of a therapeutic agent comprising solubility within a range from about 1 ug/mL to about 100 ug/mL, such as from about 1 ug/mL to about 40 ug/mL. For example, the therapeutic agent may comprise a suspension of triamcinolone acetonide having a solubility of approximately 19 ug/mL in the buffer at 37 C when implanted.

The release rate index may comprise many values, and the release rate index with the suspension may be somewhat higher than for a solution in many embodiments, for example. The release rate index may be no more than about 5, and can be no more than about 2.0, for example no more than about 1.5, and in many embodiments may be no more than about 1.2, so as to release the therapeutic agent with therapeutic amounts for the extended time.

The therapeutic device, including for example, the retention structure and the porous structure, may be sized to pass through a lumen of a catheter.

The porous structure may comprise a needle stop that limits penetration of the needle. The porous structure may comprise a plurality of channels configured for the extended release of the therapeutic agent. The porous structure may comprise a rigid sintered material having characteristics suitable for the sustained release of the material.

FIG. 6A-2 shows a therapeutic device as in FIG. 6A comprising a rounded distal end.

Figure 6B:
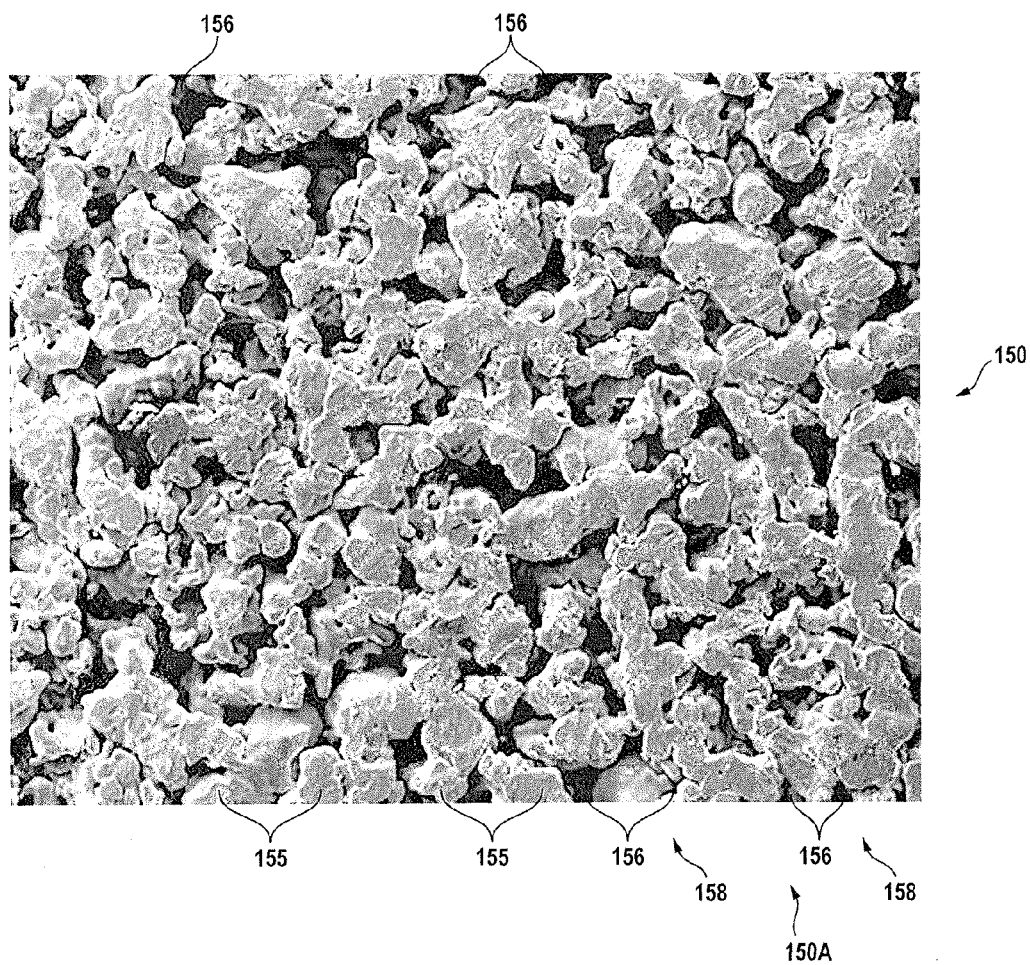
FIG. 6B shows a rigid porous structure configured for sustained release with a device as in FIG. 6A.
Figures 1, 6B:
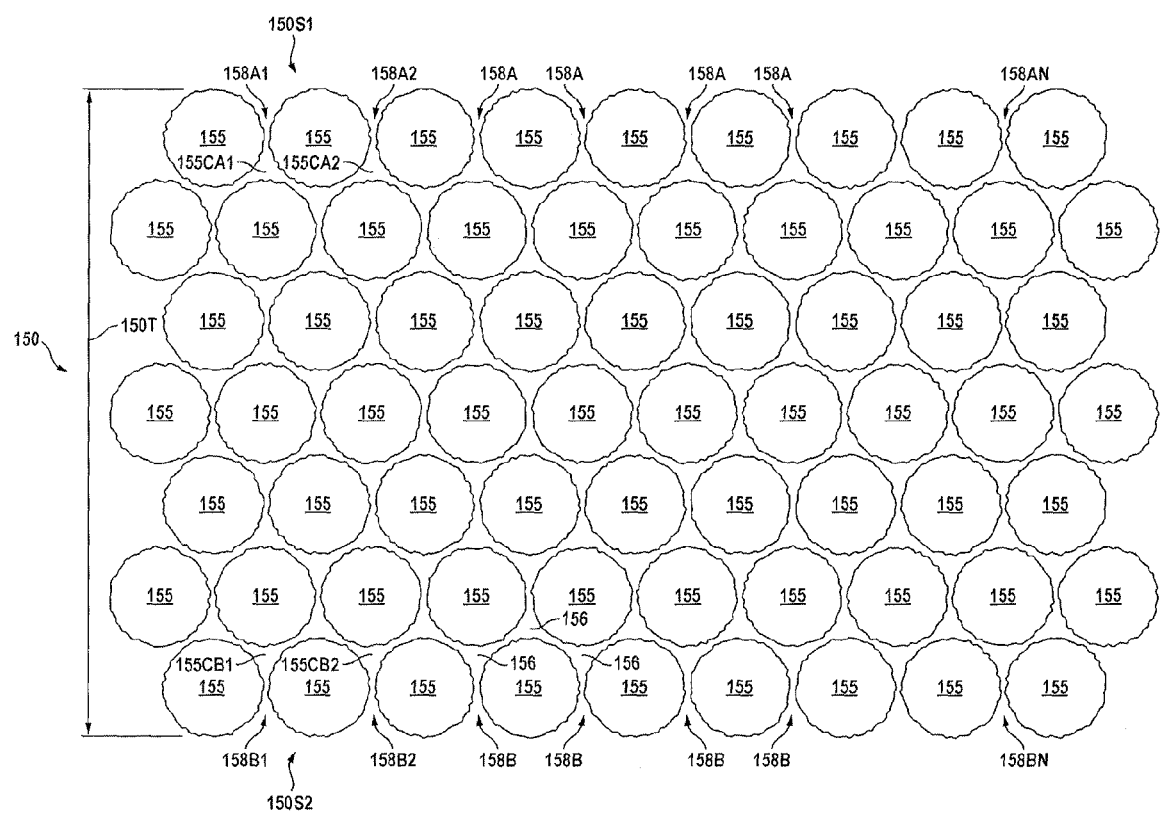
Figures 2, 6B:
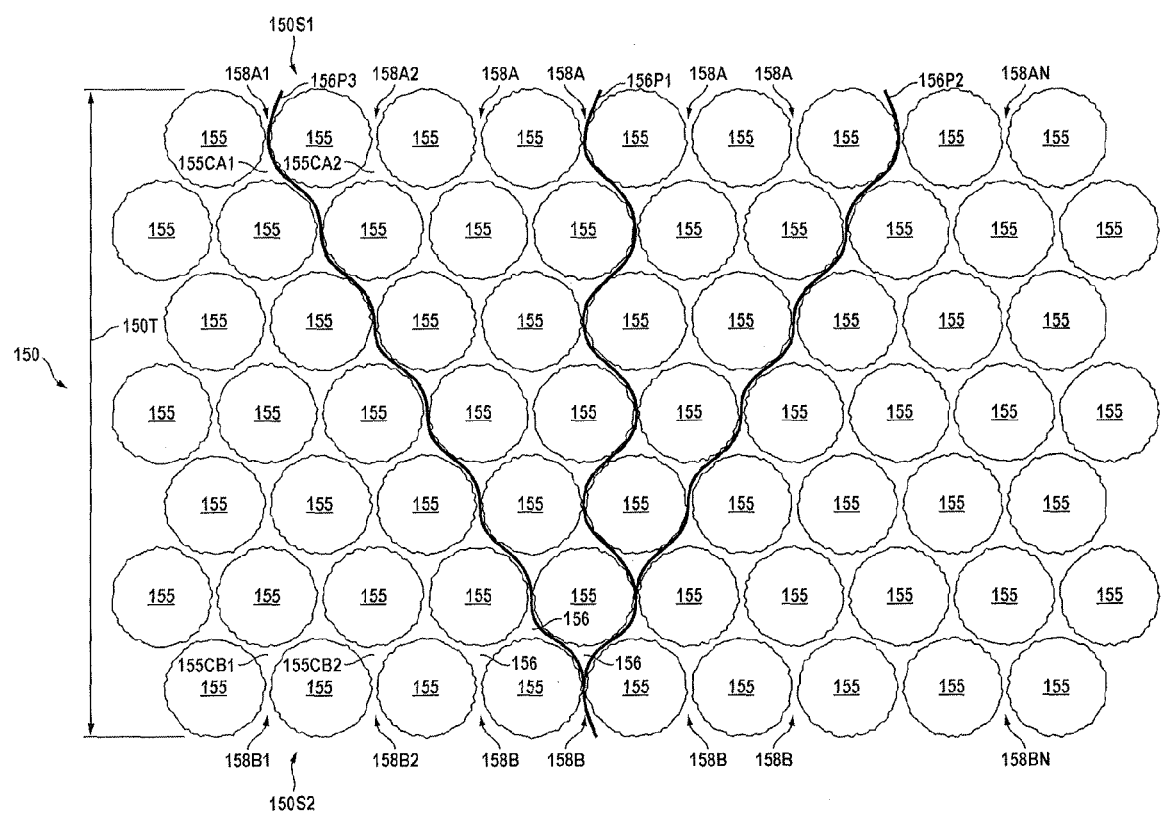
Figures 3, 6B:
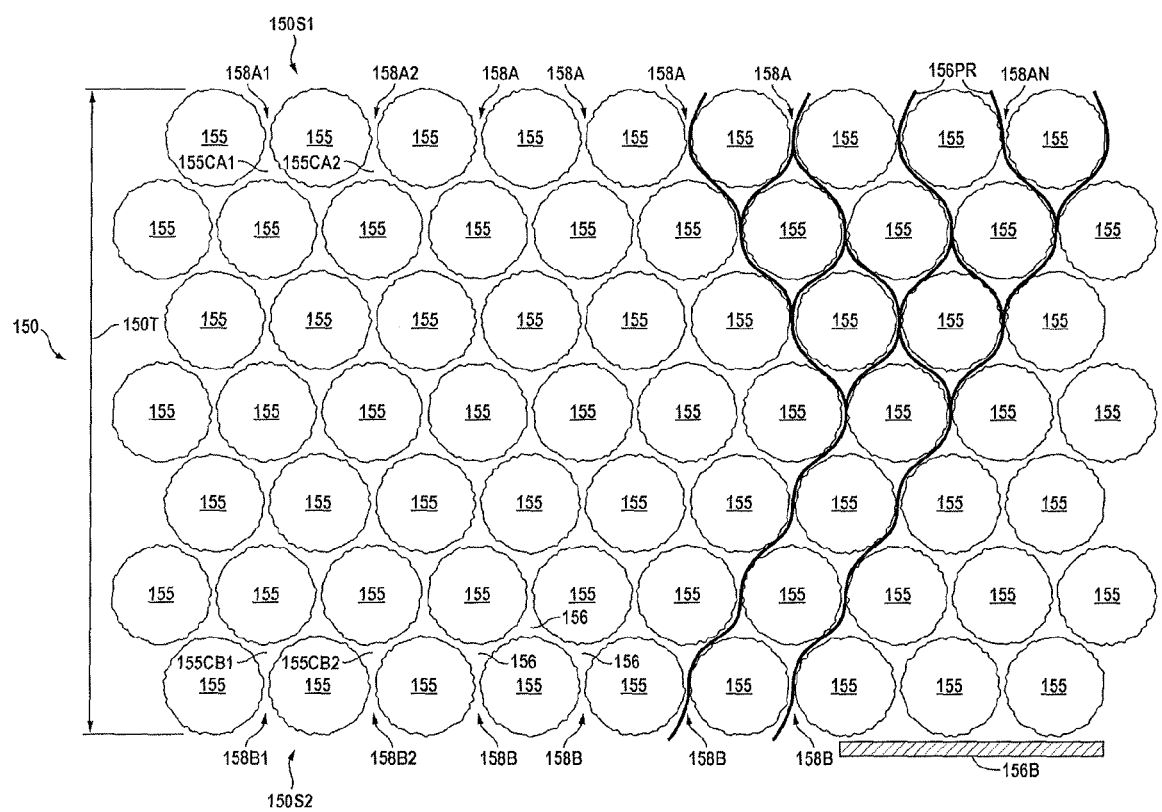

FIG. 6B shows a rigid porous structure as in FIG. 6A. The rigid porous structure 158 comprises a plurality of interconnecting channels 156. The porous structure comprises a sintered material composed of interconnected grains 155 of material. The interconnected grains of material define channels that extend through the porous material to release the therapeutic agent. The channels may extend around the sintered grains of material, such that the channels comprise interconnecting channels extending through the porous material.

The rigid porous structure can be configured for injection of the therapeutic agent into the container in many ways. The channels of the rigid porous structure may comprise substantially fixed channels when the therapeutic agent is injected into the reservoir with pressure. The rigid porous structure comprises a hardness parameter within a range from about 160 Vickers to about 500 Vickers. In some embodiments the rigid porous structure is formed from sintered stainless steel and comprises a hardness parameter within a range from about 200 Vickers to about 240 Vickers. In some embodiments it is preferred to inhibit ejection of the therapeutic agent through the porous structure during filling or refilling the reservoir of the therapeutic device with a fluid. In these embodiments the channels of the rigid porous structure comprise a resistance to flow of an injected solution or suspension through a thirty gauge needle such that ejection of said solution or suspension through the rigid porous structure is substantially inhibited when said solution or suspension is injected into the reservoir of the therapeutic device. Additionally, these embodiments may optionally comprise an evacuation vent or an evacuation reservoir under vacuum or both to facilitate filling or refilling of the reservoir.

The reservoir and the porous structure can be configured to release therapeutic amounts of the therapeutic agent in many ways. The reservoir and the porous structure can be configured to release therapeutic amounts of the therapeutic agent corresponding to a concentration of at least about 0.1 ug per ml of vitreous humor for an extended period of at least about three months. The reservoir and the porous structure can be configured to release therapeutic amounts of the therapeutic agent corresponding to a concentration of at least about 0.1 ug per ml of vitreous humor and no more than about 10 ug per ml for an extended period of at least about three months. The therapeutic agent may comprise at least a fragment of an antibody and a molecular weight of at least about 10 k Daltons. For example, the therapeutic agent may comprise one or more of ranibizumab or bevacizumab. Alternatively or in combination, the therapeutic agent may comprise a small molecule drug suitable for sustained release. The reservoir and the porous structure may be configured to release therapeutic amounts of the therapeutic agent corresponding to a concentration of at least about 0.1 ug per ml of vitreous humor and no more than about 10 ug per ml for an extended period of at least about 3 months or at least about 6 months. The reservoir and the porous structure can be configured to release therapeutic amounts of the therapeutic agent corresponding to a concentration of at least about 0.1 ug per ml of vitreous humor and no more than about 10 ug per ml for an extended period of at least about twelve months or at least about two years or at least about three years. The reservoir and the porous structure may also be configured to release therapeutic amounts of the therapeutic agent corresponding to a concentration of at least about 0.01 ug per ml of vitreous humor and no more than about 300 ug per ml for an extended period of at least about 3 months or 6 months or 12 months or 24 months.

The channels of the rigid porous structure comprise a hydrogel configured to limit a size of molecules passed through the channels of the rigid porous structure. For example, the hydrogel can be formed within the channels and may comprise an acrylamide gel. The hydrogel comprises a water content of at least about 70%. For example, the hydrogel may comprise a water content of no more than about 90% to limit molecular weight of the therapeutic agent to about 30 k Daltons. The hydrogel comprises a water content of no more than about 95% to limit molecular weight of the therapeutic agent to about 100 k Daltons. The hydrogel may comprise a water content within a range from about 90% to about 95% such that the channels of the porous material are configured to pass Lucentis™ and substantially not pass Avastin™.

The rigid porous structure may comprise a composite porous material that can readily be formed in or into a wide range of different shapes and configurations. For example, the porous material can be a composite of a metal, aerogel or ceramic foam (i.e., a reticulated inter-cellular structure in which the interior cells are interconnected to provide a multiplicity of pores passing through the volume of the structure, the walls of the cells themselves being substantially continuous and non-porous, and the volume of the cells relative to that of the material forming the cell walls being such that the overall density of the intercellular structure is less than about 30 percent theoretical density) the through pores of which are impregnated with a sintered powder or aerogel. The thickness, density, porosity and porous characteristics of the final composite porous material can be varied to conform with the desired release of the therapeutic agent.

Embodiments comprise a method of making an integral (i.e., single-component) porous structure. The method may comprise introducing particles into a mold having a desired shape for the porous structure. The shape includes a proximal end defining a plurality of proximal porous channel openings to couple to the reservoir, a distal end defining a plurality of outlet channel openings to couple to the vitreous humor of the eye, a plurality of blind inlet cavities extending into the filter from the proximal openings, and a plurality of blind outlet cavities extending into the porous structure from the outlet channel openings. The method further includes applying pressure to the mold, thereby causing the particles to cohere and form a single component, and sintering the component to form the porous structure. The particles can be pressed and cohere to form the component without the use of a polymeric binder, and the porous structure can be formed substantially without machining.

The mold can be oriented vertically with the open other end disposed upwardly, and metal powder having a particle size of less than 20 micrometers can be introduced into the cavity through the open end of the mold while vibrating the mold to achieve substantially uniform packing of the metal powder in the cavity. A cap can be placed on the open other end of the mold, and pressure is applied to the mold and thereby to the metal powder in the cavity to cause the metal powder to cohere and form a cup-shaped powdered metal structure having a shape corresponding to the mold. The shaped powdered metal structure can be removed from the mold, and sintered to obtain a porous sintered metal porous structure.

The metal porous structure can be incorporated into the device by a press fit into an impermeable structure with an opening configured to provide a tight fit with the porous structure. Other means, such as welding, known to those skilled in the art can be used to incorporate the porous structure into the device. Alternatively, or in combination, the powdered metal structure can be formed in a mold where a portion of the mold remains with the shaped powdered metal structure and becomes part of the device. This may be advantageous in achieving a good seal between the porous structure and the device.

The release rate of therapeutic agent through a porous body, such as a sintered porous metal structure or a porous glass structure, may be described by diffusion of the of the therapeutic agent within the porous structure with the channel parameter, and with an effective diffusion coefficient equal to the diffusion coefficient of the therapeutic agent in the liquid that fills the reservoir multiplied by the Porosity and a Channel Parameter of the porous body:

Release Rate=$(D\,P/F)A(c_R-c_V)/L$, where:

$c_R$=Concentration in reservoir
$c_V$=Concentration outside of the reservoir or in the vitreous
D=Diffusion coefficient of the therapeutic agent in the reservoir solution
P=Porosity of porous structure
F=Channel parameter that may correspond to a tortuosity parameter of channels of porous structure
A=Area of porous structure
L=Thickness (length) of porous structure Cumulative Release=$1-cR/cR0=1-\exp((-D\,PA/FL\,V_R)t)$, where t=time, Vr=reservoir volume The release rate index can (hereinafter RRI) be used to determine release of the therapeutic agent. The RRI may be defined as (PA/FL), and the RRI values herein will have units of mm unless otherwise indicated. Many of the porous structures used in the therapeutic delivery devices described here have an RRI of no more than about 5.0, often no more than about 2.0, and can be no more than about 1.2 mm.

The channel parameter can correspond to an elongation of the path of the therapeutic agent released through the porous structure. The porous structure may comprise many interconnecting channels, and the channel parameter can correspond to an effective length that the therapeutic agent travels along the interconnecting channels of the porous structure from the reservoir side to the vitreous side when released. The channel parameter multiplied by the thickness (length) of the porous structure can determine the effective length that the therapeutic agent travels along the interconnecting channels from the reservoir side to the vitreous side. For example, the channel parameter (F) of about 1.5 corresponds to interconnecting channels that provide an effective increase in length traveled by the therapeutic agent of about 50%, and for a 1 mm thick porous structure the effective length that the therapeutic agent travels along the interconnecting channels from the reservoir side to the vitreous side corresponds to about 1.5 mm. The channel parameter (F) of at least about 2 corresponds to interconnecting channels that provide an effective increase in length traveled by the therapeutic agent of about 100%, and for a 1 mm thick porous structure the effective length that the therapeutic agent travels along the interconnecting channels from the reservoir side to the vitreous side corresponds to at least about 2.0 mm. As the porous structure comprises many interconnecting channels that provide many alternative paths for release of the therapeutic agent, blockage of some of the channels provides no substantial change in the effective path length through the porous structure as the alternative interconnecting channels are available, such that the rate of diffusion through the porous structure and the release of the therapeutic agent are substantially maintained when some of the channels are blocked.

If the reservoir solution is aqueous or has a viscosity similar to water, the value for the diffusion coefficient of the therapeutic agent (TA) in water at the temperature of interest may be used. The following equation can be used to estimate the diffusion coefficient at 37° C. from the measured value of $D_{BSA,20C}$=6.1 e-7 cm2/s for bovine serum albumin in water at 20° C. (Molokhia et al, *Exp Eye Res* 2008):

$$D_{TA,37C}=D_{BSA,20C}(\eta_{20C}/\eta_{37C})(MW_{BSA}/MW_{TA})^{1/3}$$
where

MW refers to the molecular weight of either BSA or the test compound and $\eta$ is the viscosity of water. The following lists diffusion coefficients of proteins of interest.

| Compound | MW | Temp C. | Diff Coeff (cm^2/s) |
|---|---|---|---|
| BSA | 69,000 | 20 | 6.1E−07 |
| BSA | 69,000 | 37 | 9.1E−07 |
| Ranibizumab | 48,000 | 20 | 6.9E−07 |
| Ranibizumab | 48,000 | 37 | 1.0E−06 |
| Bevacizumab | 149,000 | 20 | 4.7E−07 |
| Bevacizumab | 149,000 | 37 | 7.1E−07 |

Small molecules have a diffusion coefficient similar to fluorescein (MW=330, D=4.8 to 6 e-6 cm$^2$/s from Stay, M S et al. *Pharm Res* 2003, 20 (1), pp. 96-102). For example, the small molecule may comprise a glucocorticoid such as triamcinolone acetonide having a molecular weight of about 435.

The porous structure comprises a porosity, a thickness, a channel parameter and a surface area configured to release therapeutic amounts for the extended period. The porous material may comprise a porosity corresponding to the fraction of void space of the channels extending within the material. The porosity comprises a value within a range from about 3% to about 70%. In other embodiments, the porosity comprises a value with a range from about 5% to about 10% or from about 10% to about 25%, or for example from about 15% to about 20%. Porosity can be determined from the weight and macroscopic volume or can be measured via nitrogen gas adsorption The porous structure may comprise a plurality of porous structures, and the area used in the above equation may comprise the combined area of the plurality of porous structures.

The channel parameter may comprise a fit parameter corresponding to the tortuosity of the channels. For a known porosity, surface area and thickness of the surface parameter, the curve fit parameter F, which may correspond to tortuosity of the channels can be determined based on experimental measurements. The parameter PA/FL can be used to determine the desired sustained release profile, and the values of P, A, F and L determined. The rate of release of the therapeutic agent corresponds to a ratio of the porosity to the channel parameter, and the ratio of the porosity to the channel parameter can be less than about 0.5 such that the porous structure releases the therapeutic agent for the extended period. For example, the ratio of the porosity to the channel parameter is less than about 0.1 or for example less than about 0.2 such that the porous structure releases the therapeutic agent for the extended period. The channel parameter may comprise a value of at least about 1, such as at least about 1.2. For example, the value of the channel parameter may comprise at least about 1.5, for example at least about 2, and may comprise at least about 5. The channel parameter can be within a range from about 1.1 to about 10, for example within a range from about 1.2 to about 5. A person of ordinary skill in the art can conduct experiments based on the teachings described herein to determine empirically the channel parameter to release the therapeutic agent for an intended release rate profile.

The area in the model originates from the description of mass transported in units of flux; i.e., rate of mass transfer per unit area. For simple geometries, such as a porous disc mounted in an impermeable sleeve of equal thickness, the area corresponds to one face of the disc and the thickness, L, is the thickness of the disc. For more complex geometries, such as a porous body in the shape of a truncated cone, the effective area is a value in between the area where therapeutic agent enters the porous body and the area where therapeutic agent exits the porous body.

A model can be derived to describe the release rate as a function of time by relating the change of concentration in the reservoir to the release rate described above. This model assumes a solution of therapeutic agent where the concentration in the reservoir is uniform. In addition, the concentration in the receiving fluid or vitreous is considered negligible ($c_V$=0). Solving the differential equation and rearrangement yields the following equations describing the concentration in the reservoir as a function of time, t, and volume of the reservoir, $V_R$, for release of a therapeutic agent from a solution in a reservoir though a porous structure.

$$c_R=c_{R0}\exp((-D\,PA/FL\,V_R)t)$$

and Cumulative Release=$1-c_R/c_{R0}$

When the reservoir contains a suspension, the concentration in reservoir, $c_R$, is the dissolved concentration in equilibrium with the solid (i.e., the solubility of the therapeutic agent). In this case, the concentration in the reservoir is constant with time, the release rate is zero order, and the cumulative release increases linearly with time until the time when the solid is exhausted.

Therapeutic concentrations for many ophthalmic therapeutic agents may be determined experimentally by measuring concentrations in the vitreous humor that elicit a therapeutic effect. Therefore, there is value in extending predictions of release rates to predictions of concentrations in the vitreous. A one-compartment model may be used to describe elimination of therapeutic agent from eye tissue.

Current intravitreal administration of therapeutic agents such as Lucentis™ involves a bolus injection. A bolus injection into the vitreous may be modeled as a single exponential with rate constant, k=0.693/half-life and a cmax=dose/$V_v$ where $V_v$ is the vitreous volume. As an example, the half-life for ranibizumab is approximately 3 days in the rabbit and the monkey (Gaudreault et al) and 9 days in humans (Lucentis™ package insert). The vitreous volume is approximately 1.5 mL for the rabbit and monkey and 4.5 mL for the human eye. The model predicts an initial concentration of 333 ug/mL for a bolus injection of 0.5 mg Lucentis™ into the eye of a monkey. This concentration decays to a vitreous concentration of 0.1 ug/mL after about a month.

For devices with extended release, the concentration in the vitreous changes slowly with time. In this situation, a model can be derived from a mass balance equating the release rate from the device (described by equations above) with the elimination rate from the eye, k $c_v$ $V_v$. Rearrangement yields the following equation for the concentration in the vitreous:

$$c_v=\text{Release rate from device}/kV_v.$$

Since the release rate from a device with a solution of therapeutic agent decreases exponentially with time, the concentration in the vitreous decreases exponentially with the same rate constant. In other words, vitreous concentration decreases with a rate constant equal to D PA/FL $V_R$ and, hence, is dependent on the properties of the porous structure and the volume of the reservoir.

Since the release rate is zero order from a device with a suspension of therapeutic agent, the vitreous concentration will also be time-independent. The release rate will depend on the properties of the porous structure via the ratio, PA/FL, but will be independent of the volume of the reservoir until the time at which the drug is exhausted.

The channels of the rigid porous structure can be sized in many ways to release the intended therapeutic agent. For example, the channels of the rigid porous structure can be sized to pass therapeutic agent comprising molecules having a molecular weight of at least about 100 Daltons or for example, at least about 50 k Daltons. The channels of the rigid porous structure can be sized to pass therapeutic agent comprising molecules comprising a cross-sectional size of no more than about 10 nm. The channels of the rigid porous structure comprise interconnecting channels configured to pass the therapeutic agent among the interconnecting channels. The rigid porous structure comprises grains of rigid material and wherein the interconnecting channels extend at least partially around the grains of rigid material to pass the therapeutic agent through the porous material. The grains of rigid material can be coupled together at a loci of attachment and wherein the interconnecting channels extend at least partially around the loci of attachment.

The porous structure and reservoir may be configured to release the glucocorticoid for an extended time of at least about six months with a therapeutic amount of glucocorticoid of corresponding to an in situ concentration within a range from about 0.05 ug/mL to about 4 ug/mL, for example from 0.1 ug/mL to about 4 ug/mL, so as to suppress inflammation in the retina-choroid.

The porous structure comprises a sintered material. The sintered material may comprise grains of material in which the grains comprise an average size of no more than about 20 um. For example, the sintered material may comprise grains of material in which the grains comprise an average size of no more than about 10 um, an average size of no more than about 5 um, or an average size of no more than about 1 um. The channels are sized to pass therapeutic quantities of the therapeutic agent through the sintered material for the extended time based on the grain size of the sintered material and processing parameters such as compaction force and time and temperature in the furnace. The channels can be sized to inhibit penetration of microbes including bacteria and fungal spores through the sintered material.

The sintered material comprises a wettable material to inhibit bubbles within the channels of the material.

The sintered material comprises at least one of a metal, a ceramic, a glass or a plastic. The sintered material may comprises a sintered composite material, and the composite material comprises two or more of the metal, the ceramic, the glass or the plastic. The metal comprises at least one of Ni, Ti, nitinol, stainless steel including alloys such as 304, 304L, 316 or 316L, cobalt chrome, elgiloy, hastealloy, c-276 alloy or Nickel 200 alloy. The sintered material may comprise a ceramic. The sintered material may comprise a glass. The plastic may comprise a wettable coating to inhibit bubble formation in the channels, and the plastic may comprise at least one of polyether ether ketone (PEEK), polyethylene, polypropylene, polyimide, polystyrene, polycarbonate, polyacrylate, polymethacrylate, or polyamide.

The rigid porous structure may comprise a plurality of rigid porous structures coupled to the reservoir and configured to release the therapeutic agent for the extended period. For example, additional rigid porous structure can be disposed along the container, for example the end of the container may comprise the porous structure, and an additional porous structure can be disposed along a distal portion of the container, for example along a tubular sidewall of the container.

The therapeutic device can be tuned to release therapeutic amounts of the therapeutic agent above the minimum inhibitory concentration for an extended time based on bolus injections of the therapeutic agent. For example, the volume of the chamber of the reservoir can be sized with the release rate of the porous structure based on the volume of the bolus injection. A formulation of a therapeutic agent can be provided, for example a known intravitreal injection formulation. The therapeutic agent can be capable of treating the eye with bolus injections, such that the formulation has a corresponding period between each of the bolus injections to treat the eye. For example the bolus injections may comprise monthly injections. Each of the bolus injections comprises a volume of the formulation, for example 50 uL. Each of the bolus injections of the therapeutic agent may correspond to a range of therapeutic concentrations of the therapeutic agent within the vitreous humor over the time course between injections, and the device can be tuned so as to release therapeutic amounts of the therapeutic agent such that the vitreous concentrations of the released therapeutic agent from the device are within the range of therapeutic concentrations of the corresponding bolus injections. For example, the therapeutic agent may comprise a minimum inhibitory concentration to treat the eye, for example at least about 3 ug/mL, and the values of the range of therapeutic concentrations can be at least about 3 ug/mL. The therapeutic device can be configured to treat the eye with an injection of the monthly volume of the formulation into the device, for example through the penetrable barrier. The reservoir of the container has a chamber to contain a volume of the therapeutic agent, for example 35 uL, and a mechanism to release the therapeutic agent from the chamber to the vitreous humor.

The volume of the container and the release mechanism can be tuned to treat the eye with the therapeutic agent with vitreous concentrations within the therapeutic range for an extended time with each injection of the quantity corresponding to the bolus injection, such that the concentration of the therapeutic agent within the vitreous humor remains within the range of therapeutic concentrations and comprises at least the minimum inhibitory concentration. The extended time may comprise at least about twice the corresponding period of the bolus injections. The release mechanism comprises one or more of a porous frit, a sintered porous frit, a permeable membrane, a semi-permeable membrane, a capillary tube or a tortuous channel, nano-structures, nano-channels or sintered nano-particles. For example, the porous frit may comprises a porosity, cross sectional area, and a thickness to release the therapeutic agent for the extended time. The volume of the container reservoir can be sized in many ways in relation to the volume of the injected formulation and can be larger than the volume of injected formulation, smaller than the volume of injected formulation, or substantially the same as the volume of injected formulation. For example, the volume of the container may comprise no more than the volume of the formulation, such that at least a portion of the formulation injected into the reservoir passes through the reservoir and comprises a bolus injection to treat the patient immediately. As the volume of the reservoir is increased, the amount of formulation released to the eye through the porous structure upon injection can decrease along with the concentration of active ingredient of the therapeutic agent within the reservoir, and the release rate index can be increased appropriately so as to provide therapeutic amounts of therapeutic agent for the extended time. For example, the volume of the reservoir of the container can be greater than the volume corresponding to the bolus injection, so as to provide therapeutic amounts for at least about five months, for example 6 months, with an injection volume corresponding to a monthly injection of Lucentis™. For example, the formulation may comprise commercially available Lucentis™, 50 uL, and the reservoir may comprise a volume of about 100 uL and provide therapeutic vitreous concentrations of at least about 3 ug/mL for six months with 50 uL of Lucentis™ injected into the reservoir.

The chamber may comprise a substantially fixed volume and the release rate mechanism comprises a substantially rigid structure to maintain release of the therapeutic agent above the minimum inhibitory concentration for the extended time with each injection of a plurality of injections.

A first portion of the injection may pass through the release mechanism and treat the patient when the formulation is injected, and a second portion of the formulation can be contained in the chamber when the formulation is injected.

FIG. 6B-1 shows interconnecting channels 156 extending from first side 150S1 to second side 150S2 of the porous structure as in FIG. 6B. The interconnecting channels 156 extend to a first opening 158A1, a second opening 158A2 and an Nth opening 158AN on the first side 150S1. The interconnecting channels 156 extend to a first opening 158B1, a second opening 158B2 and an Nth opening 158BN on the second side 150S2. Each of the openings of the plurality of channels on the first side is connected to each of the openings of plurality of channels on the second side, such that effective length traveled along the channels is greater than thickness 150T. The channel parameter can be within a range from about 1.1 to about 10, such that the effective length is within a range from about 1.1 to 10 times the thickness 150T. For example, the channel parameter can be about 1 and the porosity about 0.2, such that the effective length corresponds to at least about 5 times the thickness 150T.

FIG. 6B-2 shows a plurality of paths of the therapeutic agent along the interconnecting channels extending from a first side 150S1 to a second side 150S2 of the porous structure as in FIGS. 6B and 6B-1. The plurality of paths comprises a first path 156P1 extending from the first side to the second side, a second path 156P2 extending from the first side to the second side and a third path 156P3 extending from the first side to the second side, and many additional paths. The effect length of each of first path P1, second path P2 and third path P3 is substantially similar, such that each opening on the first side can release the therapeutic agent to each interconnected opening on the second side. The substantially similar path length can be related to the sintered grains of material and the channels that extend around the sintered material. The porous structure may comprise randomly oriented and connected grains of material, packed beads of material, or combinations thereof. The channel parameter can be related to the structure of the sintered grains of material and corresponding interconnecting channels, porosity of the material, and percolation threshold. Work in relation to embodiments shows that the percolation threshold of the sintered grains may be below the porosity of the porous frit structure, such that the channels are highly inter-connected. The sintered grains of material can provide interconnected channels, and the grains can be selected to provide desired porosity and channel parameters and RRI as described herein.

The channel parameter and effective length from the first side to the second side can be configured in many ways. The channel parameter can be greater than 1 and within a range from about 1.2 to about 5.0, such that the effective length is within a range about 1.2 to 5.0 times the thickness 150T, although the channel parameter may be greater than 5, for example within a range from about 1.2 to 10. For example, the channel parameter can be from about 1.3 to about 2.0, such that the effective length is about 1.3 to 2.0 times the thickness 150T. For example, experimental testing has shown the channel parameter can be from about 1.4 to about 1.8, such that the effective length is about 1.4 to 1.8 times the thickness 150T, for example about 1.6 times the thickness. These values correspond to the paths of the channels around the sintered grains of material, and may correspond, for example, to the paths of channels around packed beads of material.

FIG. 6B-3 shows blockage of the openings with a covering 156B and the plurality of paths of the therapeutic agent along the interconnecting channels extending from a first side to a second side of the porous structure as in FIGS. 6B and 6B-1. A plurality of paths 156PR extend from the first side to the second side couple the first side to the second side where one of the sides is covered, such that the flow rate is maintained when one of the sides is partially covered.

Figures 4, 6B:
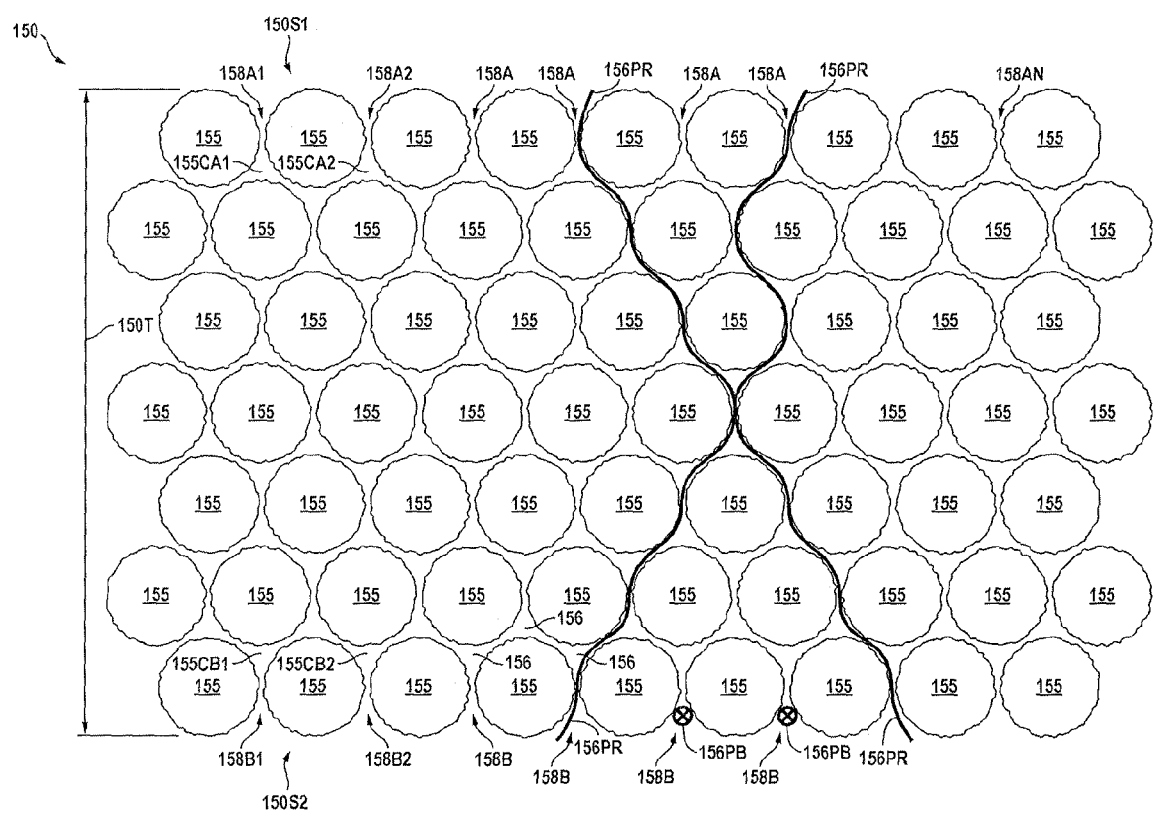
Figures 5, 6B:
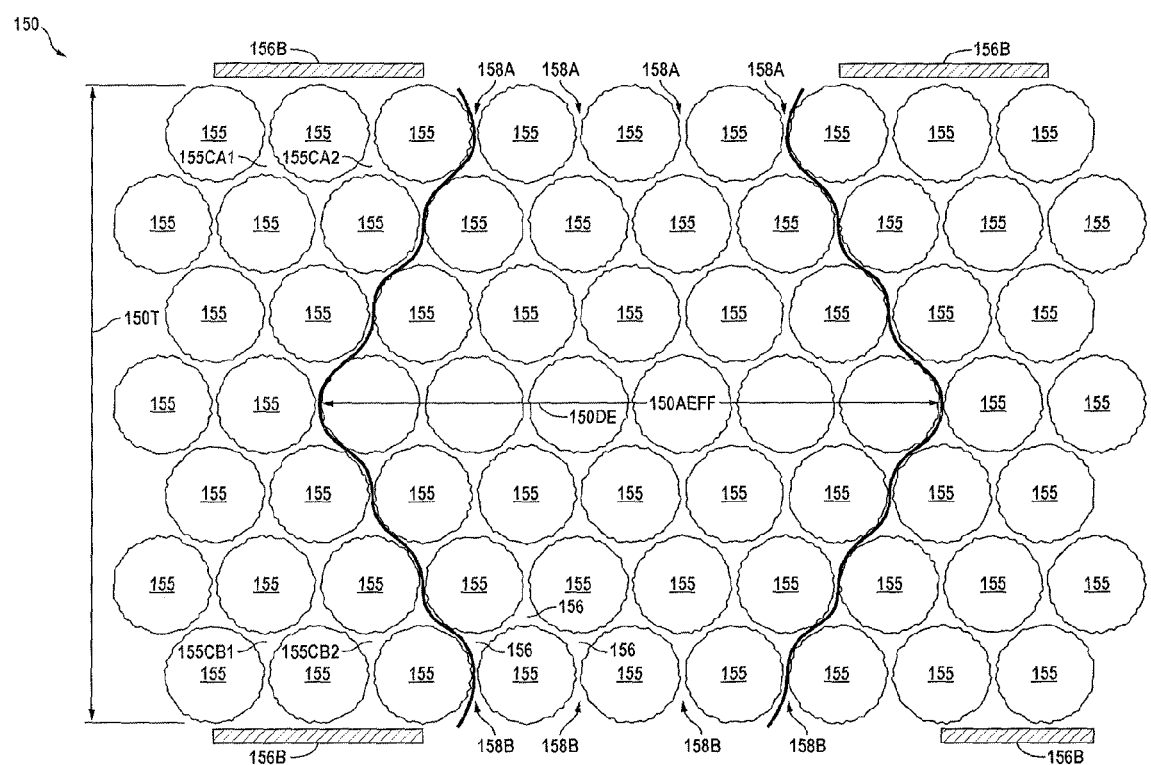

FIG. 6B-4 shows blockage of the openings with particles 156PB and the plurality of paths of the therapeutic agent along the interconnecting channels extending from a first side to a second side of the porous structure as in FIGS. 6B and 6B-1. The plurality of paths 156PR extend from the first side to the second side couple the first side to the second side where one of the sides is covered, such that the flow rate is maintained when one of the sides is partially covered FIG. 6B-5 shows an effective cross-sectional size 150DE and area 150EFF corresponding to the plurality of paths of the therapeutic agent along the interconnecting channels extending from a first side to a second side of the porous structure as in FIGS. 6B and 6B-1. The effective cross sectional area of the interconnecting channels corresponds to the internal cross-sectional area of the porous structure disposed between the openings of the first side and the openings of the second side, such that the rate of release can be substantially maintained when the channels are blocked on the first side and the second side.

The rigid porous structure can be shaped and molded in many ways for example with tubular shapes, conical shapes, discs and hemispherical shapes. The rigid porous structure may comprise a molded rigid porous structure. The molded rigid porous structure may comprises at least one of a disk, a helix or a tube coupled to the reservoir and configured to release the therapeutic agent for the extended period.

Figure 6C:
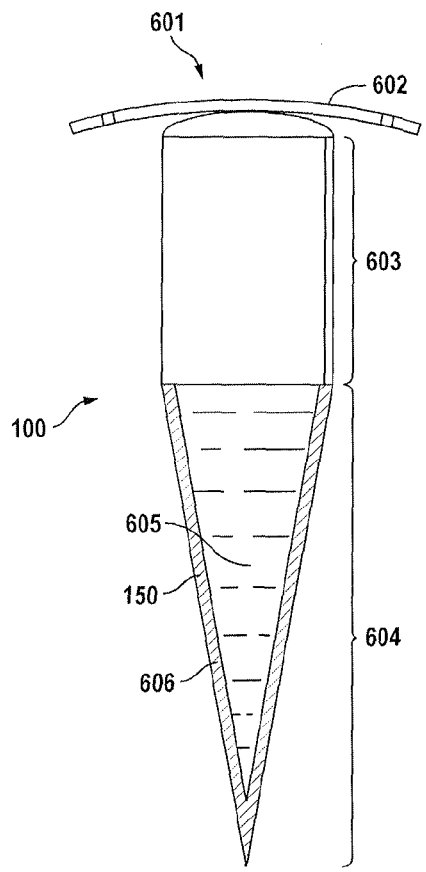
FIG. 6C shows a rigid porous structure as in FIG. 6B incorporated into a scleral tack.

FIG. 6C shows a rigid porous structure as in FIG. 6B incorporated into a scleral tack 601 as described in U.S. Pat. No. 5,466,233. The scleral tack comprises a head 602, a central portion 603 and a post 604. The post may comprise the reservoir 605 and the rigid porous structure 606 as described above. The porous structure may comprise a molded conical structure having a sharp tip configured for insertion into the patient. Alternatively or in combination, the tip may be rounded.

Figure 6D:
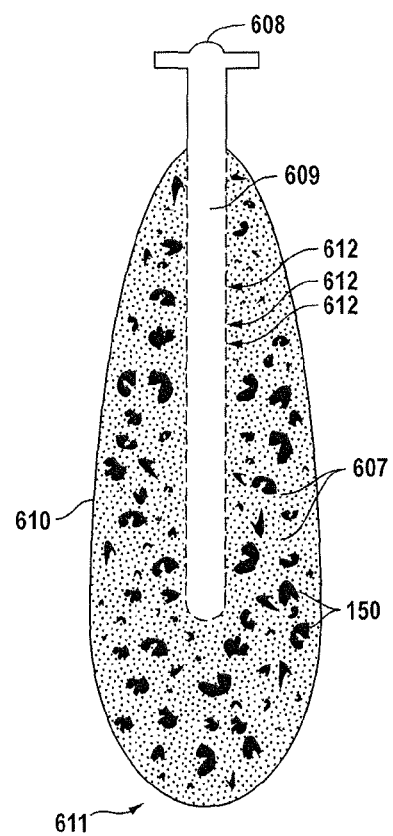
FIG. 6D, shows a rigid porous structure as in FIG. 6B coupled with a reservoir for sustained release.
Figure 6E:
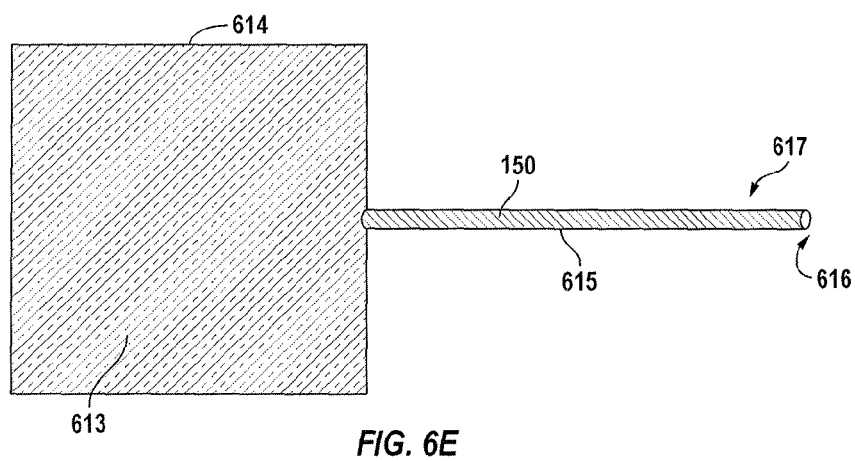
FIG. 6E shows a rigid porous structure as in FIG. 6B comprising a hollow body or tube for sustained release.

FIG. 6E, shows a plurality of rigid porous structures as in FIG. 6B incorporated with a drug delivery device for sustained release as described in U.S. Pat. No. 5,972,369. The therapeutic device comprises a reservoir 613 to contain the therapeutic agent and an impermeable and non-porous outer surface 614. The reservoir is coupled to a rigid porous structure 615 that extends to a distal end 617. The rigid porous structure comprises an exposed area 616 on the distal end to release the therapeutic agent, and the impermeable and non-porous outer surface may extend to the distal end.

FIG. 6D shows a rigid porous structure as in FIG. 6B incorporated with a delivery device for sustained release as described in U.S. Pat. Pub. 2003/0014036 A1. The drug delivery device comprises an inlet port 608 on the proximal end and a hollow body 609 coupled to the inlet port. The hollow body comprises many openings 612 that allow a solution injected into the inlet port to pass from the hollow body into a balloon 610. The balloon comprises a distal end 611 disposed opposite the injection port. The balloon comprises a plurality of the rigid porous structures 607, as described above. Each of the plurality of porous rigid structures comprises a first surface exposed to the interior of the balloon and a second surface configured to contact the vitreous. The calculated area can be the combined area of the plurality of porous rigid structures as noted above.

Figure 6F:
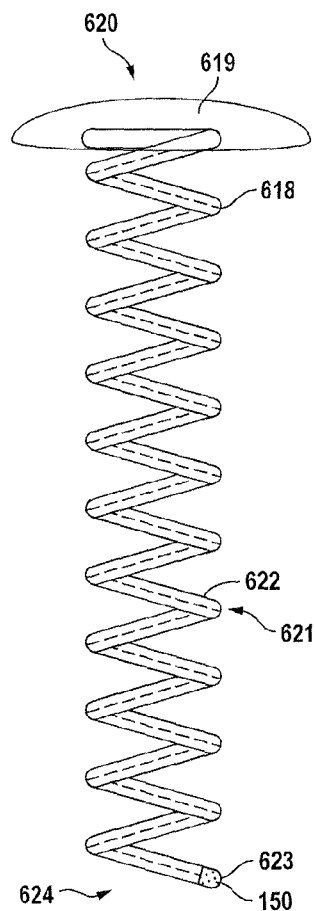
FIG. 6F shows a rigid porous structure as in FIG. 6B comprising a non-linear helical structure for sustained release.

FIG. 6F shows a rigid porous structure as in FIG. 6B incorporated with a non-linear body member 618 for sustained release as described in U.S. Pat. No. 6,719,750. The non-linear member may comprise a helical shape. The non-linear member can be coupled to a cap 619 on the proximal end 620. The non-linear member may comprise a lumen 621 filled with therapeutic agent so as to comprise a reservoir 622. The porous structure 623 can be disposed on a distal end 624 of the non-linear member to release the therapeutic agent. The porous structure may be located at additional or alternative locations of the non-linear member. For example a plurality of porous structures may be disposed along the non-linear member at locations disposed between the cap and distal end so as to release therapeutic agent into the vitreous humor when the cap is positioned against the sclera.

Figure 6G:
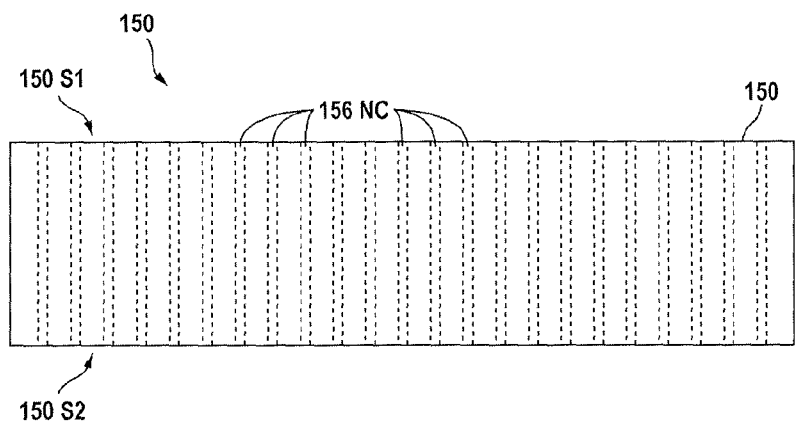
FIG. 6G shows porous nanostructures, in accordance with embodiments.

FIG. 6G shows porous nanostructures, in accordance with embodiments. The porous structure 150 may comprise a plurality of elongate nano-channels 156NC extending from a first side 150S1 of the porous structure to a second side 150S2 of the porous structure. The porous structure 150 may comprise a rigid material having the holes formed thereon, and the holes may comprise a maximum dimension across such as a diameter. The diameter of the nano-channels may comprise a dimension across, for example from about 10 nm across, to about 1000 nm across, or larger. The channels may be formed with etching of the material, for example lithographic etching of the material. The channels may comprise substantially straight channels such that the channel parameter F comprises about 1, and the parameters area A, and thickness or length L correspond to the combined cross-sectional area of the channels and the thickness or length of the porous structure.

The porous structure 150 may comprise interconnecting nano-channels, for example formed with a sintered nano-material.

The injection of therapeutic agent into the device 100 as described herein can be performed before implantation into the eye or alternatively when the therapeutic device is implanted into the eye.

FIG. 7 shows a therapeutic device 100 coupled to an injector 701 that removes material from the device and injects therapeutic agent 702 into the device. The injector picks up spent media 703 and refills the injector with fresh therapeutic agent. The therapeutic agent is injected into the therapeutic device. The spent media is pulled up into the injector. The injector may comprise a stopper mechanism 704.

The injector 701 may comprise a first container 702C to contain a formulation of therapeutic agent 702 and a second container 703C to receive the spent media 703. Work in relation to embodiments suggests that the removal of spent media 703 comprising material from the container reservoir of the therapeutic device can remove particulate from the therapeutic device, for example particles comprised of aggregated therapeutic agent such as protein. The needle 189 may comprise a double lumen needle with a first lumen coupled to the first container and a second lumen coupled to the second container, such that spent media 703 passes from the container reservoir of device 100 to the injector. A valve 703V, for example a vent, can be disposed between the second lumen and the second container. When the valve is open and therapeutic agent is injected, spent media 703 from the container reservoir of the therapeutic device 100 passes to the second container of the injector, such that at least a portion of the spent media within the therapeutic device is exchanged with the formulation. When the valve is closed and the therapeutic agent is injected, a portion of the therapeutic agent passes from the reservoir of the therapeutic device into the eye. For example, a first portion of formulation of therapeutic agent can be injected into therapeutic device 100 when the valve is open such that the first portion of the formulation is exchanged with material disposed within the reservoir; the valve is then closed and a second portion of the formulation is injected into therapeutic device 100 such that at least a portion of the first portion passes through the porous structure into the eye. Alternatively or in combination, a portion of the second portion of injected formulation may pass through the porous structure when the second portion is injected into the eye. The second portion of formulation injected when the valve is closed may correspond to a volume of formulation that passes through the porous structure into the vitreous humor to treat the patient immediately.

The needle 189 may comprise a dual lumen needle, for example as described with reference to FIG. 7A2 shown below.

FIG. 7A shows a therapeutic device 100 coupled to an injector 701 to inject and remove material from the device. The injector may comprise a two needle system configured to insert into a container of the device. The injector may simultaneously inject therapeutic agent through the first needle 705 (the injection needle) while withdrawing liquid from the device through the second needle 706 (the vent needle). The injection needle may be longer and/or have a smaller diameter than the vent needle to facilitate removal of prior material from the device. The vent needle may also be attached to a vacuum to facilitate removal of prior material from the device.

FIG. 7A-1 shows a therapeutic device 100 comprising a penetrable barrier coupled to an injector needle 189 comprising a stop 189S that positions the distal end of the needle near the proximal end of the reservoir 130 of the device to flush the reservoir with ejection of liquid formulation through the porous frit structure, in accordance with embodiments. For example, the injector needle may comprise a single lumen needle having a bevel that extends approximately 0.5 mm along the shaft of the needle from the tip of the needle to the annular portion of the needle. The stop can be sized and positioned along an axis of the needle such that the needle tip extends a stop distance 189SD into the reservoir as defined by the length of the needle from the stop to the tip and the thickness of the penetrable barrier, in which the stop distance is within a range from about 0.5 to about 2 mm. The reservoir may extend along an axis of the therapeutic device distance within a range from about 4 to 8 mm. A volume comprising a quantity of liquid formulation within a range from about 20 to about 200 uL, for example about 50 uL can be injected into the therapeutic device with the needle tip disposed on the distal end. The volume of the reservoir can be less than the injection volume of the formulation of therapeutic agent, such that liquid is flushed through the porous structure 150. For example, the reservoir may comprise a volume within a range from about 20 to 40 uL, and the injection volume of the liquid formulation of therapeutic agent may comprise about 40 to 100 uL, for example about 50 uL.

FIG. 7A-2 shows a therapeutic device comprising a penetrable barrier coupled to a needle 189 of an injector 701 to inject and remove material from the device such that the liquid in the reservoir 130 is exchanged with the injected formulation. The needle comprises at least one lumen and may comprise a concentric double lumen needle 189DL with a distal end coupled to the inner lumen to inject formulation of the therapeutic agent into the therapeutic device and a proximal vent 189V to receive liquid into the needle when the formulation is injected. Alternatively, the vent may correspond to an opening on the distal end of the inner lumen of the needle and the outer lumen may comprise a proximal opening to inject therapeutic agent formulation into a proximal portion of the container reservoir.

Work in relation to the injector embodiments indicates that a filling efficiency of at least about 80%, for example 90% or more can be achieved with injector apparatus and needles as described above.

FIG. 7B-1 shows a side cross-sectional view of therapeutic device 100 comprising a retention structure having a cross-section sized to fit in an elongate incision. The cross-section sized to fit in the elongate incision may comprise a narrow portion 120N of retention structure 120 that is sized smaller than the flange 122. The narrow portion 120N sized to fit in the elongate incision may comprise an elongate cross section 120NE sized to fit in the incision. The narrow portion 120N may comprise a cross-section having a first cross-sectional distance across, or first dimensional width, and a second cross-sectional distance across, or second dimensional width, in which the first cross-sectional distance across is greater than the second cross-sectional distance across such that the narrow portion 120N comprises an elongate cross-sectional profile.

The elongate cross section 120NE of the narrow portion 120N can be sized in many ways to fit the incision. The elongate cross section 120NE comprises a first dimension longer than a second dimension and may comprise one or more of many shapes such as dilated slit, dilated slot, lentoid, oval, ovoid, or elliptical. The dilated slit shape and dilated slot shape may correspond to the shape sclera tissue assumes when cut and dilated. The lentoid shape may correspond to a biconvex lens shape. The elongate cross-section of the narrow portion may comprise a first curve along an first axis and a second curve along a second axis different than the first curve.

Similar to the narrow portion 120N of the retention structure, the container reservoir may comprise a cross-sectional profile FIG. 7B-2 shows an isometric view of the therapeutic device as in FIG. 7B-1.

FIG. 7B-3 shows a top view of the therapeutic device as in FIG. 7B-1.

FIG. 7B-4 shows a side cross sectional view along the short side of the retention structure of the therapeutic device as in FIG. 7B-1.

FIG. 7B-5 shows a bottom view of the therapeutic device as in FIG. 7B-1 implanted in the sclera.

FIG. 7B-5A shows a cutting tool 710 comprising a blade 714 having a width 712 corresponding to perimeter 160P of the barrier 160 and the perimeter 160NP of the narrow portion. The cutting tool can be sized to the narrow portion 120N so as to seal the incision with the narrow portion when the narrow portion is positioned against the sclera. For example, the width 712 may comprise about one half of the perimeter 160P of the barrier 160 and about one half of the perimeter 160NP of the narrow portion 160N. For example, the outside diameter of the tube of barrier 160 may comprise about 3 mm such that the perimeter of 160P comprises about 6 mm, and the narrow portion perimeter 160NP may comprise about 6 mm. The width 712 of the blade 710 may comprise about 3 mm such that the incision comprises an opening having a perimeter of about 6 mm so as to seal the incision with the narrow portion 160P. Alternatively, perimeter 160P of barrier 160 may comprise a size slightly larger than the incision and the perimeter of the narrow portion.

The retention structure comprises a narrow section 120N having a short distance 120NS and a long distance 120NL so as to fit in an elongate incision along the pars plana of the eye. The retention structure comprises an extension 122. The extension of the retention structure 120E comprises a short distance across 122S and a long distance across 122S, aligned with the short distance 122NS and long distance 122NL of the narrow portion 120N of the retention structure 120. The narrow portion 120 may comprise an indentation 120I sized to receive the sclera.

FIGS. 7B-6A and 7B-6B show distal cross-sectional view and a proximal cross-sectional view, respectively, of therapeutic device 100 comprising a non-circular cross-sectional size. The porous structure 150 can be located on a distal end portion of the therapeutic device, and the retention structure 120 can be located on a proximal portion of therapeutic device 100. The barrier 160 defines a size of reservoir 130. The barrier 160 and reservoir 130 may each comprise an elliptical or oval cross-sectional size, for example. The barrier 160 comprises a first cross-sectional distance across reservoir 130, and a second cross-sectional distance across reservoir 130, and the first distance across may extend across a long (major) axis of an ellipse and the second distance across may extend across a short (minor) axis of the ellipse. This elongation of the device along one direction can allow for increased drug in the reservoir with a decrease interference in vision, for example, as the major axis of the ellipse can be aligned substantially with the circumference of the pars plana region of the eye extending substantially around the cornea of the eye, and the minor axis of the ellipse can be aligned radially with the eye so as to decrease interference with vision as the short axis of the ellipse extends toward the optical axis of the eye corresponding to the patient's line of sight through the pupil. Although reference is made to an elliptical or oval cross-section, many cross-sectional sizes and shapes can be used such as rectangular with a short dimension extending toward the pupil of the eye and the long dimension extending along the pars plana of the eye.

The retention structure 120 may comprise structures corresponding to structure of the cross-sectional area. For example, the extension 122 may comprise a first distance across and a second distance across, with the first distance across greater than the second distance across. The extension may comprise many shapes, such as rectangular, oval, or elliptical, and the long distance across can correspond to the long distance of the reservoir and barrier. The retention structure 120 may comprise the narrow portion 120N having an indentation 120I extending around an access port to the therapeutic device, as described above. The indentation 120I and extension 122 may each comprise an elliptical or oval profile with a first long (major) axis of the ellipse extending in the first direction and a second short (minor) axis of the ellipse extending in the second direction. The long axis can be aligned so as to extend circumferentially along the pars plana of the eye, and the short axis can be aligned so as to extend toward the pupil of the eye, such that the orientation of device 100 can be determined with visual examination by the treating physician.

FIG. 7B-6C shows an isometric view of the therapeutic device having a retention structure comprising a narrow portion 120N with an elongate cross-sectional size 120NE.

FIG. 7B-6D shows a distal end view of the therapeutic device as in FIG. 7B-6C.

FIG. 7B-6E1 shows a side view of the short distance 120NS of the narrow portion 120N of the therapeutic device as in FIG. 7B-6C.

FIG. 7B-6E2 shows a side view of the long distance 120NL of the narrow portion 120N of the therapeutic device 100 as in FIG. 7B-6C.

FIG. 7B-6F shows a proximal view of the therapeutic device as in FIG. 7B-6C.

FIG. 7B-6G to FIG. 7B-6I show exploded assembly drawings for the therapeutic device 100 as in FIGS. 7B-6C to 7B-6F. The assembly drawings of FIGS. 7B-6G, FIG. 7B-6H and FIG. 7B-6I show isometric and thin side profiles views, respectively, of the elongate portion 120NE of the narrow portion of the retention structure 120N. The therapeutic device 100 has an elongate axis 100A.

The penetrable barrier 184, for example the septum, can be inserted into the access port 180. The penetrable barrier may comprise an elastic material sized such that the penetrable barrier can be inserted into the access port 180. The penetrable barrier may comprise one or more elastic materials such as siloxane or rubber. The penetrable barrier may comprise tabs 184T to retain the penetrable barrier in the access port. The penetrable barrier 184 may comprise a beveled upper rim 184R sized to seal the access port 180. The access port 180 of the reservoir container 130 may comprise a beveled upper surface to engage the beveled rim and seal the penetrable barrier against the access port 180 when the tabs 184T engage an inner annular or elongate channel of the access port. The penetrable barrier 184 may comprise an opaque material, for example a grey material, for example silicone, such that the penetrable barrier can be visualized by the patient and treating physician.

The reservoir container 130 of the device may comprise a rigid biocompatible material that extends at least from the retention structure to the rigid porous structure, such that the reservoir comprises a substantially constant volume when the therapeutic agent is released with the rigid porous structure so as to maintain a stable release rate profile, for example when the patient moves. Alternatively or in combination, the reservoir container 130 may comprise an optically transmissive material such that the reservoir container 130 can be translucent, for example transparent, such that the chamber of reservoir 140 can be visualized when the device is loaded with therapeutic agent outside the patient prior to implantation, for example when injected with a formulation of therapeutic agent prior to implantation in the physician's office. This visualization of the reservoir 140 can be helpful to ensure that the reservoir 140 is properly filled with therapeutic agent by the treating physician or assistant prior to implantation. The reservoir container may comprise one or more of many biocompatible materials such as acrylates, polymethylmethacrylate, siloxanes, metals, titanium stainless steel, polycarbonate, polyetheretherketone (PEEK), polyethylene, polyethylene terephthalate (PET), polyimide, polyamide-imide, polypropylene, polysulfone, polyurethane, polyvinylidene fluoride or PTFE. The biocompatible material of the reservoir container may comprise an optically transmissive material such as one or more of acrylate, polyacrylate, methlymethacraylate, polymethlymethacrylate (PMMA), polyacarbonate or siloxane. The reservoir container 130 can be machined from a piece of material, or injection molded, so as to form the retention structure 120 comprising flange 122 and the elongate narrow portion 120NE. The flange 122 may comprise a translucent material such that the physician can visualize tissue under the flange to assess the patient and to decrease appearance of the device 100 when implanted. The reservoir container 130 may comprise a channel extending along axis 100A from the access port 180 to porous structure 150, such that formulation injected into device 100 can be release in accordance with the volume of the reservoir and release rate of the porous structure 150 as described herein. The porous structure 150 can be affixed to the distal end of therapeutic device 100, for example with glue. Alternatively or in combination, the distal end of the reservoir container 130 may comprise an inner diameter sized to receive the porous structure 150, and the reservoir container 130 may comprise a stop to position the porous structure 150 at a predetermined location on the distal end so as to define a predetermined size of reservoir 140.

FIG. 7C-1 shows an expandable therapeutic device 790 comprising expandable barrier material 160 and support 160S in an expanded configuration for extended release of the therapeutic agent. The expanded configuration can store an increased amount of therapeutic agent, for example from about 30 uL to about 100 uL. The expandable device comprises a retention structure 120, an expandable reservoir 140. The support 160S may comprise a resilient material configured for compression, for example resilient metal or thermoplastic. Alternatively, the expandable support may be bent when expanded. The expandable device comprises the porous structure 150 disposed on a distal end, and affixed to the expandable support. The expandable device may comprise an access port 180, for example with a penetrable barrier 184. In the expanded configuration, the device is substantially clear from a majority of the optical path OP of the patient The support 160S of the barrier 160 can provide a substantially constant volume of the reservoir in the expanded configuration. The substantially constant volume, for example +/−25%, can be combined with the release rate index of the porous structure 150 so as to tune the expanded reservoir and porous structure to the volume of therapeutic agent to be injected into the therapeutic device as described herein. The barrier 160 may comprise a thin compliant material, for example a membrane, and the support 160S can urge the barrier 160 to an expanded configuration so as to define the reservoir chamber having the substantially constant volume.

FIG. 7C-1A shows the distal end portion of the support 160S. The support 160S may comprise struts that extend to an annular flange 160SF that supports the porous structure 150 on the distal end of device 100.

FIG. 7C-1B shows the support 160S disposed inside the barrier 160 so as to provide the substantially constant expanded volume of the reservoir chamber.

FIG. 7C-1C shows the support 160S disposed along the inner surface of the barrier 160 so as to provide the substantially constant expanded volume of the reservoir chamber. The support 160 can be bonded to the barrier 160 in many ways, for example with a bonding agent such as glue or resin, or with thermal bonding. The support 160S can be disposed on the outside of barrier 160.

FIG. 7C-2 shows the expandable therapeutic device 790 as in FIG. 7C-1 in a narrow profile configuration suitable for use in an injection lumen.

FIG. 7C-3 shows the expandable therapeutic device as in FIG. 7C-1 in an expanded profile configuration, suitable for retention, for example with the sclera.

FIGS. 7C-4A and 7C-4B show an expandable retention structure 792. The expandable retention structure 792 can be used with the expandable therapeutic device 790, or with a substantially fixed reservoir and container device as described above. The expandable retention structure 792 comprises many compressible or expandable or resilient materials or combinations thereof. The expandable retention structure 792 comprises an extension 120E that can expand from the narrow profile configuration to the expanded configuration, for example with tabs and flanges comprising resilient material. The upper portion can be inclined proximally and the distal portion can be inclined distally, such that the retention structure expands to engage opposite sides of the sclera. The resilient material may comprise a thermoplastic material, a resilient metal, a shape memory material, and combinations thereof.

Figure 7D:
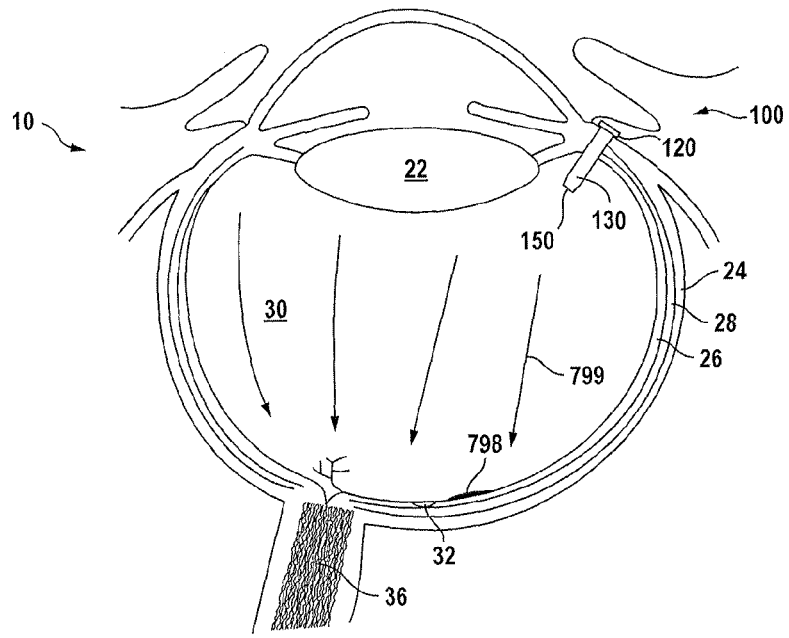
FIG. 7D shows a therapeutic device comprising a porous structure positioned in an eye to deliver a therapeutic agent to a target location on the retina, in accordance with embodiments

FIG. 7D shows therapeutic device 100 comprising porous structure 150 positioned in an eye 10 to deliver a therapeutic agent to a target location on or near the retina 26, for example choroidal neovascularization of a lesion on or near the retina. For example, the lesion may comprise one or more buckling, folding, bending or separation of the retina from the choroid related to neovascularization of corresponding vascular tissue associated with blood supply to the retina, and the neovascular tissue corresponding to the lesion of the retina may be targeted. Work in relation to embodiments indicates that the vitreous humor 30 of the eye may comprise convective current flows that extend along flow paths 799. The convective flow paths may comprise flow channels. Although small molecules can be delivered to a target location of the retina 26 in accordance with the flow paths, therapeutic agent comprising large molecules, for example with antibody fragments or antibodies, can be delivered substantially with the convective flow paths as the molecular diffusion of large molecules in the vitreous humor can be somewhat lower than small molecules.

The therapeutic device can be sized such that porous structure 150 is positioned along a flow path extending toward a target location of the retina. The therapeutic agent can be released along the flow path, such that the flow of vitreous humor transports the therapeutic agent to the retina. The porous structure can be disposed on a distal portion of the therapeutic device, for example on a distal end, and the reservoir 130 can be sized for delivery for the extended time. The retention structure 120 can be located on the proximal. The therapeutic device 100 can be sized such that the porous structure is positioned in the flow patch corresponding to the target region. The surgeon may identify a target region 798 of the retina, for example corresponding to a lesion, and the therapeutic device 100 can be positioned along the pars plana or other location such that the therapeutic agent is released to the target region.

Figure 7E:
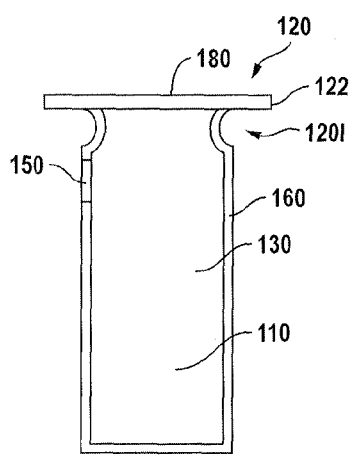
FIG. 7E shows a therapeutic device comprising a porous structure located on the device to deliver a therapeutic agent to one or more of the ciliary body or the trabecular meshwork when positioned in the eye, in accordance with embodiments.

FIG. 7E shows therapeutic device 100 comprising porous structure 150 located on a proximal portion of the device to deliver a therapeutic agent to one or more of the ciliary body or the trabecular meshwork when implanted in the eye. The porous structure 150 can be located near retention structure 120 such that the porous structure is positioned in the vitreous substantially away from the flow paths extending to retina, as noted above. The porous structure can be located on a side of the therapeutic device so as to release the therapeutic agent toward a target tissue. While many therapeutic agents can be used, the therapeutic agent may comprise a prostaglandin or analog, such as bimatoprost or latanoprost, such that the therapeutic agent can be released toward one or more of the ciliary body or trabecular meshwork when implanted in the vitreous humor with the retention structure coupled to the sclera.

Figure 7F:
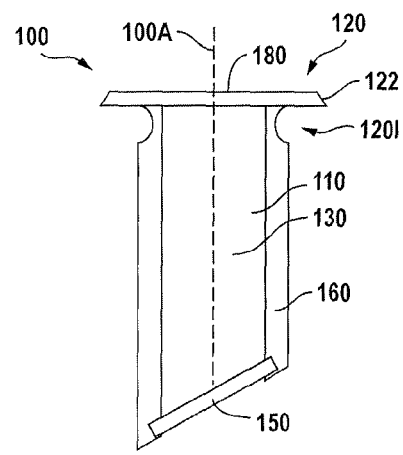
FIG. 7F shows therapeutic device 100 comprising porous structure 150 oriented to release the therapeutic agent away from the lens and toward the retina, in accordance with embodiments.

FIG. 7F shows therapeutic device 100 comprising porous structure 150 oriented to release the therapeutic agent 110 away from the lens and toward the retina. For example, the therapeutic agent 110 may comprise a steroid, and the steroid can be released from porous structure 150 away from the lens and toward the retina. For example, the porous structure can be oriented relative to an axis 100A of the therapeutic device. The outer side of porous structure 150 can be oriented at least partially toward the retina and away from the lens, for example along a flow path as described above so as to treat a target region of the retina. The barrier 160 can extend between the porous structure 160 and the lens of the eye when implanted such that release of therapeutic agent toward the lens can be inhibited with barrier 160. The retention structure 120 may comprise a long distance across and a short distance across as described above. The porous structure can be oriented in relation to the short and long distances of the extensions 122, such that the outer side of porous structure 150 is oriented at least partially toward the retina and along the flow path when the long distance of the retention structure extends along the pars plana and the short distance extends toward the pupil.

FIG. 7G shows a kit 789 comprising a placement instrument 750, a container 780, and a therapeutic device 100 disposed within the container. The reservoir of the therapeutic device 100 disposed in the container may comprise a non-therapeutic solution, for example saline, such that the channels of the porous structure comprise liquid water to inhibit bubble formation when the formulation of therapeutic agent is injected into the device 100. The kit may also comprise the syringe 188, needle 189 and stop 189S to insert the needle tip to a maximum stop distance within the reservoir as described above. The kit may contain instructions for use 789I, and may contain a container 110C comprising a formulation of therapeutic agent.

Tuning of Therapeutic Device for Sustained Release Based on an Injection of a Formulation The therapeutic device 100 can be tuned to deliver a target therapeutic concentration profile based on the volume of formulation injected into the device. The injected volume may comprise a substantially fixed volume, for example within about +/−30% of an intended pre-determined target volume. The volume of the reservoir can be sized with the release rate index so as to release the therapeutic agent for an extended time substantially greater than the treatment time of a corresponding bolus injection. The device can also be tuned to release the therapeutic agent based on the half life of the therapeutic agent in the eye. The device volume and release rate index comprise parameters that can be tuned together based on the volume of formulation injected and the half life of the therapeutic agent in the eye. The following equations can be used to determine therapeutic device parameters suitable for tuning the device.

$$\text{Rate} = V_r(dC_r/dt) = -D(PA/TL)C_r$$

where Rate=Rate of release of therapeutic agent from device
Cr=concentration of therapeutic agent in reservoir
Vr=volume of reservoir
D=Diffusion constant
PA/TL=RRI
P=porosity
A=area
T=tortuosity=F=channel parameter.
For a substantially fixed volume injection,
Cr0=(Injection Volume)(Concentration of Formulation)/Vr
Where Cr0=initial concentration in reservoir following injection of formulation
For Injection Volume=50 uL
Cr0=(0.05 mL)(10 mg/mL)/Vr(1000 ug/1 mg)=500 ug/Vr
Rate=x(500 ug)exp(−xt)

where t=time
x=(D/Vr)(PA/TL)
With a mass balance on the vitreous
Vv(dCv/dt)=Rate from device=kVvCv
where Vv=volume of vitreous (about 4.5 ml)
Cv=concentration of therapeutic agent in vitreous
k=rate of drug from vitreous (proportional to 1/half life of drug in vitreous)
For the situation appropriate for the embodiments as described herein where Cv remains substantially constant and changes slowly with time (i.e. dCv/dt is approximately 0),
Cv=(Rate from device)/(kVv)
Since kVv is substantially constant, the max value of Cv will correspond to conditions that maximize the Rate from the device. At a given time since injection into the device (e.g., 180 days), the maximum Cv is found at the value of x that provides the maximum rate. The optimal value of x satisfies
d(Rate)/dx=0 at a given time.
Rate=500(x)exp(-xt)=f(x)g(x) where f(x)=500x and g(x)=exp(-xt)
d(Rate)/dx=f'(x)g(x)+f(x)g'(x)=500(1-xt)exp(-xt)
For a given time, t, d(Rate)/dx=0 when 1-xt=0 and xt=1
The rate is maximum when (D/Vr)(PA/TL)t=1.
For a given volume, optimal PA/TL=optimal RRI=Vr/(Dt)
Therefore the highest Cv at a given time, t, occurs for the optimal RRI=(PA/FL) for a given Vr.
Also, the ratio (Vr)/(RRI)=(Vr)/(PA/TL)=Dt will determine the optimal rate at the time.

The above equations provide approximate optimized values that, when combined with numerical simulations, can provide optimal values of Vr and PA/TL. The final optimum value can depend on additional parameters, such as the filling efficiency.

The above parameters can be used to determine the optimal RRI, and the therapeutic device can be tuned to the volume of formulation injected into the device with a device reservoir volume and release rate index within about +/−50% of the optimal values, for example +/−30% of the optimal values. For example, for an optimal release rate index of the porous structure and an optimal reservoir volume sized to receive a predetermined quantity of therapeutic agent, e.g. 50 uL, so as to achieve therapeutic concentrations above a minimum inhibitory concentration for a predetermined extended time such as 90 days, the maximum volume of the reservoir can be limited to no more than about twice the optimal volume. This tuning of the reservoir volume and the porous structure to the injected volume of the commercially available formulation can increase the time of release of therapeutic amounts from the device as compared to a much larger reservoir volume that receives the same volume of commercially available injectable formulation. Although many examples as described herein show a porous frit structure and reservoir volume tuned together to receive a quantity of formulation and provide release for an extended time, the porous structure tuned with the reservoir may comprise one or more of a porous frit, a permeable membrane, a semi-permeable membrane, a capillary tube or a tortuous channel, nano-structures, nano-channels or sintered nano-particles, and a person of ordinary skill in the art can determine the release rate characteristics, for example a release rate index, so as to tune the one or more porous structures and the volume to receive the quantity of the formulation and release therapeutic amounts for an extended time.

As an example, the optimal RRI at 180 days can be determined for a reservoir volume of about 125 uL. Based on the above equations (Vr/Dt)=optimal RRI, such that the optimal RRI at 180 days is about 0.085 for the 50 uL formulation volume injected into the device. The corresponding Cv is about 3.19 ug/mL at 180 days based on the Rate of drug released from the device at 180 days and the rate of the drug from the vitreous (k corresponding to a half life of about 9 days). A device with a container reservoir volume of 63 uL and RRI of 0.044 will also provide the optimal Cv at 180 days since the ratio of Vr to PA/TL is also optimal. Although an optimal value can be determined, the therapeutic device can be tuned to provide therapeutic amounts of drug at a targeted time, for example 180 days, with many values of the reservoir volume and many values of the release rate index near the optimal values, for example within about +/−50% of the optimal values. Although the volume of the reservoir can be substantially fixed, the volume of the reservoir can vary, for example within about +/−50% as with an expandable reservoir such as a balloon reservoir.

The half life of the drug in the vitreous humor of the eye can be determined based on the therapeutic agent and the type of eye, for example human, rabbit or monkey, such that the half life may be determined based on the species of the eye, for example. With at least some animal models the half life of the therapeutic agent in the vitreous humor can be shorter than for human eyes, for example by a factor of about two in at least some instances. For example, the half-life of the therapeutic agent Lucentis™ (ranibizumab) can be about nine days in the human eye and about two to four days in the rabbit and monkey animal models. For small molecules, the half life in the vitreous humor of the human eye can be about two to three hours and can be about one hour in the monkey and rabbit animal models. The therapeutic device can be tuned to receive the volume of formulation based on the half life of the therapeutic agent in the human vitreous humor, or an animal vitreous humor, or combinations thereof. Based on the teachings described herein, a person of ordinary skill in the art can determine empirically the half life of the therapeutic agent in the eye based on the type of eye and the therapeutic agent, such that the reservoir and porous structure can be tuned together so as to receive the volume of formulation and provide therapeutic amounts for the extended time.

EXPERIMENTAL

Example 1

FIG. 8 shows reservoirs with exit ports of defined diameters fabricated from 1 mL syringes with Luer-Lok™ tips and needles of varying diameter. The needles were trimmed to a total length of 8 mm, where 2 mm extended beyond the needle hub. Metal burrs were removed under a microscope. FIG. 8-1 shows the needles attached to syringes which were then filled with a solution of 2.4 mg/mL fluorescein sodium, molecular weight 376 Da, in phosphate buffer (Spectrum Chemicals, B-210.). Bubbles were removed and the syringes were adjusted to be able to dispense 0.05 mL. The shape of the resulting reservoir is shown in FIG. 8-1. The first expanded region is defined by the inside of the needle hub and the tip of the syringe. The second expanded region is inside the syringe. The total volume of the reservoir is 0.14 mL.

Once filled, the outsides of the reservoirs were rinsed of excess fluorescein by submerging in PBS.

FIG. 8-2 shows the reservoirs placed into 4 mL vials containing 1.5 mL buffer at room temperature. Collars cut from rubber tubing were placed around the syringe barrels to position the top of the reservoir to match the height of buffer in the vial to avoid any pressure differential. The tops of the vials were sealed with parafilm to avoid evaporation. At periodic intervals, the reservoirs were moved to new vials containing buffer. The amount of fluorescein transported from the reservoir through the exit port was determined by measuring the amount of fluorescein in the vials via absorption of visible light (492 nm).

Example 1

TABLE 1C

Release of Fluorescein through Exit Port

| Reservoir Number | Needle Gauge | Needle ID (mm) | Area (mm^2) | Release Rate (ug/day) |
|---|---|---|---|---|
| 1 | 18 | 0.838 | 0.552 | 10.8 |
| 2 | 18 | 0.838 | 0.552 | 9.4 |
| 3 | 23 | 0.318 | 0.079 | 1.0 |
| 4 | 23 | 0.318 | 0.079 | 1.2 |
| 5 | 30 | 0.14 | 0.015 | 0.6 |
| 6 | 30 | 0.14 | 0.015 | 0.6 |

The initial release rate (averaged over 0.5-4 days) is proportional to the area of the exit port opening.

Figure 9:
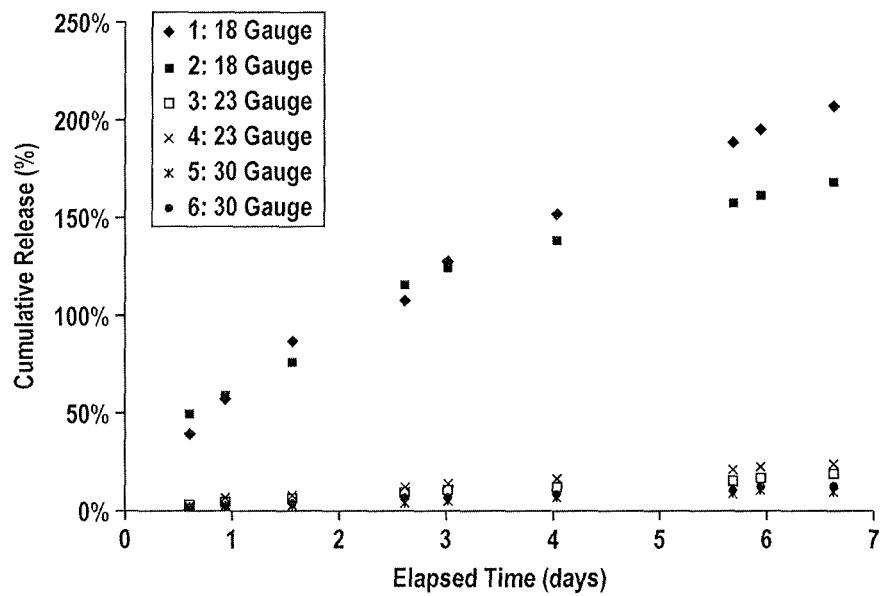
FIG. 9 shows cumulative release through the needles of varying diameter.
Figure 10:
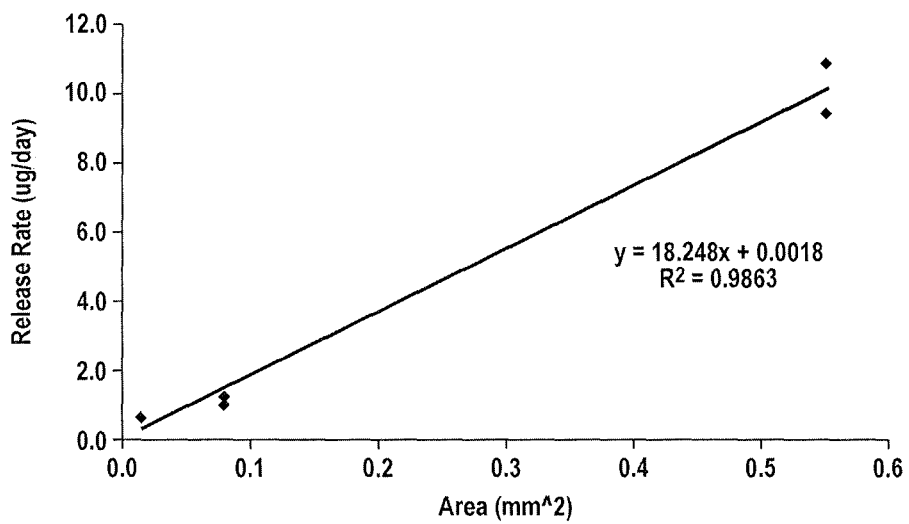
FIG. 10 shows release rate as a function of area.

The cumulative amount released into the vials is shown in FIG. 9. The amount released in a week ranged from 2 to 20%. An average delivery rate was determined from the slope for data collected between 0.5 and 4.5 days and is reported in Table 1C. FIG. 10 shows that the initial release rate is approximately proportional to the area of the exit port opening.

Example 2

Figure 11:
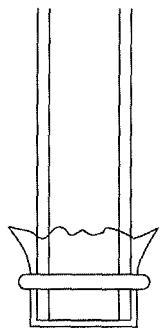
FIG. 11 shows a reservoir with a porous membrane fabricated by cutting off the Luer-Lok tip on a 1 mL syringe.
Figures 1, 11:
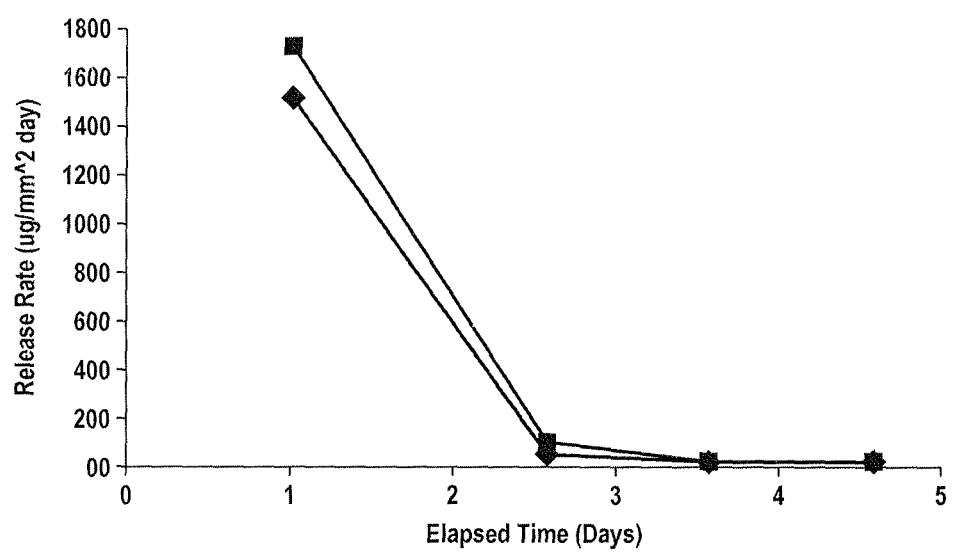
Figure 12:
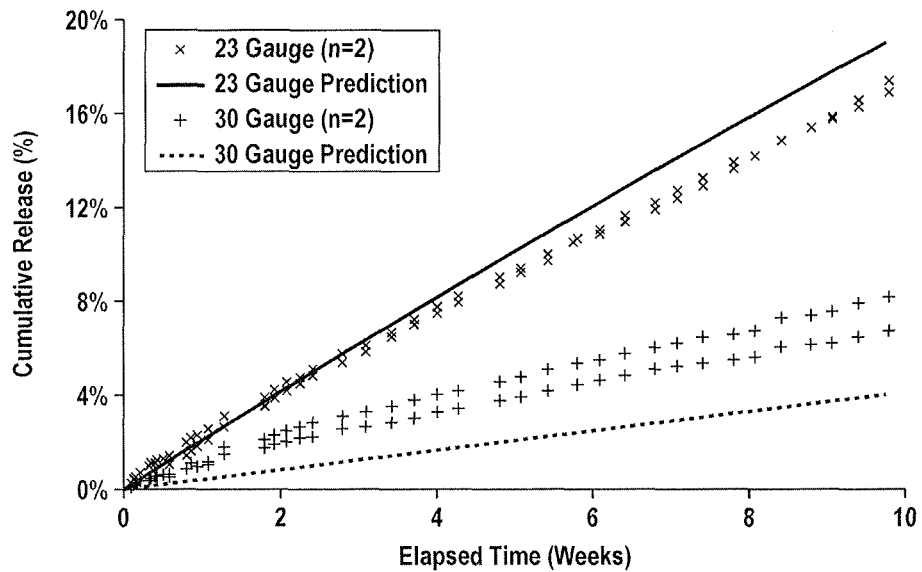
FIG. 12 shows the cumulative release of fluorescein through cut-off needles.

FIG. 11 shows reservoirs with a porous membrane fabricated by cutting off the Luer-Lok tip on 1 mL syringes. The end of the syringe was smoothed and beveled. A nylon membrane with 0.2 µm pore size was placed over the end of the syringe and secured with a piece of silicone tubing. The inner diameter of the syringe was 4.54 mm, yielding an exposed membrane area of 16 mm$^2$. The piston was removed so that approximately 100 mL of 300 mg/mL bovine serum albumin (BSA, Sigma A7906-100G) in PBS could be added. The piston was replaced and moved to remove the air and to push a small amount of the liquid through the membrane. The outside of the membrane and syringe was rinsed by submerging briefly in water. The reservoirs were then placed into 15 mL vials containing 5 mL PBS. The tops of the vials were sealed with parafilm to avoid evaporation. At periodic intervals of 0.5-1 day, the reservoirs were moved to new vials containing PBS. Diffusion through the membrane was determined by measuring the amount of BSA that accumulated in the vials via absorption of visible light (280 nm). The delivery rates from two replicates are shown in FIG. 11-1. This data suggests that therapeutic agents of interest with molecular weight on the order of 100 kDa will transport easily through porous membranes with pore sizes of 0.2 um.

Example 3

An experiment was performed to screen chromatographic media (Bio-Rad) for binding to Human IgG (Jackson ImmunoResearch, ChromPure). Columns were packed with the ten media listed below and were equilibrated in 20 mM acetate buffer pH 4.5.

TABLE 2

Macro-Prep t-Butyl HIC Support
Macro-Prep DEAE Support
CHT Ceramic Hydroxyapatite Type I 40 um
Macro-Prep CM Support
Macro-Prep Methyl HIC Support
Macro-Prep Ceramic Hydroxyapatite Type II 40 um
UNOsphere S Cation Exchange Support
UNOsphere Q Strong Anion Exchange Support
Macro-Prep High S Support
Macro-Prep High Q Support Then, 0.5 mL aliquots of 1 mg/mL antibody in 20 mM acetate buffer pH 4.5 were gravity-driven through the column and the collected solution was assessed qualitatively for color change using a BCA™ protein assay kit (Pierce). Of the media tested, Macro-Prep CM Support, Macro-Prep High S Support, and Macro-Prep Ceramic Hydroxyapatite Type II 40 um each successfully bound IgG. Subsequently, PBS was washed through the columns and the IgG was released from all three of these media.

Future Exit Port Studies

The experiments described in Examples 1-3 can be repeated with agitation to explore the impact of mixing induced by eye movement. In addition, the experiments can be performed at body temperature where delivery rates would be expected to be higher based upon faster diffusion rates at higher temperature.

Diffusion rates of BSA (MW 69 kDa) should be representative of diffusion rates of Lucentis™ and Avastin™, globular proteins with MW of 49 and 150 kDa, respectively. Selected experiments could be repeated to confirm individual delivery rates of these therapeutic agents.

Device prototypes closer to the embodiments described in the body of the patent could be fabricated from metals (e.g., titanium or stainless steel) or polymers (e.g., silicone or polyurethane). Exit ports of defined areas can be created via ablation or photo-etching techniques. In the case of polymers, exit ports can also be created by molding the material with a fine wire in place, followed by removal of the wire after the polymer is cured. Access ports can be created using membranes of silicone or polyurethane. Needle stops and flow diverters can be fabricated from metal or a rigid plastic.

Device prototypes can be tested with methods similar to those described in Example 1. Drug delivery rates can be measured for pristine devices as well as devices that have been refilled. Methods such as absorbance and fluorescence can be used to quantitate the amount of therapeutic agent that has been delivered as a function of time. Enzyme-Linked ImmunoSorbent Assays (ELISA) can be used to monitor the stability of the biological therapeutic agent in the formulations at 37° C. and can be used to determine the concentration of biologically active therapeutic agent delivered as a function of time.

Future Membrane Studies

Experiments could be performed with a range of candidates to identify membranes that 1) would be a barrier to bacteria and cells without much resistance during refilling; 2) may contribute to controlling the delivery rate of the therapeutic agent; and 3) would be biocompatible. Candidate membranes would have pore sizes of 0.2 µm or smaller, approaching the size of the therapeutic agents. A variety of fixtures can be used to secure a membrane between a donor solution and a receiver solution to measure permeation rates. In addition, performance of membranes can be tested in device prototypes using methods similar to what was done in Example 3.

Porous membranes could include cellulose acetate, nylon, polycarbonate, and poly(tetrafluoroethylene) (PTFE), in addition to regenerated cellulose, polyethersulfone, polyvinylidene fluoride (PVDF).

Developing Binding Formulations and Conditions

Once media and conditions have been screened via the batch or flow-through methods, devices can be fabricated containing the binding media in place or with binding media injected along with the therapeutic agent. Formulations can be prepared with the desired excipients, and therapeutic agent delivery rates can be monitored similarly to the method used in Example 1.

Additional media to test for binding include, ion exchange and bioaffinity chromatography media based on a hydrophilic polymeric support (GE Healthcare) that bind proteins with high capacity, and a hydrophilic packing material from Harvard Apparatus made from poly(vinyl alcohol) that binds more protein than silica. Other candidates would be known to those knowledgeable in the art.

A change in pH could modulate the binding of antibody to media. For example, binding of antibody would be expected in a formulation with cationic exchange media at an acidic pH. As the pH becomes more neutral, the antibody may be released from the media. Formulations could be tested that provide acidic pH for finite durations (i.e., a few months). Once the pH has become neutral, the release of antibody from the binding media could drive a higher release rate, resulting in a more constant release rate profile.

The binding media itself may have some buffering capacity that could dominate until physiological buffer diffuses into the device.

Alternatively, the formulation could include a buffer with a buffering capacity selected to dominate during the first few months. With time, the formulation buffer will diffuse out of the device and physiological buffer will diffuse into the device, which will result in a change of pH towards physiological pH (i.e., neutral). The kinetics of this change can be modulated by use of a polymeric buffer, with a higher molecular weight buffer remaining in the device for longer periods of time. Polypeptides are attractive as biocompatible polymeric buffers because they degrade to amino acids. Buffers are optimal near their pKa. The table below lists the pKa of the side chains of amino acids of interest.

TABLE 3

| Amino Acid | pKa of side chain |
|---|---|
| L-Aspartic Acid | 3.8 |
| L-Glutamic Acid | 4.3 |
| L-Arginine | 12.0 |
| L-Lysine | 10.5 |
| L-Histidine | 6.08 |
| L-Cysteine | 8.28 |
| L-Tyrosine | 10.1 |

The formulation could include a polyester, such as PLGA, or other biodegradable polymers such as polycaprolactone or poly-3-hydroxybutyrate, to generate hydrogen ions for a finite amount of time. The degradation rate could be modulated by, for example, changing the composition or molecular weight of the PLGA, such that the degradation is completed within a few months, contributing to reaching neutral pH in the last few months of delivery.

The pH could also be modulated electrochemically. Suitable electrode materials include inert or non-consumable materials such as platinum or stainless steel. Water hydrolysis occurs at the electrode interfaces and the products of hydrolysis are hydronium ions at the anode and hydroxyl ions at the cathode.

Rationale for Device Length

At least some device designs do not extend more than about 6 mm into the vitreous so as to minimize interference with vision. In addition, it can be beneficial to have the device extend into the vitreous since then drug can be released a distance from the walls of the globe. Macromolecules, such as antibodies, are primarily eliminated from the vitreous by a convection process rather than a diffusion process. (see Computer Simulation of Convective and Diffusive Transport of Controlled-Release Drugs in the vitreous Humor, by Stay, M S; Xu, J, Randolph, T W; and V H Barocas, *Pharm Res* 2003, 20(1), pp. 96-102.) Convection can be driven by the pressure generated by the secretion of aqueous humor by the ciliary body, with flow in the vitreous directed towards the retina. With exit ports extending into the vitreous, it may be more likely that drug will be convected towards the back of the eye and the central retina, as opposed to a device with ports flush with the globe likely delivering more of the therapeutic agent to the peripheral retina.

Example 4

Comparison of Predicted Vs. Measured Release Rates for a Reservoir with One Orifice The release study described in Example 1 using 23 and 30 gauge needles was continued through ten weeks. The results are compared with a model relating the change of concentration in the reservoir to the release rate from the reservoir based upon Fick's Law of diffusion. This simple model assumes the concentration in the reservoir is uniform and the concentration in the receiving fluid or vitreous is negligible. Solving the differential equation yields the following cumulative release of a therapeutic agent from a reservoir with one orifice:

$$\text{Cumulative Release}=1-cR/cR0=1-\exp((-DA/L\ V_R)t),$$

where:

cR=Concentration in reservoir $V_R$=Volume of reservoir

D=Diffusion coefficient

A=Area of orifice

L=Thickness of orifice t=Time

FIG. 12 shows the cumulative amount released into the vials over 10 weeks and the predicted cumulative amount release. These data show that the release from model devices generally agrees with the trend predicted by this model with no adjustable fitting parameters.

Example 5

Release of Protein Through a Cylindrical Sintered Porous Titanium Cylinder

Reservoirs were fabricated from syringes and sintered porous titanium cylinders (available from Applied Porous Technologies, Inc., Mott Corporation or Chand Eisenmann Metallurgical). These were sintered porous cylinders with a diameter of 0.062 inches and a thickness of 0.039 inches prepared from titanium particles. The porosity is 0.17 with mean pore sizes on the order of 3 to 5 micrometers. The porous cylinder is characterized as 0.2 media grade according to measurements of bubble point. The porous cylinders were press-fit into sleeves machined from Delrin. The sleeves exposed one entire planar face to the solution in the reservoir and the other entire planar face to the receiver solution in the vials, corresponding to an area of 1.9 square millimeters. The tips were cut off of 1 mL polypropylene syringes and machined to accept a polymer sleeve with outer diameter slightly larger than the inner diameter of the syringe. The porous cylinder/sleeve was press-fit into the modified syringe.

A solution was prepared containing 300 mg/mL bovine serum albumin (BSA, Sigma, A2153-00G) in phosphate buffered saline (PBS, Sigma, P3813). Solution was introduced into the syringes by removing the piston and dispensing approximately 200 microliters into the syringe barrel. Bubbles were tapped to the top and air was expressed out through the porous cylinder. Then BSA solution was expressed through the porous cylinder until the syringe held 100 uL as indicated by the markings on the syringe. The expressed BSA solution was wiped off and then rinsed by submerging in PBS. The reservoirs were then placed into 4 mL vials containing 2 mL PBS at room temperature. Collars cut from silicone tubing were placed around the syringe barrels to position the top of the reservoir to match the height of PBS. The silicone tubing fit inside the vials and also served as a stopper to avoid evaporation. At periodic intervals, the reservoirs were moved to new vials containing PBS. The amount of BSA transported from the reservoir through the porous cylinder was determined by measuring the amount of BSA in the vials using a BCA™ Protein Assay kit (Pierce, 23227).

Figure 13:
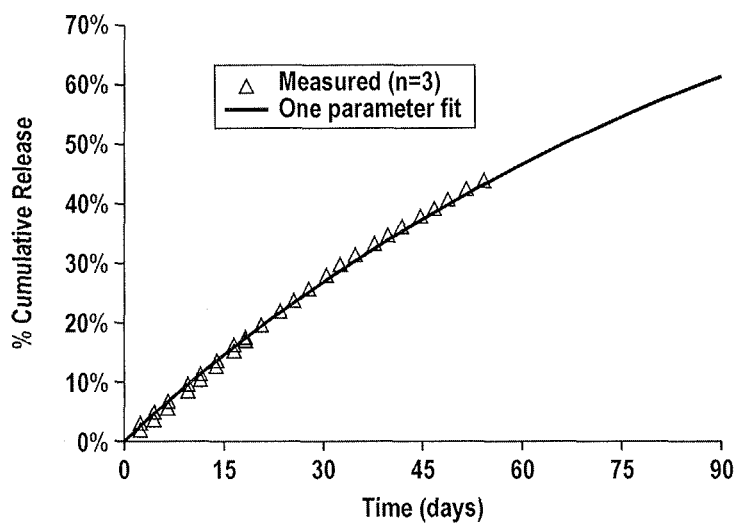
FIG. 13 shows the cumulative release of BSA protein through a sintered porous titanium cylinder.
Figures 1, 13:
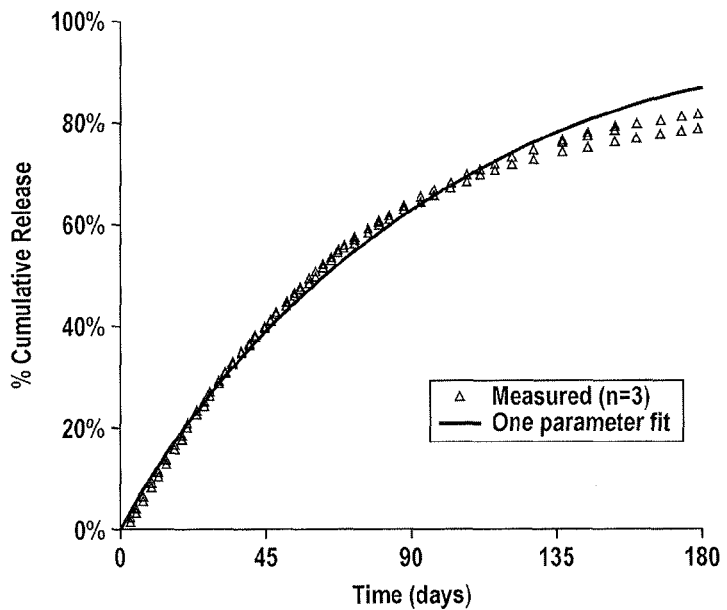

FIG. 13 shows the measured cumulative release of BSA through a sintered porous titanium disc and a prediction from the model describing release through a porous body. The Channel Parameter of 1.7 was determined via a least squares fit between the measured data and the model (Microsoft Excel). Since the porous cylinder has equal areas exposed to the reservoir and receiving solution, the Channel Parameter suggests a tortuosity of 1.7 for porous titanium cylinders prepared from 0.2 media grade.

FIG. 13-1 shows the measured cumulative release of BSA of FIG. 13 measured to 180 days. The Channel Parameter of 1.6 was determined via a least squares fit between the measured data and the model (Microsoft Excel). This corresponds to a Release Rate Index of 0.21 mm. Since the porous cylinder has equal areas exposed to the reservoir and receiving solution, the Channel Parameter corresponds to an effective path length channel parameter of 1.6 and suggests a tortuosity of 1.6 for porous titanium cylinders prepared from 0.2 media grade.

Example 6

Release of Protein Through Masked Sintered Porous Titanium Cylinders

Reservoirs were fabricated from syringes and porous sintered titanium cylinders similar to that described in Example 5. The porous sintered titanium cylinders (available from Applied Porous Technologies, Inc., Mott Corporation or Chand Eisenmann Metallurgical) had a diameter of 0.082 inch, a thickness of 0.039 inch, a media grade of 0.2 and were prepared from titanium particles. The porosity is 0.17 with mean pore sizes on the order of 3 to 5 micrometers. The porous cylinder is characterized as 0.2 media grade according to measurements of bubble point. The porous cylinders were press fit into sleeves machined from Delrin. The sleeves exposed one entire planar face to the solution in the reservoir and the other entire planar face to the receiver solution in the vials, corresponding to an area of 3.4 square millimeters. The tips were cut off of 1 mL polycarbonate syringes and machined to accept a polymer sleeve with outer diameter slightly larger than the inner diameter of the syringe. The porous cylinder/sleeve was press fit into the modified syringe. A kapton film with adhesive was affixed to the surface exposed to the receiving solution to create a mask and decrease the exposed area. In the first case, the diameter of the mask was 0.062 inches, exposing an area of 1.9 square millimeters to the receiving solution. In a second case, the diameter of the mask was 0.027 inches, exposing an area of 0.37 square millimeters.

Three conditions were run in this study: 1) 0.062 inch diameter mask, 100 uL donor volume, at room temperature in order to compare with reservoirs with unmasked porous cylinders in Example 5; 2) 0.062 inch diameter mask, 60 uL donor volume, at 37° C.; and 3) 0.027 inch diameter mask, 60 uL donor volume, at 37° C. The syringes were filled with a solution containing 300 mg/mL bovine serum albumin (BSA, Sigma, A2153-00G) in phosphate buffered saline (Sigma, P3813), similar to Example 5. In addition, 0.02 wt % of sodium azide (Sigma, 438456-5G) was added as a preservative to both the BSA solution placed in the reservoirs and the PBS placed in the receiving vials and both solutions were filtered through a 0.2 micron filter. This time, the amount of BSA solution dispensed into the syringe was weighed and the amount expressed through the porous cylinder was determined by rinsing and measuring the amount of BSA in the rinse. Assuming unit density for the BSA solution, the amount dispensed was 113+/−2 uL (Condition 1) and 66+/−3 uL (Condition 2). Subtracting off the amount in the rinse yielded a final reservoir volume of 103+/−5 uL (Condition 1) and 58+/−2 uL (Condition 2). The reservoirs were then placed into 5 mL vials containing 1 mL PBS at 37° C. in a heating block. At periodic intervals, the reservoirs were moved to new vials containing PBS and the BSA concentrations were determined in the receiving solutions using the method described in Example 5.

Figure 14:
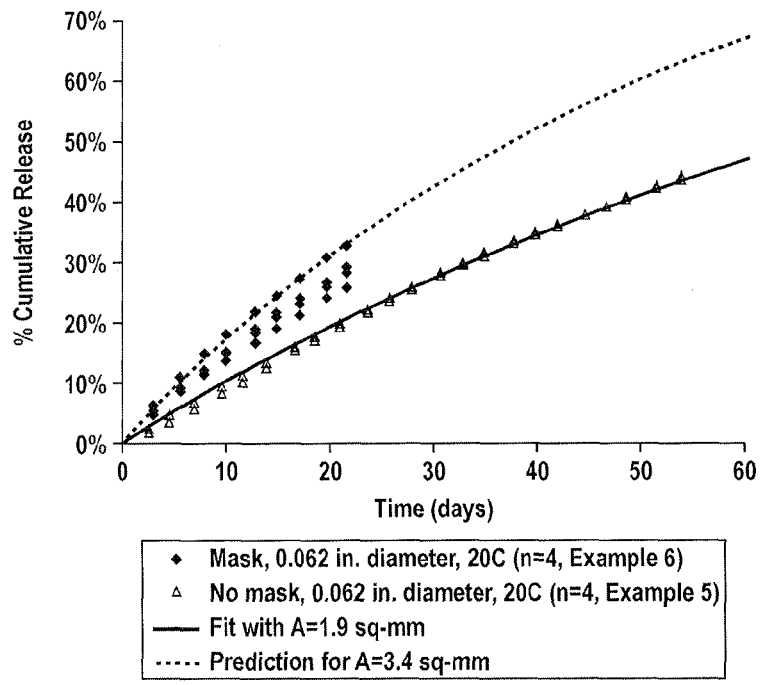
FIG. 14 shows the cumulative release of BSA protein through a masked sintered porous titanium cylinder at Condition 1, in accordance with experimental embodiments.

FIG. 14 shows the cumulative release of BSA protein through a masked sintered porous Titanium disc at Condition 1 (0.062 inch diameter mask, 100 uL donor volume, at room temperature) is faster than the release through an unmasked porous cylinder with the same exposed area (data from Example 5). Predictions are also shown using the Channel Parameter of 1.7 determined in Example 5, BSA diffusion coefficient at 20° C. (6.1e-7 cm$^2$/s), reservoir volume of 100 uL, and the area of the porous cylinder exposed to the receiver solution (A=1.9 mm$^2$) or the area of the porous cylinder exposed to the reservoir (A=3.4 mm$^2$). The data for the masked porous cylinder matches more closely with larger area exposed to the reservoir. Hence, this mask with width of 0.7 mm is not sufficient to reduce the effective area of the porous cylinder for the dimensions of this porous cylinder.

Figure 15:
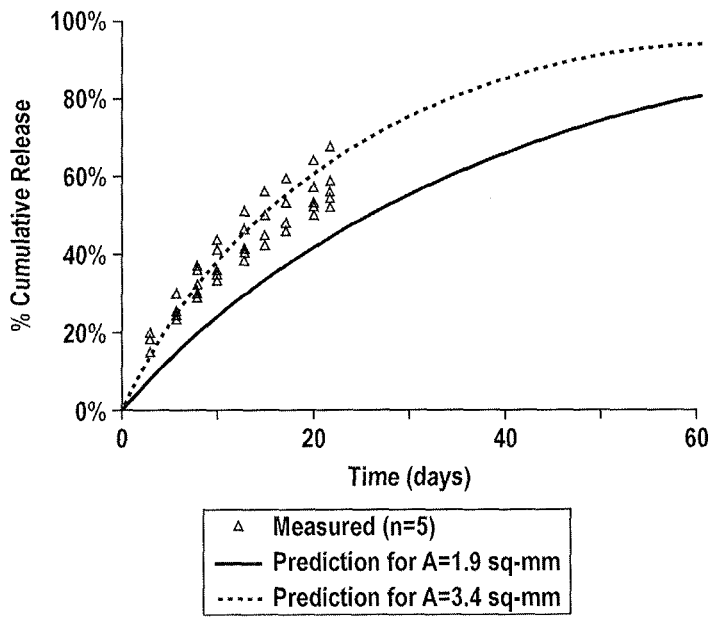
FIG. 15 shows cumulative release of BSA protein through a masked sintered porous titanium cylinder at Condition 2, in accordance with experimental embodiments.

FIG. 15 shows the cumulative release of BSA protein through a masked sintered porous titanium cylinder at Condition 2 (0.062 inch diameter mask, 60 uL donor volume, at 37° C.). The figure also displays predictions using the Channel Parameter of 1.7 determined in Example 5, BSA diffusion coefficient at 37° C. (9.1e-7 cm$^2$/s), reservoir volume of 58 uL, and the area of the porous cylinder exposed to the receiver solution (A=1.9 mm$^2$) or the area of the porous cylinder exposed to the reservoir (A=3.4 mm$^2$). Again, the data for this masked porous cylinder matches more closely with larger area exposed to the reservoir. The consistency of the data with the model at two temperatures supports how the model incorporates the effect of temperature.

Figure 16:
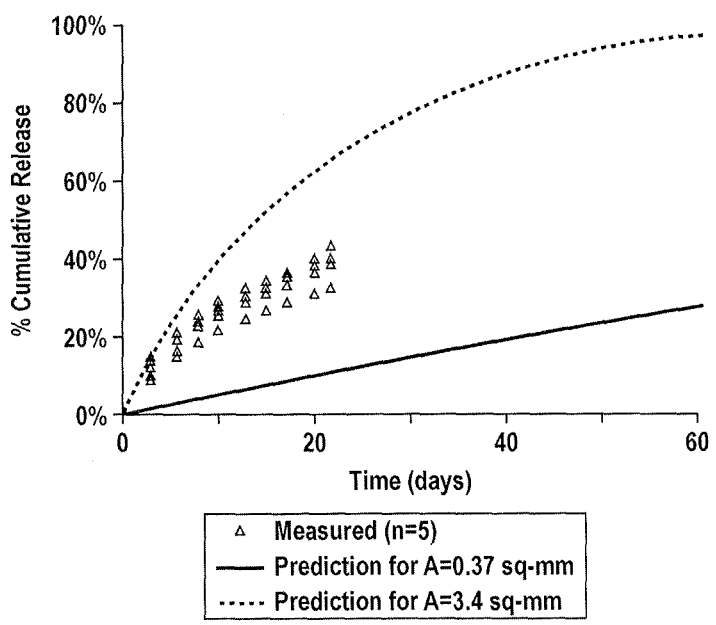
FIG. 16 shows cumulative release of BSA protein through a masked sintered porous titanium cylinder at Condition 3, in accordance with experimental embodiments.

FIG. 16 shows the cumulative release of BSA protein through a masked sintered porous titanium cylinder at Condition 3 (0.027 inch diameter mask, 60 uL donor volume, at 37° C.). The figure also displays predictions using the Channel Parameter of 1.7 determined in Example 5, BSA diffusion coefficient at 37° C. (9.1e-7 cm$^2$/s), reservoir volume of 58 uL, and the area of the porous cylinder exposed to the receiver solution (A=0.37 mm$^2$) or the area of the porous cylinder exposed to the reservoir (A=3.4 mm$^2$). This mask achieves a release rate corresponding to an effective area in between the area exposed to the reservoir and the area exposed to the receiver solution. A combination of the results in FIGS. 15 and 16 demonstrate that slower release is achieved using a mask that exposes a smaller area to the receiver solution.

FIGS. 13-16 show an unexpected result. Masking of the area of the porous frit structure so as to decrease the exposed area of the porous structure decreased the release rate less than the corresponding change in area. The release rate through the porous structure corresponds substantially to the interconnecting channels of the porous frit structure disposed between the first side exposed to the reservoir and the second side exposed to the receiver solution, such that the rate of release is maintained when a portion of the porous frit structure is covered. The rate of release of the interconnecting channels corresponds substantially to an effective area of the porous frit structure, and the effective area may correspond to an effective area of the interconnecting channels within the porous structure as shown above. As the rate of release is dependent upon the interconnecting channels, the release rate can be maintained when at least some of the channels are blocked, for example with coverage of a portion of the porous structure or blocking of a portion of the interconnecting channels with particles.

Example 7

Release of Protein Through Sintered Porous Stainless Steel Cylinder (Media Grade 0.1)

Prototype devices were fabricated from tubing and sintered porous stainless steel cylinders (available from Applied Porous Technologies, Inc., Mott Corporation or Chand Eisenmann Metallurgical) which are cylindrical with diameter 0.155 inch and thickness 0.188 inch prepared from 316L stainless steel particles. The porous cylinder is characterized as 0.1 media grade according to measurements of bubble point. This study was performed with these large, off-the-shelf porous cylinders with an area of 12 mm$^2$ in order to characterize the resistive properties of 0.1 media grade stainless steel.

These devices were prepared using Teflon-FEP heat shrink tubing (Zeus, #37950) and a hot air gun to shrink around the porous cylinders on one end and a custom prepared septum on the other end (NuSil MED1 4013 silicone molded to 0.145 inch diameter). The reservoir volume (46+/−2 uL) was determined from the difference in weight between empty systems and systems loaded with PBS. The PBS was loaded by submerging the systems in PBS and drawing a vacuum. The systems were then sterilized by heating to 250° F., 15 psi for 15 minutes, submerged in PBS in microcentrifuge tubes placed in a pressure cooker (Deni, 9760). Two 30 G needles were inserted into the septum to displace the PBS with BSA solution. One was used to inject the BSA solution and the other was bent and used as a vent for the displaced PBS. Sufficient BSA solution was injected to fill the needle hub of the vent to approximately ¾ full. Similar to Example 6, the BSA and PBS contained sodium azide and the nominal concentration was 300 mg/mL BSA. The devices were placed into 1.5 mL microcentrifuge tubes containing 1 mL PBS and kept at 37° C. in a heating block. Pieces of silicone tubing (tight fit with inside of tube, hole for septum) were used to suspend the devices in the PBS with the bottom of the septum approximately the same height as the PBS. The concentrations in the first tubes contained BSA from the filling process and were discarded. At periodic intervals, the devices were moved to new tubes containing PBS and the BSA concentrations were determined in the receiving solutions using the method described in Example 5.

Figure 17:
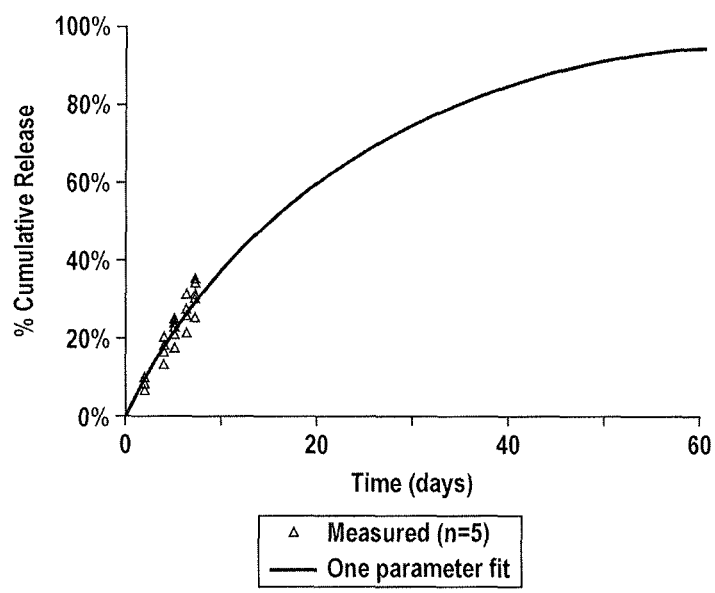
FIG. 17 shows cumulative release of BSA through 0.1 media grade sintered porous stainless steel cylinder.

FIG. 17 displays the measured cumulative release of BSA through the 0.1 media grade stainless steel sintered titanium discs. Since the Porosity, P, is not available from the vendor at this time, a single parameter of Porosity divided by Channel Parameter was determined by least squares fit of the model to the data. Since the sintered porous structure is cylindrical, the Channel Parameter can be interpreted as the Tortuosity, T, and P/T was determined to be equal to 0.07.

Example 8

Release of Protein Through a Sintered Porous Stainless Steel Cylinder (Media Grade 0.2)

Prototype devices were fabricated from tubing and sintered porous stainless steel cylinders (available from Applied Porous Technologies, Inc., Mott Corporation or Chand Eisenmann Metallurgical) which are cylindrical with diameter 0.031 inch, and thickness 0.049 inch prepared from 316L stainless steel particles. The porous cylinder is characterized as 0.2 media grade according to measurements of bubble point. This porous cylinder was obtained as a custom order with properties determined from a previous study with a large diameter 0.2 media grade porous stainless steel cylinder (data no shown) and predictions based on the model described herein. The area of each face of this porous cylinder is 0.5 mm$^2$.

These devices were prepared using Teflon-FEP heat shrink tubing (Zeus, 0.125 inch OD) and a hot air gun to shrink around the porous cylinder on one end and a custom prepared septum on the other end (NuSil MED1 4013 silicone molded to 0.113 inch diameter). The reservoir volume (17+/−1 uL) was determined from the difference in weight between empty systems and systems filled with PBS. The PBS was loaded by submerging the systems in PBS and drawing a vacuum. Dry devices were submerged in PBS in microcentrifuge tubes and sterilized by heating to 250° F., 15 psi for 15 minutes in a pressure cooker (Deni, 9760). Two 30 G needles were inserted into the septum to fill the devices with PBS. One was used to inject the PBS and the other was bent and used as a vent. After weighing the PBS filled devices, two new needles were inserted through the septum and sufficient BSA solution was injected to fill the needle hub of the vent to approximately ¾ full. The remaining details of the experiment are the same as Example 7.

Figure 18A:
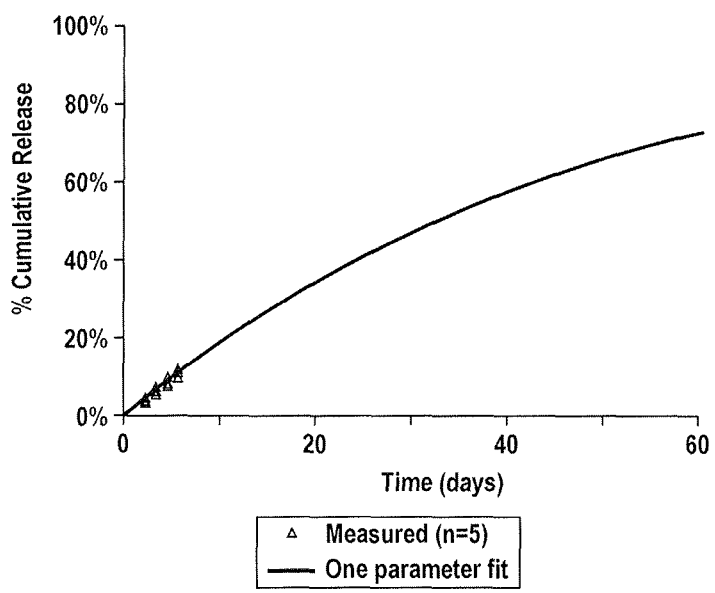
FIG. 18A shows cumulative release of BSA through 0.2 media grade sintered porous stainless steel cylinder.

FIG. 18A displays the measured cumulative release of BSA through the 0.2 media grade sintered porous stainless steel cylinder. A single parameter of Porosity divided by Channel Parameter was determined to be 0.12 by least squares fit of the model to the data. Since the sintered porous structure is cylindrical, the Channel Parameter can be interpreted as effective length of the interconnecting channels that may correspond the Tortuosity, T. Using the Porosity of 0.17 determined by the vendor, the effective length of the channel that may correspond to the Tortuosity was determined to be 1.4. Furthermore, this corresponds to a PA/FL ratio (Release Rate Index) of 0.0475 mm.

Figure 18B:
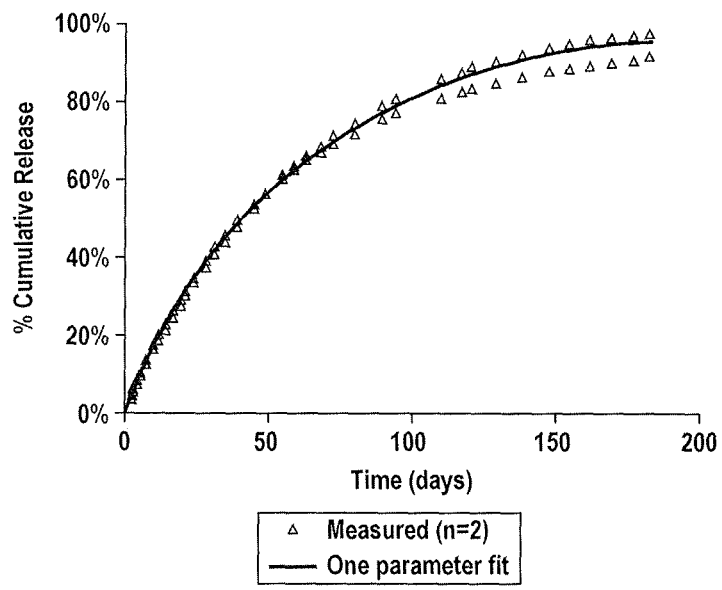
FIG. 18B shows cumulative release of BSA through 0.2 media grade sintered porous stainless steel cylinder for 180 days.

FIG. 18B displays the measured cumulative release of BSA through the 0.2 media grade sintered porous stainless steel cylinder for 180 days. A single parameter of Porosity divided by Channel Parameter was determined to be 0.10 by least squares fit of the model to the data. Since the sintered porous structure is cylindrical, the Channel Parameter can be interpreted an effective length of the inter-connecting channels that may correspond to the Tortuosity, T. Using the Porosity of 0.17 determined by the vendor, the effective channel length of the inter-connecting channels that may correspond to the Tortuosity was determined to be 1.7. Furthermore, this corresponds to a PA/FL ratio (Release Rate Index) of 0.038 mm.

Example 9

Calculations of Lucentis™ Concentrations in the Vitreous

The vitreous concentrations of a therapeutic agent can be predicted based on the equations described herein. Table 4 shows the values of the parameters applied for each of Simulation 1, Simulation 2, Simulation 3, Simulation 4, and Simulation 5. The half-life and vitreous volume correspond to a monkey model (J. Gaudreault et al., Preclinical Pharmacokinetics of Ranibizumab (rhuFabV2) after a Single Intravitreal Administration, Invest Ophthalmol Vis Sci 2005; 46: 726-733) (Z. Yao et al., Prevention of Laser Photocoagulation Induced Choroidal Neovascularization Lesions by Intravitreal Doses of Ranibizumab in Cynomolgus Monkeys, ARVO 2009 abstract D906). The parameter PA/FL can be varied to determine the release rate profile. For example, the value of A can be about 1 mm², the porosity can be about 0.1 (PA=0.1 mm²) and the length about 1 mm and the channel fit parameter that may correspond to tortuousity can be about 2 (FL=2 mm), such that PA/TL is about 0.05 mm. A person of ordinary skill in the art can determine empirically the area, porosity, length and channel fit parameter for extended release of the therapeutic agent for the extended period based on the teachings described herein.

TABLE 4A

| Parameter | Values Simulation 1 | Values Simulation 2 | Values Simulation 3 | Values Simulation 4 | Values Simulation 5 |
|---|---|---|---|---|---|
| Diffusion coeff (cm2/s) | 1.0E−06 | 1.0E−06 | 1.0E−06 | 1.0E−06 | 1.0E−06 |
| Initial Loading (ug/mL) | 10000 | 10000 | 10000 | 10000 | 10000 |
| Reservoir Vol (ml) | 0.05 | 0.01 | 0.05 | 0.01 | 0.017 |
| PA/FL (mm) | 0.0225 | 0.0225 | 0.045 | 0.045 | 0.047 |
| Half-life (days) | 2.63 | 2.63 | 2.63 | 2.63 | 2.63 |
| Rate constant, k (1/day) | 0.264 | 0.264 | 0.264 | 0.264 | 0.264 |
| Vitreous vol (ml) | 1.5 | 1.5 | 1.5 | 1.5 | 1.5 |

TABLE 4B

| Time (days) | Predicted Vitreous Conc using Meas Cmax (ug/mL) | Predicted Vitreous Conc using Calc Cmax (ug/mL) |
|---|---|---|
| 0 | 169.00 | 333.33 |
| 1 | 129.85 | 256.11 |
| 2 | 99.76 | 196.77 |
| 3 | 76.65 | 151.18 |
| 4 | 58.89 | 116.16 |
| 5 | 45.25 | 89.24 |
| 6 | 34.76 | 68.57 |
| 7 | 26.71 | 52.68 |
| 8 | 20.52 | 40.48 |
| 9 | 15.77 | 31.10 |
| 10 | 12.11 | 23.89 |
| 11 | 9.31 | 18.36 |
| 12 | 7.15 | 14.10 |
| 13 | 5.49 | 10.84 |
| 14 | 4.22 | 8.33 |
| 15 | 3.24 | 6.40 |
| 16 | 2.49 | 4.91 |
| 17 | 1.91 | 3.78 |
| 18 | 1.47 | 2.90 |
| 19 | 1.13 | 2.23 |
| 20 | 0.87 | 1.71 |
| 21 | 0.67 | 1.32 |
| 22 | 0.51 | 1.01 |
| 23 | 0.39 | 0.78 |
| 24 | 0.30 | 0.60 |
| 25 | 0.23 | 0.46 |
| 26 | 0.18 | 0.35 |
| 27 | 0.14 | 0.27 |
| 28 | 0.11 | 0.21 |
| 29 | 0.08 | 0.16 |
| 30 | 0.06 | 0.12 |
| 31 | 0.05 | 0.09 |
| 32 | 0.04 | 0.07 |

Tables 4C1, 4C2, 4C3 4C4, and 4C5 show the calculated concentration of Lucentis™ in the vitreous humor for Simulation 1, Simulation 2, Simulation 3, Simulation 4, and Simulation 5 respectively. These results indicate Lucentis™ vitreous concentrations may be maintained above the minimum therapeutic level for about a year or more when released from Table 4B shows the vitreous concentrations calculated for a 0.5 mg bolus injection of Lucentis™ injected into the eye of a monkey using equations described herein and the half-life measured for the monkey listed in Table 4A. The first column used the measured Cmax (Gaudreault et al.) while the second used a calculated Cmax based on the dose and volume of the vitreous. The average concentration of Lucentis™ is about 46 ug/ml. The minimum therapeutic concentration of Lucentis™ is about 0.1 ug/mL, which may correspond to about 100% VGEF inhibition (Gaudreault et al.). Table 4B indicates that a bolus injection of 0.5 mg Lucentis™ maintains a vitreous concentration above 0.1 ug/mL for about a month whether using the measured or calculated Cmax. This is consistent with monthly dosing that has been shown to be therapeutic in clinical studies.

a device with porous structure characterized by PA/FL≤0.0225 mm and a reservoir volume ≥10 uL.

Simulation 5 corresponds to the devices used in the experiment described in Example 8. This device had a reservoir volume of 17 uL and porous structure characterized by PA/FL=0.047 mm. When this device is loaded with Lucentis™, the loading dose corresponds to ⅓ of the 50 uL currently injected monthly. Calculations that predict vitreous concentrations indicate that this device with one-third of the monthly dose may maintain Lucentis™ therapeutic concentrations for about 6 months. While half of the dose is delivered in the first month and more than 98% delivered at 6 months, therapeutic levels may still be maintained for 6 months.

The ability of the device to release therapeutic agent for an extended time can be described by an effective device half-life. For the device in Example 8, the effective device half-life is 29 days for delivery of Lucentis™. The device can be configured by selection of the reservoir volume and a porous structure with an appropriate PA/FL to achieve the desired effective half-life.

TABLE 4C1

Simulation 1

| Time (days) | Predicted Rate (ug/day) | Predicted % CR | Predicted Vitreous Conc (ug/mL) |
|---|---|---|---|
| 0 | 1.9 | 0.0% | 4.9 |
| 10 | 1.9 | 3.8% | 4.7 |
| 20 | 1.8 | 7.5% | 4.5 |
| 30 | 1.7 | 11.0% | 4.4 |
| 40 | 1.7 | 14.4% | 4.2 |
| 50 | 1.6 | 17.7% | 4.0 |
| 60 | 1.5 | 20.8% | 3.9 |
| 70 | 1.5 | 23.8% | 3.7 |
| 80 | 1.4 | 26.7% | 3.6 |
| 90 | 1.4 | 29.5% | 3.5 |
| 100 | 1.3 | 32.2% | 3.3 |
| 110 | 1.3 | 34.8% | 3.2 |
| 120 | 1.2 | 37.3% | 3.1 |
| 130 | 1.2 | 39.7% | 3.0 |
| 140 | 1.1 | 42.0% | 2.9 |
| 150 | 1.1 | 44.2% | 2.7 |
| 160 | 1.0 | 46.3% | 2.6 |
| 170 | 1.0 | 48.4% | 2.5 |
| 180 | 1.0 | 50.3% | 2.4 |
| 190 | 0.9 | 52.2% | 2.3 |
| 200 | 0.9 | 54.0% | 2.3 |
| 210 | 0.9 | 55.8% | 2.2 |
| 220 | 0.8 | 57.5% | 2.1 |
| 230 | 0.8 | 59.1% | 2.0 |
| 240 | 0.8 | 60.7% | 1.9 |
| 250 | 0.7 | 62.2% | 1.9 |
| 260 | 0.7 | 63.6% | 1.8 |
| 270 | 0.7 | 65.0% | 1.7 |
| 280 | 0.7 | 66.3% | 1.7 |
| 290 | 0.6 | 67.6% | 1.6 |
| 300 | 0.6 | 68.9% | 1.5 |
| 310 | 0.6 | 70.0% | 1.5 |
| 320 | 0.6 | 71.2% | 1.4 |
| 330 | 0.5 | 72.3% | 1.4 |
| 340 | 0.5 | 73.3% | 1.3 |
| 350 | 0.5 | 74.4% | 1.3 |
| 360 | 0.5 | 75.3% | 1.2 |

TABLE 4C2

Simulation 2

| Time (days) | Predicted Rate (ug/day) | Predicted % CR | Predicted Vitreous Conc (ug/mL) |
|---|---|---|---|
| 0 | 1.9 | 0.0% | 4.92 |
| 10 | 1.6 | 17.7% | 4.05 |
| 20 | 1.3 | 32.2% | 3.33 |
| 30 | 1.1 | 44.2% | 2.74 |
| 40 | 0.9 | 54.0% | 2.26 |
| 50 | 0.7 | 62.2% | 1.86 |
| 60 | 0.6 | 68.9% | 1.53 |
| 70 | 0.5 | 74.4% | 1.26 |
| 80 | 0.4 | 78.9% | 1.04 |
| 90 | 0.3 | 82.6% | 0.85 |
| 100 | 0.3 | 85.7% | 0.70 |
| 110 | 0.2 | 88.2% | 0.58 |
| 120 | 0.2 | 90.3% | 0.48 |
| 130 | 0.2 | 92.0% | 0.39 |
| 140 | 0.1 | 93.4% | 0.32 |
| 150 | 0.1 | 94.6% | 0.27 |
| 160 | 0.1 | 95.5% | 0.22 |
| 170 | 0.1 | 96.3% | 0.18 |
| 180 | 0.1 | 97.0% | 0.15 |
| 190 | 0.0 | 97.5% | 0.12 |
| 200 | 0.0 | 98.0% | 0.10 |
| 210 | 0.0 | 98.3% | 0.08 |
| 220 | 0.0 | 98.6% | 0.07 |
| 230 | 0.0 | 98.9% | 0.06 |
| 240 | 0.0 | 99.1% | 0.05 |
| 250 | 0.0 | 99.2% | 0.04 |
| 260 | 0.0 | 99.4% | 0.03 |
| 270 | 0.0 | 99.5% | 0.03 |
| 280 | 0.0 | 99.6% | 0.02 |
| 290 | 0.0 | 99.6% | 0.02 |
| 300 | 0.0 | 99.7% | 0.01 |
| 310 | 0.0 | 99.8% | 0.01 |
| 320 | 0.0 | 99.8% | 0.01 |
| 330 | 0.0 | 99.8% | 0.01 |
| 340 | 0.0 | 99.9% | 0.01 |
| 350 | 0.0 | 99.9% | 0.01 |
| 360 | 0.0 | 99.9% | 0.00 |

TABLE 4C3

Simulation 3

| Time (days) | Predicted Rate (ug/day) | Predicted % CR | Predicted Vitreous Conc (ug/mL) |
|---|---|---|---|
| 0 | 3.9 | 0.0% | 9.8 |
| 10 | 3.6 | 7.5% | 9.1 |
| 20 | 3.3 | 14.4% | 8.4 |
| 30 | 3.1 | 20.8% | 7.8 |
| 40 | 2.8 | 26.7% | 7.2 |
| 50 | 2.6 | 32.2% | 6.7 |
| 60 | 2.4 | 37.3% | 6.2 |
| 70 | 2.3 | 42.0% | 5.7 |
| 80 | 2.1 | 46.3% | 5.3 |
| 90 | 1.9 | 50.3% | 4.9 |
| 100 | 1.8 | 54.0% | 4.5 |
| 110 | 1.7 | 57.5% | 4.2 |
| 120 | 1.5 | 60.7% | 3.9 |
| 130 | 1.4 | 63.6% | 3.6 |
| 140 | 1.3 | 66.3% | 3.3 |
| 150 | 1.2 | 68.9% | 3.1 |
| 160 | 1.1 | 71.2% | 2.8 |
| 170 | 1.0 | 73.3% | 2.6 |
| 180 | 1.0 | 75.3% | 2.4 |
| 190 | 0.9 | 77.2% | 2.2 |
| 200 | 0.8 | 78.9% | 2.1 |
| 210 | 0.8 | 80.5% | 1.9 |
| 220 | 0.7 | 81.9% | 1.8 |
| 230 | 0.7 | 83.3% | 1.6 |
| 240 | 0.6 | 84.5% | 1.5 |
| 250 | 0.6 | 85.7% | 1.4 |
| 260 | 0.5 | 86.8% | 1.3 |
| 270 | 0.5 | 87.7% | 1.2 |
| 280 | 0.4 | 88.7% | 1.1 |
| 290 | 0.4 | 89.5% | 1.0 |
| 300 | 0.4 | 90.3% | 1.0 |
| 310 | 0.3 | 91.0% | 0.9 |
| 320 | 0.3 | 91.7% | 0.8 |
| 330 | 0.3 | 92.3% | 0.8 |
| 340 | 0.3 | 92.9% | 0.7 |
| 350 | 0.3 | 93.4% | 0.6 |
| 360 | 0.2 | 93.9% | 0.6 |

TABLE 4C4

Simulation 4

| Time (days) | Predicted Rate (ug/day) | Predicted % CR | Predicted Vitreous Conc (ug/mL) |
|---|---|---|---|
| 0 | 3.89 | 0.0% | 9.83 |
| 10 | 2.64 | 32.2% | 6.67 |
| 20 | 1.79 | 54.0% | 4.52 |
| 30 | 1.21 | 68.9% | 3.06 |
| 40 | 0.82 | 78.9% | 2.08 |
| 50 | 0.56 | 85.7% | 1.41 |
| 60 | 0.38 | 90.3% | 0.95 |
| 70 | 0.26 | 93.4% | 0.65 |
| 80 | 0.17 | 95.5% | 0.44 |
| 90 | 0.12 | 97.0% | 0.30 |
| 100 | 0.08 | 98.0% | 0.20 |
| 110 | 0.05 | 98.6% | 0.14 |
| 120 | 0.04 | 99.1% | 0.09 |
| 130 | 0.02 | 99.4% | 0.06 |
| 140 | 0.02 | 99.6% | 0.04 |
| 150 | 0.01 | 99.7% | 0.03 |
| 160 | 0.01 | 99.8% | 0.02 |
| 170 | 0.01 | 99.9% | 0.01 |
| 180 | 0.00 | 99.9% | 0.01 |
| 190 | 0.00 | 99.9% | 0.01 |
| 200 | 0.00 | 100.0% | 0.00 |
| 210 | 0.00 | 100.0% | 0.00 |
| 220 | 0.00 | 100.0% | 0.00 |
| 230 | 0.00 | 100.0% | 0.00 |
| 240 | 0.00 | 100.0% | 0.00 |
| 250 | 0.00 | 100.0% | 0.00 |
| 260 | 0.00 | 100.0% | 0.00 |
| 270 | 0.00 | 100.0% | 0.00 |
| 280 | 0.00 | 100.0% | 0.00 |
| 290 | 0.00 | 100.0% | 0.00 |
| 300 | 0.00 | 100.0% | 0.00 |
| 310 | 0.00 | 100.0% | 0.00 |
| 320 | 0.00 | 100.0% | 0.00 |
| 330 | 0.00 | 100.0% | 0.00 |
| 340 | 0.00 | 100.0% | 0.00 |
| 350 | 0.00 | 100.0% | 0.00 |
| 360 | 0.00 | 100.0% | 0.00 |

TABLE 4C5

Simulation 5

| Time (days) | Predicted Rate (ug/day) | Predicted % CR | Predicted Vitreous Conc (ug/mL) |
|---|---|---|---|
| 0 | 4.1 | 0.0% | 10.27 |
| 10 | 3.2 | 21.2% | 8.09 |
| 20 | 2.5 | 38.0% | 6.37 |
| 30 | 2.0 | 51.2% | 5.02 |
| 40 | 1.6 | 61.5% | 3.95 |
| 50 | 1.2 | 69.7% | 3.11 |
| 60 | 1.0 | 76.1% | 2.45 |
| 70 | 0.8 | 81.2% | 1.93 |
| 80 | 0.6 | 85.2% | 1.52 |
| 90 | 0.5 | 88.3% | 1.20 |
| 100 | 0.4 | 90.8% | 0.94 |
| 110 | 0.3 | 92.8% | 0.74 |
| 120 | 0.2 | 94.3% | 0.58 |
| 130 | 0.2 | 95.5% | 0.46 |
| 140 | 0.1 | 96.5% | 0.36 |
| 150 | 0.1 | 97.2% | 0.29 |
| 160 | 0.1 | 97.8% | 0.22 |
| 170 | 0.1 | 98.3% | 0.18 |
| 180 | 0.1 | 98.6% | 0.14 |
| 190 | 0.0 | 98.9% | 0.11 |
| 200 | 0.0 | 99.2% | 0.09 |
| 210 | 0.0 | 99.3% | 0.07 |
| 220 | 0.0 | 99.5% | 0.05 |
| 230 | 0.0 | 99.6% | 0.04 |
| 240 | 0.0 | 99.7% | 0.03 |
| 250 | 0.0 | 99.7% | 0.03 |
| 260 | 0.0 | 99.8% | 0.02 |
| 270 | 0.0 | 99.8% | 0.02 |
| 280 | 0.0 | 99.9% | 0.01 |
| 290 | 0.0 | 99.9% | 0.01 |
| 300 | 0.0 | 99.9% | 0.01 |
| 310 | 0.0 | 99.9% | 0.01 |
| 320 | 0.0 | 100.0% | 0.00 |
| 330 | 0.0 | 100.0% | 0.00 |
| 340 | 0.0 | 100.0% | 0.00 |
| 350 | 0.0 | 100.0% | 0.00 |
| 360 | 0.0 | 100.0% | 0.00 |

Z. Yao et al. (Prevention of Laser Photocoagulation Induced Choroidal Neovascularization Lesions by Intravitreal Doses of Ranibizumab in Cynomolgus Monkeys, ARVO 2009 abstract D906) have performed a preclinical study to determine the lowest efficacious Lucentis™ dose in cynomolgus monkeys that leads to 100% prevention of laser photocoagulation treatment-induced Grade IV choroidal neovascularization (CNV) lesions. This model has been shown to be relevant to AMD. Intravitreal injection of Lucentis™ at all doses tested completely inhibited the development of Grade IV CNV lesions. Table 4D shows predictions of Lucentis™ vitreous concentrations for the lowest total amount of Lucentis™ investigated (intravitreal injection of 5 ug on days 1, 6, 11, 16, 21 and 26), using the equations described herein and pharmacokinetic parameters listed in Table 4A. This data indicates that it is not necessary to achieve the high Cmax of a 0.5 mg single bolus injection in order to be therapeutic.

Figure 19A:
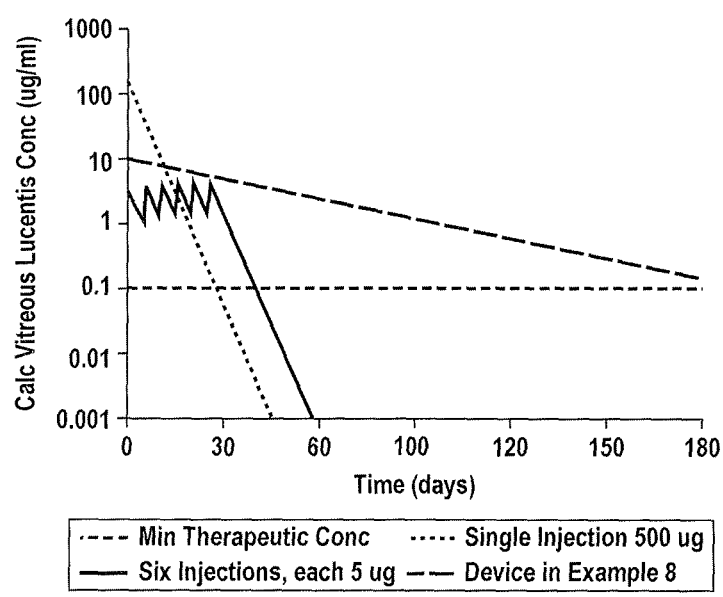
FIG. 19A compares calculated Lucentis™ pharmacokinetics profiles to the pharmacokinetics profiles predicted for the device in Example 8.

FIG. 19A compares this predicted profile with that predicted for the device in Example 8. This data further supports that the release profile from a device in accordance with embodiments of the present invention may be therapeutic for at least about 6 months. The single injection of 500 ug corresponds to a 50 uL bolus injection of Lucentis™ that can given at monthly intervals, and the range of therapeutic concentrations of Lucentis™ (ranibizumab) in the vitreous extends from about 100 ug/mL to the minimum inhibitory (therapeutic) concentration of about 0.1 ug/mL at about 1 month, for example. The minimum inhibitory concentration corresponding to the lower end of the range of therapeutic concentrations in the vitreous humor can be determined empirically by one of ordinary skill in the art in accordance with the examples described herein. For example, a lose does study of a series of six Lucentis™ injections, 5 ug each, can be administered so as to provide a concentration in the vitreous of at least about 1 ug/mL, and the therapeutic benefit of the injections assessed as described herein.

TABLE 4D

| Time (days) | Predicted Lucentis Vitreous Conc (ug/mL) |
|---|---|
| 0 | 0.00 |
| 1 | 3.33 |
| 2 | 2.56 |
| 3 | 1.97 |

TABLE 4D-continued

| Time (days) | Predicted Lucentis Vitreous Conc (ug/mL) |
| --- | --- |
| 4 | 1.51 |
| 5 | 1.16 |
| 6 | 4.23 |
| 7 | 3.25 |
| 8 | 2.49 |
| 9 | 1.92 |
| 10 | 1.47 |
| 11 | 4.46 |
| 12 | 3.43 |
| 13 | 2.64 |
| 14 | 2.02 |
| 15 | 1.56 |
| 16 | 4.53 |
| 17 | 3.48 |
| 18 | 2.67 |
| 19 | 2.05 |
| 20 | 1.58 |
| 21 | 4.55 |
| 22 | 3.49 |
| 23 | 2.68 |
| 24 | 2.06 |
| 25 | 1.58 |
| 26 | 4.55 |
| 27 | 3.50 |
| 28 | 2.69 |
| 29 | 2.06 |
| 30 | 1.59 |
| 35 | 0.42 |
| 40 | 0.11 |
| 45 | 0.03 |
| 50 | 0.01 |
| 60 | 0.00 |
| 70 | 0.00 |
| 80 | 0.00 |
| 90 | 0.00 |

The concentration profiles of a therapeutic agent comprising Lucentis™ were determined as shown below based on the teachings described herein and with drug half-life of nine days for Lucentis™ in the human eye. The examples shown below for injections of the commercially available formulation Lucentis™ and the nine day half life show unexpected results, and that a volume of formulation corresponding to a monthly bolus injection into the device as described herein can provide therapeutic benefit for at least about two months. The device volume and the porous structure can be tuned to receive the predetermined volume of formulation and provide sustained release for an extended time. Additional tuning of the device can include the half-life of the therapeutic agent in the eye, for example nine days for Lucentis™, and the minimum inhibitory concentration of the therapeutic agent as determined based on the teachings as described herein.

Figure 19B:
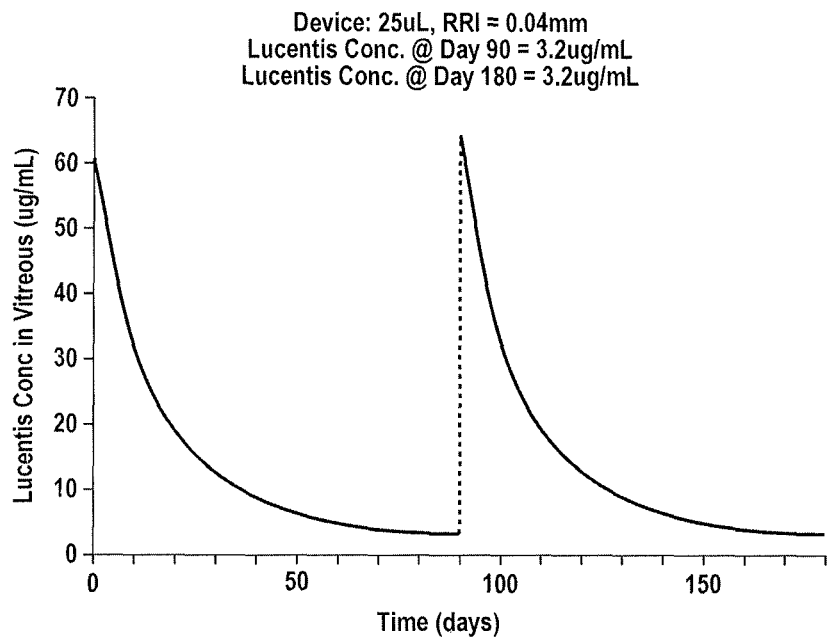
FIG. 19B shows determined concentrations of ranibizumab in the vitreous humor for a first 50 uL Lucentis™ injection into a 25 uL reservoir of the device and a second 50 uL injection at 90 days, in accordance with embodiments.

FIG. 19B shows determined concentrations of Lucentis™ in the vitreous humor for a first 50 uL injection into a 25 uL device and a second 50 uL injection at 90 days. The calculations show that the 50 uL dosage of the monthly FDA approved bolus injection can be used to treat the eye for about 90 days, and that the injections can be repeated to treat the eye, for example at approximately 90 day intervals. The Lucentis™ may comprise a predetermined amount of the commercially available formulation injected into the device. The commercially available formulation of Lucentis™ has a concentration of ranibizumab of 10 mg/mL, although other concentrations can be used for example as described herein below with reference to a 40 mg/mL solution of injected ranibizumab. The predetermined amount corresponds to the amount of the monthly bolus injection, for example 50 uL. The therapeutic device may comprise a substantially fixed volume container reservoir having a volume of 25 uL, such that a first 25 uL portion of the 50 uL injection is contained in the reservoir for sustained and/or controlled release and a second 25 uL portion of the 50 uL injection is passed through the porous structure and released into the vitreous with a 25 uL bolus. The filling efficiency of the injection into the device may comprise less than 100%, and the reservoir volume and injection volume can be adjusted based on the filling efficiency in accordance with the teachings described herein. For example, the filling efficiency may comprise approximately 90%, such that the first portion comprises approximately 22.5 uL contained in the chamber of the container reservoir and the second portion comprises approximately 27.5 uL passed through the device for the 50 uL injected into the therapeutic device. The initial concentration of Lucentis™ in the vitreous humor corresponds to about 60 ug/mL immediately following injection into the reservoir device. The concentration of Lucentis™ in the vitreous humor decreases to about 3.2 ug/mL at 90 days. A second 50 uL injection of Lucentis™ approximately 90 days after the first injection increases the concentration to about 63 ug/mL. The concentration of Lucentis™ in the vitreous humor decreases to about 3.2 ug/mL at 180 days after the first injection and 90 days after the second injection. These calculations show that the concentration of Lucentis™ can be continuously maintained above a minimum inhibitory concentration of about 3 ug per ml with the 50 uL injection into the device. Additional injections can be made, for example every 90 days for several years to deliver the therapeutic agent to treat the patient.

Figure 19C:
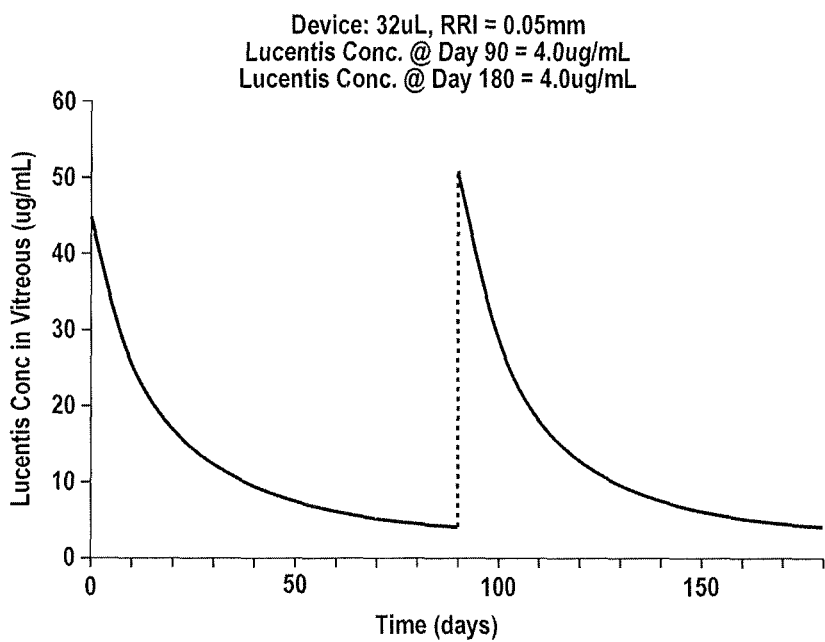
FIG. 19C shows determined concentrations of ranibizumab in the vitreous humor for a first 50 uL Lucentis™ injection into a 32 uL reservoir of the device and a second 50 uL injection at 90 days, in accordance with embodiments.

FIG. 19C shows determined concentrations of Lucentis™ in the vitreous humor for a first 50 uL injection into a 32 uL device and a second 50 uL injection at a time greater than 90 days. The calculations show that the 50 uL dosage of the monthly FDA approved bolus injection can be used to treat the eye for about 90 days, and that the injections can be repeated to treat the eye, for example at approximately 90 day intervals. The Lucentis™ may comprise a predetermined amount of the commercially available formulation injected into the device. The predetermine amount corresponds to the amount of the monthly bolus injection, for example 50 uL. The therapeutic device may comprise a substantially fixed volume container reservoir having a volume of 32 uL, such that a first 32 uL portion of the 50 uL injection is contained in the reservoir for sustained and/or controlled release and a second 18 uL portion of the 50 uL injection is passed through the porous structure and released into the vitreous with an 18 uL bolus. The filling efficiency of the injection into the device may comprise less than 100%, and the reservoir volume and injection volume can be adjusted based on the filling efficiency in accordance with the teachings described herein. For example, the filling efficiency may comprise approximately 90%, such that the first portion comprises approximately 29 uL contained in the chamber of the reservoir container and the second portion comprises approximately 21 uL passed through the device for the 50 uL of Lucentis™ injected into the therapeutic device. The initial concentration of Lucentis™ in the vitreous humor corresponds to about 45 ug/mL immediately following injection into the reservoir device. The concentration of Lucentis™ in the vitreous humor decreases to about 4 ug/mL at 90 days. A second 50 uL injection of Lucentis™ approximately 90 days after the first injection increases the concentration to about 50 ug/mL. The concentration of Lucentis™ in the vitreous humor decreases to about 4 ug/mL at 180 days after the first injection and 90 days after the second injection. These calculations show that the concentration of Lucentis™ can be continuously maintained above a minimum inhibitory concentration of about 4 ug per ml with the 50 uL injection into the device. Additional injections can be made every 120 days for several years to deliver the therapeutic agent to treat the patient. The injections can be made more frequently or less frequently, depending upon the minimum inhibitory concentration, the release rate profile, and the discretion of the treating physician.

Figure 19D:
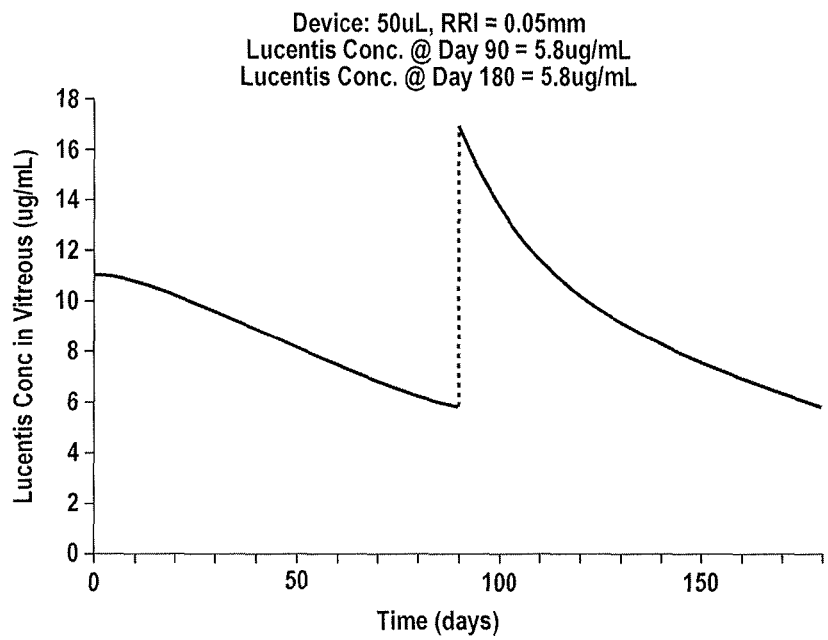
FIG. 19D shows determined concentrations of ranibizumab in the vitreous humor for a first 50 uL Lucentis™ injection into a 50 uL reservoir of the device and a second 50 uL injection at 90 days, in accordance with embodiments.

FIG. 19D shows determined concentrations of Lucentis™ in the vitreous humor for a first 50 uL injection into a 50 uL device and a second 50 uL injection at 90 days. The calculations show that the 50 uL dosage of the monthly FDA approved bolus injection can be used to treat the eye for about 90 days, and that the injections can be repeated to treat the eye, for example at approximately 90 day intervals. The Lucentis™ may comprise a predetermined amount of the commercially available formulation injected into the device. The filling efficiency of the injection into the device may comprise less than 100%, and the reservoir volume and injection volume can be adjusted based on the filling efficiency in accordance with the teachings described herein. For example, the filling efficiency may comprise approximately 90%, such that the first portion comprises approximately 45 uL contained in the chamber of the reservoir container and the second portion comprises approximately 5 uL passed through the device for the 50 uL of Lucentis™ injected into the therapeutic device. The initial concentration of Lucentis™ in the vitreous humor corresponds to about 11 ug/mL immediately following injection into the reservoir device. The concentration of Lucentis™ in the vitreous humor decreases to about 5.8 ug/mL at 90 days. A second 50 uL injection of Lucentis™ approximately 90 days after the first injection increases the concentration to about 17 ug/mL. The concentration of Lucentis™ in the vitreous humor decreases to about 5.8 ug/mL at 180 days after the first injection and 90 days after the second injection. These calculations show that the concentration of Lucentis™ can be continuously maintained above a minimum inhibitory concentration of about 5 ug per ml with the 50 uL injection into the device. Additional injections can be made, for example every 90 days for several years to deliver the therapeutic agent to treat the patient.

Figure 19E:
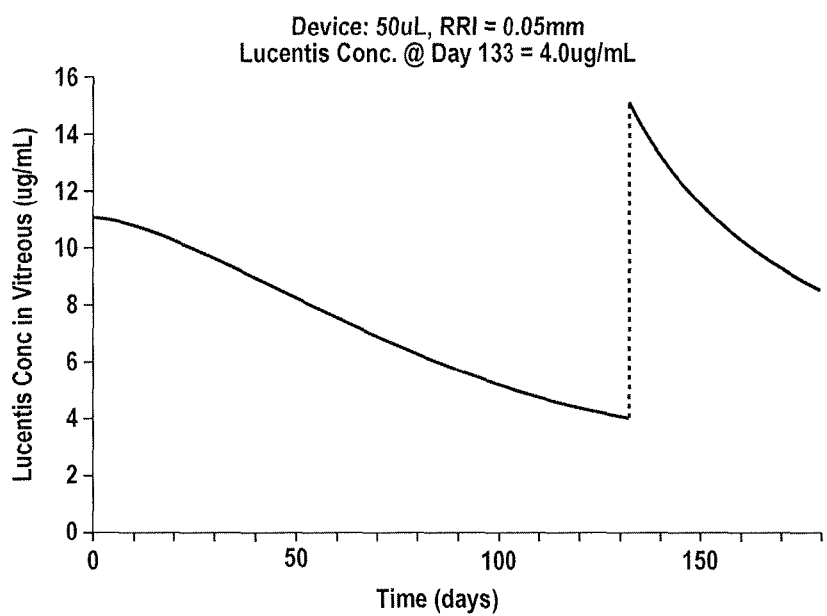
FIG. 19E shows determined concentrations of ranibizumab in the vitreous humor for a first 50 uL Lucentis™ injection into a 50 uL reservoir of the device and a second 50 uL injection at 130 days, in accordance with embodiments.

FIG. 19E shows determined concentrations of Lucentis™ in the vitreous humor for a first 50 uL injection into a 50 uL device and a second 50 uL injection at 90 days. The calculations show that the 50 uL dosage of the monthly FDA approved bolus injection can be used to treat the eye for about 130 days, and that the injections can be repeated to treat the eye, for example at approximately 120 day intervals. The Lucentis™ may comprise a predetermined amount of the commercially available formulation injected into the device. The filling efficiency of the injection into the device may comprise less than 100%, and the reservoir volume and injection volume can be adjusted based on the filling efficiency in accordance with the teachings described herein. For example, the filling efficiency may comprise approximately 90%, such that the first portion comprises approximately 45 uL contained in the chamber of the reservoir container and the second portion comprises approximately 5 uL passed through the device for the 50 uL of Lucentis™ injected into the therapeutic device. The initial concentration of Lucentis™ in the vitreous humor corresponds to about 11 ug/mL immediately following injection into the reservoir device. The concentration of Lucentis™ in the vitreous humor decreases to about 4 ug/mL at 133 days. A second 50 uL injection of Lucentis™ approximately 130 days after the first injection increases the concentration to about 15 ug/mL. Based on these calculations, the concentration of Lucentis™ in the vitreous humor decreases to about 4 ug/mL at 266 days after the first injection and 90 days after the second injection. These calculations show that the concentration of Lucentis™ can be continuously maintained above a minimum inhibitory concentration of about 4 ug per ml with the 50 uL injection into the device. Additional injections can be made, for example every 90 days for several years to deliver the therapeutic agent to treat the patient.

Figure 19F:
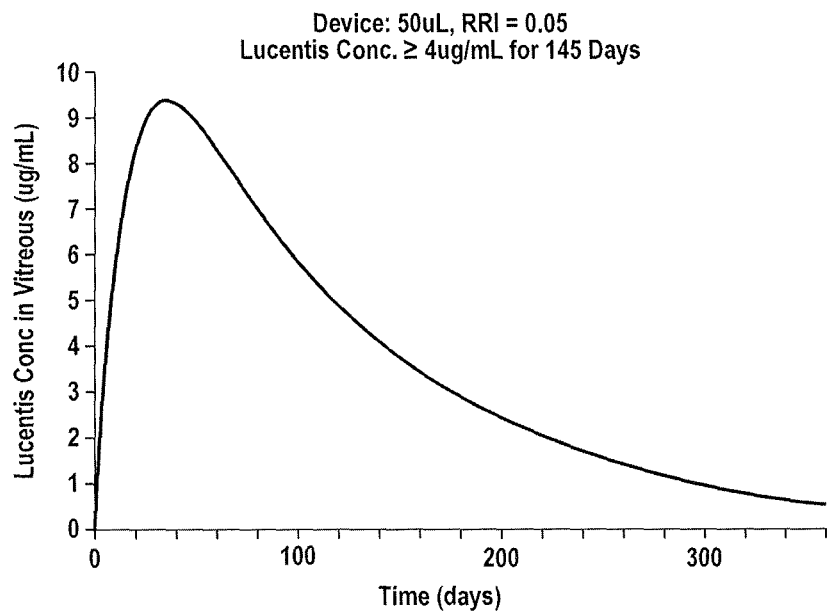
FIG. 19F shows determined concentrations of ranibizumab in the vitreous humor for a 50 uL Lucentis™ injection into a 50 uL device having a release rate index of 0.05, in accordance with embodiments.
Figure 19G:
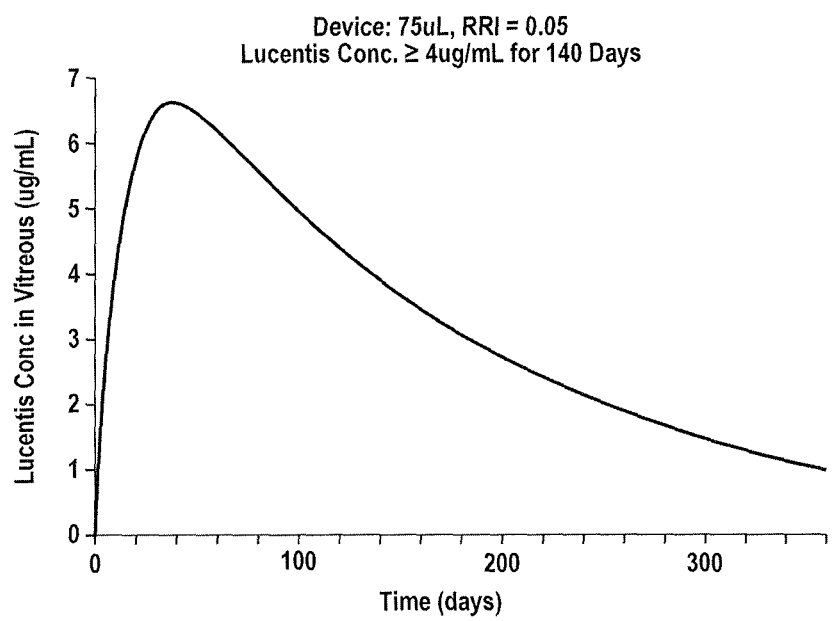
FIG. 19G shows determined concentrations of ranibizumab in the vitreous humor for a 50 uL Lucentis™ injection into a 75 uL device having a release rate index of 0.05, in accordance with embodiments.
Figure 19H:
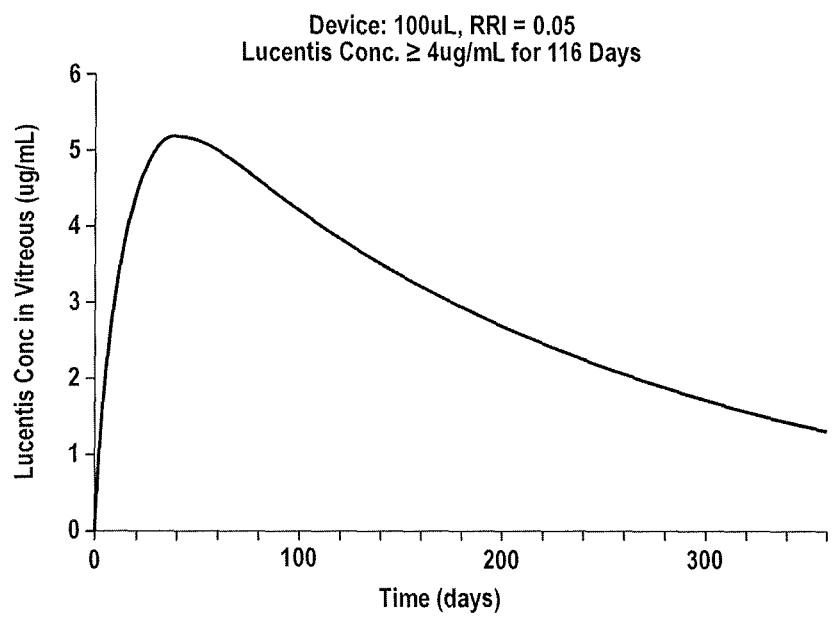
FIG. 19H shows determined concentrations of ranibizumab in the vitreous humor for a 50 uL Lucentis™ injection into a 100 uL device having a release rate index of 0.05, in accordance with embodiments.
Figure 19I:
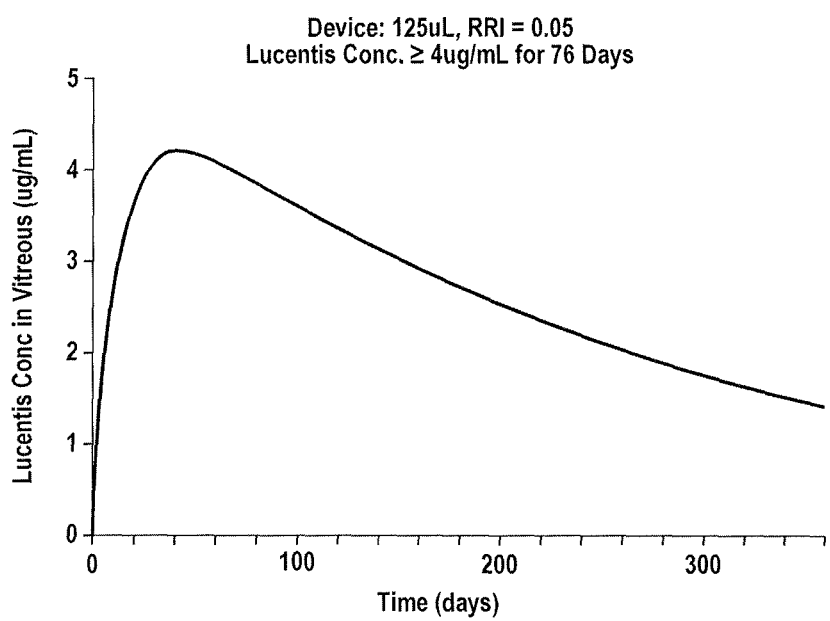
FIG. 19I shows determined concentrations of ranibizumab in the vitreous humor for a 50 uL Lucentis™ injection into a 125 uL device having a release rate index of 0.05, in accordance with embodiments.
Figure 19J:
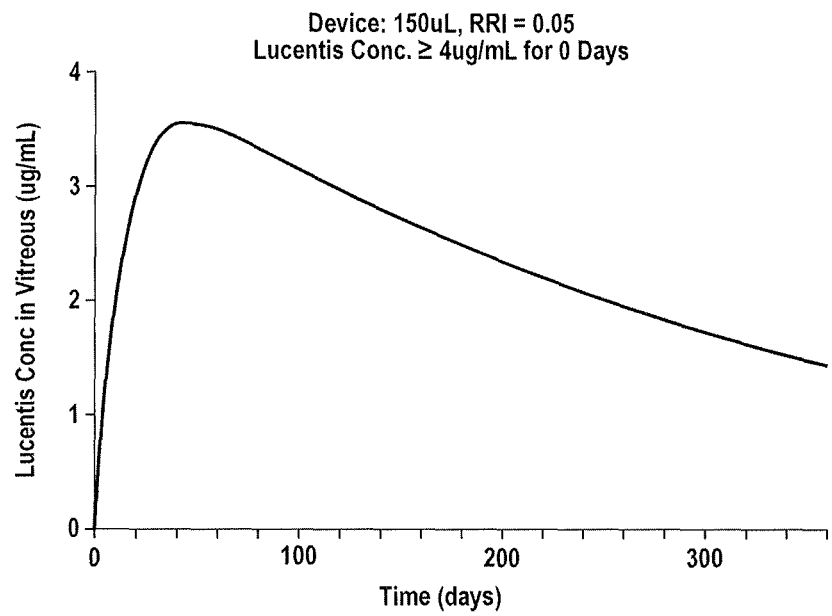
FIG. 19J shows determined concentrations of ranibizumab in the vitreous humor for a 50 uL Lucentis™ injection into a 150 uL device having a release rate index of 0.05, in accordance with embodiments.
Figure 19K:
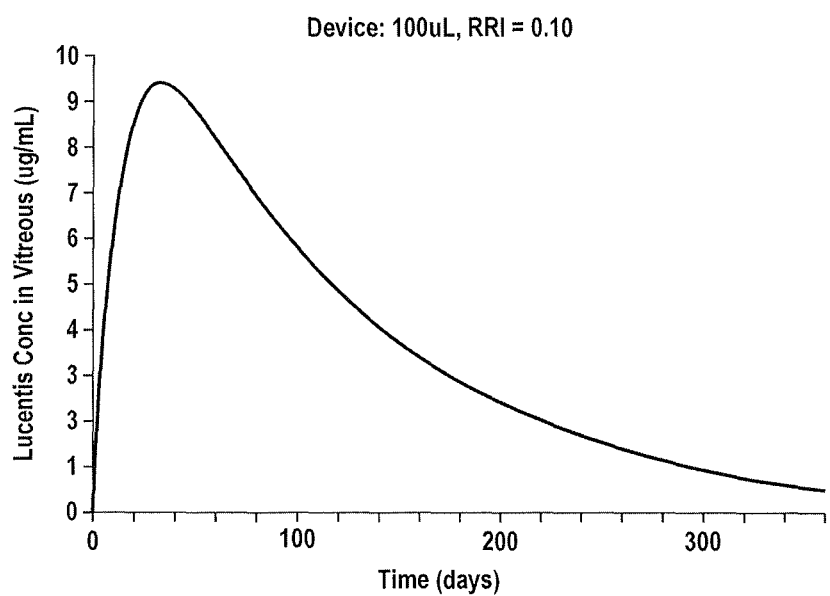
FIG. 19K shows determined concentrations of ranibizumab in the vitreous humor for a 50 uL Lucentis™ injection into a 100 uL device having a release rate index of 0.1, in accordance with embodiments.
Figure 19L:
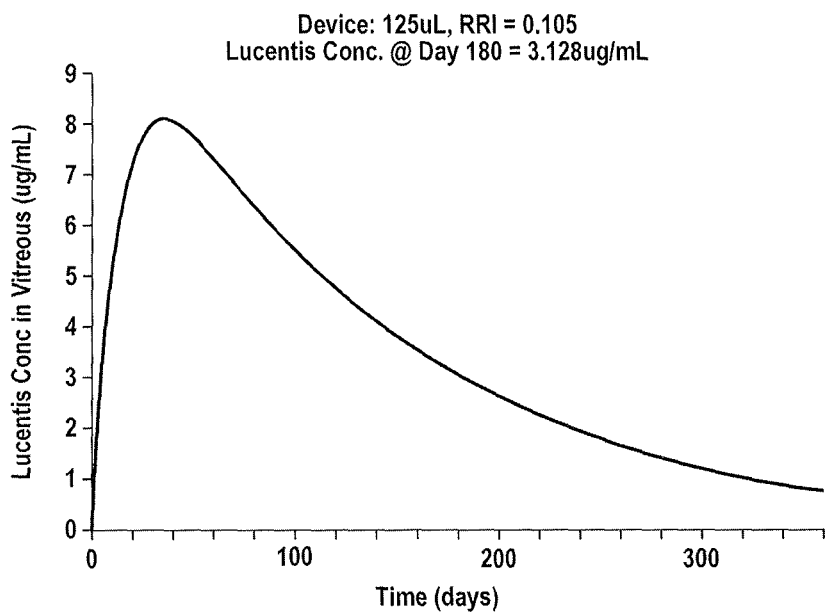
FIG. 19L shows determined concentration profiles of ranibizumab in the vitreous humor for a 50 uL Lucentis™ injection into a 125 uL reservoir device having a release rate index of 0.105, in accordance with embodiments.
Figure 19M:
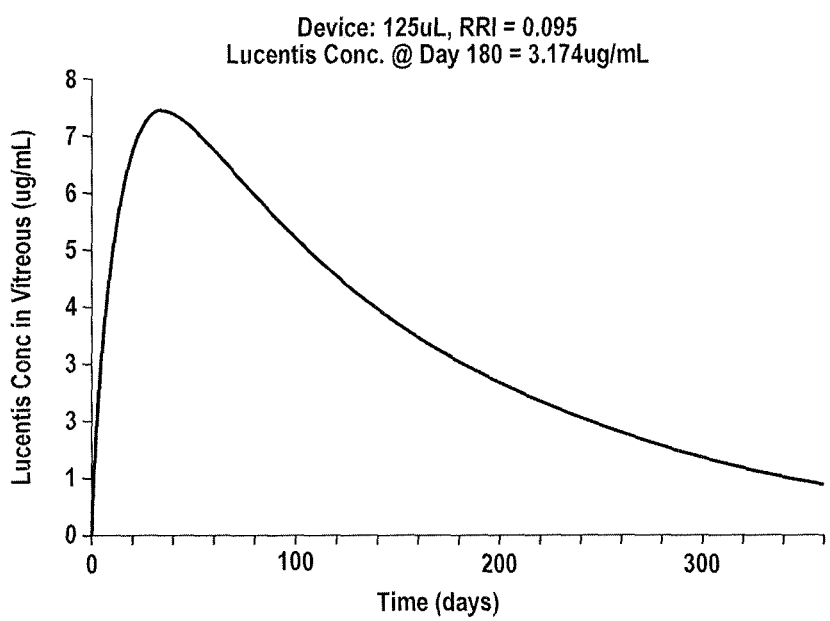
FIG. 19M shows determined concentration profiles of ranibizumab in the vitreous humor for a 50 uL Lucentis™ injection into a 125 uL reservoir device having a release rate index of 0.095, in accordance with embodiments.
Figure 19N:
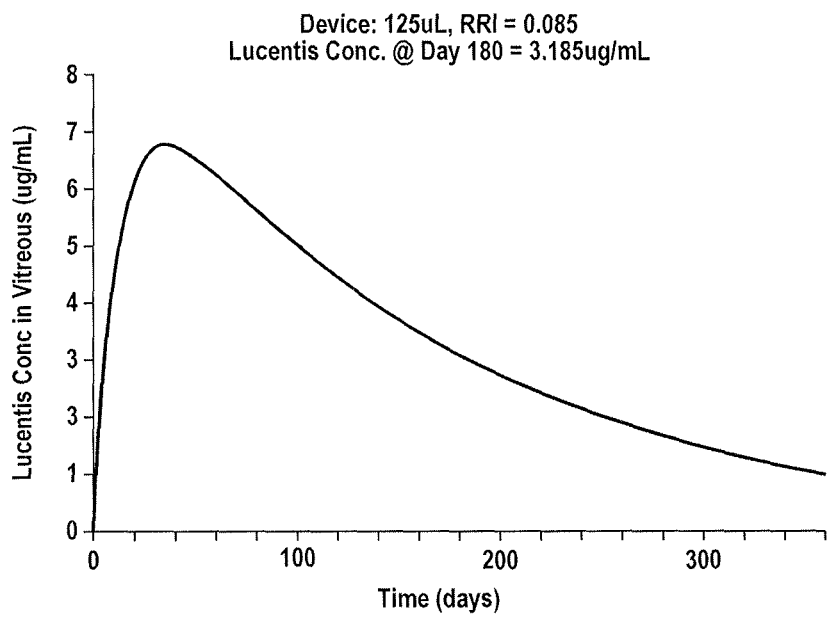
FIG. 19N shows determined concentration profiles of ranibizumab in the vitreous humor for a 50 uL Lucentis™ injection into a 125 uL reservoir device having a release rate index of 0.085, in accordance with embodiments.
Figure 19O:
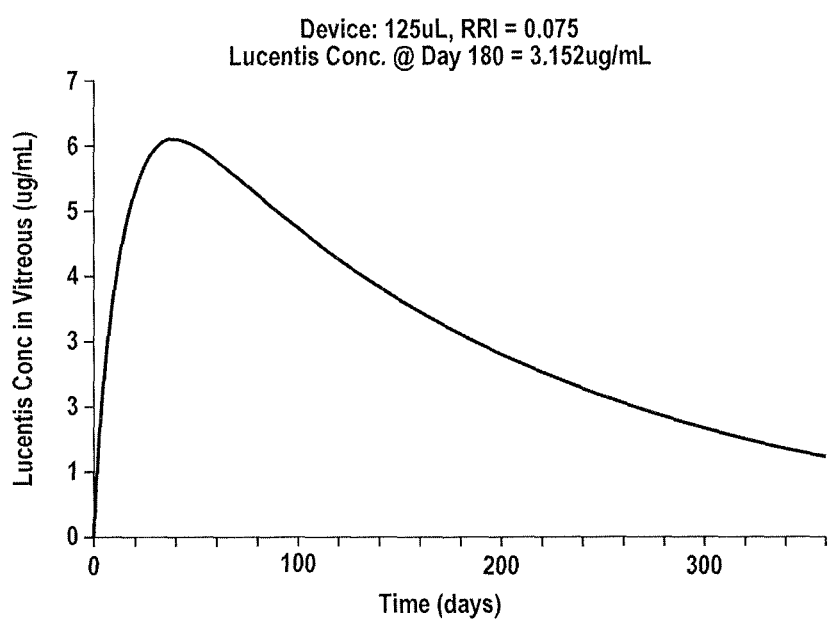
FIG. 19O shows determined concentration profiles of ranibizumab in the vitreous humor for a 50 uL Lucentis™ injection into a 125 uL reservoir device having a release rate index of 0.075, in accordance with embodiments.
Figure 19P:
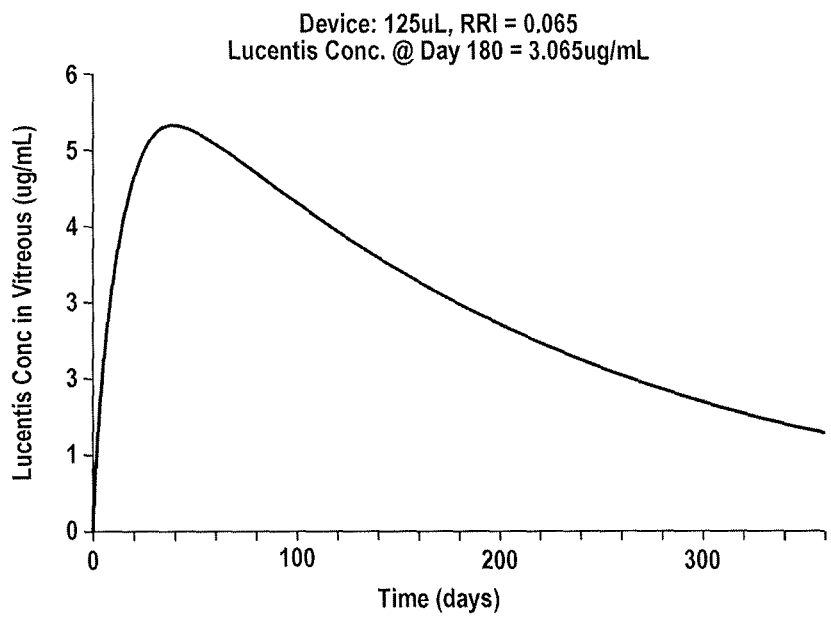
FIG. 19P shows determined concentration profiles of ranibizumab in the vitreous humor for a 50 uL Lucentis™ injection into a 125 uL reservoir device having a release rate index of 0.065, in accordance with embodiments.

Although FIGS. 19B to 19P make reference to injections of commercially available off the shelf formulations of Lucentis™, therapeutic device 100 can be similarly configured to release many formulations of the therapeutic agents as described herein, for example with reference to Table 1A and the Orange Book of FDA approved formulations and similar books of approved drugs in many countries, unions and jurisdictions such as the European Union. For example, based on the teachings described herein, one can determine empirically the parameters of therapeutic device 100 so as to tune the device to receive a injection of a commercially available formulation corresponding to a monthly bolus injections and release the injected therapeutic agent with amounts above the minimum inhibitory concentration for an extended time of at least about two months, for example, at least about three months, for example, or about four months, for example.

FIG. 19F shows determined concentrations of ranibizumab in the vitreous humor for a 50 uL Lucentis™ injection into a 50 uL device having a release rate index of 0.05. The concentration of ranibizumab in the vitreous humor peaks at around 9 ug/mL and is at or above 4 ug/mL for about 145 days. The concentration remains above about 1 ug/mL for about 300 days. The concentration is about 0.6 ug/mL at 360 days, and can be suitable for treatment with a single injection up to one year, based on a minimum inhibitory concentration of about 0.5. The minimum inhibitory concentration can be determined empirically by a person of ordinary skill in the art based on the teachings described herein.

FIG. 19G shows determined concentrations of ranibizumab in the vitreous humor for a 50 uL Lucentis™ injection into a 75 uL device having a release rate index of 0.05. The concentration of ranibizumab in the vitreous humor peaks at around 6.5 ug/mL and is at or above 4 ug/mL for about 140 days. The concentration remains above about 1 ug/mL for about 360 days.

FIG. 19H shows determined concentrations of ranibizumab in the vitreous humor for a 50 uL Lucentis™ injection into a 100 uL device having a release rate index of 0.05. The concentration of ranibizumab in the vitreous humor peaks at around 5 ug/mL and is at or above 4 ug/mL for about 116 days. The concentration remains above about 1 ug/mL for more than 360 days and is about 1.5 ug/mL at 360 days.

FIG. 19I shows determined concentrations of ranibizumab in the vitreous humor for a 50 uL Lucentis™ injection into a 125 uL device having a release rate index of 0.05. The concentration of ranibizumab in the vitreous humor peaks at around 4.3 ug/mL and does not equal or exceed 4 ug/mL. The concentration remains above about 1 ug/mL for more than 360 days and is about 1.5 ug/mL at 360 days.

FIG. 19J shows determined concentrations of ranibizumab in the vitreous humor for a 50 uL Lucentis™ injection into a 150 uL device having a release rate index of 0.05. The concentration of ranibizumab in the vitreous humor peaks at around 3.5 ug/mL and does not equal or exceed 4 ug/mL. The concentration remains above about 1 ug/mL for more than 360 days and is about 1.5 ug/mL at 360 days.

FIG. 19K shows determined concentrations of ranibizumab in the vitreous humor for a 50 uL Lucentis™ injection into a 100 uL device having a release rate index of 0.1. These determined concentrations are similar to the determined concentrations of FIG. 19F, and show that the release rate index of the porous structure can be tuned with the device volume to provide therapeutic concentration profile for an extended time. For example, by doubling the volume of the reservoir so as to half the concentration of therapeutic agent in the vitreous, the release rate index can be doubled so as to provide a similar therapeutic concentration profile. The concentration of ranibizumab in the vitreous humor peaks at around 9 ug/mL and is at or above 4 ug/mL for about 145 days. The concentration remains above about 1 ug/mL for about 300 days. The concentration is about 0.6 ug/mL at 360 days.

FIGS. 19L to 19P show examples of release rate profiles with 125 uL reservoir devices having the RRI vary from about 0.065 to about 0.105, such that these devices are tuned to receive the 50 uL injection of Lucentis™ and provide sustained release above a minimum inhibitory concentration for at least about 180 days. These calculations used a drug half life in the vitreous of 9 days to determine the profiles and 100% efficiency of the injection.

FIG. 19L shows determined concentration profiles of ranibizumab in the vitreous humor for a 50 uL Lucentis™ injection into a 125 uL reservoir device having a release rate index of 0.105. The concentration of ranibizumab in the vitreous at 180 days is about 3.128 ug/mL.

FIG. 19M shows determined concentration profiles of ranibizumab in the vitreous humor for a 50 uL Lucentis™ injection into a 125 uL reservoir device having a release rate index of 0.095. The concentration of ranibizumab in the vitreous at 180 days is about 3.174 ug/mL.

FIG. 19N shows determined concentration profiles of ranibizumab in the vitreous humor for a 50 uL Lucentis™ injection into a 125 uL reservoir device having a release rate index of 0.085. The concentration of ranibizumab in the vitreous at 180 days is about 3.185 ug/mL.

FIG. 19O shows determined concentration profiles of ranibizumab in the vitreous humor for a 50 uL Lucentis™ injection into a 125 uL reservoir device having a release rate index of 0.075. The concentration of ranibizumab in the vitreous at 180 days is about 3.152 ug/mL.

FIG. 19P shows determined concentration profiles of ranibizumab in the vitreous humor for a 50 uL Lucentis™ injection into a 125 uL reservoir device having a release rate index of 0.065. The concentration of ranibizumab in the vitreous at 180 days is about 3.065 ug/mL.

The optimal RRI for the concentration of ranibizumab at 180 days for a reservoir volume of 125 uL and a 50 uL injection of Lucentis™ can be calculated based on the equations as described herein, and is about 0.085. Although the optimal value is 0.085, the above graphs show that the reservoir and release rate index can be tuned to provide therapeutic amounts of ranibizumab above a minimum inhibitory concentration of 3 ug/mL with many values of the RRI and reservoir volume, for example values within about +/−30% to +/−50% of the optimal values for the predetermined quantity of Lucentis™ formulation.

Table 4E shows values of parameters used to determine the ranibizumab concentration profiles as in FIGS. 19K to 19P.

TABLE 4E

| | |
|---|---|
| Diffusion coeff (cm2/s) | 1.0E−06 |
| Initial Loading (ug/mL) | 10000 |
| Reservoir Vol (ml) | 0.125 |
| PA/TL (mm) | varied |
| Half-life (days) | 9 |
| Rate constant, k (1/day) | 0.077 |
| Vitreous vol (ml) | 4.5 |
| Volume injected (mL) | 0.05 |
| Time step (days) | 0.1 |

TABLE 4E-continued

| | |
|---|---|
| Time between refills (days) | 180 |
| Refill Efficiency | 100% |

The therapeutic concentration profiles of examples of FIGS. 19B to 19P were determined with a nine day half-life of the drug in the vitreous humor of the human eye. The therapeutic concentration profiles can be scaled in accordance with the half life of the therapeutic agent in the eye. For example, with an eighteen day half life, the concentration in these examples will be approximately twice the values shown in the graph at the extended times, and with a 4.5 day half-life, the concentrations will be approximately half the values shown with the extended times. As an example, a drug half life of eighteen days instead of nine days will correspond to a concentration of about 1.4 ug/mL at 360 days instead of about 0.6 ug/mL as shown in FIGS. 19F and 19K. This scaling of the concentration profile based on drug half life in the vitreous can be used to tune the volume and sustained release structures of the therapeutic device, for example in combination with the minimum inhibitory concentration. Although the above examples were calculated for Lucentis™, similar calculations can be performed for therapeutic agents and formulations as described herein, for example as described herein with reference to Table 1A.

Based on the teachings described herein, a person of ordinary skill in the art can determine the release rate index and volume of the therapeutic agent based on the volume of formulation injected into the device and minimum inhibitory concentration. This tuning of the device volume and release rate index based on the volume of formulation injected can produce unexpected results. For example, with a clinically beneficial minimum inhibitory concentration of about 4 ug/mL, a single bolus injection corresponding to a one month injection can provide a therapeutic benefit for an unexpected three or more months, such as four months. Also, for a clinically beneficial minimum inhibitory concentration of at least about 1.5 ug/mL, a single bolus injection corresponding to a one month injection can provide a therapeutic benefit for an unexpected twelve or more months. The clinically beneficial minimum inhibitory concentration can be determined empirically based on clinical studies as described herein.

Although the examples of FIGS. 19F to 19K assumed a filling efficiency of one hundred percent, a person of ordinary skill in the art based on the teachings as described herein can determine the release rate profiles for filling efficiencies less than 100%, for example with 90% filling efficiency as shown above. Such filling efficiencies can be achieved with injector apparatus and needles as described herein, for example with reference to FIGS. 7, 7A, 7A1 and 7A2.

Figure 19Q:
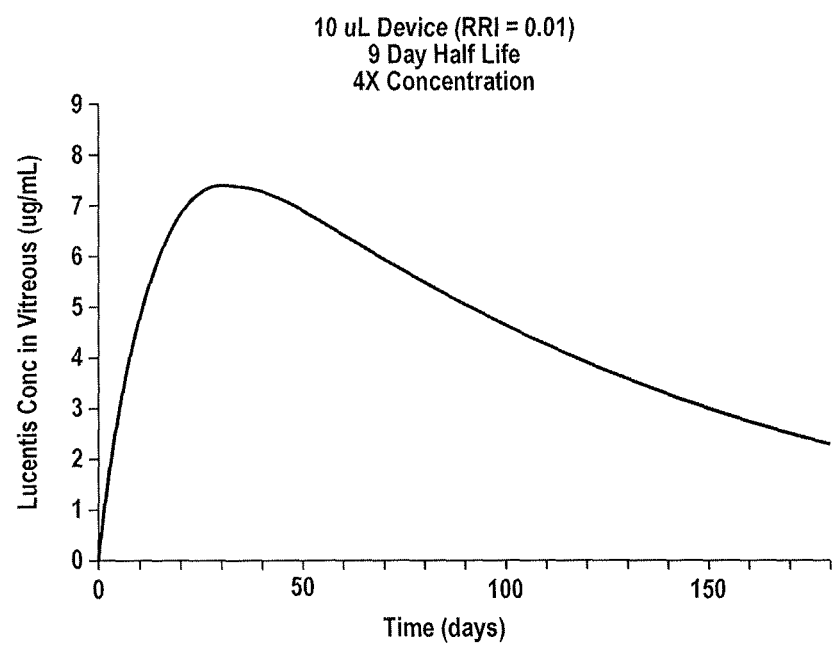
FIG. 19Q shows determined concentrations of ranibizumab in the vitreous humor for a 10 uL concentrated Lucentis™ (40 mg/mL) injection into a 10 uL device having a release rate index of 0.01 and in which the ranibizumab has a half life in the vitreous humor of about nine days, in accordance with embodiments.

FIG. 19Q shows determined concentrations of ranibizumab in the vitreous humor for a 10 uL concentrated Lucentis™ (40 mg/mL) injection into a 10 uL device having a release rate index of 0.01 and in which the ranibizumab has a half life in the vitreous humor of about nine days. These data show that an injection of 10 uL of concentrated (40 mg/mL) Lucentis™ into a 10 uL reservoir device can maintain the concentration of Lucentis™ above at least about 2 ug/mL for at least about 180 days when the half life of Lucentis™ in the vitreous is at least about nine days, and that the device can provide therapeutic concentrations for an extended time of at least about 180 days when the minimum inhibitory concentration comprises no more than about 2 ug/mL.

Figure 19R:
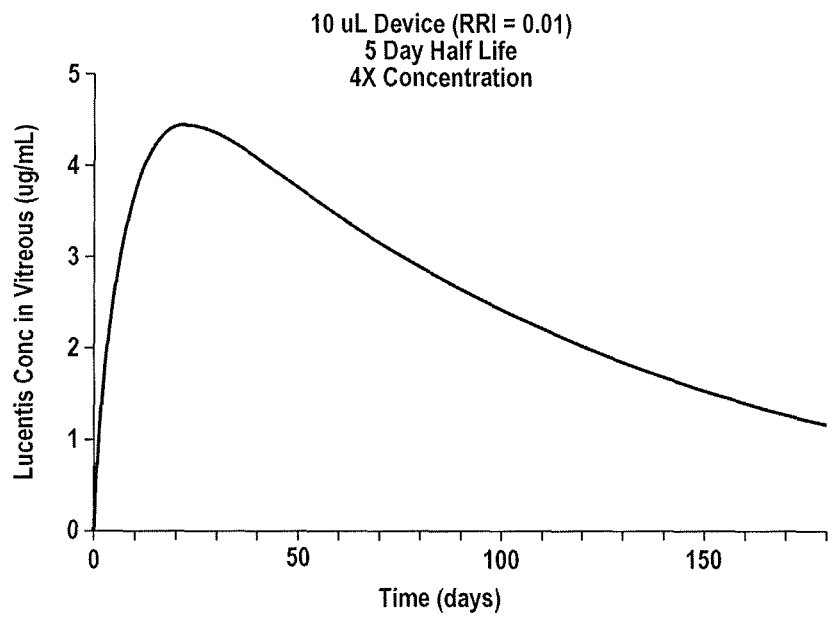
FIG. 19R shows determined concentrations of ranibizumab in the vitreous humor for a 10 uL concentrated Lucentis™ (40 mg/mL) injection into a 10 uL device having a release rate index of 0.01 and in which the ranibizumab has a half life in the vitreous humor of about five days, in accordance with embodiments.

FIG. 19R shows determined concentrations of ranibizumab in the vitreous humor for a 10 uL concentrated Lucentis™ (40 mg/mL) injection into a 10 uL device having a release rate index of 0.01 and in which the ranibizumab has a half life in the vitreous humor of about five days. These data show that an injection of 10 uL of concentrated (40 mg/mL) Lucentis™ into a 10 uL reservoir device can maintain the concentration of Lucentis™ above at least about 1 ug/mL for at least about 180 days when the half life of Lucentis™ in the vitreous is at least about five days, and that the device can provide therapeutic concentrations for an extended time of at least about 180 days when the minimum inhibitory concentration comprises no more than about 1 ug/mL.

Figure 19S:
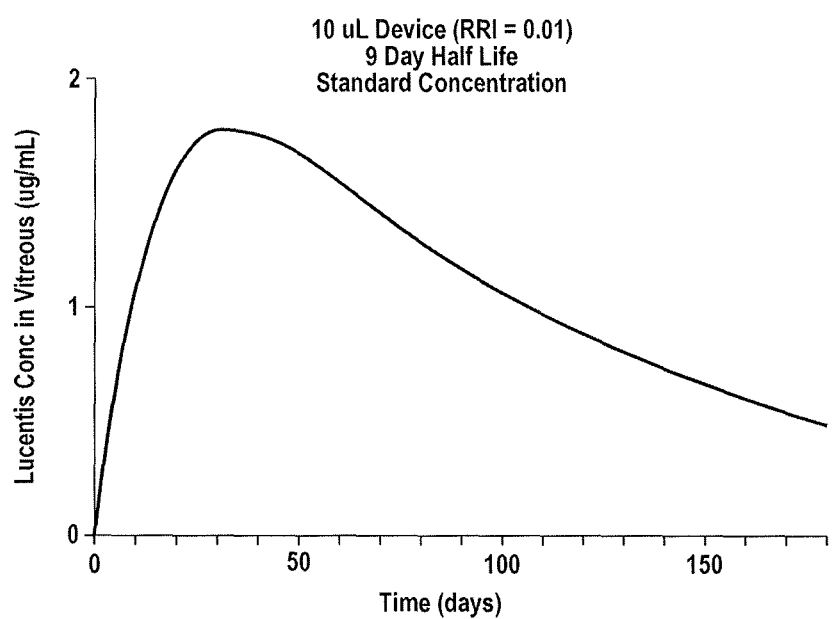
FIG. 19S shows determined concentrations of ranibizumab in the vitreous humor for a 10 uL standard Lucentis™ (10 mg/mL) injection into a 10 uL device having a release rate index of 0.01 and in which the ranibizumab has a half life in the vitreous humor of about nine days, in accordance with embodiments.

FIG. 19S shows determined concentrations of ranibizumab in the vitreous humor for a 10 uL standard Lucentis™ (10 mg/mL) injection into a 10 uL device having a release rate index of 0.01 and in which the ranibizumab has a half life in the vitreous humor of about nine days. These data show that an injection of 10 uL of standard commercially available (10 mg/mL) Lucentis™ into a 10 uL reservoir device can maintain the concentration of Lucentis™ above at least about 0.5 ug/mL for at least about 180 days when the half life of Lucentis™ in the vitreous is at least about nine days, and that the device can provide therapeutic concentrations for an extended time of at least about 180 days when the minimum inhibitory concentration comprises no more than about 0.5 ug/mL.

Figure 19T:
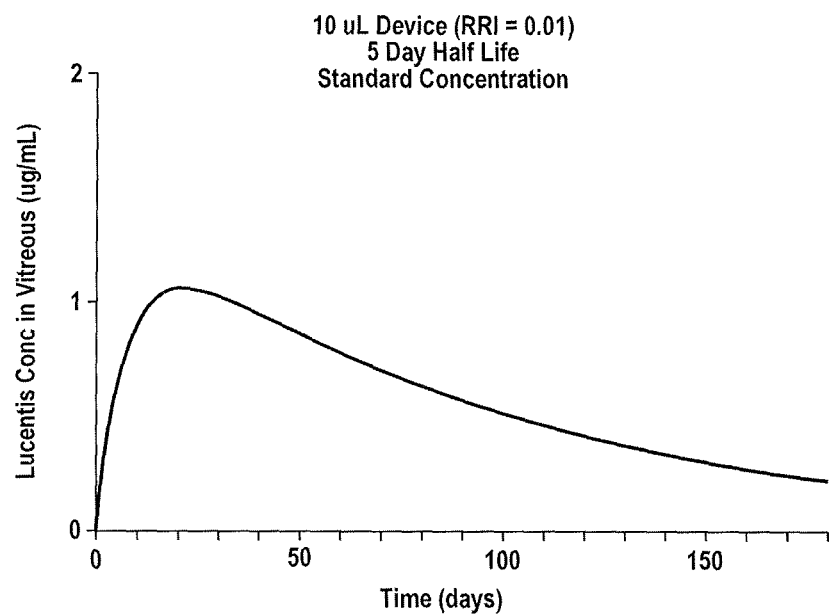
FIG. 19T shows determined concentrations of ranibizumab in the vitreous humor for a 10 uL standard Lucentis™ (10 mg/mL) injection into a 10 uL device having a release rate index of 0.01 and in which the ranibizumab has a half life in the vitreous humor of about five days, in accordance with embodiments.

FIG. 19T shows determined concentrations of ranibizumab in the vitreous humor for a 10 uL standard Lucentis™ (10 mg/mL) injection into a 10 uL device having a release rate index of 0.01 and in which the ranibizumab has a half life in the vitreous humor of about five days. These data show that an injection of 10 uL of standard commercially available (10 mg/mL) Lucentis™ into a 10 uL reservoir device can maintain the concentration of Lucentis™ above at least about 0.25 ug/mL for at least about 180 days when the half life of Lucentis™ in the vitreous is at least about five days, and that the device can provide therapeutic concentrations for an extended time of at least about 180 days when the minimum inhibitory concentration comprises no more than about 0.25 ug/mL.

Example 10

Calculations of Target Device Characteristics for a Device Releasing Drug from a Suspension Triamcinolone acetonide is a corticosteroid used to treat uveitis and other diseases involving ocular inflammation. A 4 mg intravitreal injection of a suspension of triamcinolone acetonide may be administered to patients unresponsive to topical corticosteroids. Calculations as described herein were performed to determine the characteristics of a device that would release therapeutic amounts for an extended period of time.

Consider a device with 10 uL reservoir volume loaded with 0.4 mg using a commercial drug product (40 mg/mL triamcinolone acetonide). Calculations were performed using a value of 19 ug/mL for the solubility of triamcinolone acetonide measured at 37° C. in 0.2 M potassium chloride and a diffusion coefficient of 5 e-6 $cm^2$/s representative of a small molecule. The target release rate is 1 ug/day based upon published clinical data. As an example, consider the 0.2 media grade stainless steel characterized in Example 8 with P/F=0.12 and a thickness of 0.5 mm. Using these values, the calculations suggest that therapeutic release rates could be achieved with a device containing a porous cylinder with an area of 5 $mm^2$. This could be achieved with a cylindrical device having an inner diameter of 2 mm and a length of porous tubing of 1 mm. Alternatively, the end of the device could be a porous cup with height of 0.8 mm (0.5 mm thick porous face plus 0.3 mm length) of porous tubing.

Assuming a typical value of 3 hours for the half-life of a small molecule in the vitreous, these calculations suggest the device will achieve a steady state triamcinolone acetonide vitreous concentration of 0.12 ug/mL.

Example 11

Figure 20:
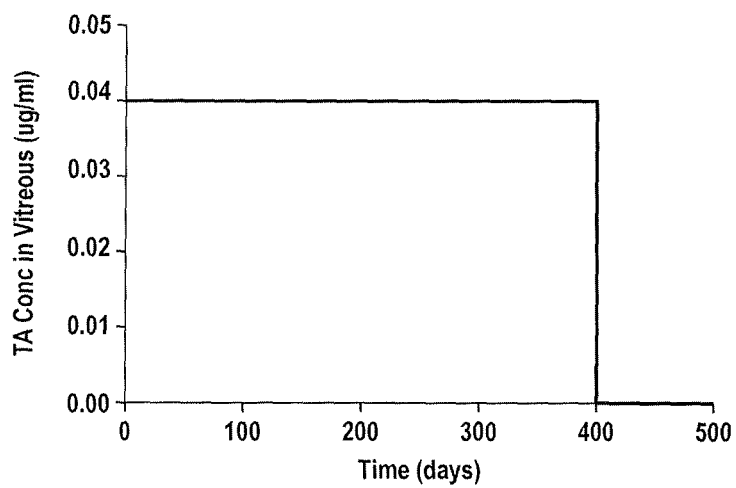
FIG. 20 shows a calculated time release profile of a therapeutic agent suspension in a reservoir, in accordance with embodiments.

Calculation of Release Rate Profile for a Therapeutic Agent Suspension Disposed in the Reservoir and Released Through the Porous Frit Structure FIG. 20 shows a calculated time release profile of a therapeutic agent suspension in a reservoir as in Example 10. Triamcinolone Acetonide concentrations in human vitreous were determined for a 10 uL device with RRI of 1.2 mm and shown. The calculations were based on the equations shown above for the suspension. The profile was generated with numerical simulation. Assuming a constant delivery rate of 1 ug/day starting instantaneously at T=0, the concentration in the vitreous of a human eye can reach within 99% of the steady state value in 1 day. At the other end of the drug release profile, the simulation shows the vitreous concentration when substantially all of the solid drug is gone; more than 99% of the dissolved drug is delivered within a day.

Assuming a typical value of 3 hours for the half-life of a small molecule in the vitreous, these calculations indicate that the device will achieve a substantially steady state triamcinolone acetonide vitreous concentration of 0.12 ug/mL in the rabbit or monkey (vitreous volume of 1.5 mL) or 0.04 ug/mL in the human eye (vitreous volume of 4.5 mL). The steady state vitreous concentration are maintained until there is no longer solid triamcinolone acetonide of the suspension in the reservoir. As shown in FIG. 20, a device with a 10 uL reservoir volume and Release Rate Index of 1.2 mm can produce substantially constant drug concentration amounts in the human vitreous for approx. 400 days. Additional experimental and clinical studies based on the teachings described herein can be conducted to determine the release rate profile in situ in human patients, and the drug reservoir volume and release rate index configured appropriately for therapeutic benefit for a target time of drug release. The substantially constant drug concentration amounts can provide substantial therapy and decrease side effects. Similar studies can be conducted with many suspensions of many therapeutic agents as described herein, for example suspensions of corticosteroids and analogues thereof as described herein.

Example 12

Figure 21:
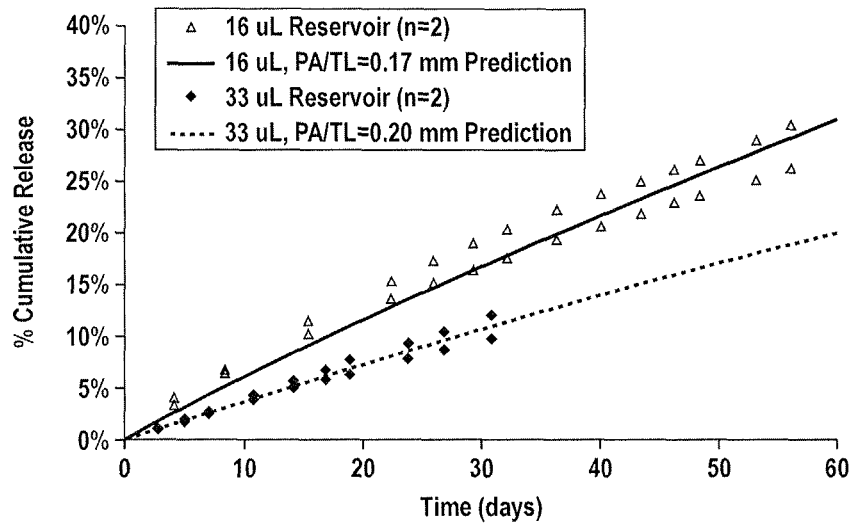
FIG. 21 shows cumulative release for Avastin™ with therapeutic devices comprising substantially similar porous frit structures and a 16 uL reservoir and a 33 uL reservoir.

Measured of Release Rate Profiles for Avastin™ Through the Porous Frit Structures Coupled to Reservoirs of Different Sizes and Dependence of Release Rate Profile on Reservoir Size FIG. 21 shows a release rate profiles of therapeutic devices comprising substantially similar porous frit structures and a 16 uL reservoir and a 33 uL reservoir. The release rate index of each frit was approximately 0.02. The release rate for two therapeutic devices each comprising a 16 uL reservoir and two therapeutic devices each comprising a 33 uL reservoir are shown. The device comprising the 33 uL reservoir released the Avastin™ at approximately twice the rate of the device comprising 16 uL reservoir. These measured data show that the release rate index and reservoir size can determine the release rate profile, such that the release rate index and reservoir can be configured to release the therapeutic agent for an extended time.

First Study: The data were measured with a 16 uL volume reservoir as follows: 25 mg/mL Avastin™; Frit #2 (0.031× 0.049", media grade 0.2 um, 316L SS, Mott Corporation); Substantially similar materials as Example 8 above (Teflon heat shrink tubing and silicone septum); 37 C; Data is truncated when one of two replicates formed a bubble. See data in Table 5A below.

Second Study: The data were measured with a 33 uL reservoir as follows: 25 mg/mL Avastin™; Frit #2 (0.031×0.049", media grade 0.2 um, 316L SS, Mott Corporation); Machined from solid beading, closed with a metal rod; 37 C; Data is truncated when one of two replicates formed a bubble.

TABLE 5A

Measured Release of Avastin ™ and RRI.

| Volume (uL) | Device | RRI (mm) | SS (ug/day)2 |
|---|---|---|---|
| 33 | 1 | 0.015 | 0.35 |
| 33 | 2 | 0.018 | 0.16 |
| 16 | 1 | 0.018 | 0.05 |
| 16 | 2 | 0.022 | 0.06 |
|  | Mean | 0.018 |  |
|  | % CV | 16% |  |

SS is the average of the squared difference between predicted and measured rates, and % CV refers to the coefficient of variation, a known statistical parameter.

Example 13

Measured Release Rate Profiles for Avastin™ Through the Porous Frit Structures

Figure 22A:
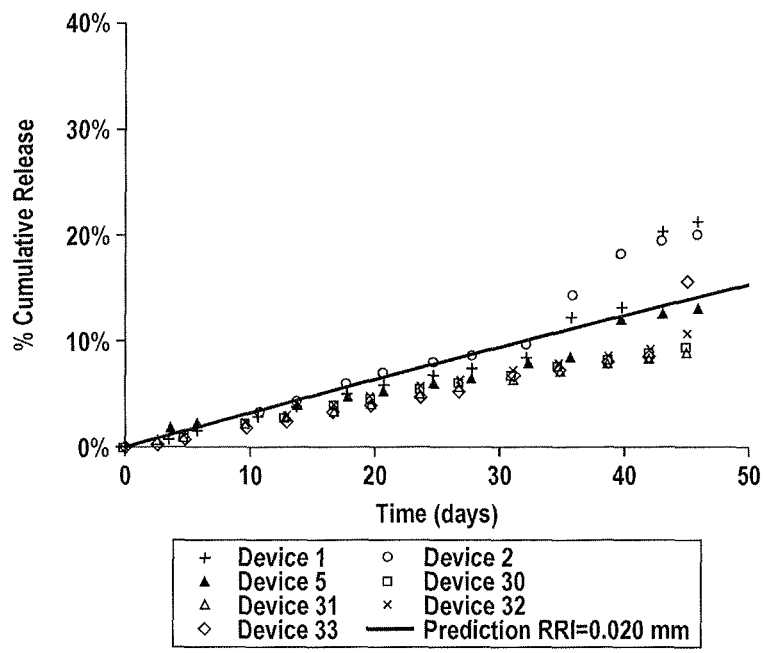
FIG. 22A shows cumulative release for Avastin™ with porous frit structures having a thickness of 0.049"

FIG. 22A shows cumulative release for Avastin™ with porous frit structures having a thickness of 0.049". The experiments used: 25 mg/mL Avastin™; Frit #2 (0.031×0.049", media grade 0.2 um, 316L SS, Mott Corporation); Machined polycarbonate surrogate with screw; Reservoir Volume 37 uL; 37 C. The device number and corresponding RRI's for each tested device are listed in Table 5B below. The determined RRI based on measurements is 0.02, consistent with the model for release of the therapeutic agent as described herein. Although some variability is noted with regards to the measured RRI for each test device, the RRI for each device can be used to determine the release of the therapeutic agent, and the porous structure can be further characterized with gas flow as described herein to determine the RRI prior to placement in the patient.

TABLE 5B

| Device | RRI (mm) | SS (ug/day)2 |
|---|---|---|
| 1 | 0.029 | 26.0 |
| 2 | 0.027 | 8.5 |
| 5 | 0.018 | 3.7 |
| 30 | 0.013 | 0.1 |
| 31 | 0.013 | 0.1 |
| 32 | 0.015 | 0.7 |
| 33 | 0.022 | 30.5 |
| Mean | 0.020 |  |
| % CV | 34% |  |

Figures 1, 22B:
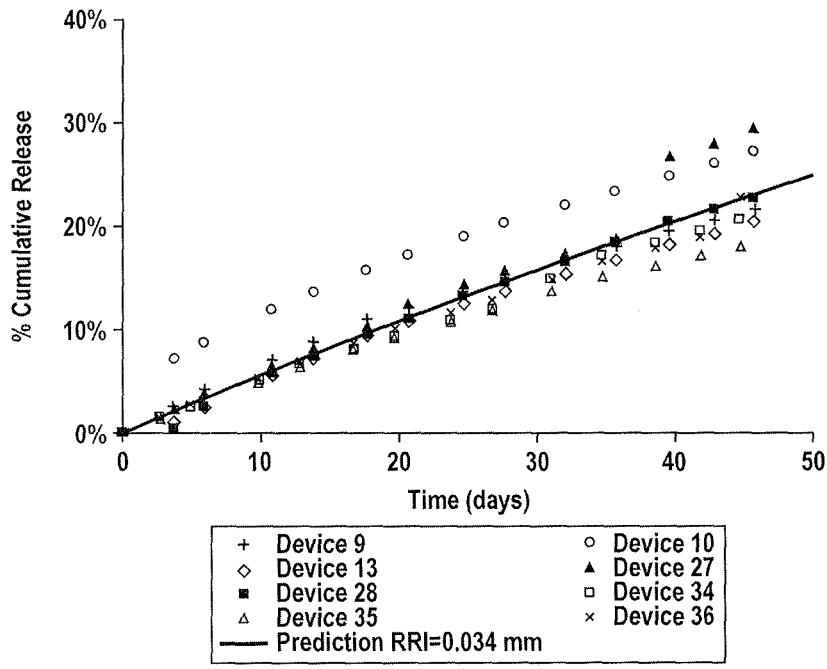
Figures 2, 22B:
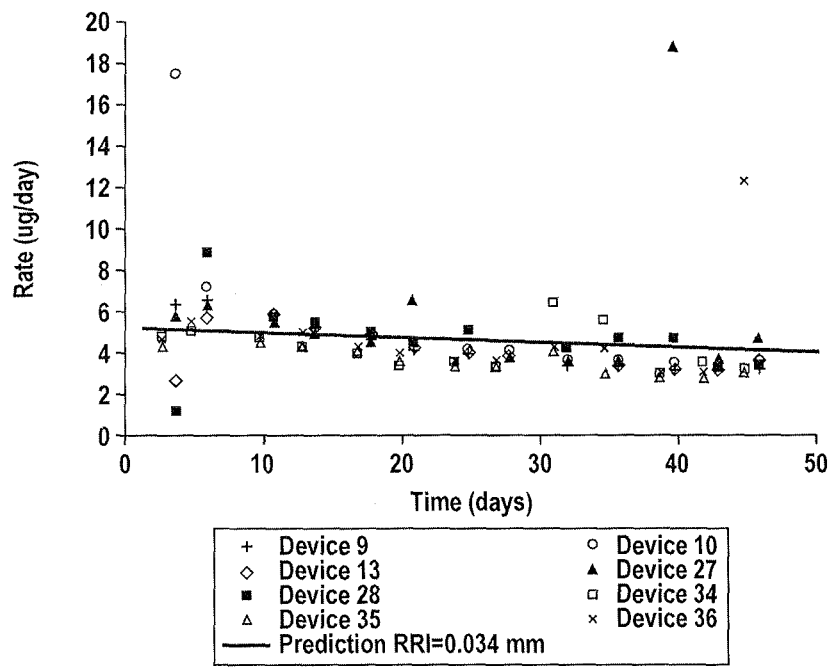

FIG. 22B1 shows cumulative release for Avastin™ with porous frit structures having a thickness of 0.029". The experiments used: 25 mg/mL Avastin™; Frit #3 (0.038×0.029", media grade 0.2 um, 316L SS, Mott Corporation); Machined polycarbonate surrogate with screw; Reservoir Volume 37 uL; 37 C. The device number and corresponding RRI's for each tested device are listed in Table 5C below. The determined RRI based on measurements is 0.034, consistent with the model for release of the therapeutic agent as described herein. Although some variability is noted with regards to the measured RRI for each test device, the RRI for each device can be used to determine the release of the therapeutic agent, and the porous structure can be further characterized with gas flow as described herein to determine the RRI prior to placement in the patient.

TABLE 5C

| Device | RRI (mm) | SS (ug/day)2 |
|---|---|---|
| 9 | 0.033 | 0.7 |
| 10 | 0.044 | 10.8 |
| 13 | 0.030 | 0.7 |
| 27 | 0.043 | 15.8 |
| 28 | 0.033 | 2.6 |
| 34 | 0.030 | 0.9 |
| 35 | 0.027 | 0.3 |
| 36 | 0.034 | 5.5 |
| Mean | 0.034 |  |
| % CV | 19% |  |

Table 5D shows an update to Table 5B showing experimental results for up to 130 days. Similarly, Table 5E is an update to Table 5C. In both cases, the RRI was determined by fitting the rate data from each device. For the analysis of data up to 130 days, the first data point is excluded from the fit because the model assumes the maximum delivery rate occurs at time zero while there is some startup time often associated with measured release profiles. The startup time may be related to the time it takes to displace all of the air in the frit. Use of different techniques to displace the air in the frit may reduce the startup time.

This early data has some noise that appears to be related to experimental issues such as contamination from excess protein that is present on the screw from filling the device and was not completely rinsed off at the start of the experiment. The contamination appears to occur randomly as receiver liquid may rinse off the protein while transferring the device from vial to vial at some time points but not others. A more accurate assessment of RRI can be obtained by using devices that had fewer or no outliers, as indicated by low values of SS. When this is done, the RRIs from Table 5D and 5E are 0.014 and 0.030 mm, respectively. Similar values for RRI are obtained from data up to 45 days and data up to 130 days, supporting the validity of the model.

TABLE 5D

|  | Up to 45 Days | | Up to 130 Days | |
|---|---|---|---|---|
| Device | RRI (mm) | SS (ug/day)^2 | RRI (mm) | SS (ug/day)^2 |
| 1 | 0.029 | 26.0 | 0.032 | 13.7 |
| 2 | 0.027 | 8.5 | 0.028 | 5.5 |
| 5 | 0.018 | 3.7 | 0.014 | 1.7 |
| 30 | 0.013 | 0.1 | 0.021 | 4.8 |
| 31 | 0.013 | 0.1 | 0.022 | 9.3 |
| 32 | 0.015 | 0.7 | 0.023 | 3.4 |
| 33 | 0.022 | 30.5 | 0.028 | 16.4 |
| Mean | 0.020 |  | 0.024 |  |

TABLE 5D-continued

| | Up to 45 Days | | Up to 130 Days | |
| --- | --- | --- | --- | --- |
| Device | RRI (mm) | SS (ug/day)^2 | RRI (mm) | SS (ug/day)^2 |
| % CV | 34% | | 24% | |
| Mean for SS < 2 | 0.014 | | 0.014 | |

TABLE 5E

| | Up to 45 Days | | Up to 130 Days | |
| --- | --- | --- | --- | --- |
| Device | RRI (mm) | SS (ug/day)^2 | RRI (mm) | SS (ug/day)^2 |
| 9 | 0.033 | 0.7 | 0.034 | 4.4 |
| 10 | 0.044 | 10.8 | 0.034 | 2.0 |
| 13 | 0.030 | 0.7 | 0.044 | 11.6 |
| 27 | 0.043 | 15.8 | 0.045 | 6.8 |
| 28 | 0.033 | 2.6 | 0.031 | 0.5 |
| 34 | 0.030 | 0.9 | 0.030 | 0.7 |
| 35 | 0.027 | 0.3 | 0.029 | 1.3 |
| 36 | 0.034 | 5.5 | 0.034 | 5.9 |
| Mean | 0.034 | | 0.035 | |
| % CV | 19% | | 17% | |
| Mean for SS < 2 | 0.030 | | 0.030 | |

FIG. 22B2 shows rate of release for Avastin™ with porous frit structures having a thickness of 0.029" as in FIG. 22B1. The rate of release can be determined from the measurements and the cumulative release. The outliers in this data can be related to measurement error, such as contamination that provides a signal in the mBCA protein assay.

Figure 23A:
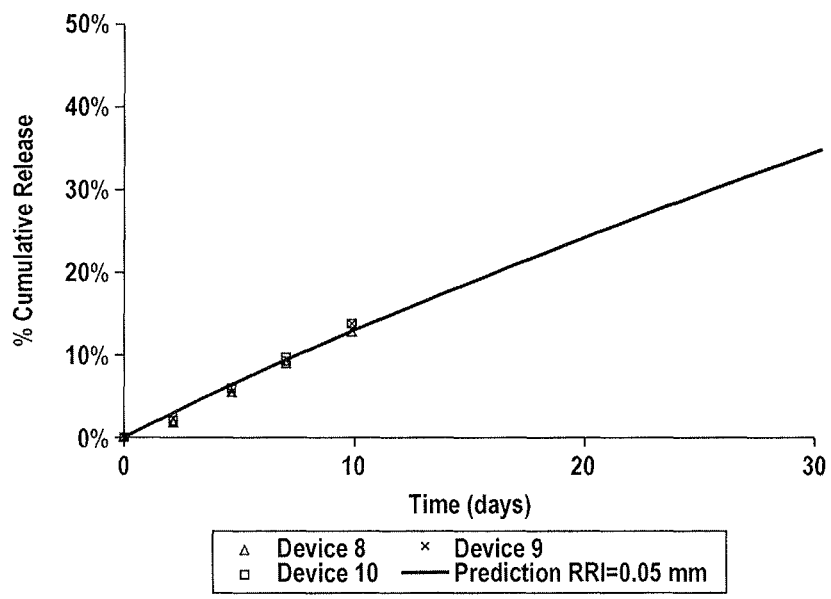
FIG. 23A shows cumulative release for Avastin™ with a reservoir volume of 20 uL.
Figures 1, 23A:
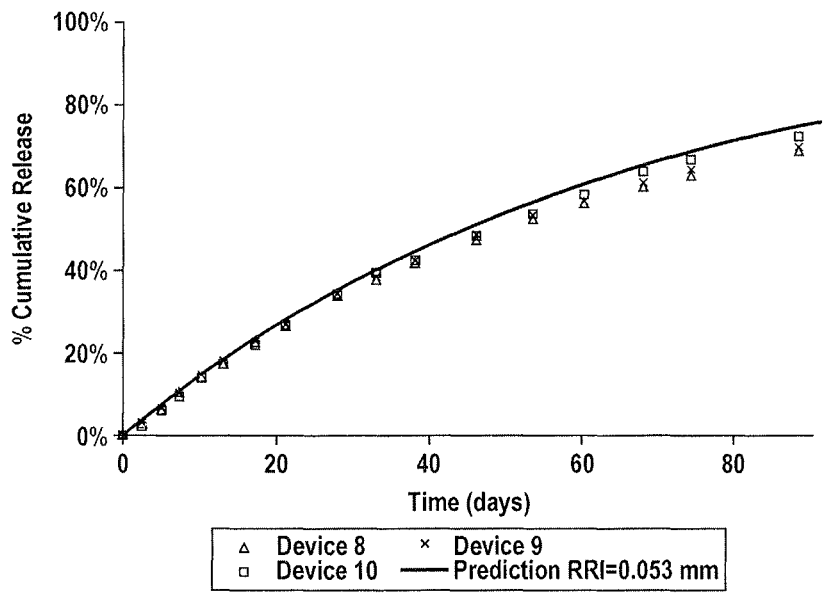

FIG. 23A shows cumulative release for Avastin™ with a reservoir volume of 20 uL. The experiment used: 25 mg/mL Avastin™; Frit #6 (0.038×0.029", media grade 0.2 um, 316L SS, Mott Corporation); Machined polycarbonate surrogate with screw; 37 C. The determined RRI based on measurements is 0.05 mm, consistent with the model for release of the therapeutic agent as described herein.

FIG. 23A-1 shows cumulative release to about 90 days for Avastin™ with a reservoir volume of 20 uL as in FIG. 23A. The RRI of 0.053 mm corresponds substantially to the RRI of 0.05 of FIG. 23 and demonstrates stability of the release of therapeutic agent through the porous structure.

Figure 23B:
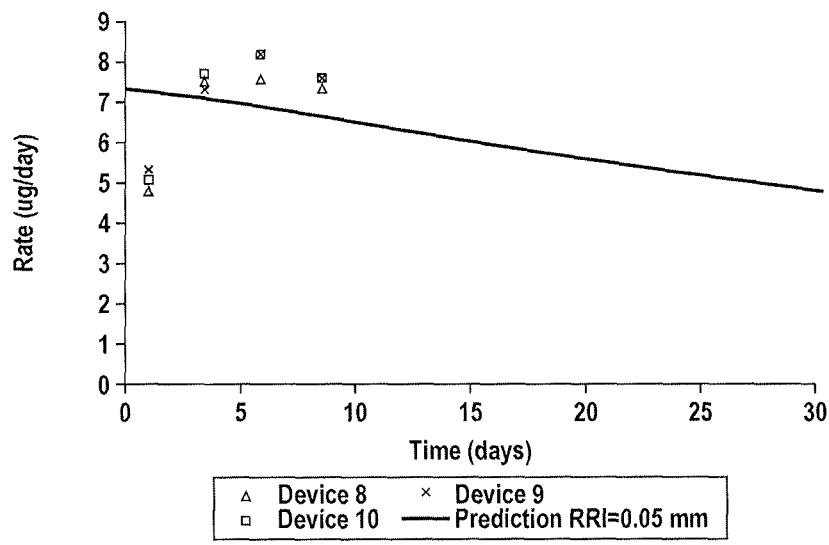
FIG. 23B shows rate of release as in FIG. 23A.
Figures 1, 23B:
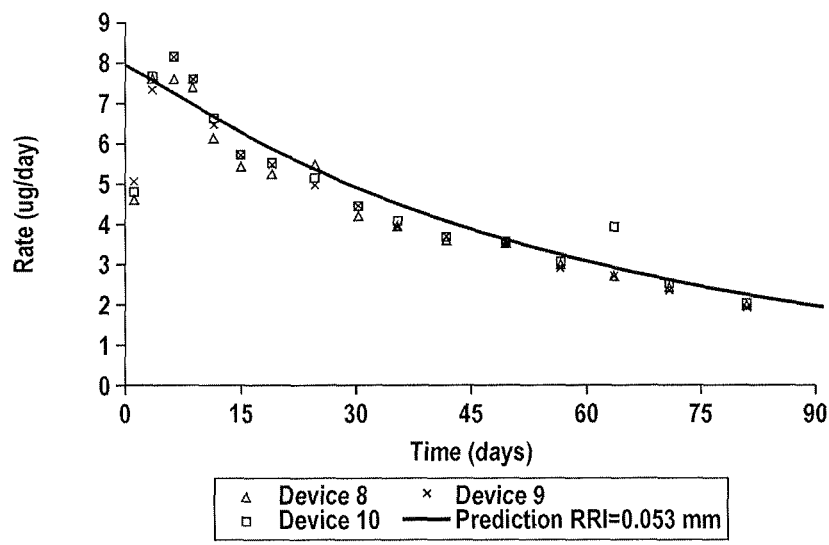

FIG. 23B shows rate of release as in FIG. 23A. The release rate data show a rate of release from about 5 ug per day to about 8 ug per day. Although the initial release rate at the first day is slightly lower than subsequent rates, the rate of release is sufficiently high to provide therapeutic effect in accordance with the drug release model. Although there can be an initial period of about a few days for the release rate profile to develop, possibly related to wetting of the interconnecting channels of the porous structure, the release rate profile corresponds substantially to the release rate index (RRI) of 0.05. Based on the teachings described herein, a person of ordinary skill in the art could determine the release rate profile with additional data for an extended time of at least about one month, for example at least about three months, six months or more, so as to determine the release rate profile for an extended time.

FIG. 23B-1 shows rate of release as in FIG. 23A-1.

Figure 24A:
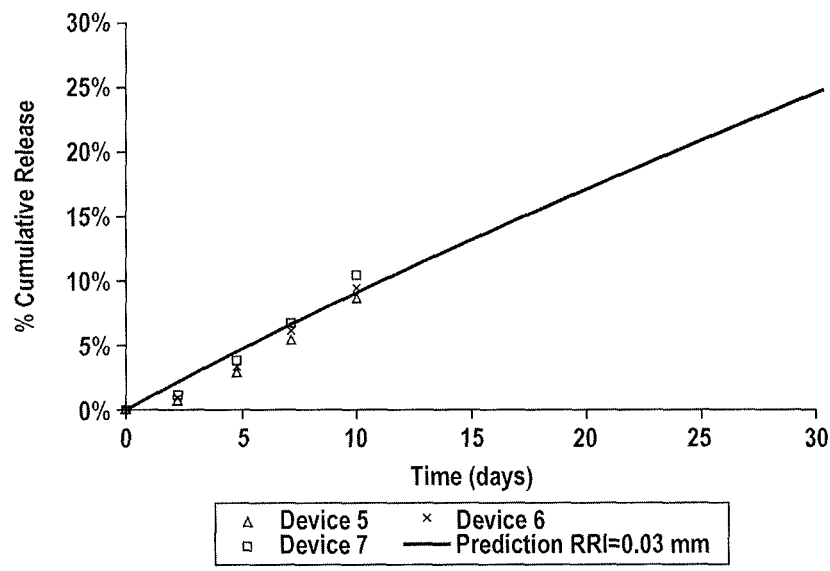
FIG. 24A shows cumulative release for Avastin™ with a 0.1 media grade porous frit structure.
Figures 1, 24A:
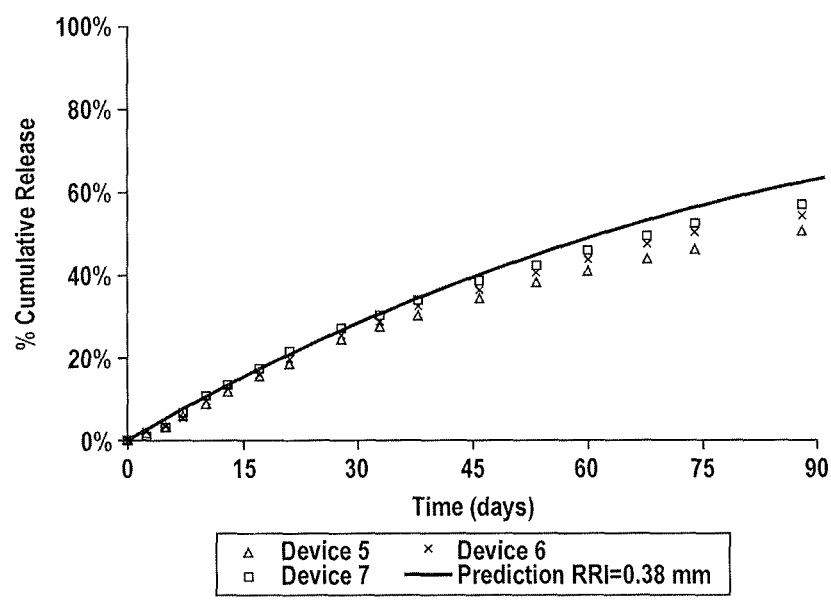

FIG. 24A shows cumulative release for Avastin™ with a 0.1 media grade porous frit structure. This experiment used: 25 mg/mL Avastin™; Frit #5 (0.038×0.029", media grade 0.1 um, 316L SS, Mott Corporation); Machined polycarbonate surrogate with screw; Reservoir Volume 20 uL; 37 C. The determined RRI based on measurements is 0.03, consistent with the model for release of the therapeutic agent as described herein.

FIG. 24A-1 shows cumulative to about 90 days release for Avastin™ with a 0.1 media grade porous frit structure as in FIG. 24A. The release rate of 0.038 mm corresponds substantially to the release rate of 0.03 of FIG. 24A and demonstrates the stability of release of the therapeutic agent through the porous structure.

Figure 24B:
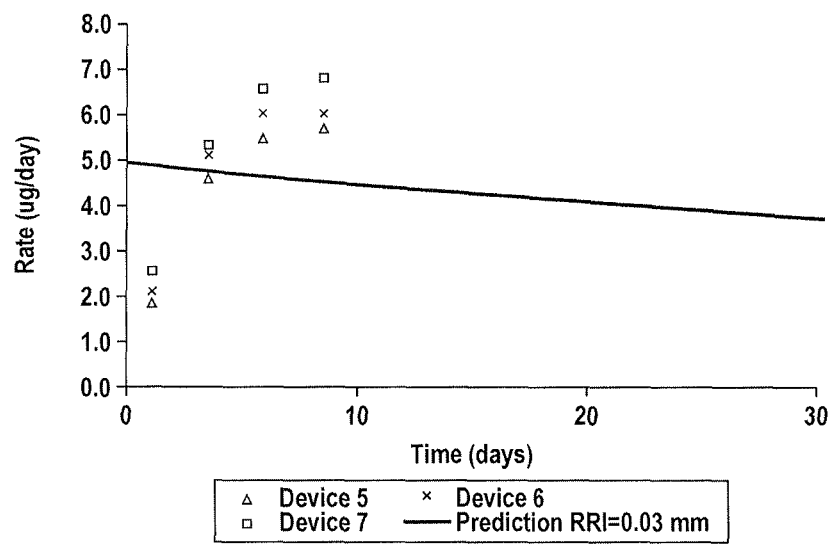
FIG. 24B shows rates of release of the devices as in FIG. 24A.
Figures 1, 24B:
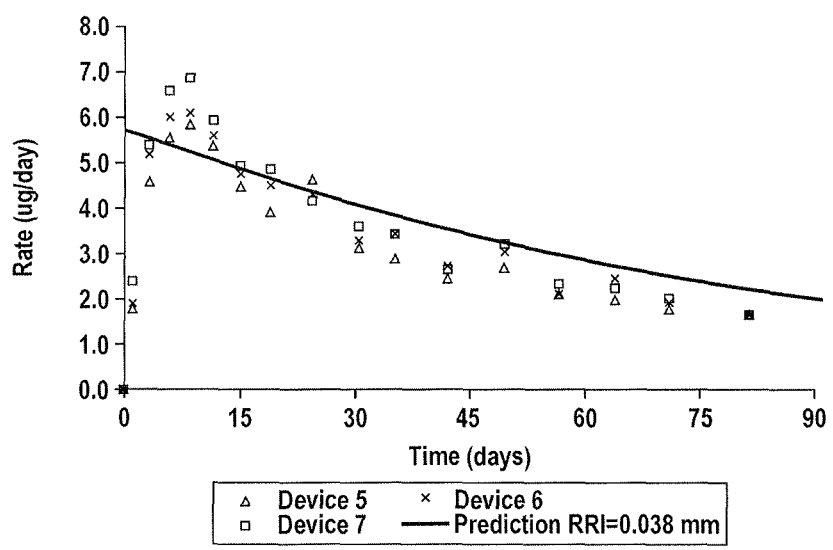

FIG. 24B shows rate of release as in FIG. 24A. The release rate data show a rate of release from about 2 ug per day to about 6 ug per day. Although the initial release rate at the first day is slightly lower than subsequent rates, the rate of release is sufficiently high to provide therapeutic effect in accordance with the drug release model. Although there can be an initial period of a few days for the release rate profile to develop, possibly related to wetting of the interconnecting channels of the porous structure, the release rate profile corresponds substantially to the release rate index (RRI) of 0.03. Based on the teachings described herein, a person of ordinary skill in the art could determine the release rate profile with additional data for an extended time of at least about one month, for example at least about three months, six months or more, so as to determine the release rate profile for an extended time.

FIG. 24B-1 shows rate of release as in FIG. 24A-1.

Example 14

Determination of Therapeutic Device Size and Lifetime Based on Minimum Inhibitory Concentration In Vivo of Therapeutic Agent Numerical calculations were performed to determine therapeutic device sizes, release rate profiles and expected therapeutic agent concentration in the reservoir. The concentration in the reservoir may correspond to the useful lifetime of the device, or time between injections of therapeutic agent into the reservoir or other replacement of the therapeutic agent.

Table 6A shows the number days of therapeutic agent is released from the device with concentration amounts at or above the MIC. These number of days correspond to an effective lifetime of the device or effective time between injections into the device. The calculations show the number of days of the extended time release based the RRI and MIC for a 20 uL reservoir volume having a drug concentration disposed therein of 10 mg/ml. The RRI ranged from 0.01 to 0.1 and the MIC ranged from 0.1 to 10, and can be determined with experimental and clinical studies as described herein. The half-life of therapeutic agent in the vitreous was modeled as 9 days, based on human data. The Cmax indicates the maximum concentration of therapeutic agent in the vitreous humor, for example within a few days of placement or injection of the therapeutic agent in the device These data indicate that the device can maintain the concentration of therapeutic agent for about 756 days, 385 days, 224 days, and 62 day for MIC's of 0.1, 0.5, 1, 2 and 4 ug/ml, respectively. For example, the therapeutic agent may comprise Lucentis™ having an MIC of about 0.5 and the device may maintain therapeutic concentrations of the agent for one year. These numerical data also show a concentration of therapeutic agent released from the device within a range of the current clinical bolus injections. For example, the Cmax ranges from 2.1 to 11.9 based on the RRI from 0.01 to 0.1 respectively, such that the maximum release of therapeutic agent such as Lucentis™ is within a safe range for the patient.

A person of ordinary skill in the art can conduct experiments to determine the stability of the therapeutic agent such as Lucentis™ in the reservoir, and adjust the size of the reservoir, time between injections or removal. The therapeutic agent can be selected and formulated so as to comprise a stability suitable for use in the therapeutic device.

TABLE 6A

Calculations for Time (days) above MIC (20 μL Reservoir Volume, T½ = 9 days, Drug Conc. in Reservoir = 10 mg/ml)

| RRI | Cmax (μg/ml) | MIC (μg/ml) | | | | | |
|---|---|---|---|---|---|---|---|
| | | 0.1 | 0.5 | 1 | 2 | 4 | 7 | 10 |
| 0.01 | 2.1 | 756 | 385 | 224 | 62 | 0 | 0 | 0 |
| 0.02 | 3.8 | 467 | 280 | 200 | 119 | 0 | 0 | 0 |
| 0.04 | 6.5 | 281 | 188 | 148 | 108 | 66 | 0 | 0 |
| 0.06 | 8.6 | 209 | 147 | 120 | 93 | 65 | 40 | 0 |
| 0.08 | 10.4 | 170 | 124 | 103 | 83 | 61 | 42 | 14 |
| 0.1 | 11.9 | 146 | 109 | 92 | 75 | 58 | 42 | 30 |

Table 6B. Shows calculations for time (days) above the MIC for a therapeutic device comprising a 20 μL Volume, Vitreous T1/2=9 days, and Drug Conc. in Reservoir=40 mg/ml. The embodiments of Table 6B include similar components to the embodiments of Table 6A and the improved time above MIC achieved with concentration of 40 mg/ml. For example, the time above the MIC can be 1079, 706, 546, 385, 225, 95, for MIC's of 0.1 0.5, 1, 2, 4, and 7 ug/ml, respectively. For example, the therapeutic agent may comprise Lucentis™ having an MIC of about 0.5 and the device may maintain therapeutic concentrations of the therapeutic agent for about 2 years. These numerical data also show a concentration of therapeutic agent released from the device within a range of the current clinical bolus injections. For example, the Cmax ranges from 8.4 to 47.6 based on the RRI from 0.01 to 0.1 respectively, such that the maximum release of therapeutic agent such as Lucentis™ is within a safe range for the patient.

A person of ordinary skill in the art can conduct experiments to determine the stability of the therapeutic agent such as Lucentis™ in the reservoir, and adjust the size of the reservoir, time between injections or removal. The therapeutic agent can be selected and formulated so as to comprise a stability suitable for use in the therapeutic device.

TABLE 6B

Calculations for Time (days) above MIC (20 μL Volume, T½ = 9 days, Drug Conc. in Reservoir = 40 mg/ml)

| RRI | Cmax (μg/ml) | MIC (μg/ml) | | | | | |
|---|---|---|---|---|---|---|---|
| | | 0.1 | 0.5 | 1 | 2 | 4 | 7 | 10 |
| 0.01 | 8.4 | 1079 | 706 | 546 | 385 | 225 | 95 | 0 |
| 0.02 | 15.1 | 626 | 440 | 360 | 280 | 200 | 135 | 93 |
| 0.04 | 25.9 | 361 | 268 | 228 | 188 | 148 | 115 | 94 |
| 0.06 | 34.4 | 262 | 200 | 174 | 147 | 120 | 98 | 84 |
| 0.08 | 41.5 | 210 | 164 | 144 | 124 | 103 | 87 | 76 |
| 0.1 | 47.6 | 179 | 141 | 125 | 109 | 92 | 79 | 70 |

Table 6C. Shows calculations for time (days) above the MIC for a therapeutic device comprising a 50 μL Volume, Vitreous T1/2=9 days, and Drug Conc. in Reservoir=40 mg/ml. The embodiments of Table 6B include similar components to the embodiments of Table 6A and the improved time above MIC achieved with concentration of 40 mg/ml. For example, the time above the MIC can be 2706, 1737, 1347, 944, 542 and 218, for MIC's of 0.1 0.5, 1, 2, 4, and 7 ug/ml, respectively. For example, the therapeutic agent may comprise Lucentis™ having an MIC of about 0.5 and the device may maintain therapeutic concentrations of the therapeutic agent for more than about 2 years. These numerical data also show a concentration of therapeutic agent released from the device within a range of the current clinical bolus injections. For example, the Cmax ranges from 9.1 to 64.7 ug/ml based on the RRI from 0.01 to 0.1 respectively, such that the maximum release of therapeutic agent such as Lucentis™ is within a safe range for the patient.

A person of ordinary skill in the art can conduct experiments to determine the stability of the therapeutic agent such as Lucentis™ in the reservoir, and adjust the size of the reservoir, time between injections or removal. The therapeutic agent can be selected and formulated so as to comprise a stability suitable for use in the therapeutic device.

TABLE 6C

Calculations for Time (days) above MIC (50 μL Volume, T½ = 9 days, Drug Conc. in Reservoir = 40 mg/ml)

| RRI | Cmax (μg/ml) | MIC (μg/ml) | | | | | |
|---|---|---|---|---|---|---|---|
| | | 0.1 | 0.5 | 1 | 2 | 4 | 7 | 10 |
| 0.01 | 9.1 | 2706 | 1737 | 1347 | 944 | 542 | 218 | 0 |
| 0.02 | 17.2 | 1560 | 1082 | 880 | 679 | 478 | 316 | 213 |
| 0.04 | 31.5 | 887 | 648 | 547 | 446 | 346 | 265 | 213 |
| 0.06 | 43.8 | 635 | 476 | 408 | 341 | 274 | 220 | 186 |
| 0.08 | 54.8 | 501 | 381 | 331 | 281 | 230 | 190 | 164 |
| 0.1 | 64.7 | 417 | 321 | 281 | 240 | 200 | 168 | 147 |

The examples shown in Tables 6A to 6C can be modified by one of ordinary skill in the art in many ways based on the teachings described herein. For example, the 50 uL reservoir may comprise an expanded configuration of the reservoir after injection of the therapeutic device. The reservoir and/or quantity of therapeutic agent can be adjusted so as to provide release for a desired extended time.

The porous frit structure as described herein can be used with many therapeutic agents, and may limit release of therapeutic agent that has degraded so as to form a particulate, for example. Work in relation to embodiments suggests that at least some therapeutic agents can degrade so as to form a particulate and that the particulate comprising degraded therapeutic agent may have an undesired effect on the patient, and the porous frit structure as described herein may at least partially filter such particulate so as to inhibit potential side effects of degraded therapeutic agent.

Table 6D shows examples of sizes of therapeutic devices that can be constructed in accordance with the teachings described herein, so as to provide a suitable volume of the drug reservoir within the container and such devices may comprise many lengths, widths and structures as described herein. For example the frit outside diameter (hereinafter "OD") can be configured in many ways and may comprise about 1 mm, for example, or about 0.5 mm. The length of the frit (thickness) may comprise about 1 mm. The volume of the frit can be, for example, about 0.785 uL, or about 0.196 uL, for example. The volume of the reservoir can be from about 0.4 uL to about 160 uL, for example. The volume of the therapeutic device can be from about 0.6 uL to about 157 uL, and can be positioned in many ways, for example with a lumen and may comprise a substantially fixed volume reservoir or an expandable reservoir. The cross sectional width of the device may correspond to many sizes, for example many radii, and the radius can be within a range from about 0.3 mm to about 3.5 mm, for example. The cross-section width and corresponding diameters of the device can be within a range from about 0.6 mm to about 7 mm. The length of the device, including the porous structure, container and retention structure can be many sizes and can be within a range from about 2 mm to about 4 mm, for example. The device may comprise a substantially fixed diameter, or alternatively can be expandable, and may comprise fixed or expandable retention structures, as described herein.

channels of the porous structure, the release rate profile corresponds substantially to the release rate index (RRI) of 0.02. Based on the teachings described herein, a person of ordinary skill in the art could determine the release rate profile with additional data for an extended time of at least about one month, for example at least about three months, six months or more, so as to determine the release rate profile for an extended time.

FIG. 25B-1 shows rate of release as in FIG. 25A-1.

TABLE 6D

| Frit OD (mm) | 1 | 0.5 | | | | | | | | | |
|---|---|---|---|---|---|---|---|---|---|---|---|
| Frit Length (mm) | 1 | 1 | | | | | | | | | |
| Frit Vol. (uL) | 0.785 | 0.19625 | | | | | | | | | |
| Vol Res (uL) | 0.4 | 2 | 4 | 8 | 16 | 27 | 31 | 39 | 63 | 110 | 157 |
| Vol Frit (uL) | 0.19625 | 0.19625 | 0.785 | 0.785 | 0.785 | 0.785 | 0.785 | 0.785 | 0.785 | 0.785 | 0.785 |
| Vol Device (uL) | 0.59625 | 2.19625 | 4.785 | 8.785 | 16.785 | 27.785 | 31.785 | 39.785 | 63.785 | 110.785 | 157.785 |
| Radius squared | 0.09 | 0.3 | 0.4 | 0.7 | 1.3 | 2.2 | 2.5 | 3.2 | 5.1 | 8.8 | 12.6 |
| Radius (mm) | 0.3 | 0.5 | 0.6 | 0.8 | 1.2 | 1.5 | 1.6 | 1.8 | 2.3 | 3.0 | 3.5 |
| OD (mm) | 0.6(4) | 1.1(3) | 1.2(3) | 1.7(3) | 2.3(3) | 3.0(2) | 3.2(2) | 3.6(2) | 4.5(2) | 5.9(2) | 7.1(2) |
| Dev Length (mm) | 2.0(6) | 2.5(5) | 4.0(1) | 4.0(1) | 4.0(1) | 4.0(1) | 4.0(1) | 4.0(1) | 4.0(1) | 4.0(1) | 4.0(1) |

(1)Fixed penetration upper limit
(2)May use non simple cylinder design to decrease incision length, for example expandable reservoir
(3)OD accommodates 1 mm diameter porous frit structure and satisfies incision length limit
(4)Device OD may use a smaller porous frit structure
(5)Length reduced to drive OD to accommodate porous frit structure
(6)Length reduced to drive OD to accommodate porous frit structure, and Device OD may use smaller frit Example 15A Calculation and Measurement of Small Release Rate Profiles as a Model for a Therapeutic Agent Released Through the Porous Frit Structure Studies of the release of fluorescein from reservoirs through porous frit structures were conducted so as to determine the release of small molecule drugs through the porous frit structure. The fluorescein model shows that the porous frit structures and reservoirs as described herein are suitable for use with small molecule drug deliver. The release profiles of Avastin™, Lucentis™ and BSA in conjunction with the fluorescein data show that the porous frit structures and reservoirs can be used for sustained release of many drugs, molecules and therapeutic agents of many molecular weights and sizes.

FIG. 25A shows cumulative release for fluorescein through a 0.2 media grade porous frit structure. The experiment used: 2 mg/mL Fluorescein sodium; Frit #2 (0.031×0.049", media grade 0.2 um, 316L SS, Mott Corporation); Machined polycarbonate surrogate with screw; 37 C. The fluorescein samples were assayed by UV absorbance at 492 nm with a plate reader. The determined RRI based on measurements is 0.02, consistent with the model for release of the therapeutic agents as described herein.

FIG. 25A-1 shows cumulative release to about 90 days for fluorescein through a 0.2 media grade porous frit structure as in FIG. 25A. The mean RRI based upon the first four data points was 0.02 mm. The mean RRI to release for 90 days (excluding the first point) is 0.026 mm. These data show stability of the rate of release and that the porous frit structure can be used for small molecule delivery or large molecule delivery, or combinations thereof.

FIG. 25B shows rate of release as in FIG. 25A. The release rate data show a rate of release from about 1.0 ug per day to about 1.8 ug per day. Although the initial release rate at the first day is slightly lower than subsequent rates, the rate of release is sufficiently high to provide therapeutic effect in accordance with the drug release model. Although there can be an initial period of about a day for the release rate profile to develop, possibly related to wetting of the interconnecting Example 15B Measured Release Rate Profiles for Lucentis™ Through the Porous Frit Structures The experiments used: 10 mg/mL Lucentis™; Machined poly(methyl methacrylate) surrogate with screw; and a Reservoir Volume 30 uL; 37 C. All porous frit structures are 316L SS, Mott Corporation. Data shown are measured data from all devices except for a few samples that showed either bubble growth or low receiver volume.

Table 6E shows results for 39 out of 48 devices were included in the table and graphs shown below. The data from the in vitro studies shown in Table 6E show that Lucentis™ can be delivered with the device having porous frit structure. The diameter ranged from 0.031" to 0.038", and the length ranged from 0.029 to 0.049. The media grade ranged from 0.1 to 0.3, and the RRI ranged from 0.014 to 0.090. The data show very low variability suitable in in vivo human treatment, with the % CV below 10% in all instances, and less than 3% for four of five device configurations measured.

Although some of the measurements were excluded, this exclusion is appropriate and associated with in vitro testing conditions that differ substantially from the in vivo model. Five devices were excluded due to bubble growth (10%), and four were excluded due to receiver volume issues at one timepoint for that device (8%). The latter can be an experimental error associated with the volume of the receiver below the assumed value due to evaporation from inadequately sealed vials or due to pipetting error. In some instances the in vitro experimental test apparatus can be sensitive to bubble formation that may differ substantially from the in vivo model as the living eye can resorb oxygen from the therapeutic devices. Bubbles can form as receiver fluid is heated to 37° C. and gas concentrations are greater than their solubilities at 37° C. To minimize the occurrence of bubble formation, receiver solutions were degassed before insertion of the devices. These experimental in vitro studies suggest that degassing of samples can be helpful with the in vitro assays.

TABLE 6E

| Frit Dimensions | | Media Grade | RRI | % | Number of |
|---|---|---|---|---|---|
| Dia | Length | (μm) | (mm) | CV | Replicates |
| 0.038" | 0.029" | 0.3 | 0.090 | 2.1% | 6 |
| 0.038" | 0.029" | 0.2 | 0.061 | 2.8% | 14 |
| 0.038" | 0.029" | 0.1 | 0.039 | 2.3% | 5 |
| 0.031" | 0.049" | 0.2 | 0.021 | 9.9% | 12 |
| 0.031" | 0.049" | 0.1 | 0.014 | 2.5% | 2 |

FIG. 25C shows cumulative release to about thirty days for Lucentis™ through a 0.2 media grade porous frit structure having a diameter of 0.038 in and a length (thickness) of 0.029, corresponding to a release rate of 0.061 as shown in the second row of Table 6E.

FIG. 25D shows rates of release of the devices as in FIG. 25C.

FIG. 25E shows cumulative release to about thirty days for Lucentis™ for 30 uL devices having a RRI's from about 0.090 to about 0.015.

FIG. 25F shows rates of release of the devices as in FIG. 25E.

These above experimentally measured data show stable release of the Lucentis™ for 30 days for a wide range of frit diameters, thicknesses and media grades consistent with the release rate model of the porous structure and reservoir as described herein. For example, the media grade, thickness, diameter and reservoir volume can be tuned to provide sustained release for a predetermined period of time above a predetermined targeted minimum inhibitory concentration. When combined with the Avastin™ and Fluorescein data, these data show that stable release can be achieved for extended times for many therapeutic agents consistent with the release model as described herein.

Example 16

Scanning Electron Micrographs of Porous Frit Structures

FIGS. 26A and 26B show scanning electron microscope images from fractured edges of porous frit structures of 0.2 media grade and 0.5 media grade porous material, respectively. The commercially available samples were obtained from Mott Corporation and comprised 316L stainless steel. The samples were mechanically fractured so as to show the porous structure and interconnecting channels within the material to release the therapeutic agent. The micrograph images show a plurality of interconnecting channels disposed between openings of the first surface and openings of the second surface.

FIGS. 27A and 27B show scanning electron microscope images from surfaces of porous frit structures of media grade of 0.2 and 0.5, respectively, from the samples of FIGS. 26A and 26B. The images show a plurality of openings on the surface connected with interconnecting channels as in FIGS. 26A and 26B.

Example 17

Porous Frit Structure Mechanical Flow Testing to Identify Porous Frit Structures Suitable for Use with Therapeutic Agent Delivery Devices The relative characteristics of sample elements can be determined by subjecting the frit to a number of mechanical tests, including but not limited to pressure decay and flow. These tests can be combined with drug release rate information, for example the RRI, so as to determine the release profile of the devices. These tests can be used with the porous structure positioned on the therapeutic device, so as to quantify flow through the porous structure of the device and determine suitable of the porous structure. Similar tests can be used to quantify the porous structure prior to mounting on the therapeutic device. At least some of the therapeutic devices can be evaluated with the gas flow of the porous structure mounted on a partially assembled therapeutic device, for example as a quality control check In some embodiments, the flow test can be performed on the partially assembled or substantially assembled therapeutic device prior to insertion of the therapeutic agent into the reservoir and prior to insertion into the patient, so as to ensure that the porous structure is suitable for release of the therapeutic agent and affixed to the device, for example a support of the therapeutic device.

These tests may utilize a variety of working fluids, but will most likely use a readily available gas such as air or nitrogen. To date, flow and pressure decay tests have been used to identify different frit characteristics that may be correlated to other test results such as chemical or pharmacologic performance.

Fixturing

Each of the test methods above may use a mechanical connection of the test specimen to the test hardware and a number of techniques have been explored and employed. These fixtures include a both a means of reliably securing the specimen (such as heat recoverable tubing, elastic tubing, press fits into relatively rigid components, etc.) and a means of coupling (such as a Luer, barbed fitting, quick connect coupling, etc.) that allow convenient and repeatable attachment to the test hardware.

Test Hardware

Each of the desired tests can be developed using commercially available solutions, or by assembling readily available instrumentation to create a custom test arrangement. Again, both of these approaches have been evaluated. A working system will consist of a means for connecting a test specimen, a controllable source (usually, but not limited to pressure), a manometer (or other pressure measurement device), and one or more transducers (pressure, flow, etc.) used to measure the test conditions and/or gather data for further analysis.

Example 17A

Pressure Decay Test to Identify Porous Structures Suitable for Use with Therapeutic Drug Delivery Devices FIG. 28 shows a pressure decay test and test apparatus for use with a porous structure so as to identify porous frit structures suitable for use with therapeutic devices in accordance with embodiments described herein.

One method of pressure decay testing is performed with the hardware shown schematically in FIG. 28. An initial pressure is applied to the system by an outside source such as a syringe, compressed air, compressed nitrogen, etc. The manometer may be configured to display simply the source gage pressure, or the actual differential pressure across the specimen. One side of the fixtured specimen is normally open to atmosphere, creating a pressure which will decay at a rate determined by the properties of the frit being tested. The instantaneous pressure may be measured by a pressure transducer that converts and supplies a signal to a data acquisition module (DAQ) that transfers data to a computer. The rate of pressure drop is then recorded and can be used for comparison to the performance of other fits or an acceptability requirement/specification. This comparison may be made by grossly comparing the pressure at a given time, or by directly comparing the output pressure decay curves.

An example test procedure would pressurize the system to slightly greater than 400 mmHg as displayed by the manometer. The computer and DAQ are configured to begin data acquisition as the pressure drops below 400 mmHg, and a data point is taken approximately every 0.109 seconds. While the test can be stopped at any time, it is likely that standard discreet points along the course of pressure decay data would be selected so as to allow direct comparison of frit flow performance (e.g. time for decay from 400 mmHg to 300 mmHg, and from 400 mmHg to 200 mmHg.)

Example 17B

Pressure Decay Test to Identify Porous Structures Suitable for Use with Therapeutic Drug Delivery Devices FIG. 29 shows a pressure flow test and test apparatus suitable for use with a porous structure so as to identify porous frit structures suitable for use with therapeutic devices in accordance with embodiments described herein.

Using a similar hardware set-up, flow thru the test specimen can also be characterized. In this test, the source pressure is constantly regulated to a known pressure and the flow of a working fluid is allowed to flow thru a mass flow meter and then thru the fixtured test frit. As in the pressure decay test, the specific characteristics of the frit determine that rate at which the working fluid will flow through the system. For additional accuracy, pressure at the otherwise open end of the fixture test frit may be regulated to control the backpressure, and therefore the pressure drop across the specimen.

Flow testing may have advantages over pressure decay testing due to the instantaneous nature of the method. Rather than waiting for the pressure to drop, the flow thru a sample should stabilize quickly enabling testing of large number of samples to be performed in rapid fashion.

In an example test procedure, a regulated compressed cylinder would supply the system with a constant source pressure of 30 psig and a constant back pressure of 1 psig. The test fluid would flow through the test frit at a characteristic rate (which is dependent on the pressure, but is expected to be in the 10-500 sccm range) as measured by the mass flow meter.

Example 17C

Determination of Therapeutic Release Rate Based on Gas Flow

Table 7 shows a table that can be used to determine release of therapeutic agent, for example the RRI, based on the flow of a gas such as oxygen or nitrogen through the porous structure. The flow through the porous structure can be measured with a decay time of the gas pressure, for with the flow rate across the porous structure with a pressure drop across the porous frit structure, as described herein. The flow rate and RRI can be determined based on the media grade of the material, for example as commercially available media grade material available from Mott Corp. The therapeutic agent can be measured through the porous structure, or a similar test molecule. The initial measurements measured the RRI for Avastin™ with the porous frit structures shown. Based on the teachings described herein, a person of ordinary skill in the art can conduct experiments to determine empirically the correspondence of flow rate with a gas to the release rate of the therapeutic agent.

TABLE 7

| Media Grade | O.D. (in.) | Length (in.) | RRI Flow | 300 Decay | 200 Decay |
|---|---|---|---|---|---|
| 0.2 | 0.031 | 0.049 | 0.019 | 106 | 256 |
| 0.2 | 0.038 | 0.029 | 0.034 | | |
| 0.1 | 0.038 | 0.029 | 0.014 | 81 | 201 |
| 0.2 | 0.038 | 0.029 | 0.033 | 31 | 78 |

The above partially populated table shows the amount and nature of frit data that can collected. It is contemplated to use some form of non-destructive testing (i.e. not drug release testing) so as to enable:
a) QC receiving inspection testing of frits
b) QC final device assembly testing One of ordinary skill can demonstrate a correlation between one or more "flow" tests and the actual drug release testing which relies on diffusion rather than forced gas flow. The data suggests that flow testing of frits can be both repeatable and falls in line with expectations.

Preliminary testing also indicates that the test for the frit alone can be substantially similar to the frit as an assembled device.

Example 18

Determination of Minimum In Vivo Inhibitory Concentration of Lucentis™ in Humans Although administration of the standard dose of Lucentis™ (500 µg) via direct intravitreal injection has been shown to be effective in reducing symptoms of patients suffering from wet AMD, the below clinical studies indicate that a lower concentration can be used to treat wet AMD. A device as described herein can be used to treat AMD with a minimum inhibitory concentration in vivo in human patients (hereinafter "MIC") with a smaller amount than corresponds to the 500 µg monthly bolus injection. For example, 5 ug Lucentis™ injections can be administered so as to obtain a concentration profiles in situ in humans in accordance with Table 4D and FIG. 19A above.

The study was designed to detect quickly a positive response to Lucentis™ treatment. A reduction of retinal thickness is an indicator of positive response to Lucentis™ therapy and a marker of drug effect that can be used to quickly identify a positive effect of drug treatment. The reduction in retinal thickness corresponds to subsequent improvement in vision. Hence, the low dose MIC study assessed the condition of retinal thickness both before and after patient's exposure to low dose bolus administration of Lucentis™, so as to determine the MIC.

OCT (Optical Coherence Tomography) imaging was used to asses the condition of the region of the macula at the back surface of the treated eye. The OCT technique relies on the measurement of certain properties of light (e.g. echo time, intensity of reflection) that has been directed at the area of study and can measure very small amounts of reflected light. Because these cellular features are essentially transparent it is possible to use OCT methodology to generate three dimensional representations of the area.

The anatomical region of patients suffering from wet AMD typically involves disturbances to the structural make-up of the various cellular layers of the back surface of the eye, notably including areas of retinal thickening often involving accumulations of subretinal fluid. In more advanced stages these areas of fluid accumulation often involve cyst-like formations easily evaluated via OCT.

post-injection and one week post-injection, respectively of sections of the region of interest.

Table 8 shows the results for 9 patients enrolled in the study. The patients received doses from 5 to 20 ug, corresponding to initial Lucentis™ concentrations in the vitreous from 1 to 4 ug/ml. Based on the above criteria, a positive response was identified in all 9 patients. In at least some instances with the 5 um injection, the decrease in size of the lesion was noted approximately 2-4 days post-op, and the decrease was substantially attenuated by one week post-op, consistent with the approximately 9 day in vivo half-life of Lucentis™. These data indicated that the MIC for a sustained release device may be approximately 1 ug per ml or less. As the therapeutic agent may have a cumulative effect, the MIC can be lower for a sustained release as described herein than the bolus injection described with reference to the MIC study. Further studies can be conducted by one or ordinary skill in the based on the teachings described herein to determine empirically the MIC for a sustained release device and cumulative effect of the drug over the time of release.

TABLE XX

| Patient # | 1 | 2 | 3 | 4 | 5 | 6 | 7 | 8 | 9 |
|---|---|---|---|---|---|---|---|---|---|
| Lowest Dose Administered (µg) | 10 | 20 | 20 | 5 | 20 | 5 | 5 | 5 | 5 |
| Estimated Initial Drug Conc. in Vitreous (µg/mL) | 2 | 4 | 4 | 1 | 4 | 1 | 1 | 1 | 1 |
| Treatment Effect Observed? | Yes | Yes | Yes | Yes | Yes | Yes | Yes | Yes | Yes |

The OCT images generated in the study enabled of various types of assessments to be made regarding the condition of the anatomical region of interest. One type of OCT image comprises a topographic map of the entire region of the macula. This image type is referred to as the "macular cube". The macular cube OCT images are typically displayed as color images and in the case of the macular cube the image provides an indication of overall topography of the disease/lesion location. These macular cube images were used identify regions of the macular of interest.

The regions of interest were analyzed with a two dimensional representation of the cross section of the retinal wall at one longitudinal scan location of the OCT image. In these "OCT scan" images is it possible to interrogate very local areas of interest more specifically. The OCT scans were carefully selected to directly compare the thickness and anatomical structure of specific sites within a lesion, pre and post treatment, for the purpose of assessing the effect of injected drug including a reduction in sub-retinal fluid.

Macular cube images and OCT scan images were measured before and after Lucentis™ treatment for each patient enrolled in the study. The OCT images were measured the day after injection and at 2-3 days post injection. An ophthalmologist reviewed the OCT images from the patients enrolled in the study, and patients were considered to have a responded to Lucentis™ treatment when the OCT scans showed a decrease in size of the lesion from one or more of the post-injection examinations.

FIG. 30A-1 shows an example of an OCT macular cube OCT image used to identify a region of interest (black arrow) and determine the response to treatment.

FIGS. 30B-1, 30B-2 and 30B-3 shows an example of a series of OCT scan images measured at pre-injection, one day FIGS. 31A and 31B show experimental implantation of therapeutic devices into the pars plana region 25 of a rabbit eye. Approximately 4 prototypes of the device as shown in FIG. 7A to 7B-6F were implanted into the rabbit eye. The retention structure of each devices comprised a substantially clear and transparent oval flange 122 positioned on the sclera under the conjunctiva. The clear and transparent flange 122 permits visualization of the interface of the scleral incision and narrow portion 120N of the retention structure, such that sealing of the retention structure to the sclera can be evaluation. The retention structure of each device also comprise an access port 180 having a substantially clear penetrable barrier 184 so as to permit dark field visualization of the location of the implanted device. The narrow portion 120N of the retention structure is disposed under the transparent flange, and barrier 160 has the oval shape so to define the narrow portion of the retention structure.

These studies showed that the retention structure comprising the oval flange and oval narrow portion can seal the incision formed in the sclera and permit dark field visualization of the implanted device. The device can be implanted temporally in the patient, for example superior/temporally or inferior/temporally such that the implant can be disposed temporally and under the eyelid so as to have a minimal effect on vision and appearance of the patient.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

TABLE 1A

Therapeutic Agent List

| Generic Name | Brands (Companies) | Category | Indication | Molecular Weight |
|---|---|---|---|---|
| 2-Methoxyestradiol analogs | (Paloma Pharmaceuticals) | Angiogenesis inhibitors | AMD | |
| 3-aminothalidomide | | | | |
| 13-cis retinoic acid | Accutane TM (Roche Pharmaceuticals) | | | |
| A0003 | (Aqumen BioPharmaceuticals) | A0003 | AMD | |
| A5b1 integrin inhibitor | (Jerini Ophthalmic); (Ophthotech) | Inhibitors of a5b1 integrin | AMD | |
| Abarelix | Plenaxis ™ (Praecis Pharmaceuticals) | Anti-Testosterone Agents; Antineoplastic Agents | For palliative treatment of advanced prostate cancer. | 37731 |
| Abatacept | Orencia ™ (Bristol-Myers Squibb) | Antirheumatic Agents | For the second line reduction of the signs and symptoms of moderate-to-severe active rheumatoid arthritis, inducing inducing major clinical response, slowing the progression of structural damage, and improving physical function in adult patients who have | 37697 |
| Abciximab | ReoPro ™; ReoPro ™ (Centocor) | Anticoagulants; Antiplatelet Agents | For treatment of myocardial infarction, adjunct to percutaneous 170oronary intervention, unstable angina | 42632 |
| ABT-578 | (Abbott Laboratories) | Limus Immunophilin Binding Compounds | | |
| Acetonide | | | | |
| Adalimumab | Humira ™ (Abbott Laboratories) | Antirheumatic Agents; Immunomodulatory Agents | For treatment of rheumatoid arthritis | 25645 |
| Aldesleukin | Proleukin ™; Proleukin ™ (Chiron Corp) | Antineoplastic Agents | For treatment of adults with metastatic renal cell carcinoma | 61118 |
| Alefacept | Amevive ™ | Immunomodulatory Agents; Immunosuppressive Agents | For treatment of moderate to severe chronic plaque psoriasis | 42632 |
| Alemtuzumab | Campath ™; Campath ™ (ILEX Pharmaceuticals LP); MabCampath ™ | Antineoplastic Agents | For treatment of B-cell chronic lymphocytic leukemia | 6614 |
| Alpha-1-proteinase inhibitor | Aralast ™ (Baxter); Prolastin ™ (Talecris Biotherapeutics C formerly Bayer) | Enzyme Replacement Agents | For treatment of panacinar emphysema | 28518 |
| Alteplase | Activase ™ (Genentech Inc) | Thrombolytic Agents | For management of acute myocardial infarction, acute ischemic strok and for lysis of acute pulmonary emboli | 54732 |
| AMG-1470 | | | | |
| Anakinra | Kineret ™ (Amgen Inc) | Anti-Inflammatory Agents, Non-Steroidal; Antirheumatic Agents; Immunomodulatory Agents | For the treatment of adult rheumatoid arthritis. | 65403 |
| Anecortave acetate | | | | |
| Angiostatin | | | | |
| Anistreplase | Eminase ™ (Wulfing Pharma GmbH) | Thrombolytic Agents | For lysis of acute pulmonary emboli, intracoronary emboli and management of myocardial infarction | 54732 |
| Anti-angiogenesis peptides | (Eyecopharm) | Anti-angiogenesis peptides | AMD | |
| Anti-angiogenesis antibodies, TRC093, TRC105 | (TRACON Pharma) | Anti-angiogenesis antibodies | AMD | |
| Anti-angiogeric bifunctional protein | Icon-1 ™ (Iconic Therapeutics) | Anti-angiogeric bifunctional protein, Icon-1 | AMD | |
| Anti-endothelial growth factor | | | | |
| Antihemophilic Factor | Advate ™; Alphanate ™; Bioclate ™; Helixate ™; Helixate FS ™; Hemofil M ™; Humate-P ™; Hyate:C ™; Koate-HP ™; Kogenate ™; Kogenate FS ™; Monarc-M ™; Monoclate-P ™; ReFacto ™; Xyntha ™ | Coagulants; Thrombotic Agents | For the treatment of hemophilia A, von Willebrand diseae and Factor XIII deficiency | 70037 |
| Antithymocyte globulin | Genzyme); Thymoglobulin ™ (SangStat Medical | Immunomodulatory Agents | For prevention of renal transplant rejection | 37173 |
| Anti-hypertensive MC1101 | (MacuCLEAR) | Anti-hypertensive MC1101 | AMD | |
| Anti-platelet devired growth factor | | | | |
| Anti-VEGF | (Neurotech); Avastin ™ (NeoVista) | Anti-VEGF | AMD | |
| AP23841 | (Ariad) | Limus Immunophilin Binding Compounds | | |

TABLE 1A-continued

Therapeutic Agent List

| Generic Name | Brands (Companies) | Category | Indication | Molecular Weight |
|---|---|---|---|---|
| Aprotinin | Trasylol ™ | Antifibrinolytic Agents | For prophylactic use to reduce perioperative blood loss and the need for blood transfusion in patients undergoing cardiopulmonary bypass in the course of coronary artery bypass graft surgery who are at an increased risk for blood loss and blood transfusio | 90569 |
| Arcitumomab | CEA-Scan ™ | Diagnostic Agents; Imaging Agents | For imaging colorectal tumors | 57561 |
| Asparaginase | Elspar ™ (Merck & Co. Inc) | Antineoplastic Agents | For treatment of acute lympocytic leukemia and non-Hodgkins lymphoma | 132.118 |
| Axitinib | | Tyrosine Kinase Inhibitors | | 386 |
| Basiliximab | Simulect ™ (Novartis Pharmaceuticals) | Immunomodulatory Agents; Immunosuppressive Agents | For prophylactic treatment of kidney transplant rejection | 61118 |
| Becaplermin | Regranex ™; Regranex ™ (OMJ Pharmaceuticals) | Anti-Ulcer Agents; Topical | For topical treatment of skin ulcers (from diabetes) | 123969 |
| Bevacizumab | Avastin ™; Avastin ™ (Genentech Inc) | Antiangiogenesis Agents; Antineoplastic Agents | For treatment of metastatic colorectal cancer | 27043 |
| Bivalirudin | Angiomax ™; Angiomax ™ (Medicines Co or MDCO); Angiox ™ | Anticoagulants; Antithrombotic Agents | For treatment of heparin-induced thrombocytopenia | 70037 |
| Bortezomib | | Proteosome Inhibitors | | |
| Bosutinib | | Tyrosine Kinase Inhibitors | | 530 |
| Botulinum Toxin Type A | BOTOX ™ (Allegran Inc); BOTOX Cosmetic ™ (Allegran Inc); Botox ™; Dysport ™ | Anti-Wrinkle Agents; Antidystonic Agents; Neuromuscular Blocking Agents | For the treatment of cervical dystonia in adults to decrease the severity of abnormal head position and neck pain associated with cervical dystonia. Also for the treatment of severe primary axillary hyperhidrosis that is inadequately managed with topical | 23315 |
| Botulinum Toxin Type B | Myobloc ™ (Solstice Neurosciences); Neurobloc ™ (Solstice Neurosciences) | Antidystonic Agents | For the treatment of patients with cervical dystonia to reduce the severity of abnormal head position and neck pain associated with cervical dystonia. | 12902 |
| C5 inhibitor | (Jerini Ophthalmic); (Ophthotech) | Inhibitors of C5 | AMD | |
| Canstatin | | | | |
| Capromab | ProstaScint ™ (Cytogen Corp) | Imaging Agents | For diagnosis of prostate cancer and detection of intra-pelvic metastases | 84331 |
| Captopril | | ACE Inhibitors | | |
| CCI-779 | (Wyeth) | Limus Immunophilin Binding Compounds | | |
| Cediranib | | Tyrosine Kinase Inhibitors | | 450 |
| Celecoxib | | Cyclooxygenase Inhibitors | | |
| Cetrorelix | Cetrotide ™ | Hormone Antagonists; Infertility Agents | For the inhibition of premature LH surges in women undergoing controlled ovarian stimulation | 78617 |
| Cetuximab | Erbitux ™; Erbitux ™ (ImClone Systems Inc) | Antineoplastic Agents | For treatment of metastatic colorectal cancer. | 42632 |
| Choriogonadotropin alfa | Novarel ™; Ovidrel ™; Pregnyl ™; Profasi ™ | Fertility Agents; Gonadotropins | For the treatment of female infertility | 78617 |
| Cilary neurotrophic factor | (Neurotech) | Cilary neurotrophic factor | AMD | |
| Coagulation Factor IX | Benefix ™ (Genetics Institute) | Coagulants; Thrombotic Agents | For treatment of hemophilia (Christmas disease). | 267012 |
| Coagulation factor VIIa | NovoSeven ™ (Novo Nordisk) | Coagulants; Thrombotic Agents | For treatment of hemorrhagic complications in hemophilia A and B | 54732 |
| Colchicines | | | | |
| Collagenase | Cordase ™; Santyl ™ (Advance Biofactures Corp); Xiaflextm ™ | Anti-Ulcer Agents; Topical | For treatment of chronic dermal ulcers and severe skin burns | 138885 |
| Complement factor H recombinant | (Optherion); (Taligen Therapeutics) | Complement factor H recombinant | AMD | |
| Compstatin derivative peptide, POT-4 | (Potentia Pharmaceuticals) | Complement Factor C3 Inhibitors; Compstatin Derivative Peptides | AMD | |
| Corticotropin | ACTH ™; Acethropan ™; Acortan ™; Acthar ™; Exacthin ™; H.P. Acthar Gel ™; Isactid ™; Purified cortrophin gel ™; Reactin ™; Solacthyl ™; Tubex | Diagnostic Agents | For use as a diagnostic agent in the screening of patients presumed to have adrenocortical insufficiency. | 33927 |
| Cosyntropin | Cortrosyn ™; Synacthen depot ™ | Diagnostic Agents | For use as a diagnostic agent in the screening of patients presumed to have adrenocortical insufficiency. | 33927 |
| Cyclophilins | | Limus Immunophilin Binding Compounds | | |

TABLE 1A-continued

Therapeutic Agent List

| Generic Name | Brands (Companies) | Category | Indication | Molecular Weight |
|---|---|---|---|---|
| Cyclosporine | Gengraf ™ (Abbott labs); Neoral ™ (Novartis); Restasis ™; Restasis ™ (Allergan Inc); Sandimmune ™ (Novartis); Sangcya ™ | Antifungal Agents; Antirheumatic Agents; Dermatologic Agents; Enzyme Inhibitors; Immunomodulatory Agents; Immunosuppressive Agents | For treatment of transplant rejection, rheumatoid arthritis, severe psoriasis | 32953 |
| Daclizumab | Zenapax ™ (Hoffmann-La Roche Inc) | Immunomodulatory Agents; Immunosuppressive Agents | For prevention of renal transplant rejection | 61118 |
| Darbepoetin alfa | Aranesp ™ (Amgen Inc.) | Antianemic Agents | For the treatment of anemia (from renal transplants or certain HIV treatment) | 55066 |
| Dasatinib | | Tyrosine Kinase Inhibitors | | 488 |
| Defibrotide | Dasovas ™; Noravid ™; Prociclide ™ | Antithrombotic Agents | Defibrotide is used to treat or prevent a failure of normal blood flow (occlusive venous disease, OVD) in the liver of patients who have had bone marrow transplants or received certain drugs such as oral estrogens, mercaptopurine, and many others. | 36512 |
| Denileukin diftitox | Ontak ™ | Antineoplastic Agents | For treatment of cutaneous T-cell lymphoma | 61118 |
| Desmopressin | Adiuretin ™; Concentraid ™; Stimate ™ | Antidiuretic Agents; Hemostatics; Renal Agents | For the management of primary nocturnal enuresis and indicated as antidiuretic replacement therapy in the management of central diabetes insipidus and for the management of the temporary polyuria and polydipsia following head trauma or surgery in the pitu | 46800 |
| Dexamethasone | Ozurdex ™ (Allergan) | Glucocorticoid | DME, inflammation, macular edema following branch retinal vein occlusion (BRVO) or central retinal vein occlusion (CRVO) | 392 |
| Diclofenac | | Cyclooxygenase Inhibitors | | |
| Dithiocarbamate | | NFκB Inhibitor | | |
| Dornase Alfa | Dilor ™; Dilor-400 ™; Lufyllin ™; Lufyllin-400 ™; Neothylline ™; Pulmozyme ™ (Genentech Inc) | Enzyme Replacement Agents | For the treatment of cystic fibrosis. | 7656 (double strand) |
| Drotrecogin alfa | Xigris ™; Xigris ™ (Eli Lilly & Co) | Antisepsis Agents | For treatment of severe sepsis | 267012 |
| Eculizumab | Soliris ™; Soliris ™ (Alexion Pharmaceuticals) | | For the treatment of patients with paroxysmal nocturnal hemoglobinuria (PNH) to reduce hemolysis. | 188333 |
| Efalizumab | Raptiva ™; Raptiva ™ (Genentech Inc) | Immunomodulatory Agents; Immunosuppressive Agents | For the treatment of adult patients with moderate to severe chronic plaque psoriasis, who are candidates for phototherapy or systemic therapy. | 128771 |
| Endostatin | | | | |
| Enfuvirtide | Fuzeon ™; Fuzeon ™ (Roche Pharmaceuticals) | Anti-HIV Agents; HIV Fusion Inhibitors | For treatment of HIV AIDS | 16768 |
| Epoetin alfa | Epogen ™ (Amgen Inc.); Epogin ™ (Chugai); Epomax ™ (Elanex); Eprex ™ (Janssen-Cilag. Ortho Biologics LLC); NeoRecormon ™ (Roche); Procrit ™ (Ortho Biotech); Recormon ™ (Roche) | Antianemic Agents | For the treatment of anemia (from renal transplants or certain HIV treatment) | 55066 |
| Eptifibatide | Integrilin ™; Integrilin ™ (Millennium Pharm) | Anticoagulants; Antiplatelet Agents; Platelet Aggregation Inhibitors | For treatment of myocardial infarction and acute coronary syndrome. | 7128 |
| Erlotinib | | Tyrosine Kinase Inhibitors | | 393 |
| Etanercept | Enbrel ™; Enbrel ™ (Immunex Corp) | Antirheumatic Agents; Immunomodulatory Agents | For treatment of severe adult and 178ocalizi rheumatoid arthritis | 25645 |
| Everolimus | | Limus Immunophilin Binding Compounds | | |
| Exenatide | Byetta ™; Byetta ™ (Amylin/Eli Lilly) | | Indicated as adjunctive therapy to improve glycemic control in patients with Type 2 diabetes mellitus who are taking metformin, a sulfonylurea, or a combination of both, but have not achieved adequate glycemic control. | 53060 |

TABLE 1A-continued

Therapeutic Agent List

| Generic Name | Brands (Companies) | Category | Indication | Molecular Weight |
|---|---|---|---|---|
| Felypressin | Felipresina ™ [INN-Spanish]; Felipressina ™ [DCIT]; Felypressin ™ [USAN:BAN:INN]; Felypressine ™ [INN-French]; Felypressinum ™ [INN-Latin]; Octapressin ™ | Renal Agents; Vasoconstrictor Agents | For use as an alternative to adrenaline as a 179ocalizing agent, provided that local ischaemia is not essential. | 46800 |
| Fenretinide | (Sirion Therapeutics) | Binding Protein Antagonist for Oral Vitamin A | AMD | |
| Filgrastim | Neupogen ™ (Amgen Inc.) | Anti-Infective Agents; Antineutropenic Agents; Immunomodulatory Agents | Increases leukocyte production, for treatment in non-myeloid cancer, neutropenia and bone marrow transplant | 28518 |
| FK605-binding proteins, FKBPs | | Limus Immunophilin Binding Compounds | | |
| Fluocinolone Acetonide | Retisert ™ (Bausch & Lomb); Iluvien ™ (Alimera Sciences, Inc.) | Glucocorticoid | Retinal inflammation, diabetic macular edema | 453 |
| Follitropin beta | Follistim ™ (Organon); Gonal F ™; Gonal-F ™ | Fertility Agents | For treatment of female infertility | 78296 |
| Fumagillin | | | | |
| Galsulfase | Naglazyme ™; Naglazyme ™ (BioMarin Pharmaceuticals) | Enzyme Replacement Agents | For the treatment of adults and children with Mucopolysaccharidosis VI. | 47047 |
| Gefitinib | | Tyrosine Kinase Inhibitors | | 447 |
| Gemtuzumab ozogamicin | Mylotarg ™; Mylotarg ™ (Wyeth) | Antineoplastic Agents | For treatment of acute myeloid leukemia | 39826 |
| Glatiramer Acetate | Copaxone ™ | Adjuvants, Immunologic; Immunosuppressive Agents | For reduction of the frequency of relapses in patients with Relapsing-Remitting Multiple Sclerosis. | 29914 |
| Glucagon recombinant | GlucaGen ™ (Novo Nordisk); Glucagon ™ (Eli Lilly) | Antihypoglycemic Agents | For treatment of severe hypoglycemia, also used in gastrointestinal imaging | 54009 |
| Goserelin | Zoladex ™ | Antineoplastic Agents; Antineoplastic Agents, Hormonal | Breast cancer; Prostate carcinoma; Endometriosis | 78617 |
| Human Serum Albumin | Albutein ™ (Alpha Therapeutic Corp) | Serum substitutes | For treatment of severe blood loss, hypervolemia, hypoproteinemia | 39000 |
| Hyaluronidase | Vitragan ™; Vitrase ™; Vitrase ™ (Ista Pharma) | Anesthetic Adjuvants; Permeabilizing Agents | For increase of absorption and distribution of other injected drugs and for rehydration | 69367 |
| Ibritumomab | Zevalin ™ (IDEC Pharmaceuticals) | Antineoplastic Agents | For treatment of non-Hodgkin's lymphoma | 33078 |
| Idursulfase | Elaprase ™ (Shire Pharmaceuticals) | Enzyme Replacement Agents | For the treatment of Hunter syndrome in adults and children ages 5 and older. | 47047 |
| Imatinib | | Tyrosine Kinase Inhibitors | | 494 |
| Immune globulin | Civacir ™; Flebogamma ™ (Instituto Grifols SA); Gamunex ™ (Talecris Biotherapeutics) | Anti-Infectives; Immunomodulatory Agents | For treatment of immunodeficiencies, thrombocytopenic purpura, Kawasaki disease, gammablobulinemia, leukemia, bone transplant | 42632 |
| Infliximab | Remicade ™ (Centocor Inc) | Immunomodulatory Agents; Immunosuppressive Agents | For treatment of Crohn's disease, psoriasis, rheumatoid 181cuminate and ankylosing spondylitis | 25645 |
| Insulin Glargine recombinant | Lantus ™ | Hypoglycemic Agents | For treatment of diabetes (type I and II) | 156308 |
| Insulin Lyspro recombinant | Humalog ™ (Eli Lily); Insulin Lispro (Eli Lily) | Hypoglycemic Agents | For treatment of diabetes (type I and II) | 154795 |
| Insulin recombinant | Novolin R ™ (Novo Nordisk) | Hypoglycemic Agents | For treatment of diabetes (type I and II) | 156308 |
| Insulin, porcine | Iletin II ™ | Hypoglycemic Agents | For the treatment of diabetes (type I and II) | 156308 |
| Interferon | | | | |
| Interferon Alfa-2a, Recombinant | Roferon A ™ (Hoffmann-La Roche Inc); Veldona ™ (Amarillo Biosciences) | Antineoplastic Agents; Antiviral Agents | For treatment of chronic hepatitis C, hairy cell leukemia, AIDS-related Kaposi's sarcoma, and chronic myelogenous leukemia. Also for the treatment of oral warts arising from HIV infection. | 57759 |
| Interferon Alfa-2b, Recombinant | Intron A ™ (Schering Corp) | Antineoplastic Agents; Antiviral Agents; Immunomodulatory Agents | For the treatment of hairy cell leukemia, malignant melanoma, and AIDS-related Kaposi's sarcoma. | 57759 |
| Interferon alfacon-1 | Advaferon ™; Infergen ™ (InterMune Inc) | Antineoplastic Agents; Antiviral Agents; Immunomodulatory Agents | For treatment of hairy cell leukemia, malignant melanoma, and AIDS-related Kaposi's sarcoma | 57759 |
| Interferon alfa-n1 | Wellferon ™ (GlaxoSmithKline) | Antiviral Agents; Immunomodulatory Agents | For treatment of venereal or genital warts caused by the Human Papiloma Virus | 57759 |
| Interferon alfa-n3 | Alferon ™ (Interferon Sciences Inc.); Alferon LDO ™; Alferon N Injection ™ | Antineoplastic Agents; Antiviral Agents; Immunomodulatory Agents | For the intralesional treatment of refractory or recurring external condylomata 182cuminate. | 57759 |
| Interferon beta-1b | Betaseron ™ (Chiron Corp) | Antiviral Agents; Immunomodulatory Agents | For treatment of relapsing/remitting multiple sclerosis | 57759 |
| Interferon gamma-1b | Actimmune ™; Actimmune ™ (InterMune Inc) | Antiviral Agents; Immunomodulatory Agents | For treatment of Chronic granulomatous disease, Osteopetrosis | 37835 |

TABLE 1A-continued

Therapeutic Agent List

| Generic Name | Brands (Companies) | Category | Indication | Molecular Weight |
|---|---|---|---|---|
| Lapatinib | | Tyrosine Kinase Inhibitors | | 581 |
| Lepirudin | Refludan ™ | Anticoagulants; Antithrombotic Agents; Fibrinolytic Agents | For the treatment of heparin-induced thrombocytopenia | 70037 |
| Lestaurtinib | | Tyrosine Kinase Inhibitors | | 439 |
| Leuprolide | Eligard ™ (Atrix Labs/QLT Inc) | Anti-Estrogen Agents; Antineoplastic Agents | For treatment of prostate cancer, endometriosis, uterine fibroids and premature puberty | 37731 |
| Lutropin alfa | Luveris ™ (Serono) | Fertility Agents | For treatment of female infertility | 78617 |
| Mecasermin | Increlex ™; Increlex ™ (Tercica); Iplex | | For the long-term treatment of growth failure in pediatric patients with Primary IGFD or with GH gene deletion who have developed neutralizing antibodies to GH. It is not indicated to treat Secondary IGFD resulting from GH deficiency, malnutrition, hypoth | 154795 |
| Menotropins | Repronex ™ | Fertility Agents | For treatment of female infertility | 78617 |
| mTOR inhibitors | | | | |
| Muromonab | Orthoclone OKT3 ™ (Ortho Biotech) | Immunomodulatory Agents; Immunosuppressive Agents | For treatment of organ transplant recipients, prevention of organ rejection | 23148 |
| Natalizumab | Tysabri ™ | Immunomodulatory Agents | For treatment of multiple sclerosis. | 115334 |
| Nepafenac | | Cyclooxygenase Inhibitors | | |
| Nesiritide | Natrecor ™ | Cardiac drugs | For the intravenous treatment of patients with acutely decompensated congestive heart failure who have dyspnea at rest or with minimal activity. | 118921 |
| Nilotinib | | Tyrosine Kinase Inhibitors | | 530 |
| NS398 | | Cyclooxygenase Inhibitors | | |
| Octreotide | Atrigel ™; Longastatin ™; Sandostatin ™; Sandostatin LAR ™; Sandostatin LAR ™ (Novartis) | Anabolic Agents; Antineoplastic Agents, Hormonal; Gastrointestinal Agents; Hormone Replacement Agents | For treatment of acromegaly and reduction of side effects from cancer chemotherapy | 42687 |
| Omalizumab | Xolair ™ (Genentech Inc) | Anti-Asthmatic Agents; Immunomodulatory Agents | For treatment of asthma caused by allergies | 29596 |
| Oprelvekin | Neumega ™; Neumega ™ (Genetics Institute Inc) | Coagulants; Thrombotics | Increases reduced platelet levels due to chemotherapy | 45223 |
| OspA lipoprotein | LYMErix ™ (SmithKline Beecham) | Vaccines | For prophylactic treatment of Lyme Disease | 95348 |
| OT-551 | (Othera) | Anti-oxidant eyedrop | AMD | |
| Oxytocin | Oxytocin ™ (BAM Biotech); Pitocin ™ (Parke-Davis); Syntocinon ™ (Sandoz) | Anti-tocolytic Agents; Labor Induction Agents; Oxytocics | To assist in labor, elective labor induction, uterine contraction induction | 12722 |
| Palifermin | Kepivance ™ (Amgen Inc) | Antimucositis Agents | For treatment of mucositis (mouth sores) | 138885 |
| Palivizumab | Synagis ™ | Antiviral Agents | For treatment of respiratory diseases casued by respiratory syncytial virus | 63689 |
| Panitumumab | Vectibix ™; Vectibix ™ (Amgen) | Antineoplastic Agents | For the treatment of EGFR-expressing, metastatic colorectal carcinoma with disease progression on or following fluoropyrimidine-, oxaliplatin-, and irinotecan-containing chemotherapy regimens. | 134279 |
| PDGF inhibitor | (Jerini Ophthalmic); (Ophthotech) | Inhibitors of PDGF | AMD | |
| PEDF (pigment epithelium derived factor) | | | | |
| Pegademase bovine | Adagen ™ (Enzon Inc.) | Enzyme Replacement Agents | For treatment of adenosine deaminase deficiency | 36512 |
| Pegaptanib | Macugen ™ | Oligonucleotide | For the treatment of neovascular (wet) age-related macular degeneration. | 103121 |
| Pegaspargase | Oncaspar ™ (Enzon Inc) | Antineoplastic Agents | For treatment of acute lymphoblastic leukemia | 132.118 |
| Pegfilgrastim | Neulasta ™ (Amgen Inc.) | Anti-Infective Agents; Antineutropenic Agents; Immunomodulatory Agents | Increases leukocyte production, for treatment in non-myeloid cancer, neutropenia and bone marrow transplant | 28518 |
| Peginterferon alfa-2a | Pegasys ™ (Hoffman-La Roche Inc) | Antineoplastic Agents; Antiviral Agents; Immunomodulatory Agents | For treatment of hairy cell leukemia, malignant melanoma, and AIDS-related Kaposi's sarcoma. | 57759 |
| Peginterferon alfa-2b | PEG-Intron (Schering Corp); Unitron PEG ™ | Antineoplastic Agents; Antiviral Agents; Immunomodulatory Agents | For the treatment of chronic hepatitis C in patients not previously treated with interferon alpha who have compensated liver disease and are at least 18 years of age. | 57759 |

TABLE 1A-continued

Therapeutic Agent List

| Generic Name | Brands (Companies) | Category | Indication | Molecular Weight |
|---|---|---|---|---|
| Pegvisomant | Somavert ™ (Pfizer Inc) | Anabolic Agents; Hormone Replacement Agents | For treatment of acromegaly | 71500 |
| Pentoxifylline | | | | |
| Perindozril | | ACE Inhibitors | | |
| Pimecrolimus | | Limus Immunophilin Binding Compounds | | |
| PKC (protein kinase C) inhibitors | | | | |
| Pramlintide | Symlin ™; Symlin ™ (Amylin Pharmaceuticals) | | For the mealtime treatment of Type I and Type II diabetes in combination with standard insulin therapy, in patients who have failed to achieve adequate glucose control on insulin monotherapy. | 16988 |
| Proteosome inhibitors | Velcade ™ | | Proteosome inhibitors | |
| Pyrrolidine | | | | |
| Quinopril | | ACE Inhibitors | | |
| Ranibizumab | Lucentis ™ | | For the treatment of patients with neovascular (wet) age-related macular degeneration. | 27043 |
| Rapamycin (sirolimus) | (MacuSight) | Limus Immunophilin Binding Compounds | AMD | |
| Rasburicase | Elitek ™; Elitek ™ (Sanofi-Synthelabo Inc); Fasturtec ™ | Antihyperuricemic Agents | For treatment of hyperuricemia, reduces elevated plasma uric acid levels (from chemotherapy) | 168.11 |
| Reteplase | Retavase ™ (Centocor); Retavase ™ (Roche) | Thrombolytic Agents | For lysis of acute pulmonary emboli, intracoronary emboli and management of myocardial infarction | 54732 |
| Retinal stimulant | Neurosolve ™ (Vitreoretinal Technologies) | Retinal stimulants | AMD | |
| Retinoid(s) | | | | |
| Rituximab | MabThera ™; Rituxan ™ | Antineoplastic Agents | For treatment of B-cell non-Hodgkins lymphoma (CD20 positive) | 33078 |
| RNAI (RNA interference of angiogenic factors) | | | | |
| Rofecoxib | Vioxx ™; Ceoxx ™; Ceeoxx ™ (Merck & Co.) | Cyclooxygenase Inhibitors | | |
| Rosiglitazone | | Thiazolidinediones | | |
| Ruboxistaurin | Eli Lilly | Protein Kinase C (PKC)-b Inhibitor | DME, diabetic peripheral retinopathy | 469 |
| Salmon Calcitonin | Calcimar ™; Miacalcin ™ (Novartis) | Antihypocalcemic Agents; Antiosteporotic Agents; Bone Density Conservation Agents | For the treatment of post-menopausal osteoporosis | 57304 |
| Sargramostim | Immunex ™; Leucomax ™ (Novartis); Leukine ™; Leukine ™ (Berlex Laboratories Inc) | Anti-Infective Agents; Antineoplastic Agents; Immunomodulatory Agents | For the treatment of cancer and bone marrow transplant | 46207 |
| SDZ-RAD | | Limus Immunophilin Binding Compounds | | |
| Secretin | SecreFlo ™; Secremax ™, SecreFlo ™ (Repligen Corp) | Diagnostic Agents | For diagnosis of pancreatic exocrine dysfunction and gastrinoma | 50207 |
| Selective inhibitor of the factor 3 complement cascade | | | | |
| Selective inhibitor of the factor 5 complement cascade | | | | |
| Semaxanib | | Tyrosine Kinase Inhibitors | | 238 |
| Sermorelin | Geref ™ (Serono Pharma) | Anabolic Agents; Hormone Replacement Agents | For the treatment of dwarfism, prevention of HIV-induced weight loss | 47402 |
| Serum albumin iodinated | Megatope ™ (IsoTex Diagnostics) | Imaging Agents | For determination of total blood and plasma volumes | 39000 |
| Siroliums reformulation (rapamycin) | (MacuSight) | Limus Immunophilin Binding Compounds | AMD | |
| siRNAi molecule synthetic, FTP-801i-14 | (Quark Pharmaceuticals) | siRNAi molecule synthetic | AMD | |

TABLE 1A-continued

Therapeutic Agent List

| Generic Name | Brands (Companies) | Category | Indication | Molecular Weight |
|---|---|---|---|---|
| Somatropin recombinant | BioTropin ™ (Biotech General); Genotropin ™ (Pfizer); Humatrope ™ (Eli Lilly); Norditropin ™ (Novo Nordisk); Nutropin ™ (Genentech Inc.); NutropinAQ ™ (Genentech Inc.); Protropin ™ (Genentech Inc.); Saizen ™ (Serono SA); Serostim ™; Serostim ™ (Serono SA); Tev-Tropin ™ (GATE) | Anabolic Agents; Hormone Replacement Agents | For treatment of dwarfism, acromegaly and prevention of HIV-induced weight loss | 71500 |
| Squalamine | | | | |
| Streptokinase | Streptase ™ (Aventis Behringer GmbH) | Thrombolytic Agents | For the treatment of acute evolving transmural myocardial infarction, pulmonary embolism, deep vein thrombosis, arterial thrombosis or embolism and occlusion of arteriovenous cannulae | 90569 |
| Sunitinib | | Tyrosine Kinase Inhibitors | | 398 |
| Tacrolimus | | Limus Immunophilin Binding Compounds | | |
| Tenecteplase | TNKase ™ (Genentech Inc) | Thrombolytic Agents | For treatment of myocardial infarction and lysis of intracoronary emboli | 54732 |
| Teriparatide | Apthela ™; Forsteo ™; Forteo ™; Fortessa ™; Opthia ™; Optia ™; Optiah ™; Zalectra ™; Zelletra ™ | Bone Density Conservation Agents | For the treatment of osteoporosis in men and postmenopausal women who are at high risk for having a fracture. Also used to increase bone mass in men with primary or hypogonadal osteoporosis who are at high risk for fracture. | 66361 |
| Tetrathiomolybdate | | | | |
| Thyrotropin Alfa | Thyrogen ™ (Genzyme Inc) | Diagnostic Agents | For detection of residueal or recurrent thyroid cancer | 86831 |
| Tie-1 and Tie-2 kinase inhibitors | | | | |
| Toceranib | | Tyrosine Kinase Inhibitors | | 396 |
| Tositumomab | Bexxar ™ (Corixa Corp) | Antineoplastic Agents | For treatment of non-Hodgkin's lymphoma (CD20 positive, follicular) | 33078 |
| TPN 470 analogue | | | | |
| Trastuzumab | Herceptin ™ (Genentech) | Antineoplastic Agents | For treatment of HER2-positive pulmonary breast cancer | 137912 |
| Triamcinolone acetonide | Triesence ™ | Glucocorticoid | DME, For treatment of inflammation of the retina | 435 |
| Troglitazone | | Thiazolidinediones | | |
| Tumistatin | | | | |
| Urofollitropin | Fertinex ™ (Serono S.A.) | Fertility Agents | For treatment of female infertility | 78296 |
| Urokinase | Abbokinase ™; Abbokinase ™ (Abbott Laboratories) | Thrombolytic Agents | For the treatment of 190ulmonary embolism, coronary artery thrombosis and IV catheter clearance | 90569 |
| Vandetanib | | Tyrosine Kinase Inhibitors | | 475 |
| Vasopressin | Pitressin ™; Pressyn ™ | Antidiuretics; Oxytocics; Vasoconstrictor Agents | For the treatment of enuresis, polyuria, diabetes insipidus, polydipsia and oesophageal varices with bleeding | 46800 |
| Vatalanib | | Tyrosine Kinase Inhibitors | | 347 |
| VEGF receptor kinase inhibitor | | | | |
| VEGF Trap | Aflibercept ™ (Regneron Pharmaceuticals, Bayer HealthCare AG) | Genetically Engineered Antibodies | DME, cancer, retinal vein occlusion, choroidal neovascularization, delay wound healing, cancer treatment | 96600 |
| Visual Cycle Modulator ACU-4229 | (Acucela) | Visual Cycle Modulator | AMD | |
| Vitamin(s) | | | | |
| Vitronectin receptor antagonists | | | | |
| Volociximabe | | Monoclonal antibody | | |

What is claimed is:

1. A method of manufacturing a drug delivery therapeutic device implantable in an eye for prolonged treatment, the method comprising:
performing a non-destructive test on at least one porous structure, the non-destructive test selected from the group consisting of a gas flow rate test, a bubble point test, and a pressure decay test, wherein the at least one porous structure has a pre-formed shape, the at least one porous structure being part of a device having a refillable reservoir for containing at least one therapeutic agent with the at least one rigid porous structure coupled to the device in fluid communication with the reservoir, the rigid porous structure having a plurality of interconnecting channels and coupled to a distal portion of the reservoir;

obtaining from the non-destructive test at least one performance result for the at least one porous structure;

measuring a diffusion rate of a molecule according to passive, concentration-gradient driven molecular diffusion to obtain a measured diffusion rate, wherein the molecule diffuses through a porous structure, the porous structure being the at least one porous structure or at least another porous structure; and correlating the at least one performance result of the at least one porous structure to the measured diffusion rate so as to form a correlation used to predict a measured diffusion rate of the molecule through at least a second porous structure.

2. The method as in claim 1, further comprising:
performing the non-destructive test on the at least a second porous structure;
obtaining from the non-destructive test at least one performance result for the at least a second porous structure; and
predicting, based on the correlation, the measured diffusion rate of the molecule through the at least a second porous structure to obtain a predicted diffusion rate.

3. The method as in claim 2, further comprising identifying the at least a second porous structure as suitable for assembly with the therapeutic device.

4. The method as in claim 2, wherein the predicted diffusion rate corresponds to the diffusion rate of the through the at least one porous structure.

5. The method as in claim 2, further comprising measuring a diffusion rate of a molecule through the at least a second porous structure to obtain a second measured diffusion rate and comparing the second measured diffusion rate to the predicted diffusion rate.

6. The method as in claim 5, wherein measuring is performed prior to manufacturing the device with the second porous structure.

7. The method as in claim 5, wherein measuring is performed after manufacturing the device with the second porous structure.

8. The method as in claim 2, further comprising manufacturing the therapeutic device with the second porous structure without measuring a diffusion rate of a molecule through the at least a second porous structure and comparing to the predicted diffusion rate.

9. The method as in claim 1, wherein the non-destructive test is performed on the at least one porous structure prior to assembling the at least one porous structure with the therapeutic device.

10. The method as in claim 1, wherein the non-destructive test is performed on the at least one porous structure after at least partially assembling the at least one porous structure with the therapeutic device.

11. The method as in claim 10, wherein the at least partially assembled therapeutic device includes the therapeutic agent contained in the reservoir.

12. The method as in claim 1, wherein the non-destructive test is performed as a quality control inspection test upon receipt of the at least one porous structure from a manufacturer.

13. The method as in claim 1, wherein the non-destructive test is performed as a quality control inspection test after final assembly of the therapeutic device.

14. The method as in claim 1, wherein the non-destructive test is a test that does not involve drug release through the at least one porous structure.

15. A therapeutic device manufactured according to the method of claim 1.

16. The method as in claim 1, wherein the at least one porous structure is a rigid porous structure manufactured from sintered grains of material including metal, ceramic, glass or plastic.

17. The method as in claim 1, wherein performing the non-destructive test comprises exposing the at least one porous structure to a gas.

18. A method of manufacturing a drug delivery device for prolonged treatment, the method comprising:
performing a non-destructive test on a first rigid porous structure, the non-destructive test selected from the group consisting of a gas flow rate test, a bubble point test, and a pressure decay test, the first rigid porous structure being part of a device having a refillable reservoir for containing at least one therapeutic agent with the first rigid porous structure coupled to the device in fluid communication with the reservoir, the first rigid porous structure having a plurality of interconnecting channels and coupled to a distal portion of the reservoir;
obtaining from the non-destructive test at least one performance result for the first rigid porous structure;
measuring a diffusion rate of a molecule according to passive, concentration-gradient driven molecular diffusion through the first rigid porous structure to obtain a measured diffusion rate; and
correlating the at least one performance result of the first rigid porous structure to the measured diffusion rate so as to form a correlation used to predict a measured diffusion rate of the molecule through at least a second porous structure.

* * * * *